United States Patent
Luo et al.

(10) Patent No.: US 11,155,523 B2
(45) Date of Patent: Oct. 26, 2021

(54) BIPHENYL COMPOUND AS CCR2/CCR5 RECEPTOR ANTAGONIST

(71) Applicant: Medshine Discovery Inc., Jiangsu (CN)

(72) Inventors: Yunfu Luo, Shanghai (CN); Yuyong Ba, Shanghai (CN); Shuhui Chen, Shanghai (CN)

(73) Assignee: Medshine Discovery, Inc., Jiangsu (CN)

( * ) Notice: Subject to any disclaimer, the term of this patent is extended or adjusted under 35 U.S.C. 154(b) by 304 days.

(21) Appl. No.: 16/468,127

(22) PCT Filed: Dec. 11, 2017

(86) PCT No.: PCT/CN2017/115453
§ 371 (c)(1),
(2) Date: Jan. 27, 2020

(87) PCT Pub. No.: WO2018/103757
PCT Pub. Date: Jun. 14, 2018

(65) Prior Publication Data
US 2020/0223801 A1   Jul. 16, 2020

(30) Foreign Application Priority Data

Dec. 9, 2016 (CN) .......................... 201611137560.7
Jan. 17, 2017 (CN) .......................... 201710037028.6

(51) Int. Cl.
| C07D 233/64 | (2006.01) |
| C07D 213/34 | (2006.01) |
| C07D 213/56 | (2006.01) |
| C07D 249/08 | (2006.01) |
| C07D 233/58 | (2006.01) |

(52) U.S. Cl.
CPC .......... C07D 233/58 (2013.01); C07D 213/34 (2013.01); C07D 213/56 (2013.01); C07D 249/08 (2013.01)

(58) Field of Classification Search
CPC .. C07D 233/64; C07D 213/34; C07D 213/56; C07D 249/08
See application file for complete search history.

(56) References Cited

U.S. PATENT DOCUMENTS

2006/0160864 A1 *   7/2006   Shiraishi ................. A61P 9/00
                                                                514/341

FOREIGN PATENT DOCUMENTS

| CA | 2304959 A1 | 7/1999 |
| CN | 1282243 A | 1/2001 |
| EP | 1422228 A1 | 5/2004 |
| EP | 1593673 A1 | 11/2005 |
| EP | 1593676 A1 | 11/2005 |
| WO | 2003014105 A1 | 2/2003 |
| WO | 2004069808 A1 | 8/2004 |

OTHER PUBLICATIONS

Berge, S. M., et al., "Pharmaceutical Salts", Journal of Pharmaceutical Sciences, Jan. 1977, vol. 66, No. 1, pp. 1-19.
Seto, Masaki et al., "Highly Potent and Orally Active CCR5 Antagonists as Anti-HIV-1 Agents: Synthesis and Biological Activities of 1-Benzazocine Derivatives Containing a Sulfoxide Moiety", J. Med. Chem., 2006, 49, 2037-2048, DOI: 10.1021/jm0509703, American Chemical Society.
Oct. 12, 2020 First office action issued in Chinese Application No. 2017800749290.
Nov. 30, 2020 First office action issued in European Application No. 17877947.6.

* cited by examiner

*Primary Examiner* — Laura L Stockton
(74) *Attorney, Agent, or Firm* — Verrill Dana, LLP

(57) ABSTRACT

Provided is a CCR2/CCR5 receptor antagonist and the use thereof in the preparation of a drug for treating diseases associated with the CCR2/CCR5. In particular, disclosed are a compound represented by formula (I) and a pharmaceutically acceptable salt thereof.

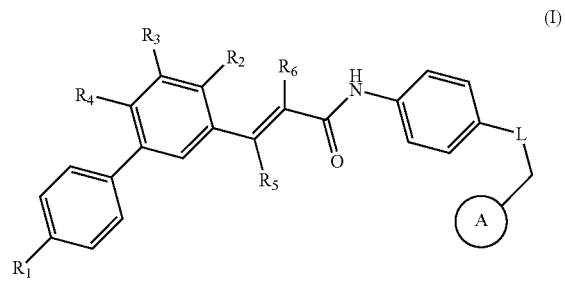

25 Claims, No Drawings

BIPHENYL COMPOUND AS CCR2/CCR5 RECEPTOR ANTAGONIST

RELATED APPLICATION REFERENCE

The present application claims priorities to the Chinese Patent Application CN201611137560.7 filed with National Intellectual Property Administration, PRC on Dec. 9, 2016 and the Chinese Patent Application CN201710037028.6 filed with National Intellectual Property Administration, PRC on Jan. 17, 2017, the contents of which are incorporated herein by reference in their entireties.

FIELD OF INVENTION

The present invention relates to a class of CCR2/CCR5 receptor antagonist, and a use thereof in manufacturing a medicament for treating CCR2/CCR5 related diseases. Specifically disclosed are a compound as shown in formula (I) and a pharmaceutically acceptable salt thereof.

PRIOR ARTS

Chemokines are a small family of pro-inflammatory cytokines that act as the chemoattractants for leukocytes. They promote the transportation of leukocytes from the vascular bed to the surrounding tissues that respond to inflammatory signals. Chemotaxis starts with the binding of the chemokines to the receptors (GPCR), and the initiation involves an increase in calcium flux, inhibition of cyclic adenosine production, cytoskeletal rearrangement, integrin activation, and signaling pathways in cell motility and increased expression of adhesion proteins.

Chemical inducer cytokines (i.e., chemokines) are relatively small proteins (8-10 kD) that stimulate cells migration. The chemokine family is classified into four subfamilies based on the number of amino acid residues between the first and the second highly conserved cysteines. Monocyte chemoattractant protein-1 (MCP-1) is a member of the CC chemokine subfamily (wherein, CC represents a subfamily with the adjacent first and second cysteines) and binds to cell surface chemokines receptor 2 (CCR2). MCP-1 is a potent chemokine that mediates the migration (i.e., chemotaxis) of monocytes and lymphocytes to the sites of inflammation after binding to CCR2. MCP-1 is also expressed by cardio-myocytes, vascular endothelial cells, fibroblasts, chondrocytes, smooth muscle cells, mesangial cells, alveolar cells, T lymphocytes, esophageal cancer, and the like. After entering the inflammatory tissues, monocytes differentiate into CCR5-expressing macrophages, providing secondary sources of several pro-inflammatory regulators, including tumor necrosis factor-α (TNF-α), interleukin-1 (IL-1), an IL-8 CXC chemokine subfamily, wherein CXC represents an amino acid residue between the first and the second cysteines, IL-12, an arachidonic acid metabolite (e.g., PGE 2 and LTB 4), oxygen-derived free radicals, matrix metalloproteinases and complement components.

CCR2 (also known as CKR-2, MCP-1RA or MCIRB) is mainly expressed on monocytes and macrophages and is essential for macrophage-dependent inflammation. CCR2 is a G-protein coupled receptor (GPCR) that binds to several members of the chemokine MCP family (CCL2, CCL7, CCL8, etc.) with high affinity, triggering chemotaxis signals and resulting in directional receptor-carrying cells migration. Animal model studies of the chronic inflammatory diseases have demonstrated that the antagonists inhibit inflammatory responses by inhibiting the binding of MCP-1 and CCR2.

CCR5 is a G-protein coupled receptor that binds to a variety of CC chemokine ligands, including CCL3, CCL3L1, CCL4, CCL5, CCL7, CCL11 and CCL13. The in vivo function of CCR5 is more indefinite than that of CCR2. Compared to CCR2, CCR5 is mainly expressed in activated Th1 cells and tissue macrophages differentiated from blood monocytes, which is accompanied by the down-modulation of CCR2 expression. It has been shown that CCR5 contributes to the survival of macrophages during inflammation and infection, and can also has role in retaining the macrophages in inflamed tissues. In addition, CCR5 mediates the recruitment and activation of Th1 cells in inflammation. CCR5 is also expressed on the osteoclasts and is crucial for the osteoclast formation, indicating a contributing role of CCR5 in the pathology of rheumatoid arthritis. The activation of vascular smooth cells by CCL4/CCR5 may also contribute to the atherosclerosis and the pathology of AIH (accelerated intimal hyperplasia).

The complementary cell distribution and differential cellular function of CCR2 and CCR5 provide dual targeting of two receptors, which may have greater efficacy in the theoretical basis than targeting individual receptors. In monocyte/macrophage biology, CCR2 plays an important role in mediating the migration from bone marrow to blood and the migration from blood to tissue monocytes, wherein, CCR5 primarily regulates the activation, survival and possible retention of the macrophages in inflamed tissues. Furthermore, CCR5 blockade can improve the therapeutic potential of dual antagonists by inhibiting T cell responses in addition to effects on monocytes/macrophages. Based on the advantages of dual targeting of CCR2 and CCR5, CCR2/5 dual antagonists have also been intensively studied, and there are four drugs in clinical phase, namely Tobira's Cenicriviroc, Bristol-Myers Squibb's BMS-813160 and Pfizer's PF-04634817. Therefore, the CCR2/5 dual antagonists have a good pharmacological potential, and here we patent the biphenyl compounds of the CCR2/5 dual antagonists.

*J. Med. Chem.* 2006, 49, 2037-2048 reports a compound Cenicriviroc, the structure of which is shown as below.

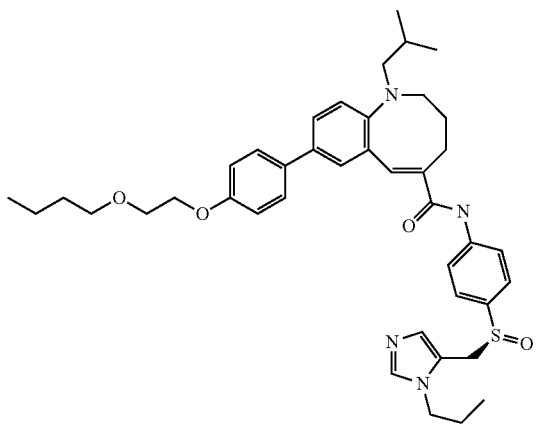

Cenicriviroc

Content of the Present Invention

The present invention provides a compound as shown in formula (I) or a pharmaceutically acceptable salt thereof,

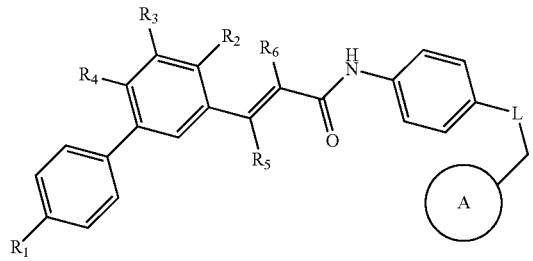

wherein,

R₁ is selected from the group consisting of $C_{1-6}$ alkoxy and 5-6 membered heterocycloalkyl, each of which is optionally substituted by 1, 2 or 3 R;

each of R₂, R₃ and R₄ is independently H, halogen, OH, CN, or selected from the group consisting of $C_{1-6}$ alkyl, $C_{1-6}$ alkoxy, $C_{1-6}$ alkylthio, $C_{1-6}$ alkyl-S(=O)—, $C_{1-6}$ alkyl-S(=O)₂— and $C_{3-6}$ cycloalkyl, each of which is optionally substituted by 1, 2 or 3 R;

each of R₅ and R₆ is independently H, or $C_{1-3}$ alkyl, which is optionally substituted by 1, 2 or 3 R ring A is

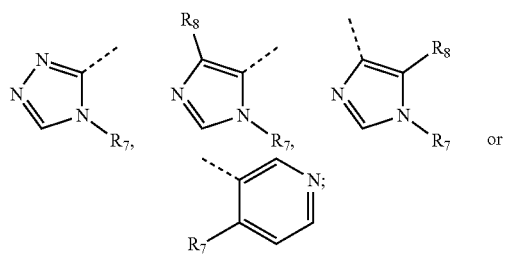

R₇ is $C_{1-6}$ alkyl, which is optionally substituted by 1, 2 or 3 R;

R₈ is H, or $C_{1-6}$ alkyl, which is optionally substituted by 1, 2 or 3 R;

L is —S(=O)— or —S(=O)₂—;

R is halogen, OH, or selected from the group consisting of $C_{1-6}$ alkyl, $C_{1-6}$ heteroalkyl and $C_{3-6}$ cycloalkyl, each of which is optionally substituted by 1, 2 or 3 R';

R' is F, Cl, Br, I, OH, CH₂F, CHF₂ or CF₃;

each of the "hetero" in the 5-6 membered heterocycloalkyl is independently —NH—, —O— or N;

in any of the above cases, the number of the heteroatom or the heteroatom group is independently 1, 2 or 3.

In some embodiments of the present invention, the above R is F, Cl, Br, I, OH, or selected from the group consisting of $C_{1-3}$ alkyl, $C_{1-4}$ alkoxy and $C_{3-6}$ cycloalkyl, each of which is optionally substituted by 1, 2 or 3 R'.

In some embodiments of the present invention, the above R is F, Cl, Br, I, OH, or selected from the group consisting of Me,

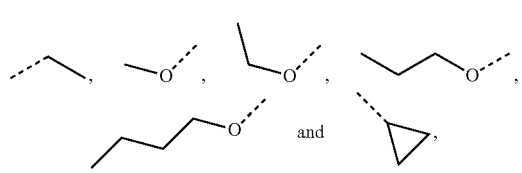

each of which is optionally substituted by 1, 2 or 3 R'.

In some embodiments of the present invention, the above R is F, Cl, Br, I, OH, CH₃, CH₂F, CHF₂, CF₃,

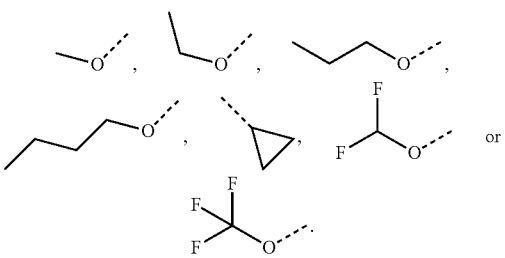

In some embodiments of the present invention, the above R₁ is selected from the group consisting of $C_{1-4}$ alkoxy and pyrrolidinyl, each of which is optionally substituted by 1, 2 or 3 R.

In some embodiments of the present invention, the above R₁ is selected from the group consisting of

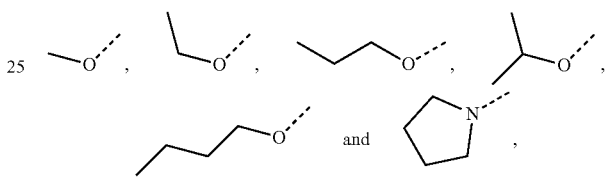

each of which is optionally substituted by 1, 2 or 3 R.

In some embodiments of the present invention, the above R₁ is

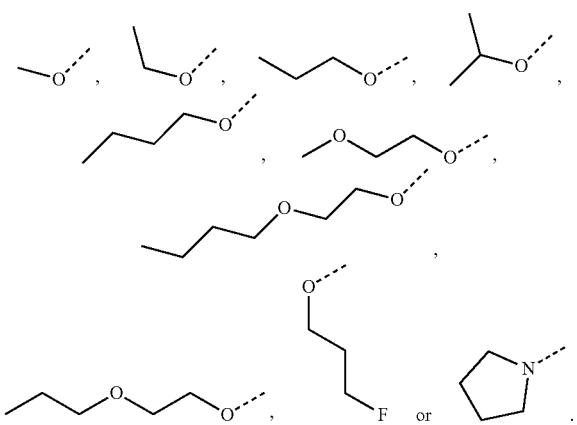

In some embodiments of the present invention, each of the above R₂, R₃ and R₄ is independently H, halogen, OH, CN, or selected from the group consisting of $C_{1-3}$ alkyl, $C_{1-3}$ alkoxy, $C_{1-3}$ alkylthio, $C_{1-3}$ alkyl-S(=O)—, $C_{1-3}$ alkyl-S(=O)₂— and $C_{4-5}$ cycloalkyl, each of which is optionally substituted by 1, 2 or 3 R.

In some embodiments of the present invention, each of the above R₂, R₃ and R₄ is independently H, F, Cl, Br, I, OH, CN, or selected from the group consisting of Me,

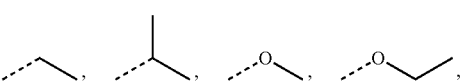

-continued

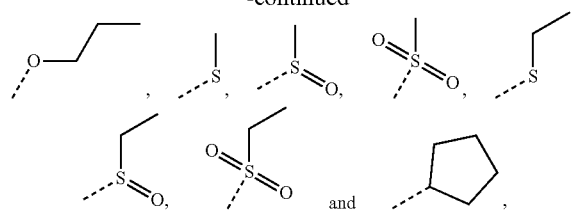

each of which is optionally substituted by 1, 2 or 3 R.

In some embodiments of the present invention, each of the above $R_2$, $R_3$ and $R_4$ is independently H, F, Cl, Br, I, OH, CN, Me,

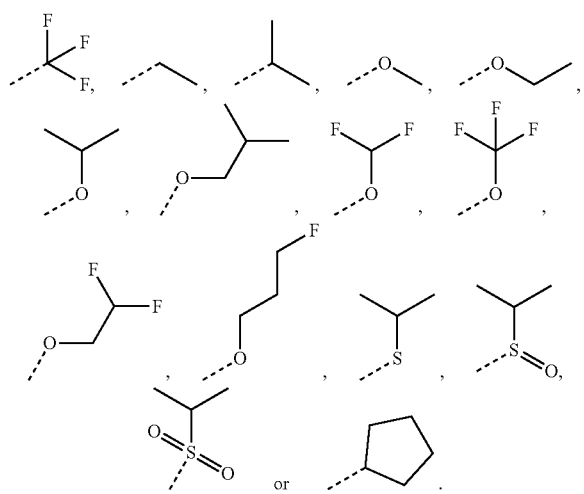

In some embodiments of the present invention, the above $R_2$ is H, F, Cl, OH, CN, Me,

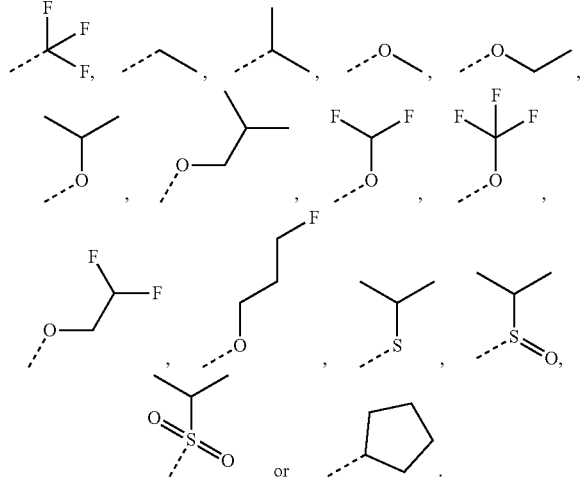

In some embodiments of the present invention, the above $R_3$ is H, F, Cl, Me or In some embodiments of the present invention, the above $R_4$ is H or Cl.

In some embodiments of the present invention, each of the above $R_5$ and $R_6$ is independently H or Me.

In some embodiments of the present invention, the above $R_7$ is selected from the group consisting of Me,

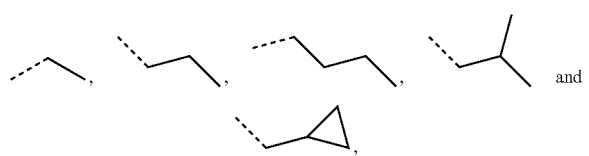

each of which is optionally substituted by 1, 2 or 3 R.

In some embodiments of the present invention, the above $R_7$ is Me, or

In some embodiments of the present invention, the above $R_8$ is H, or selected from the group consisting of Me and each of which is optionally substituted by 1, 2 or 3 R.

In some embodiments of the present invention, the above $R_8$ is H, Me or

.

In some embodiments of the present invention, the above ring A is

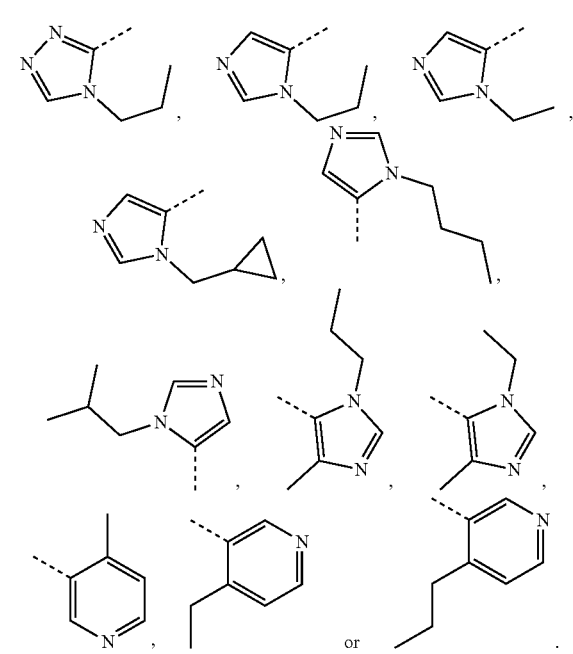

or

In some embodiments of the present invention, the above compound or the pharmaceutically acceptable salt thereof is selected from the group consisting of

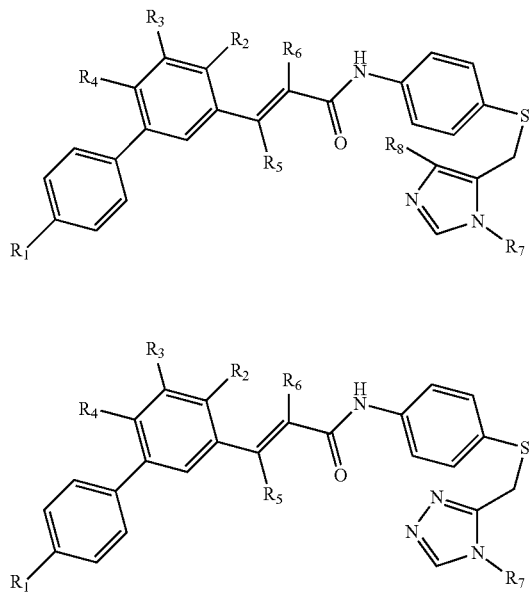

(I-1)

(I-2)

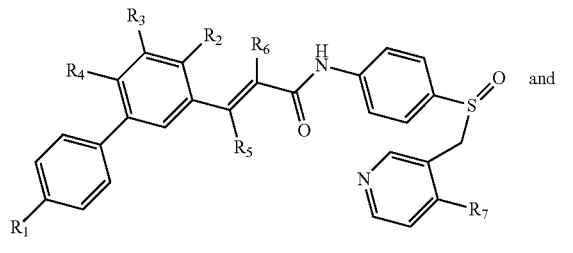

(I-3)

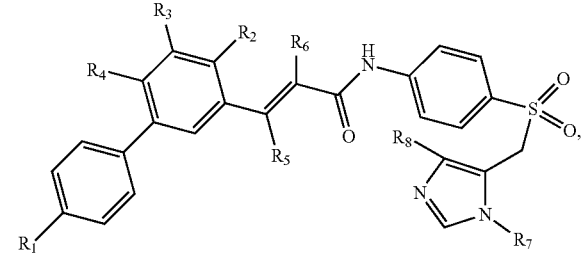

(I-4)

wherein,
$R_1$, $R_2$, $R_3$, $R_4$, $R_5$, $R_6$, $R_7$ and $R_8$ are as defined above.

The present invention also provides a compound shown as the following formula or a pharmaceutically acceptable salt thereof, which is selected from the group consisting of

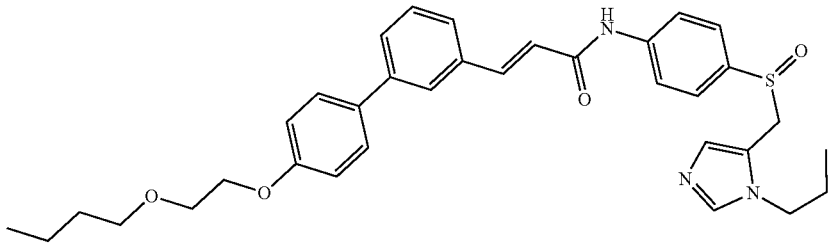

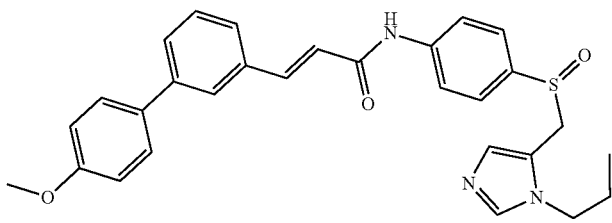

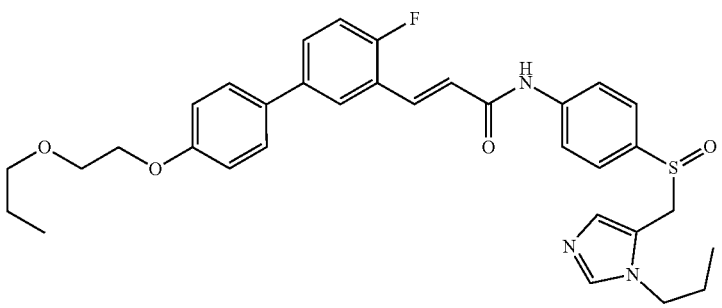

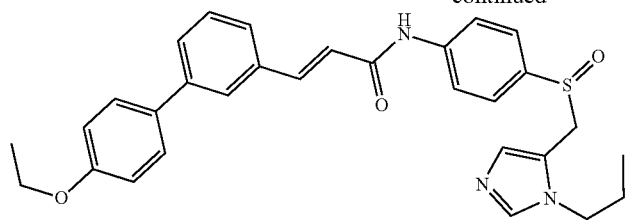
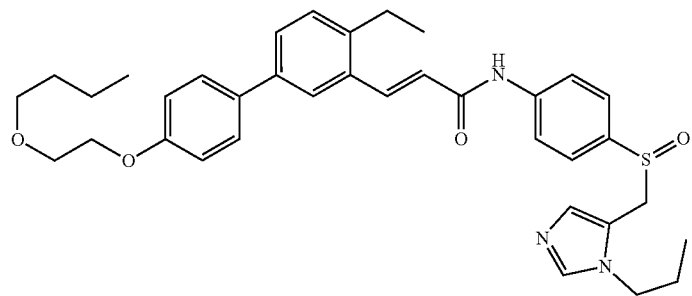
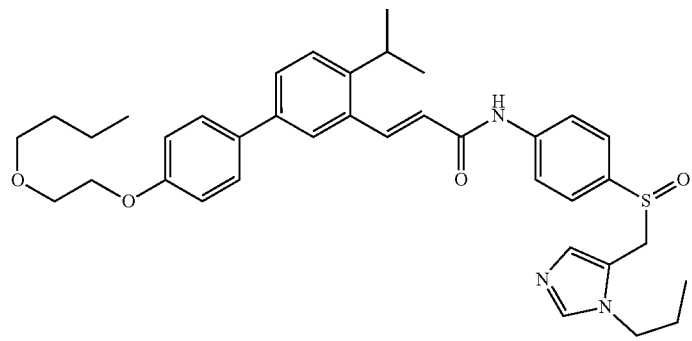
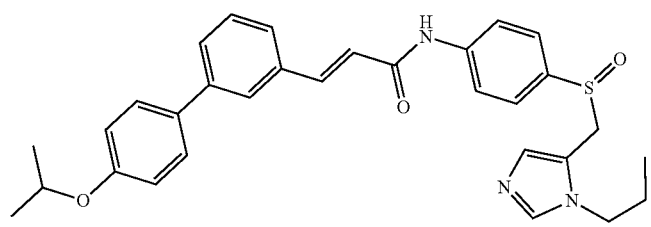
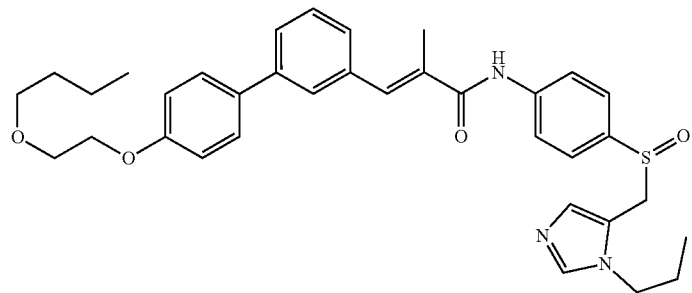
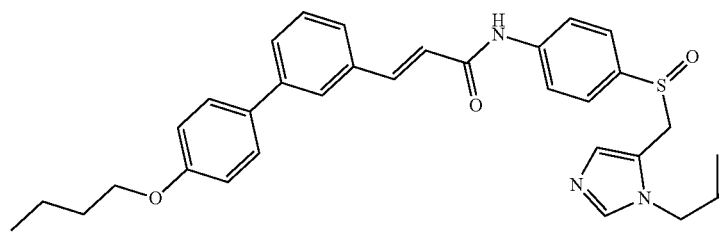

-continued
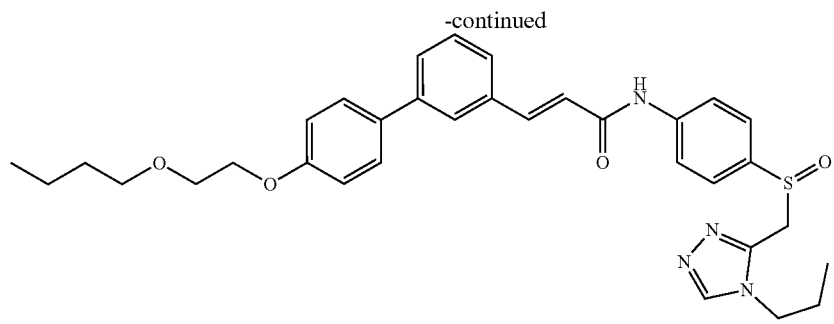
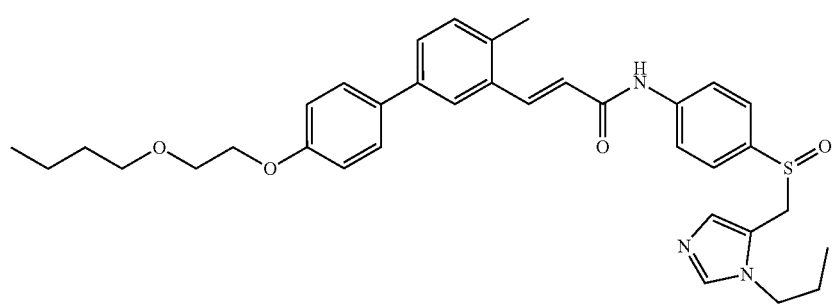
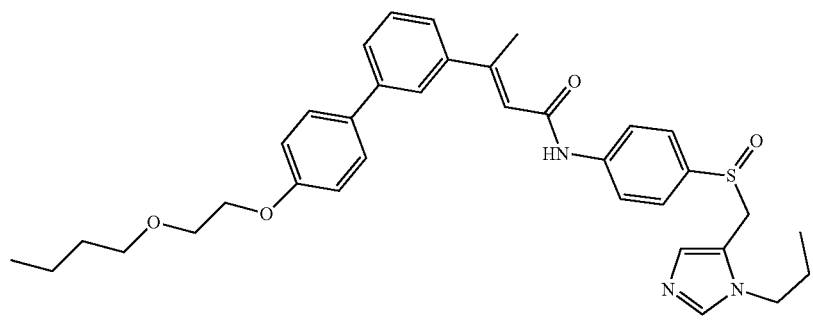
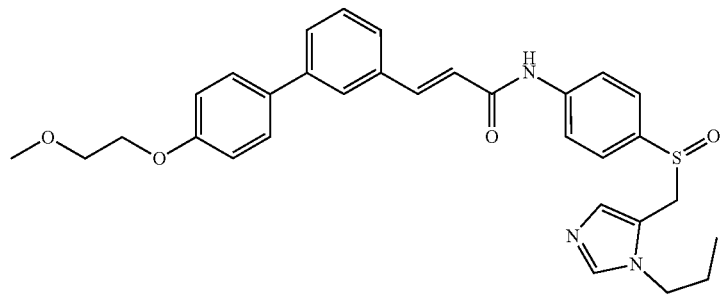
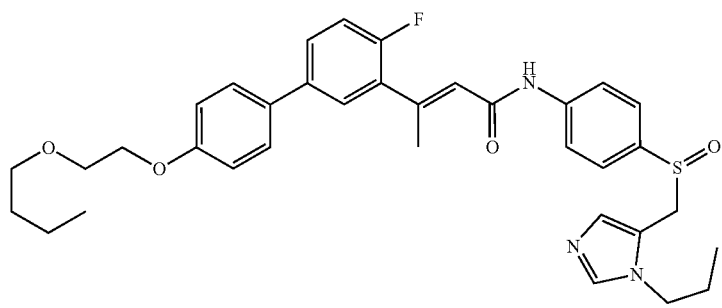

-continued
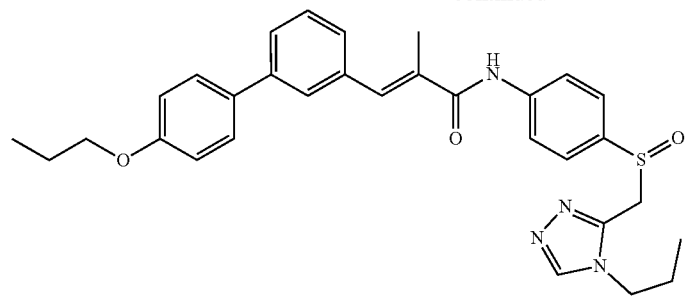
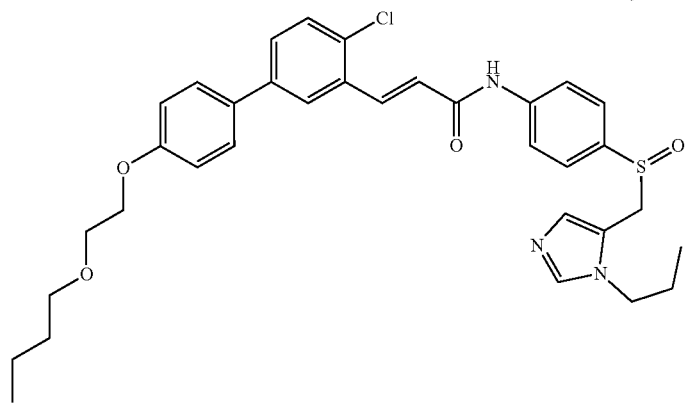
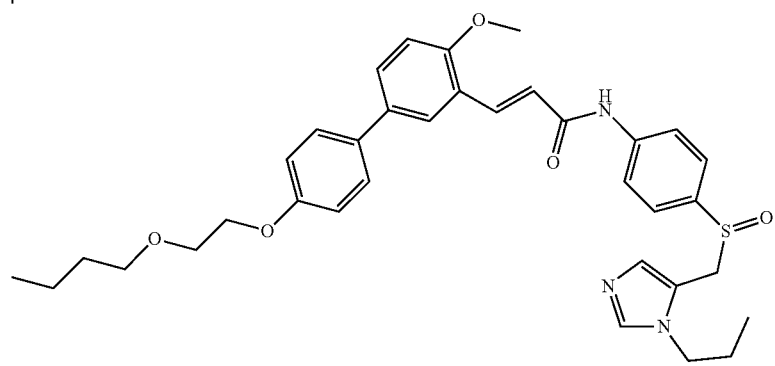
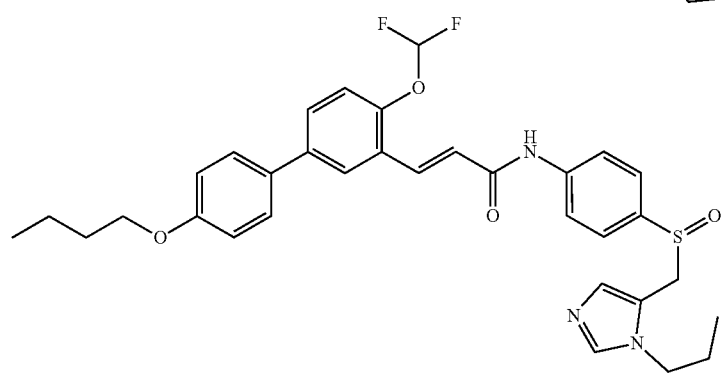
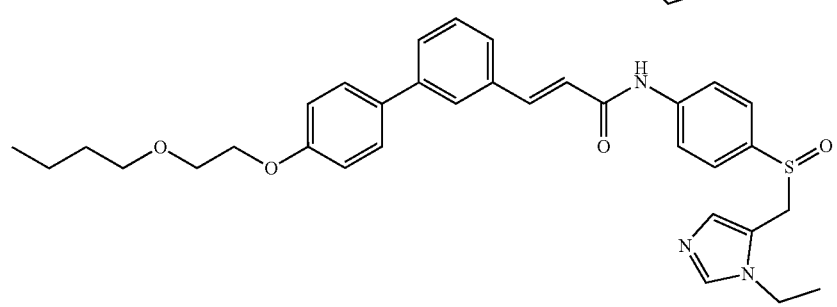

-continued
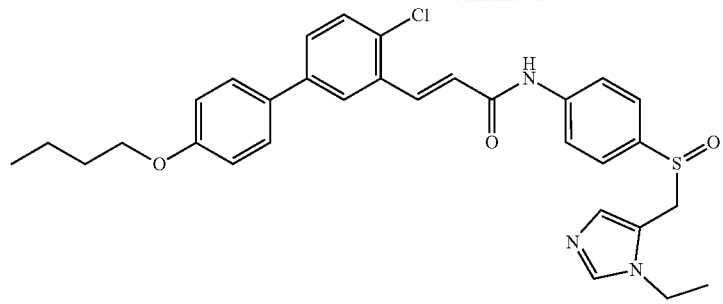
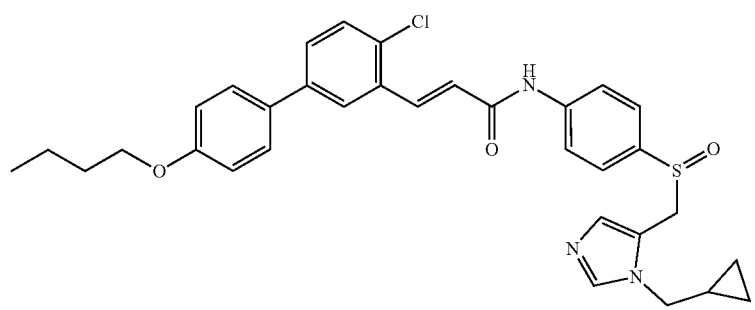
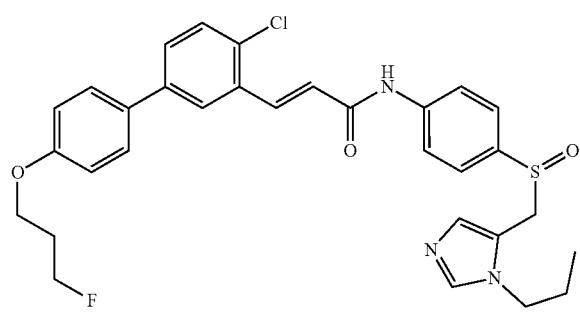
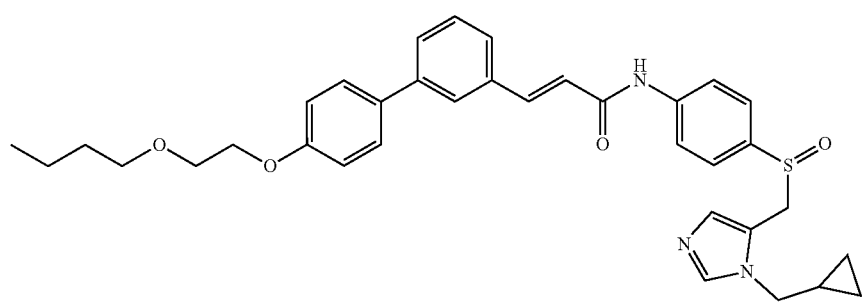
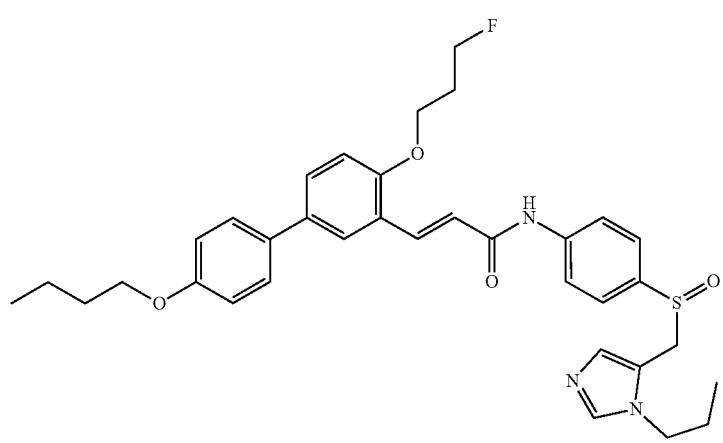

-continued
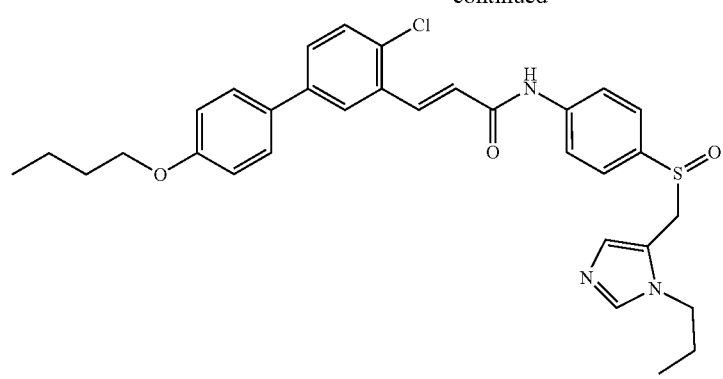
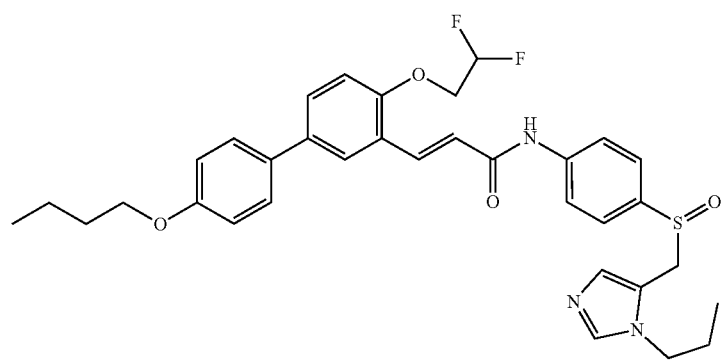
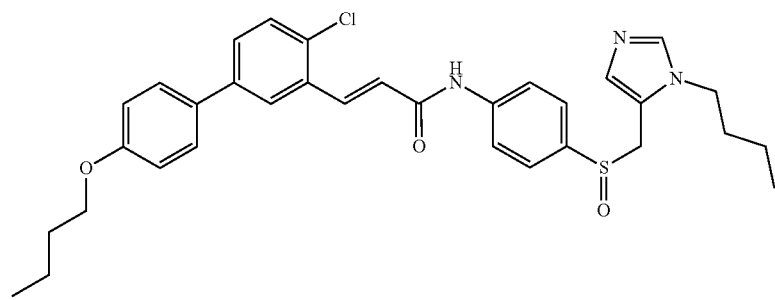
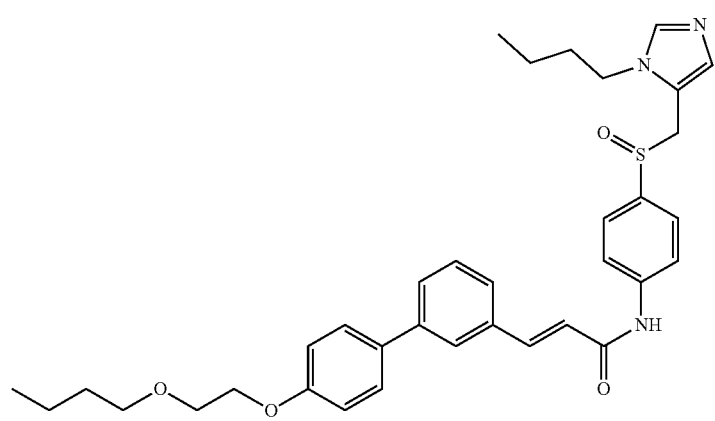

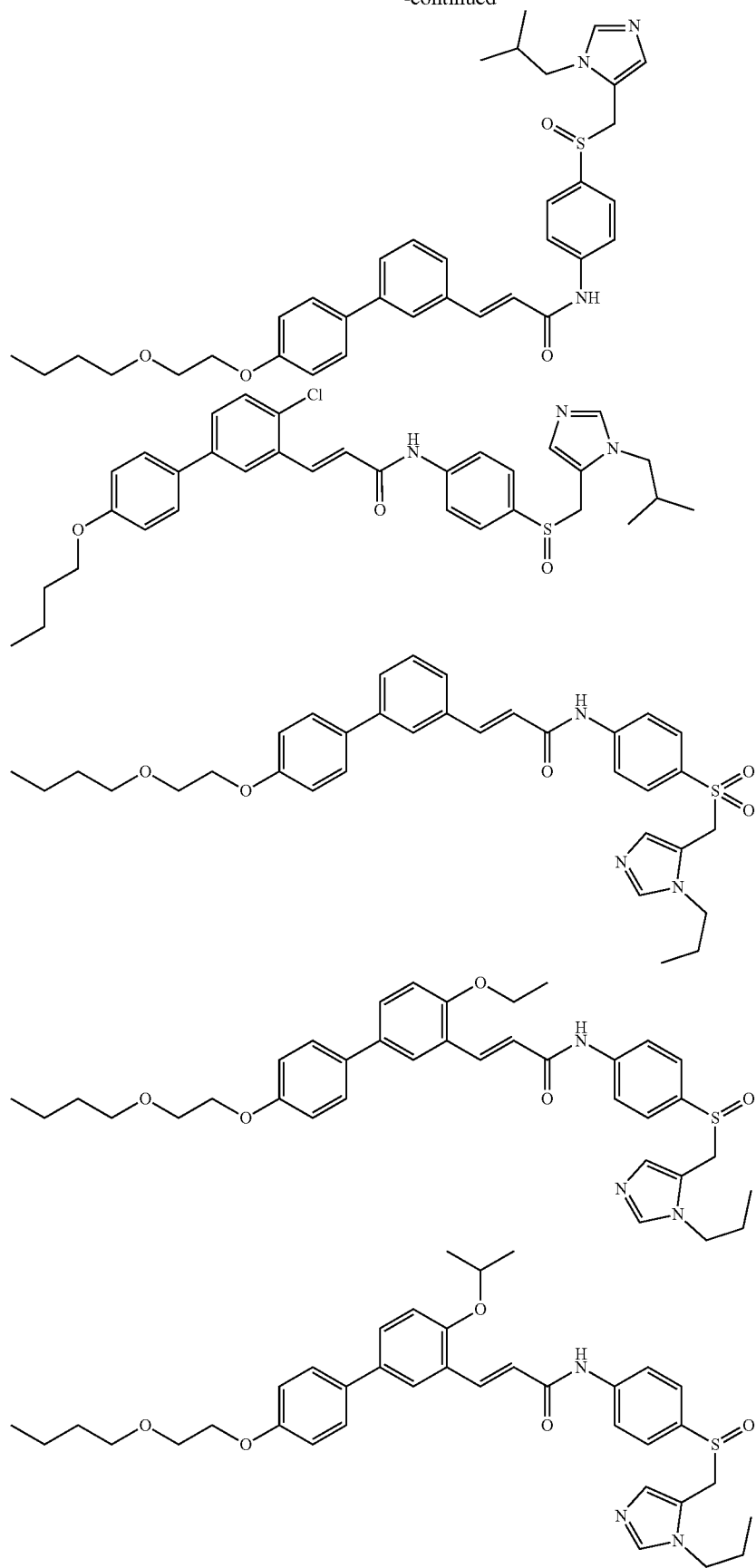

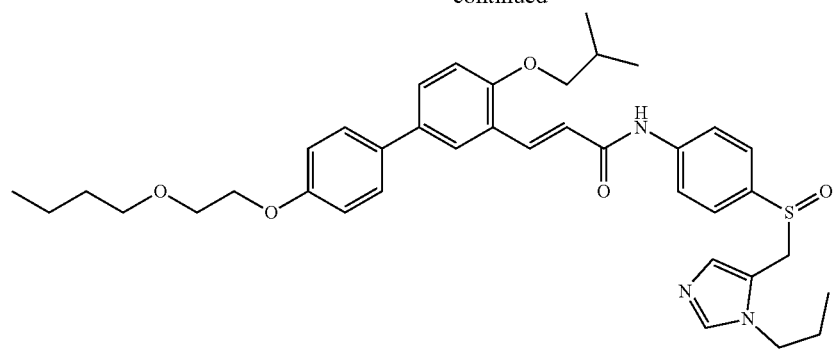
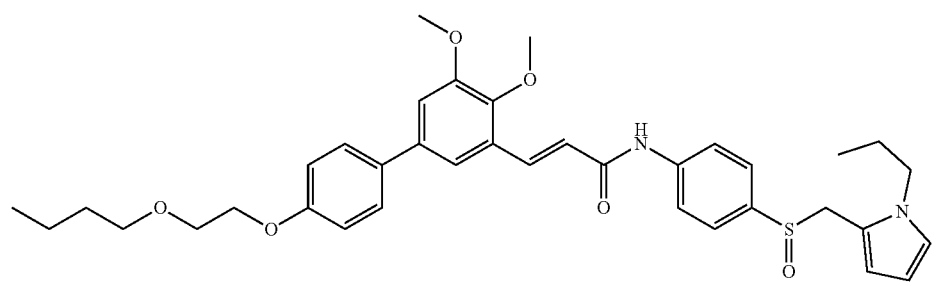
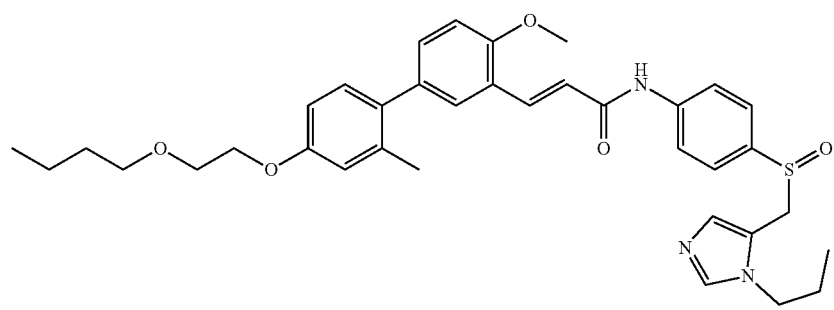
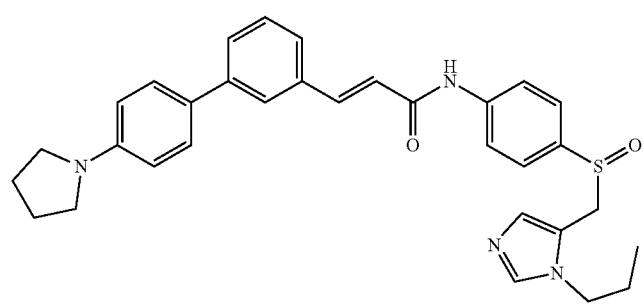
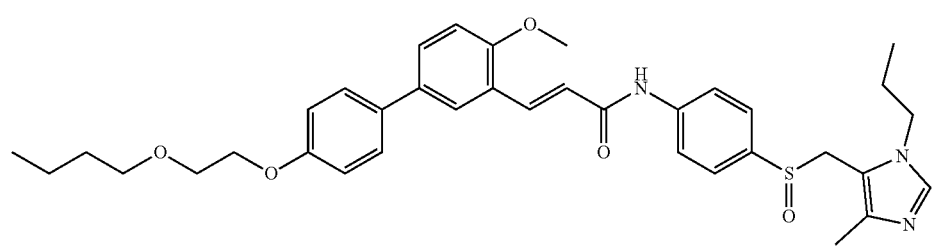

-continued
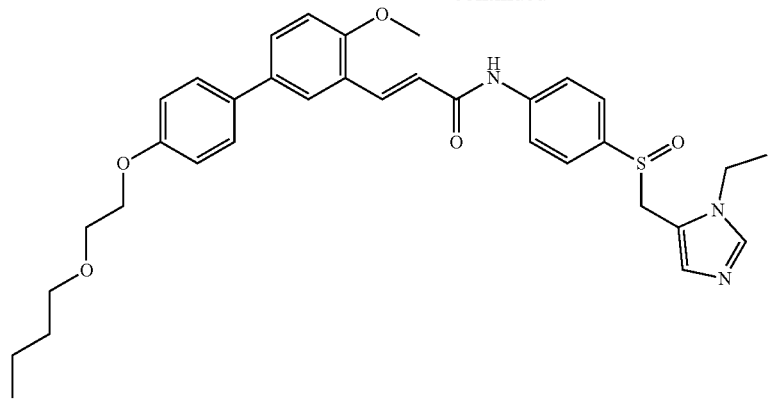
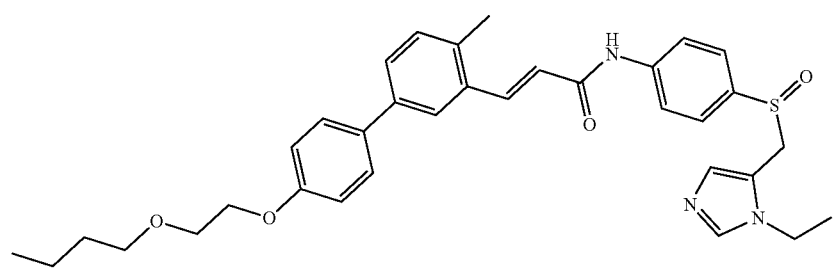
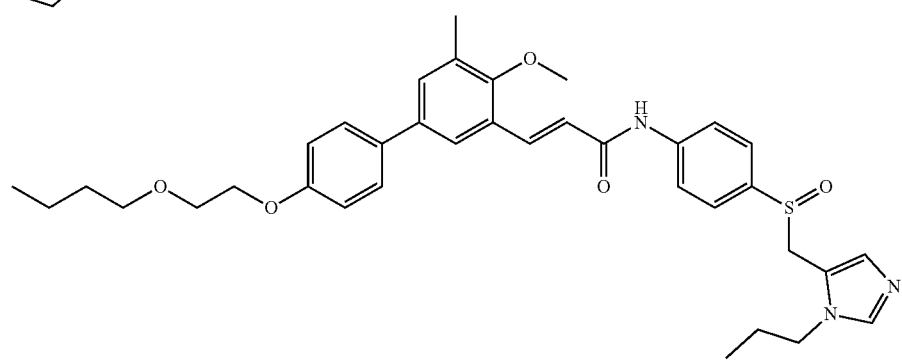
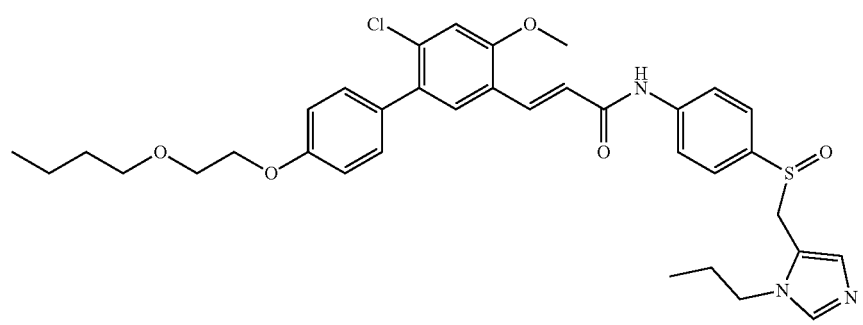
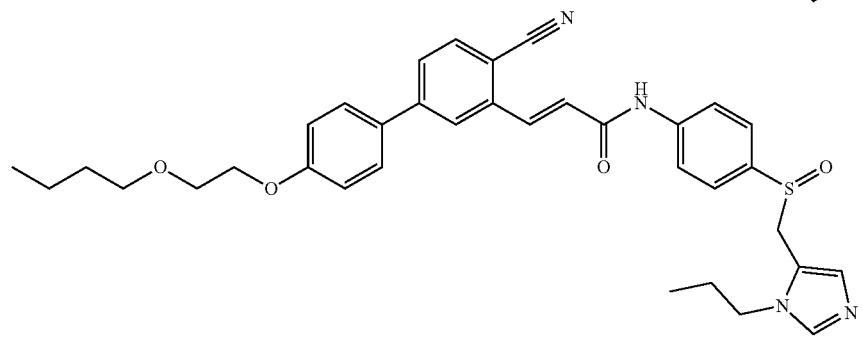

-continued
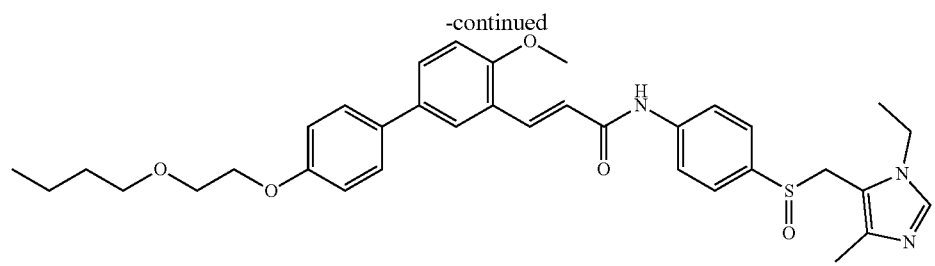
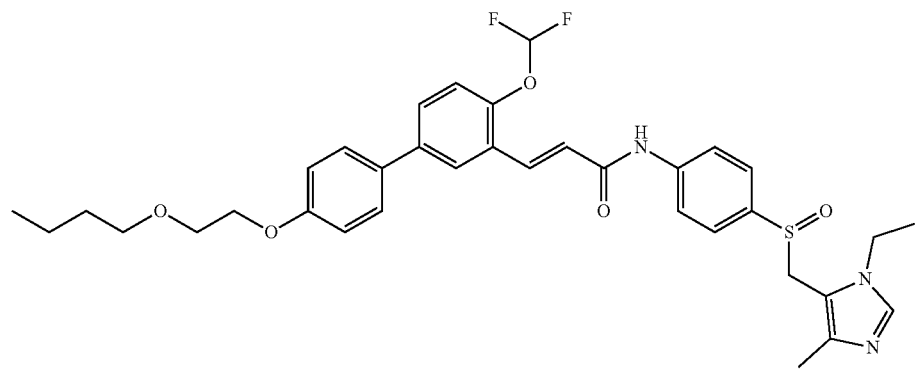
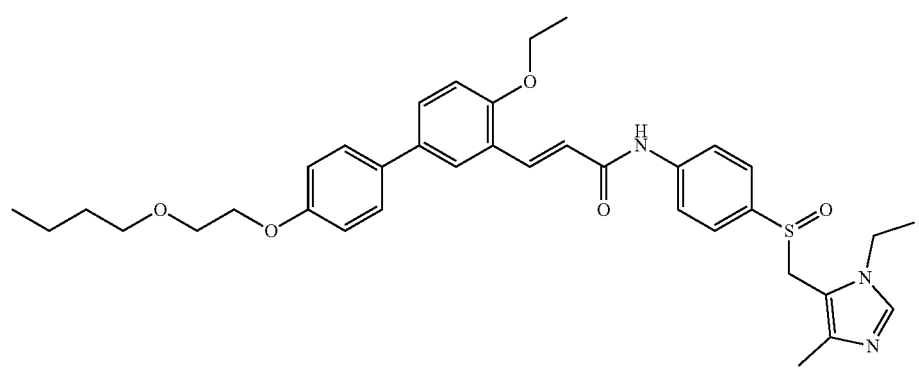
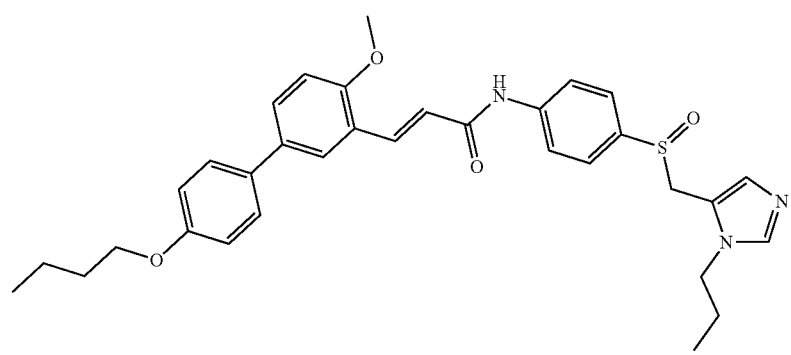
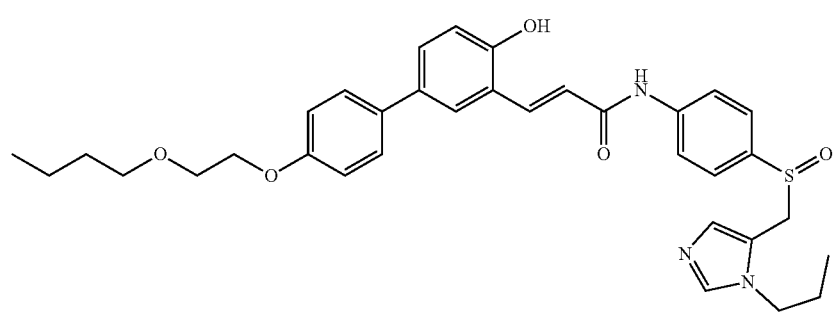

-continued
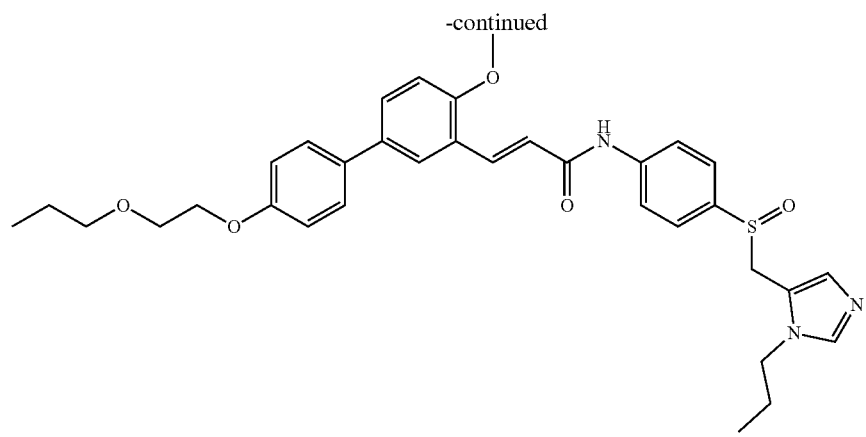
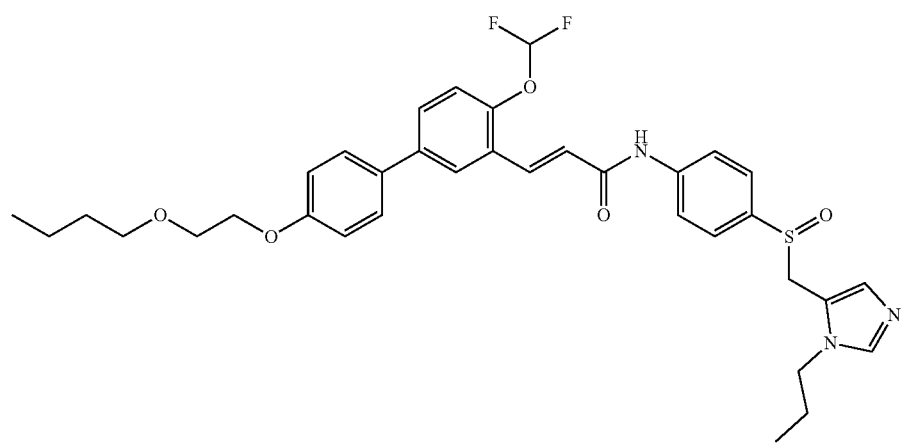
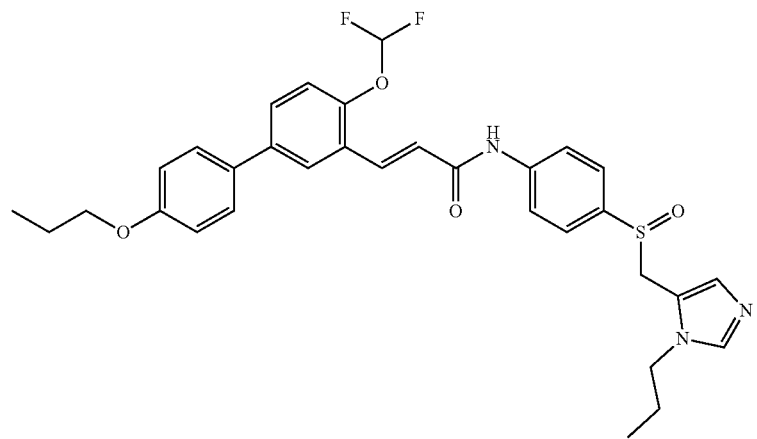
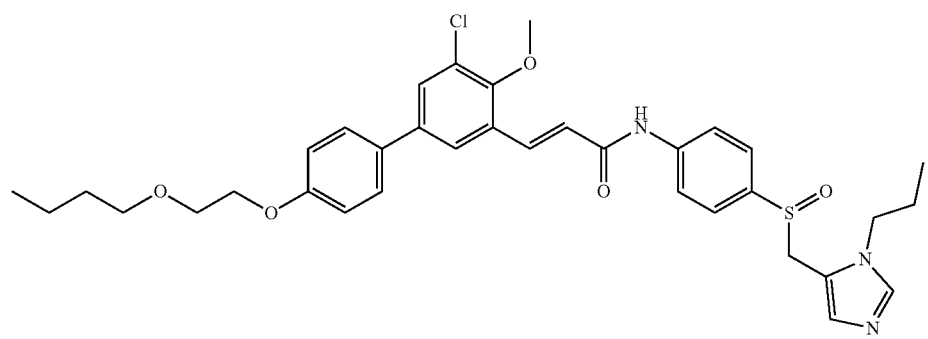

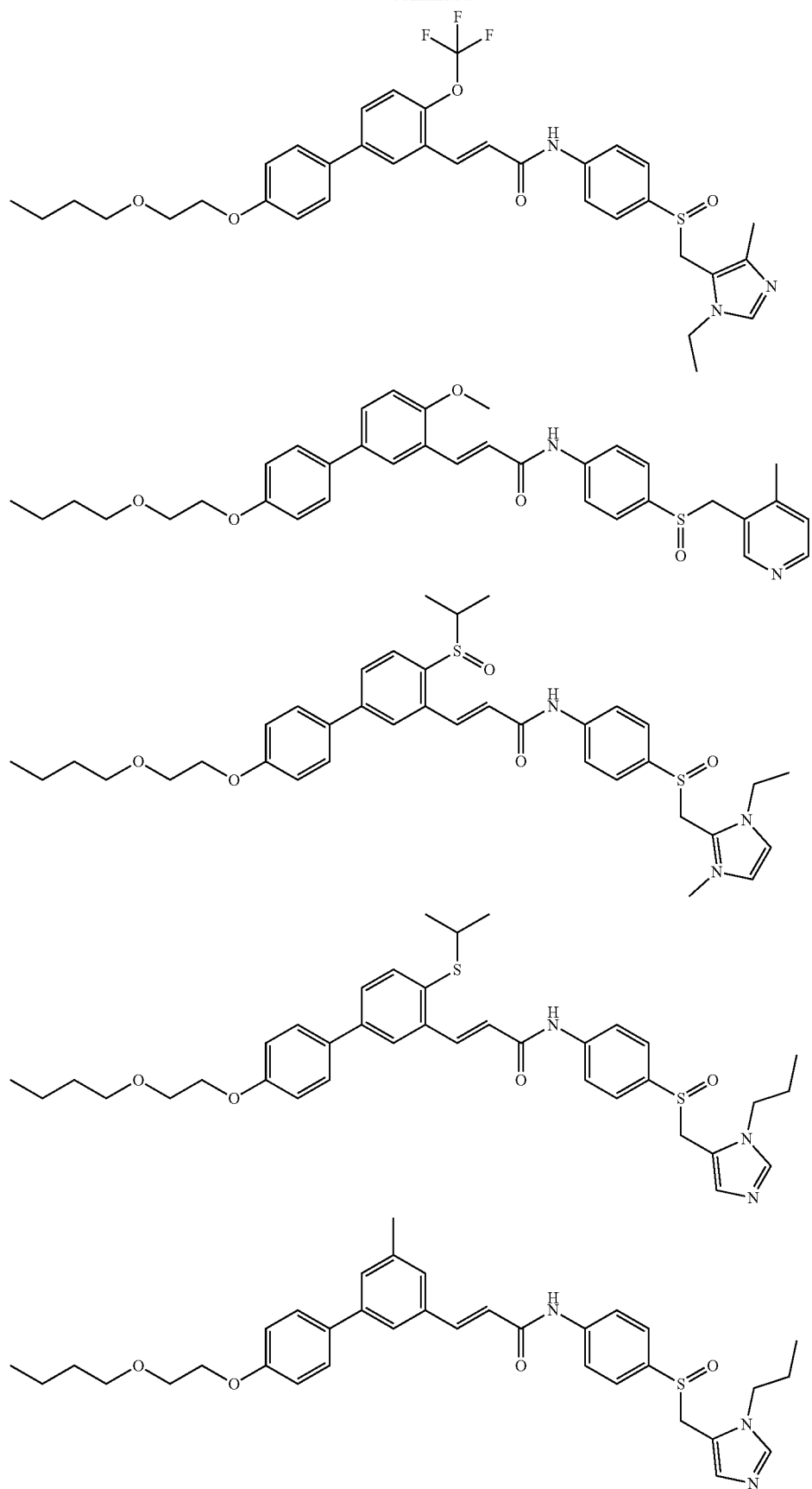

-continued
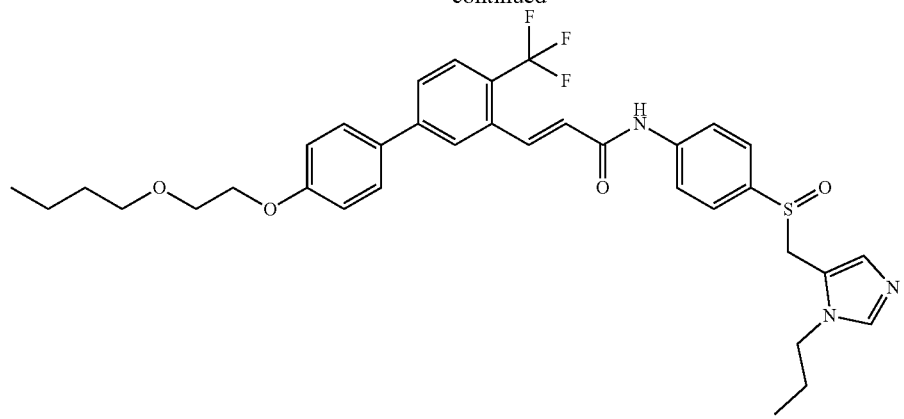
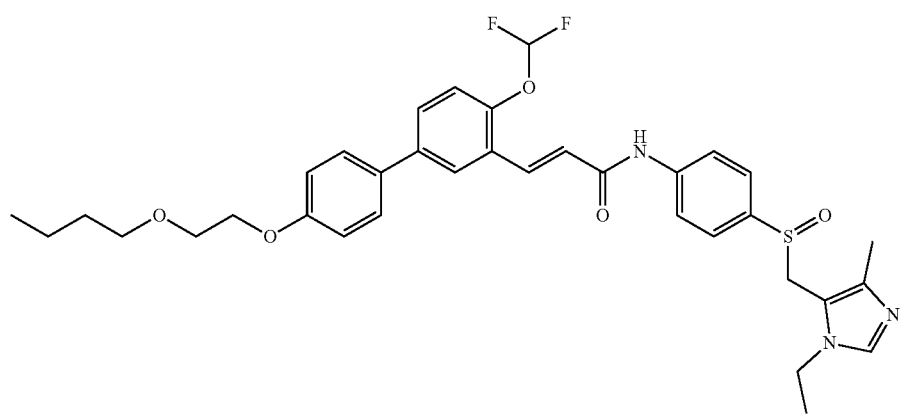
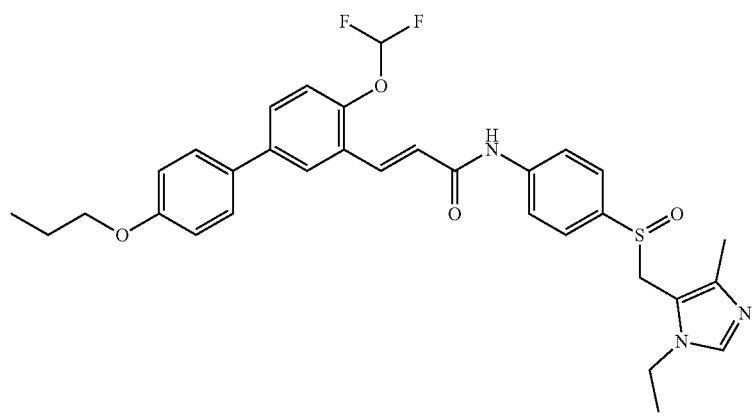
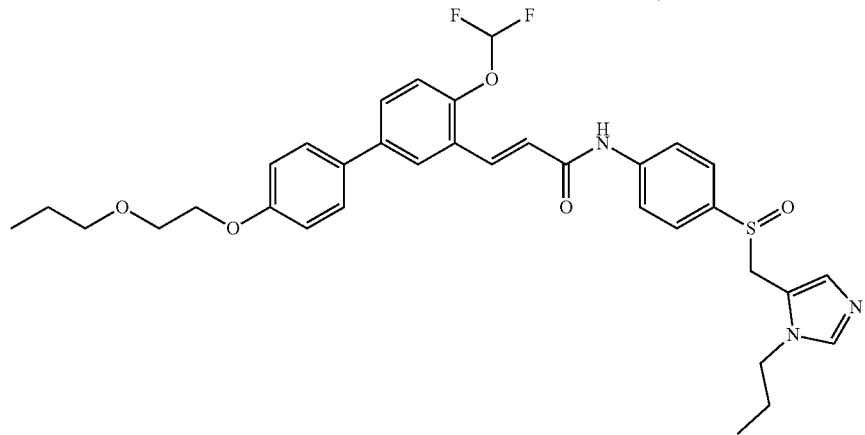

-continued
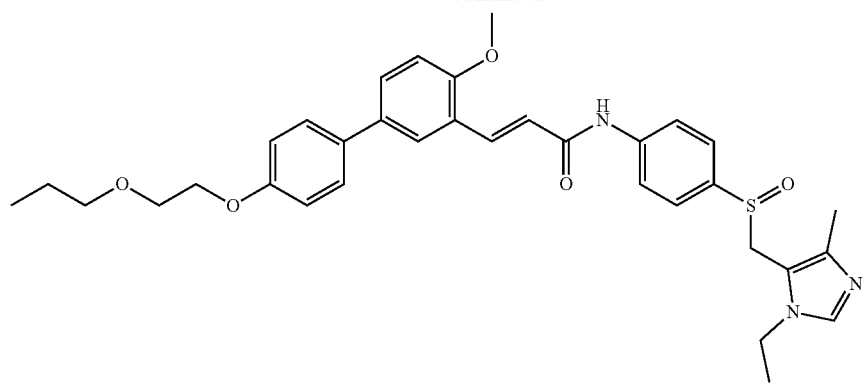
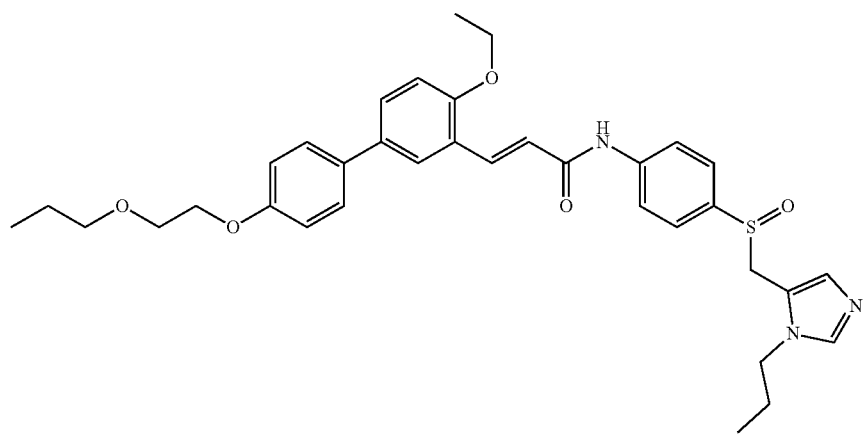
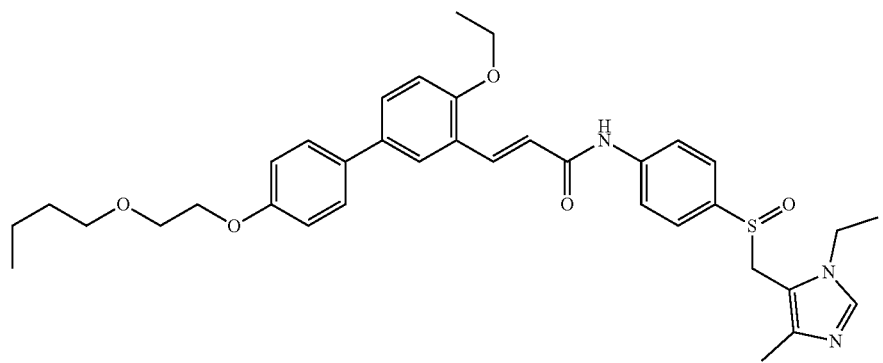
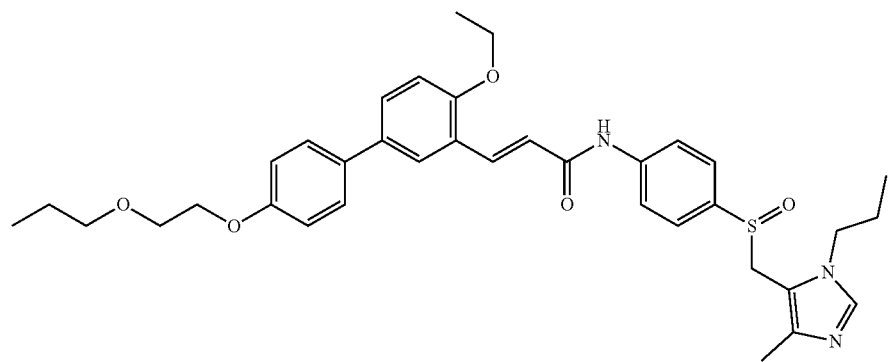

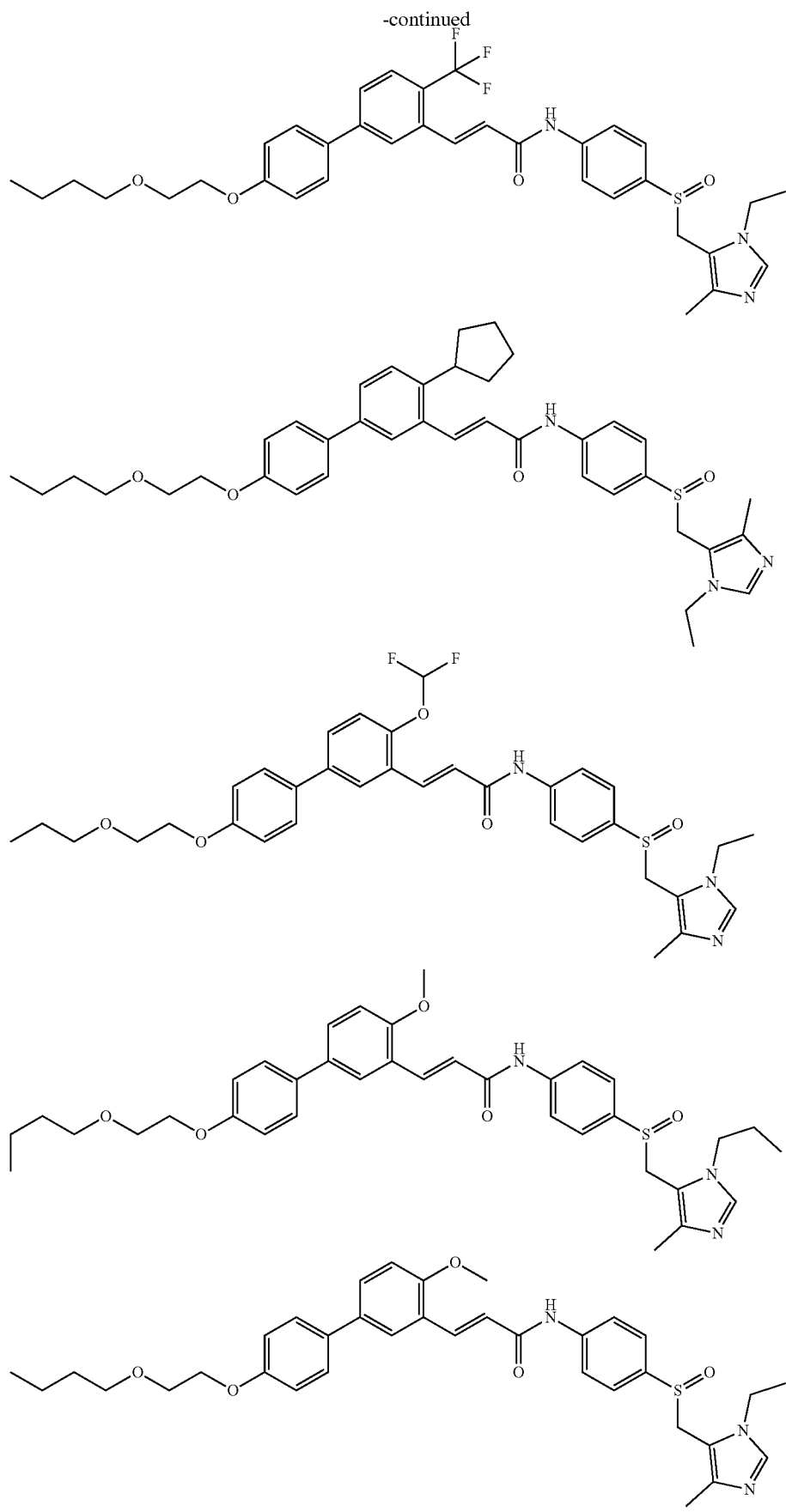

-continued
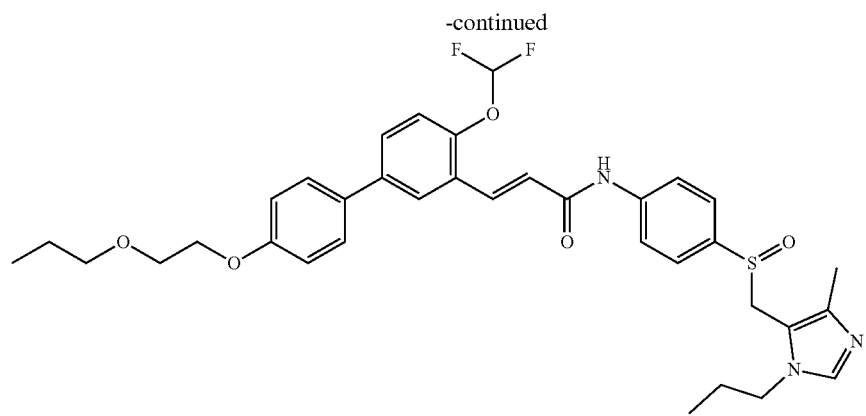
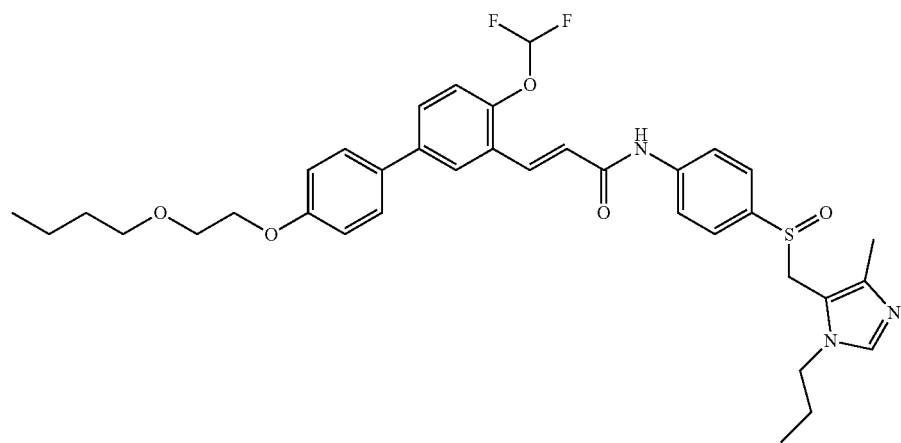
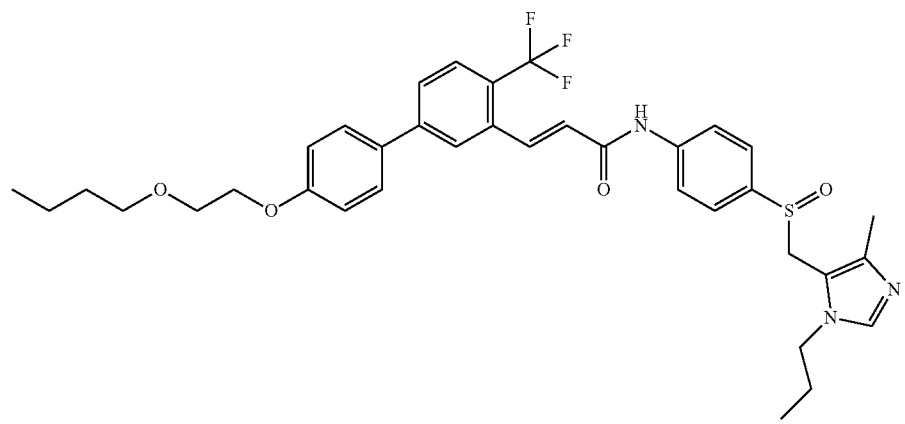
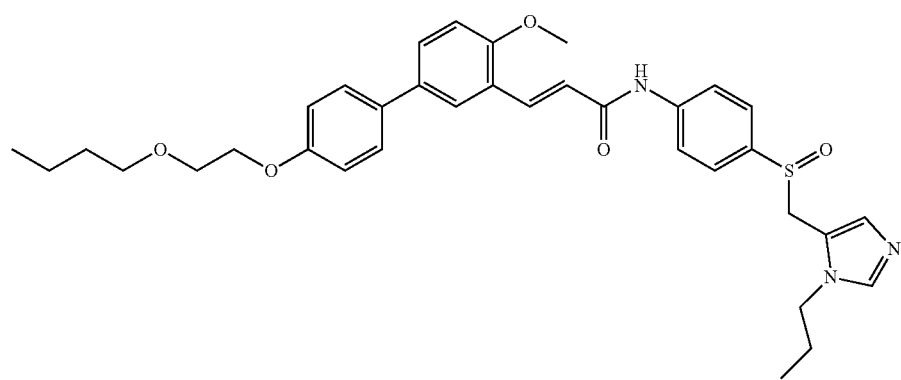

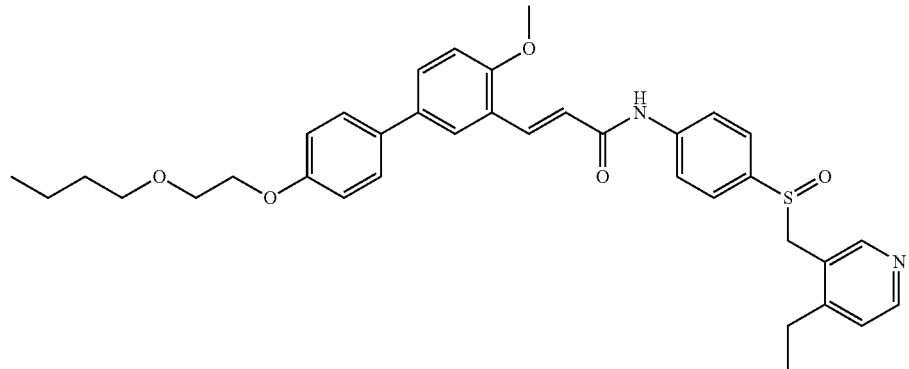
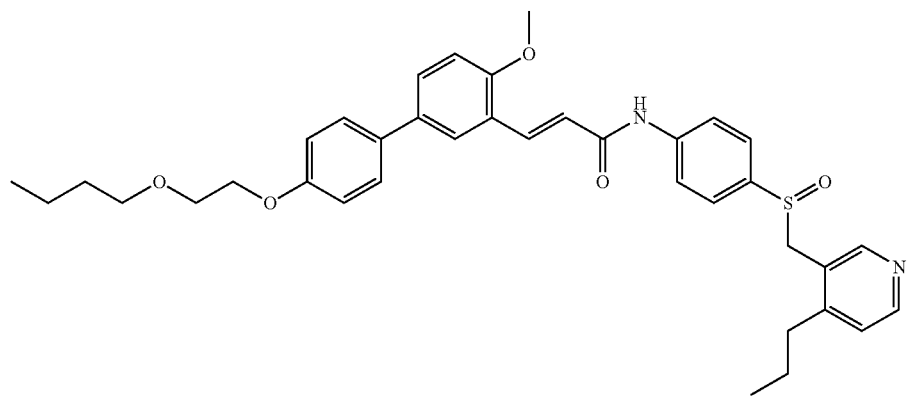
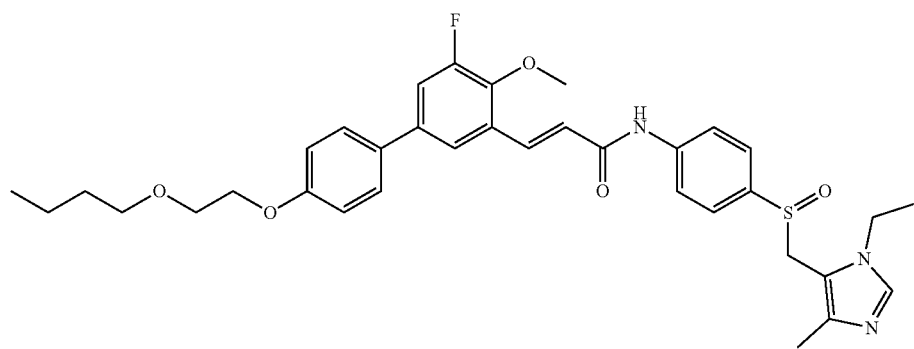
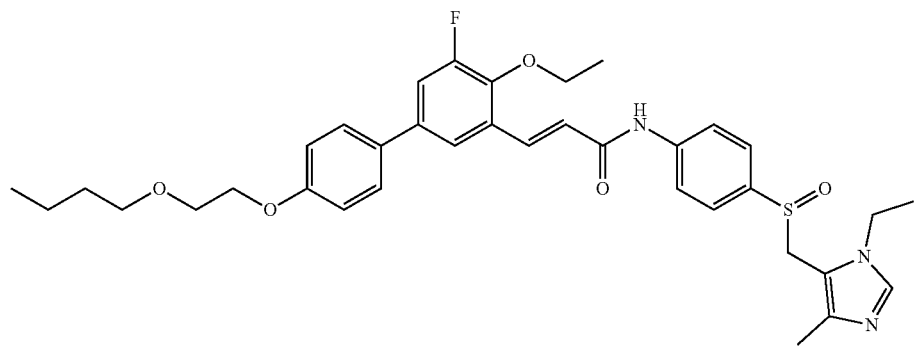

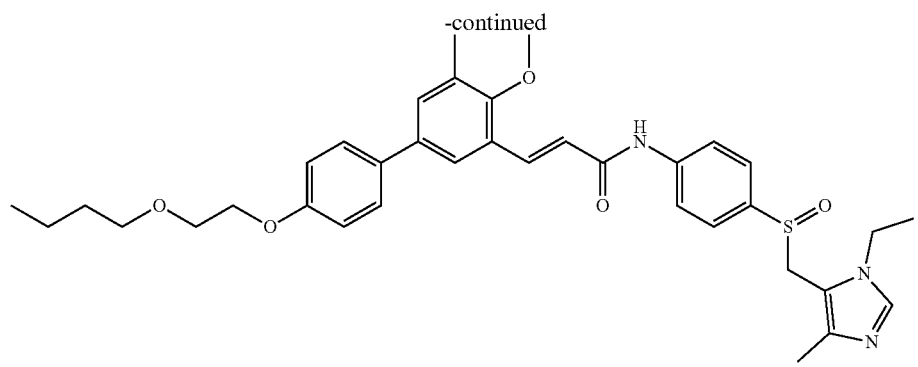
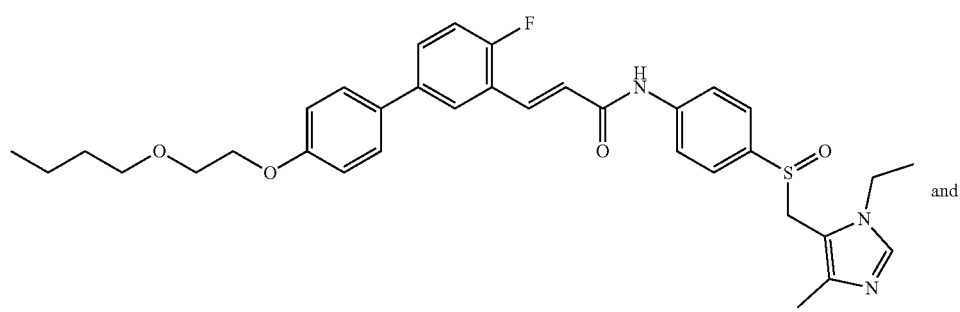
and
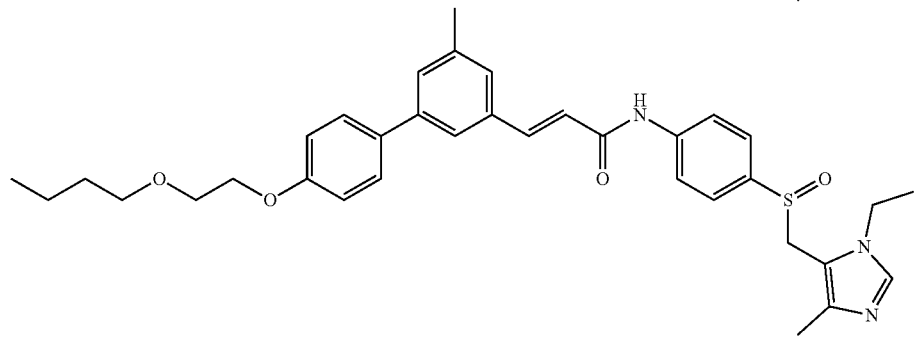
In some embodiments of the present invention, the above compound or the pharmaceutically acceptable salt thereof is selected from the group consisting of
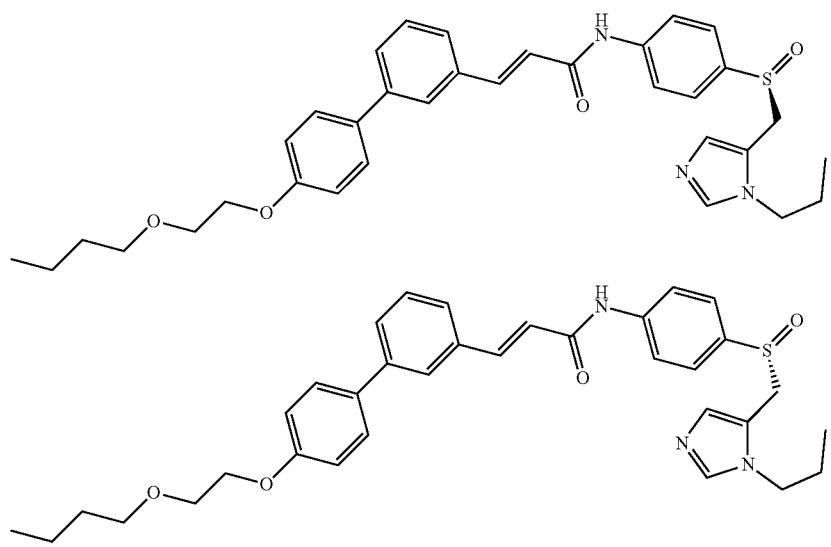

-continued
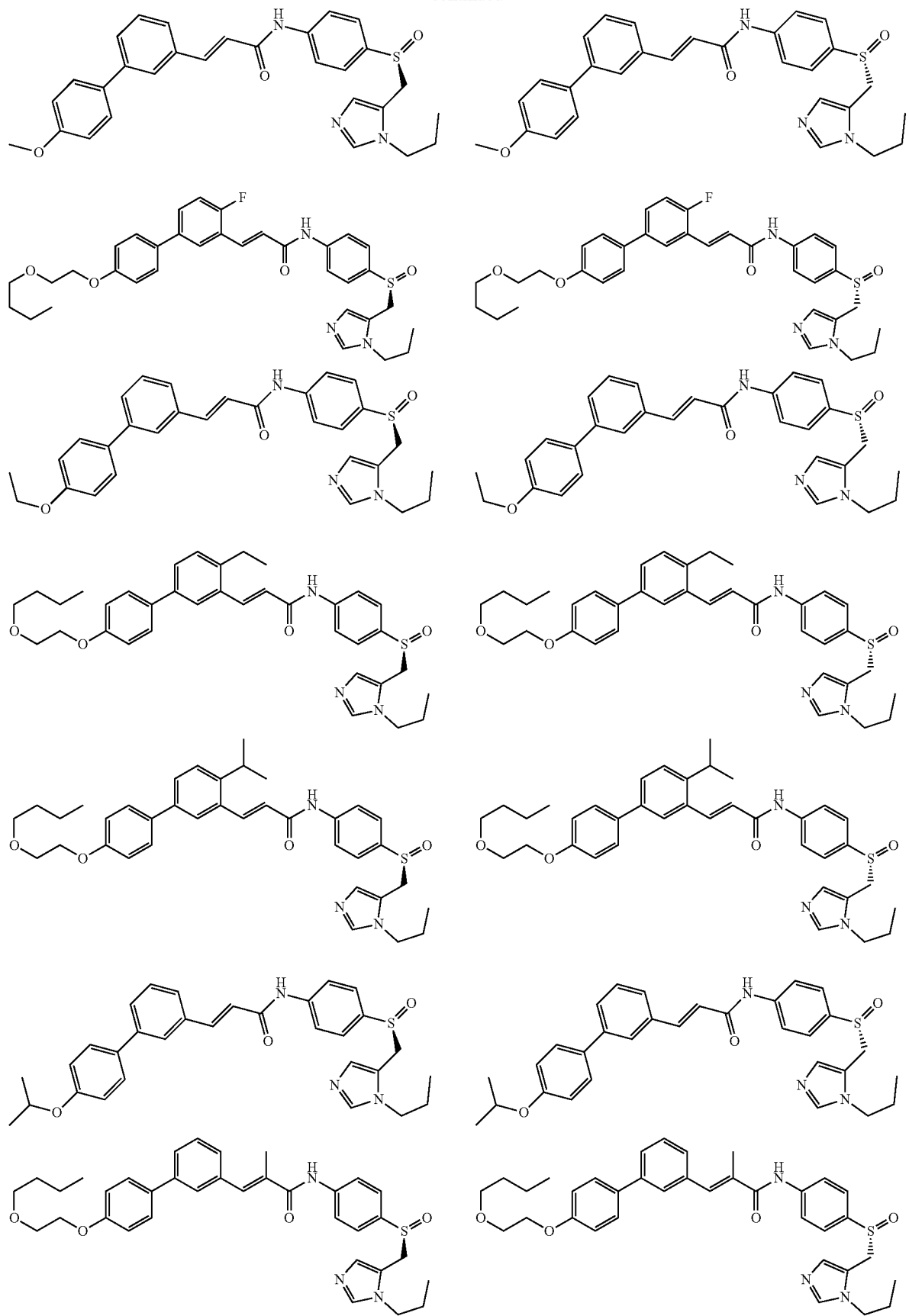

-continued
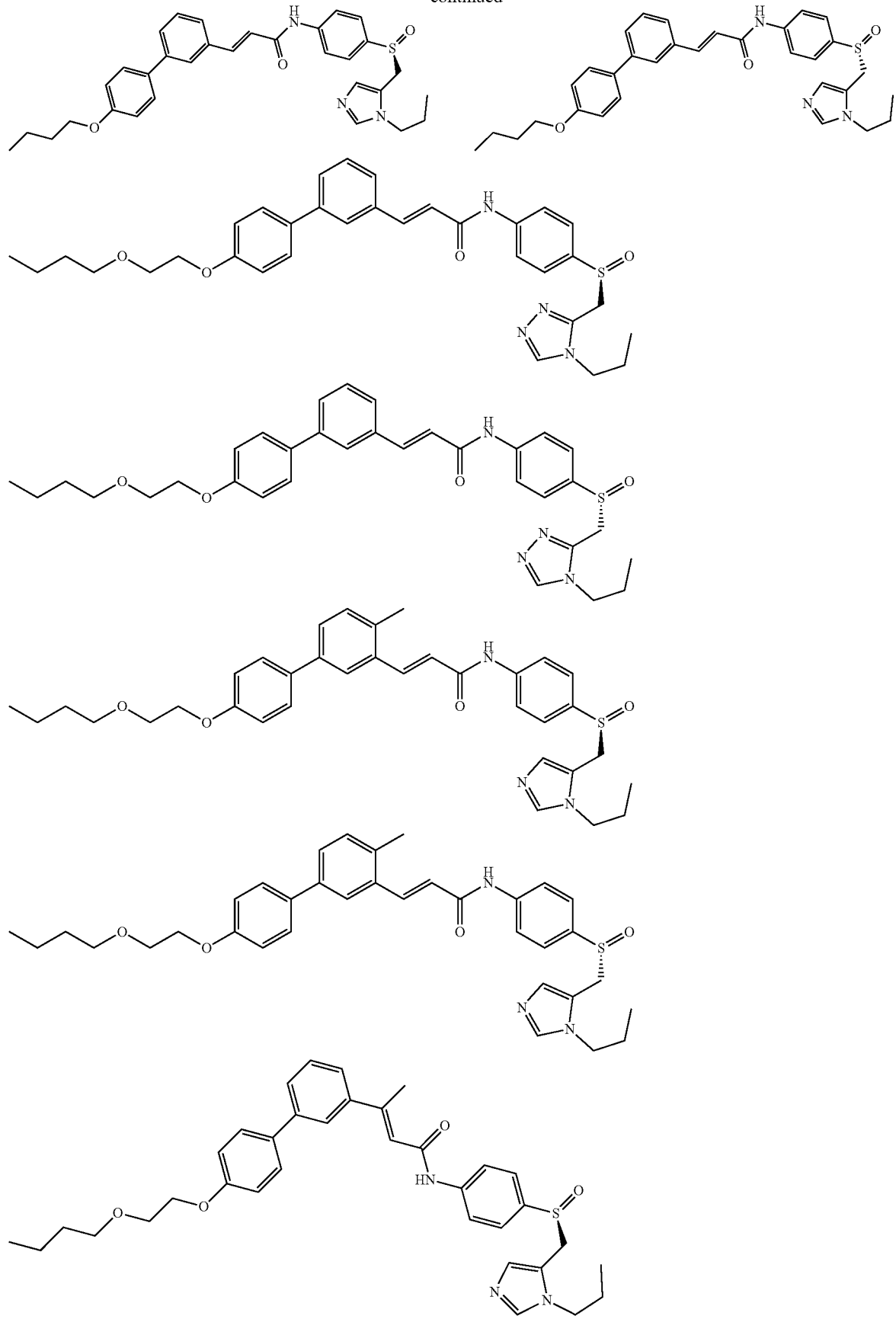

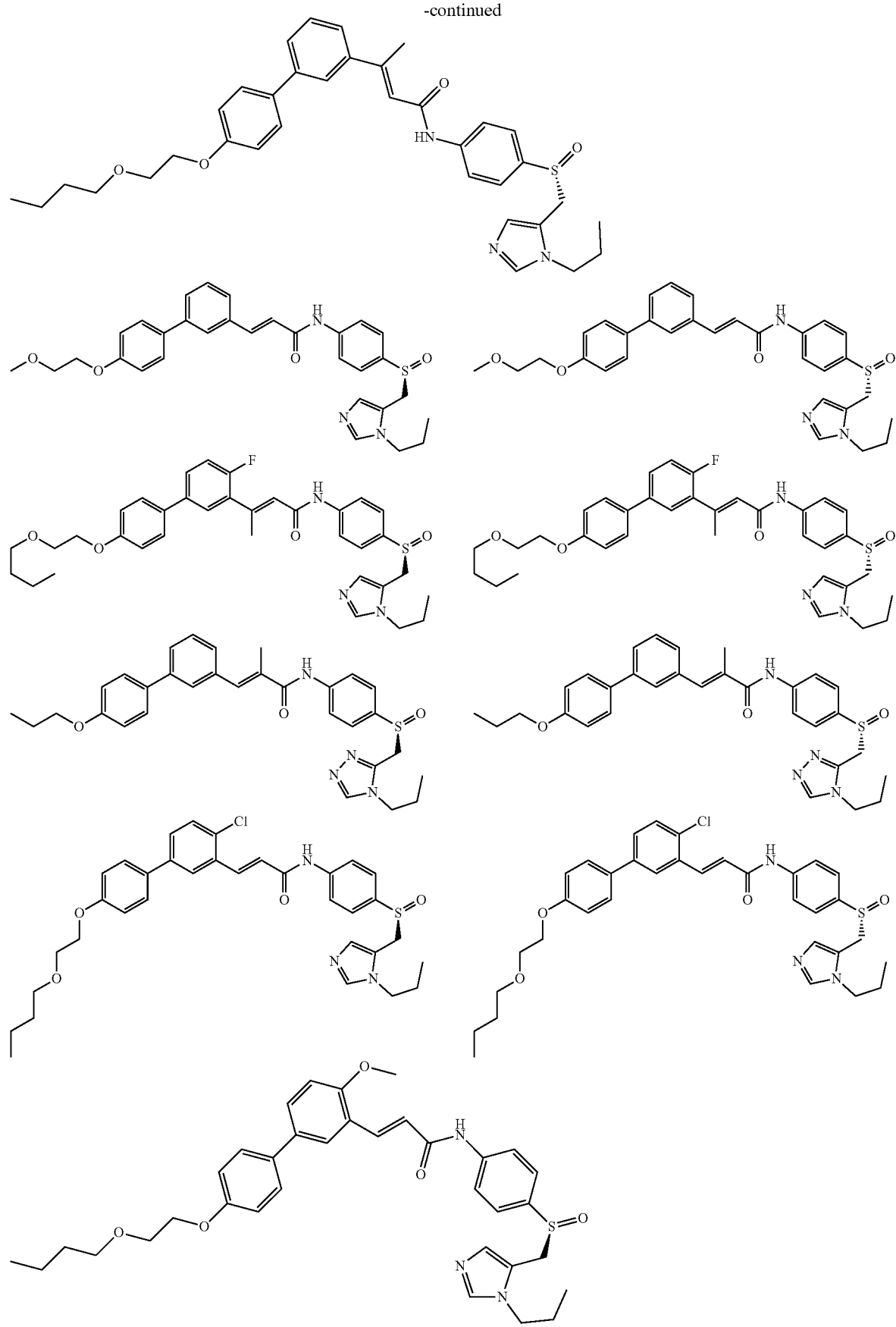

-continued
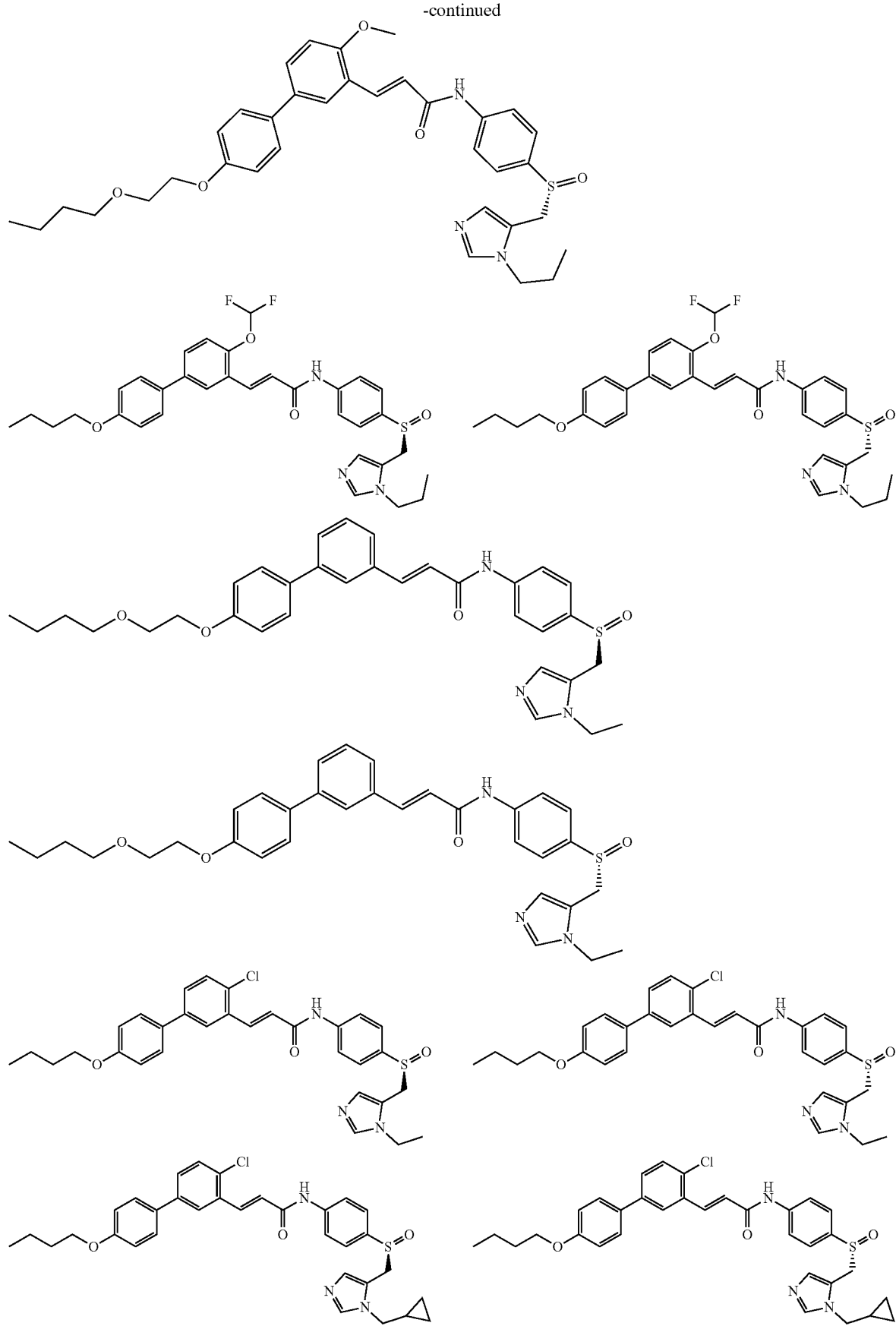

-continued
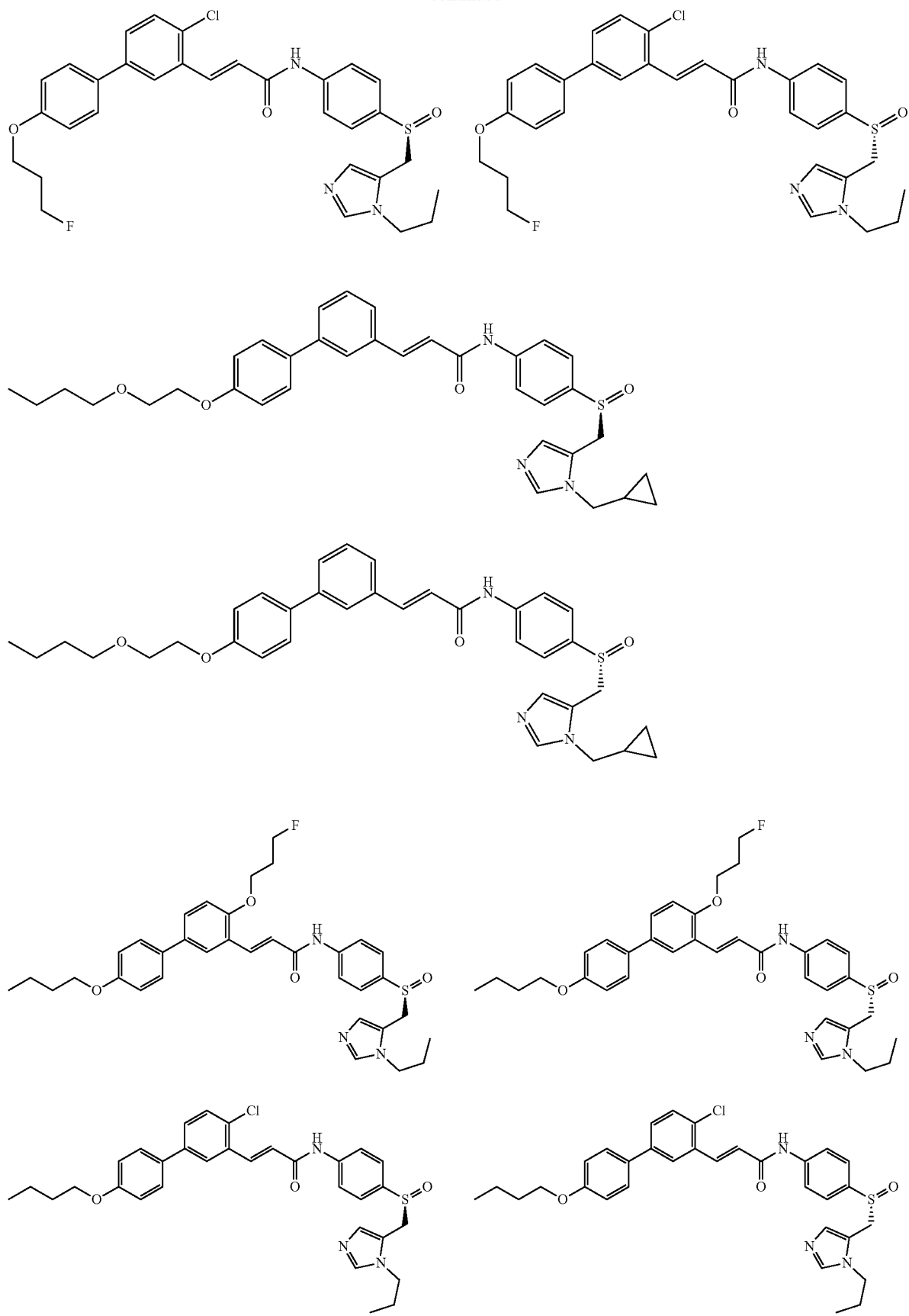

53 54
-continued
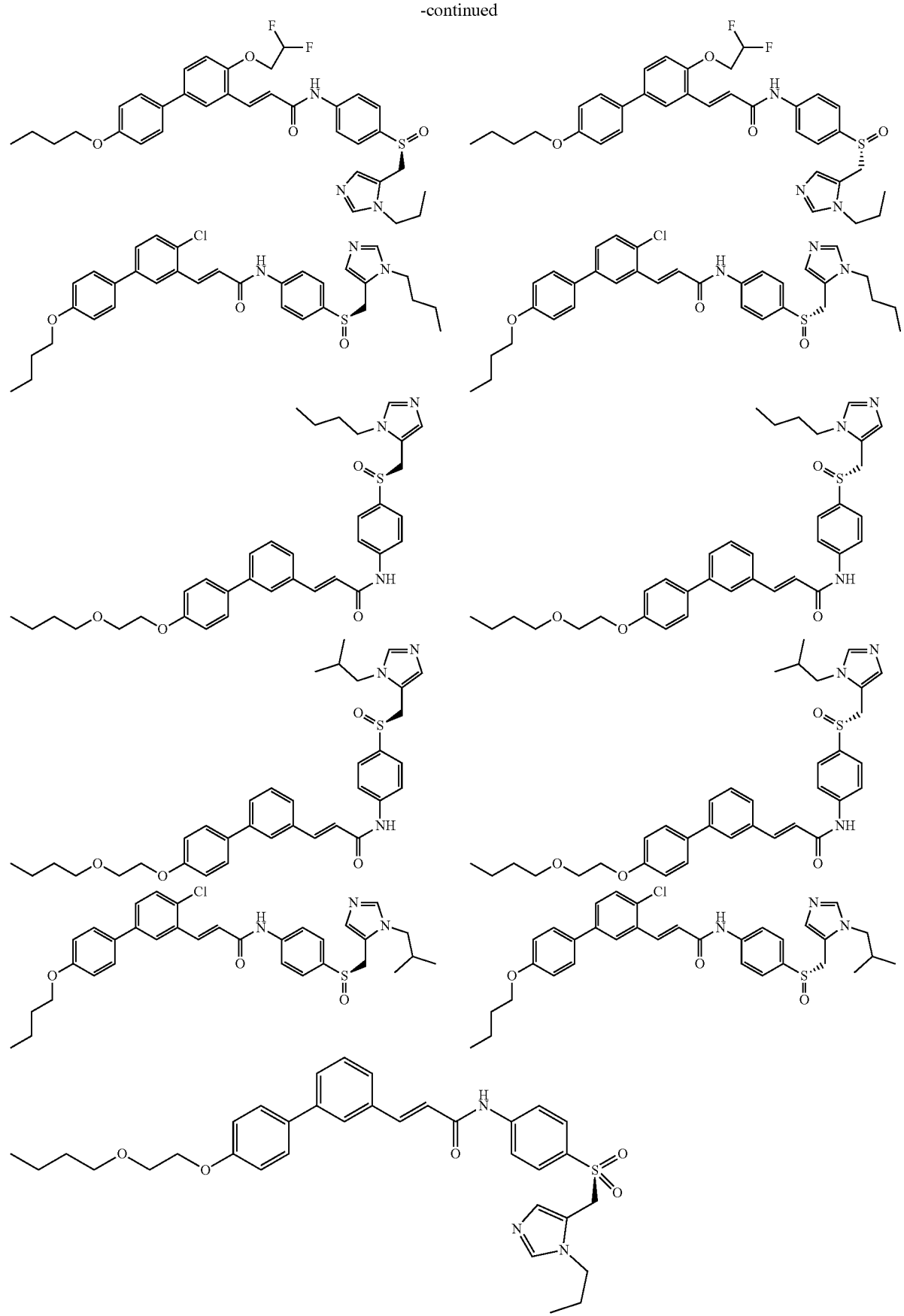

-continued
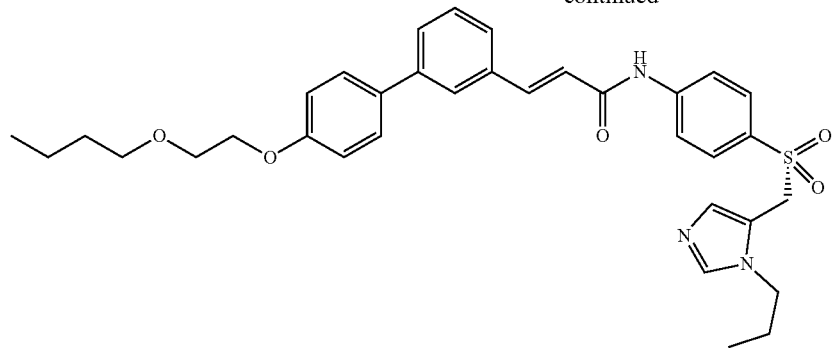
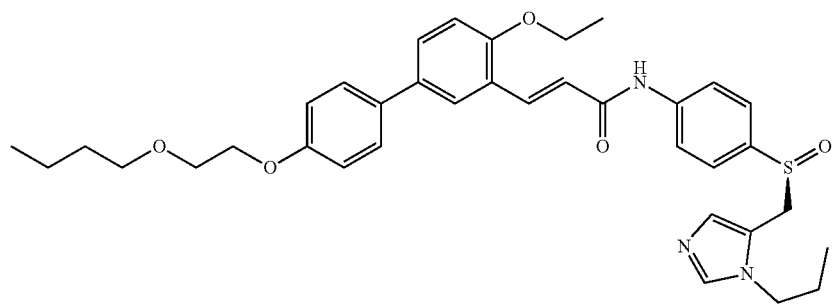
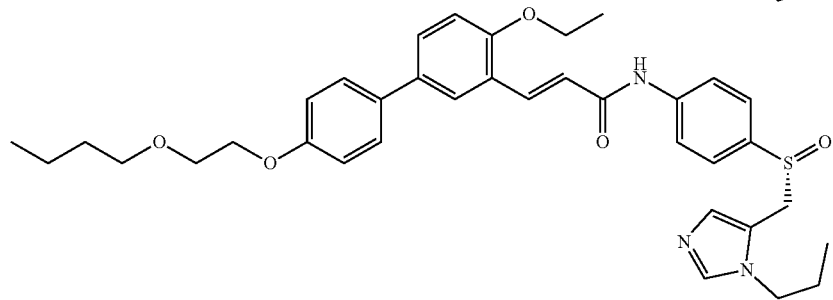
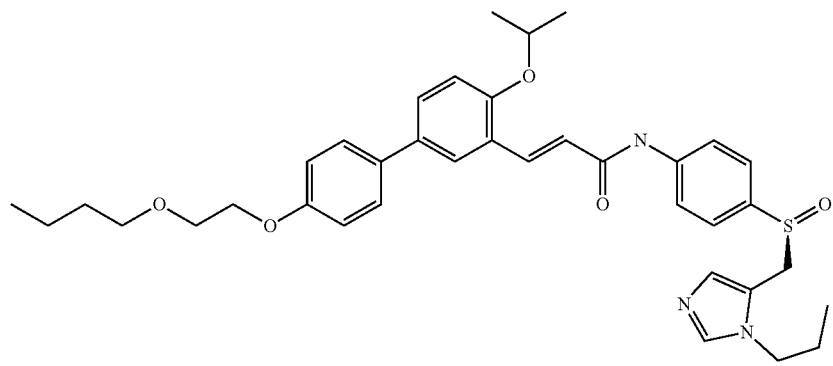
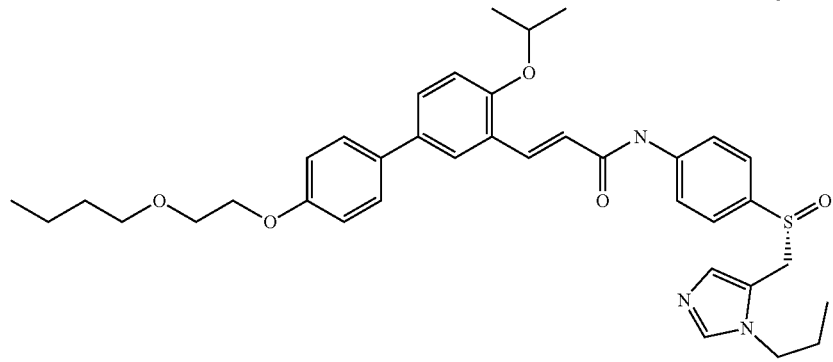

-continued
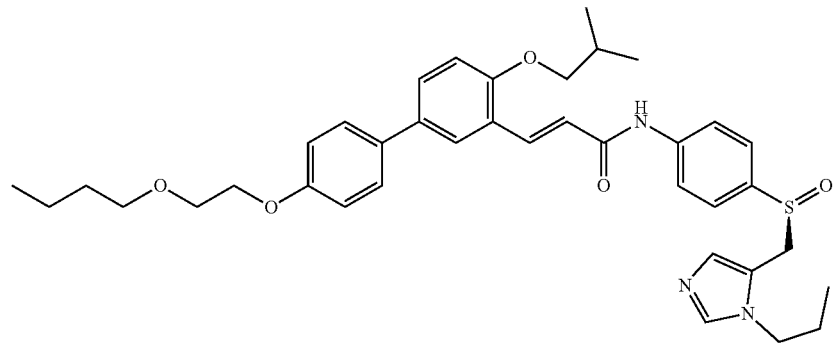
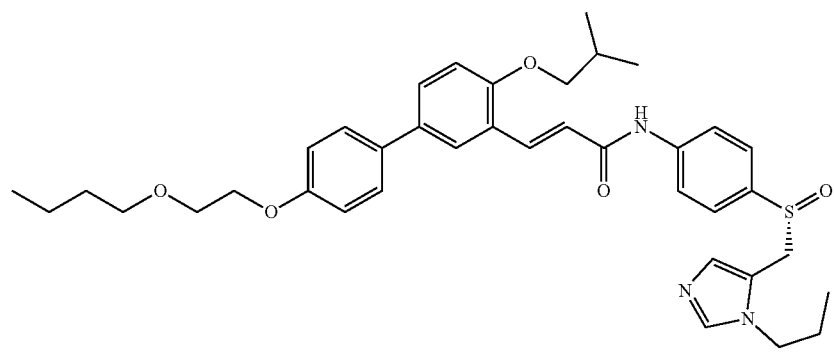
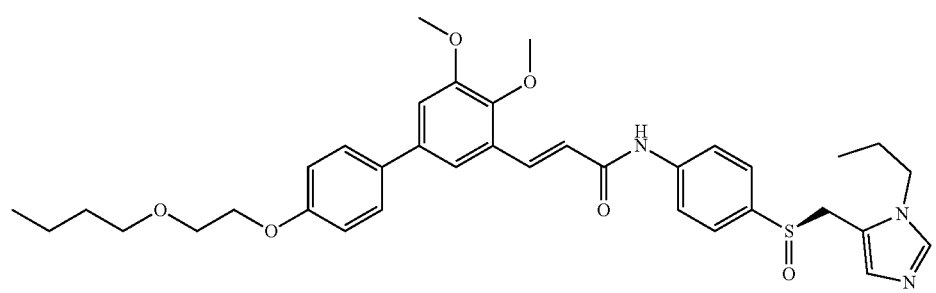
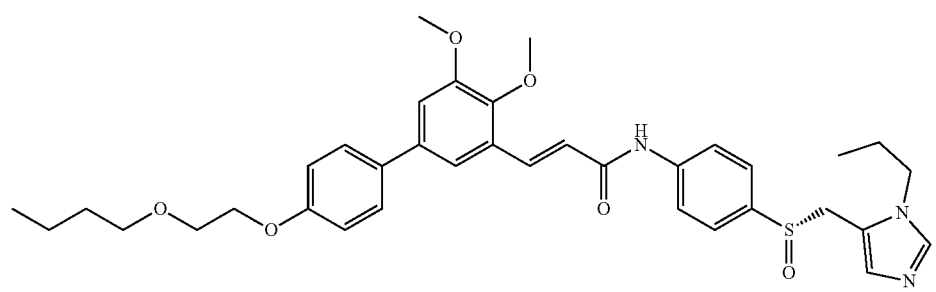
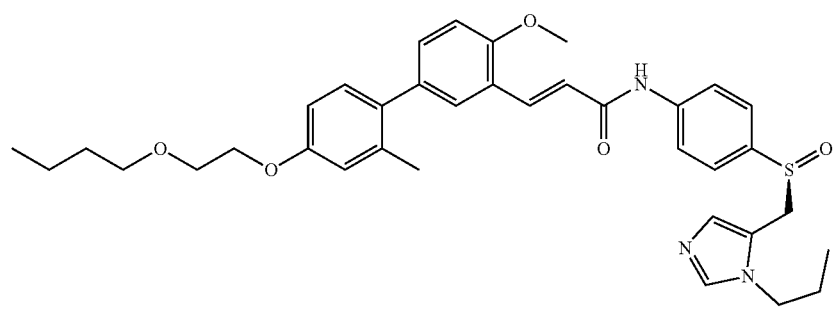

-continued
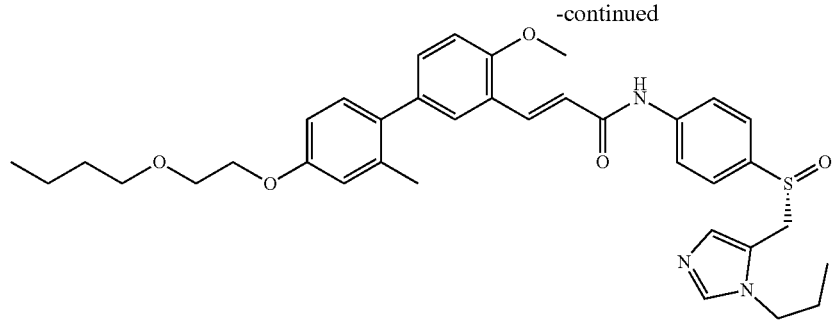
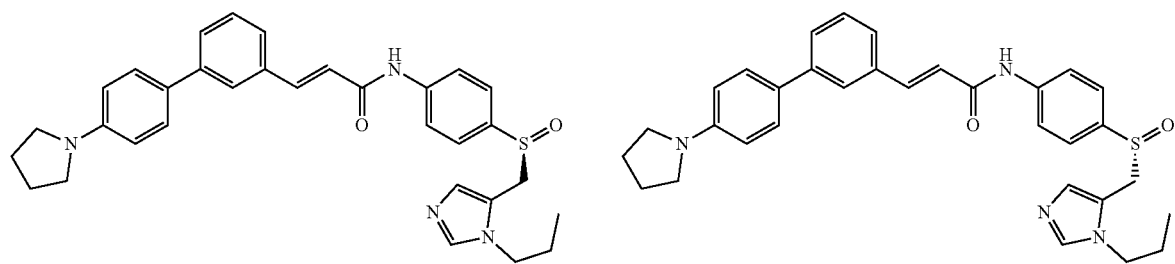
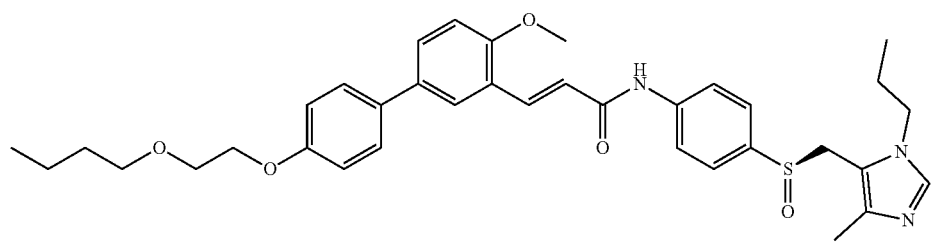
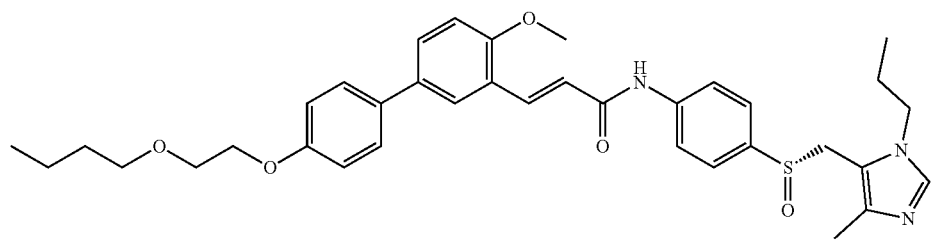
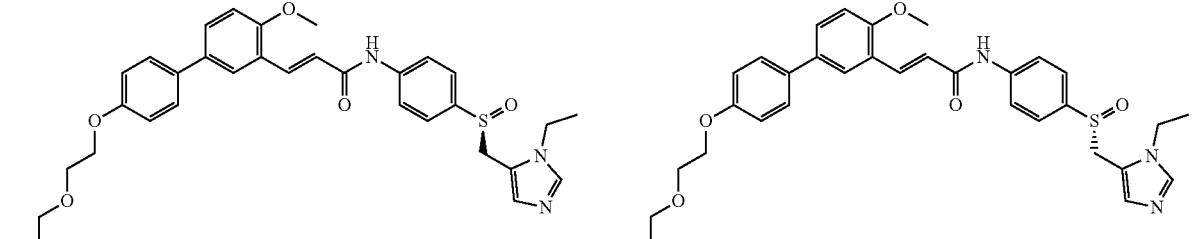
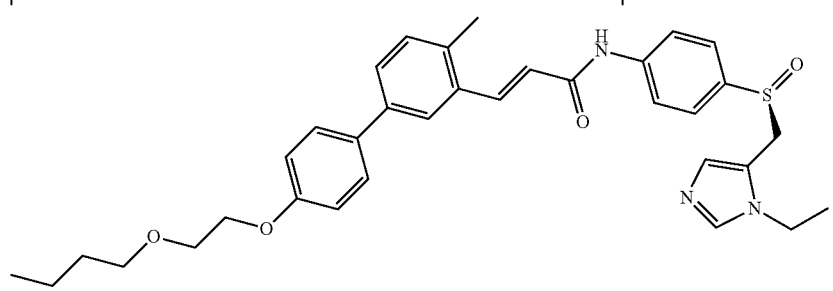

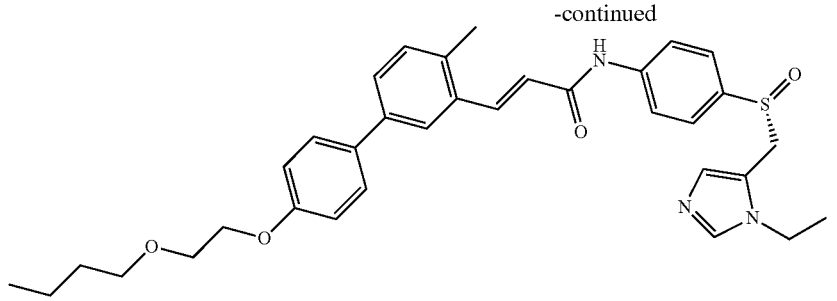
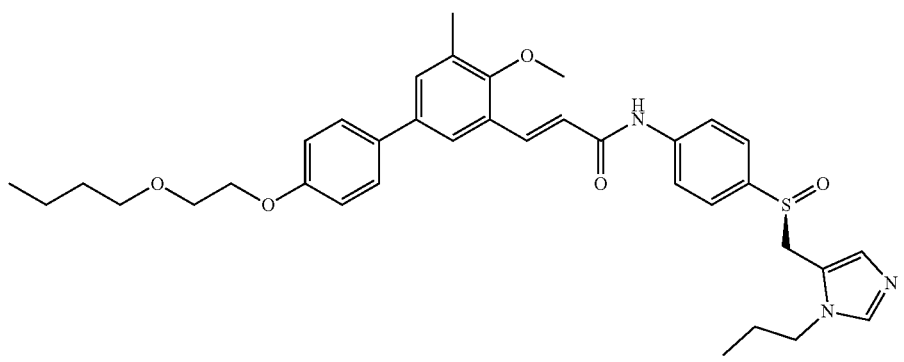
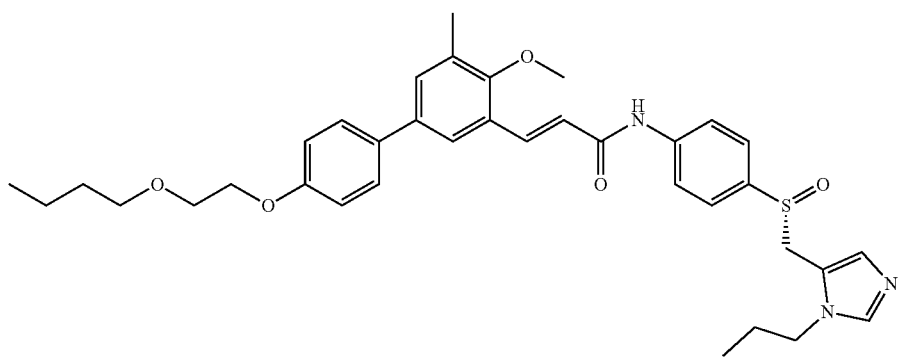
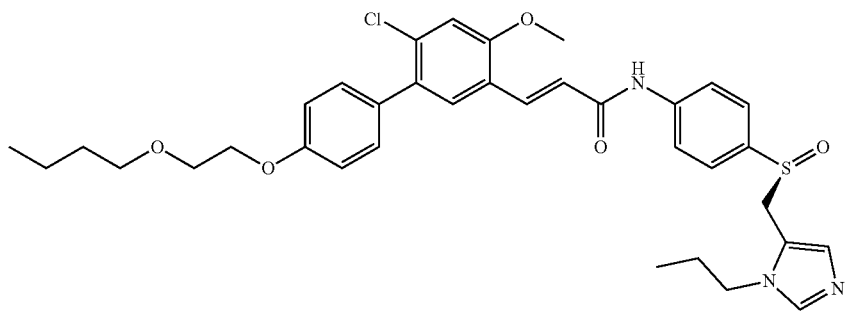
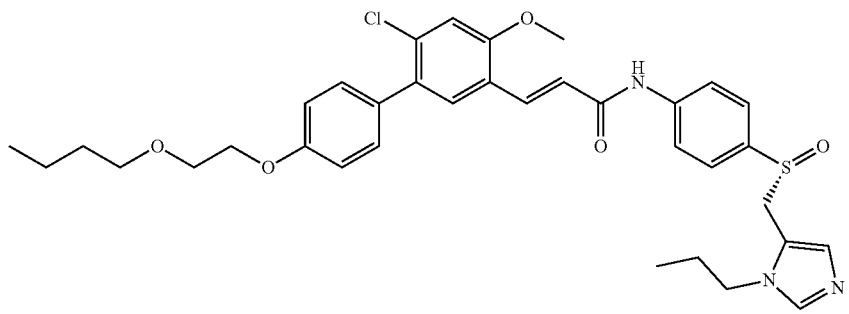

-continued
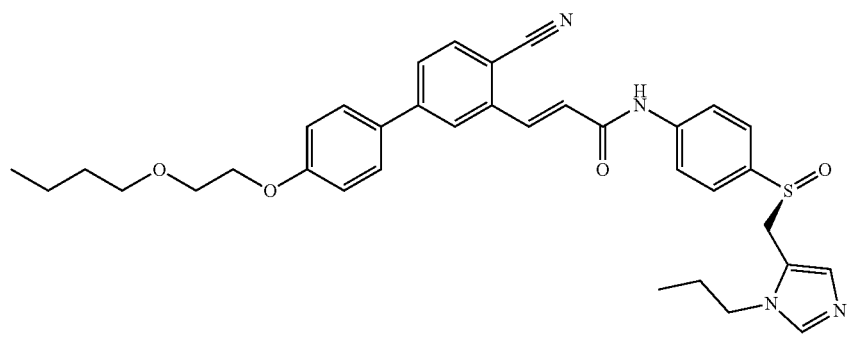
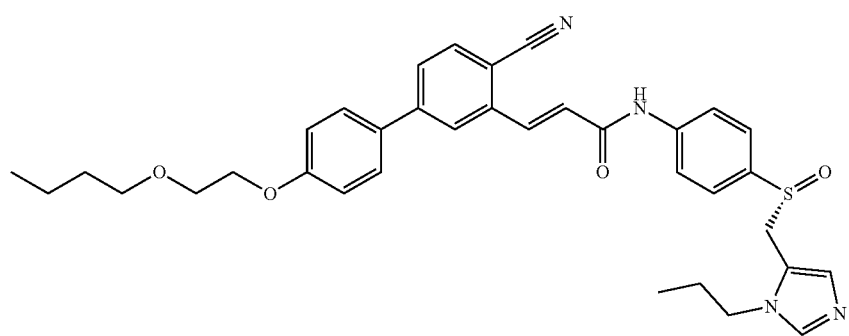
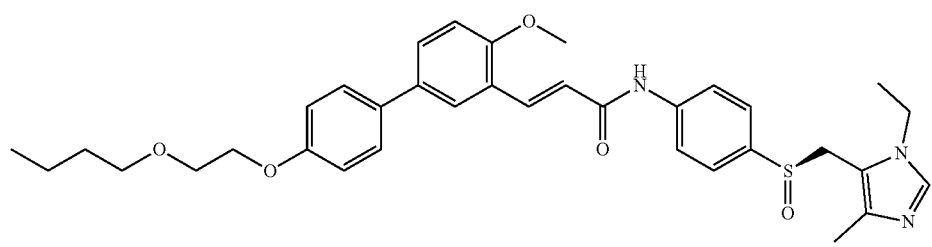
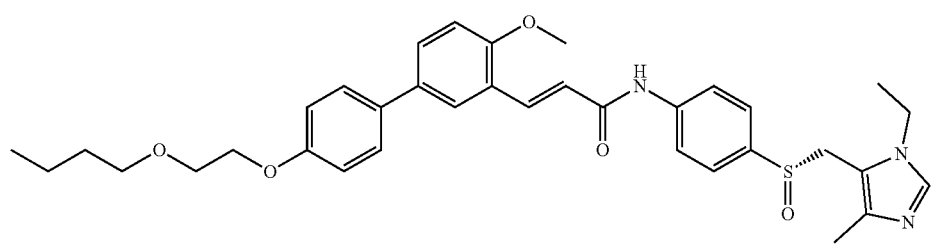
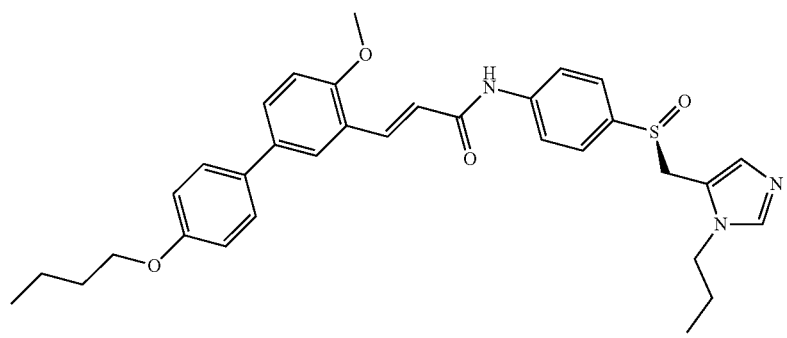

-continued
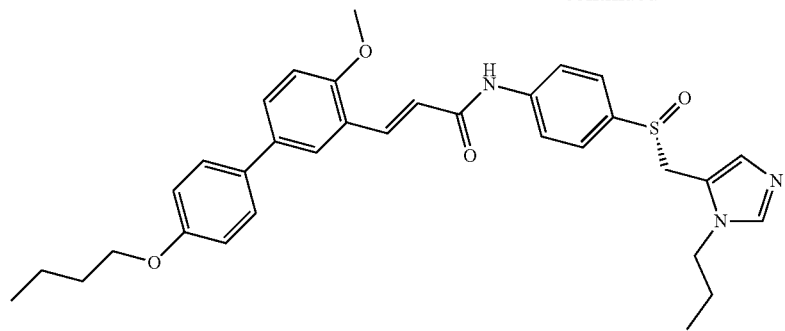
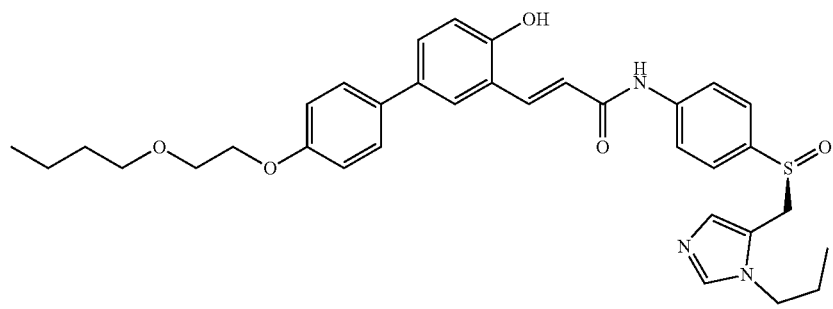
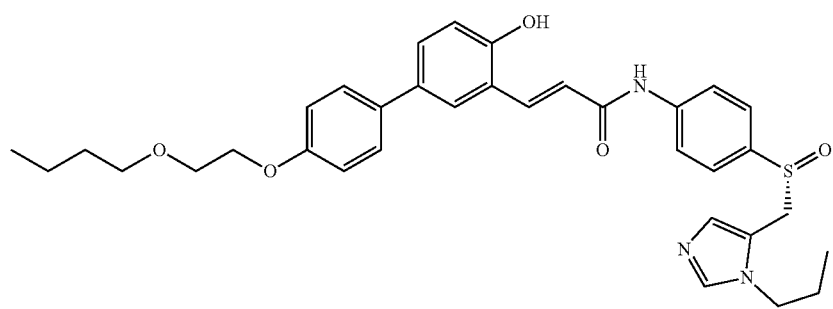
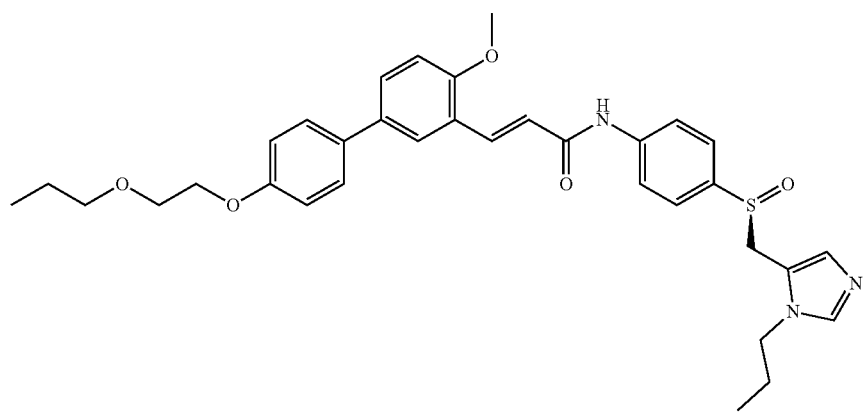

-continued
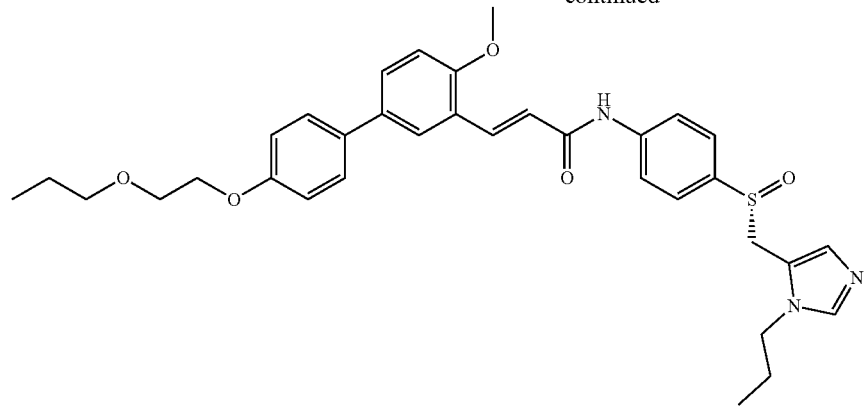
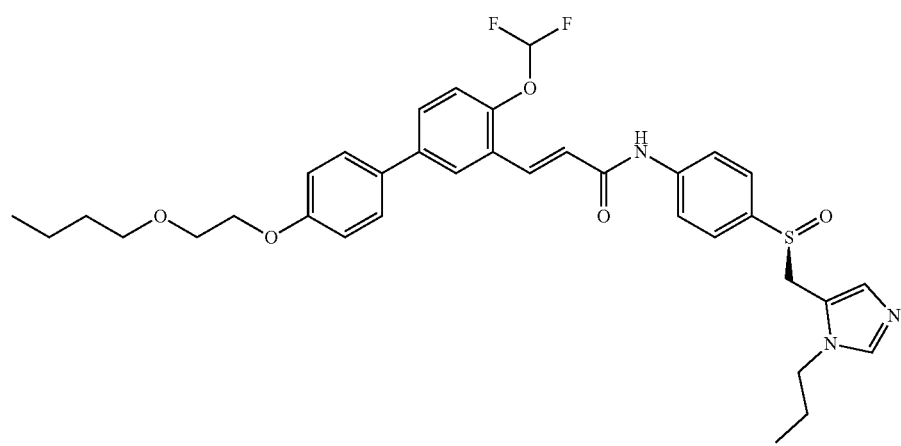
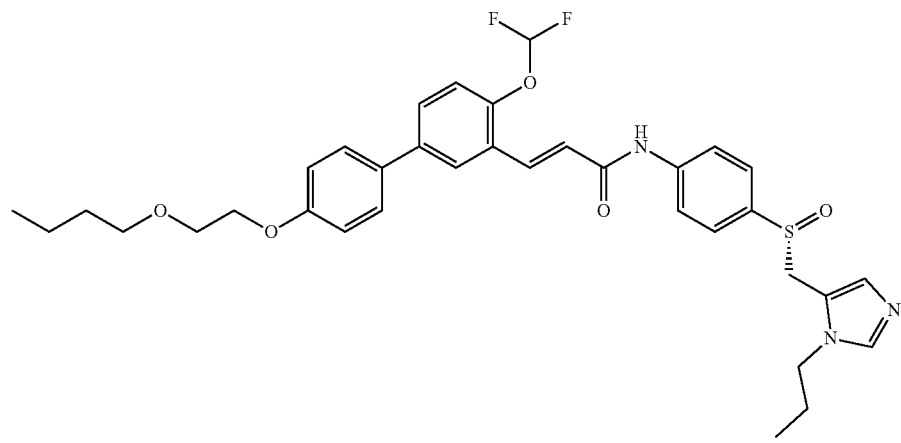
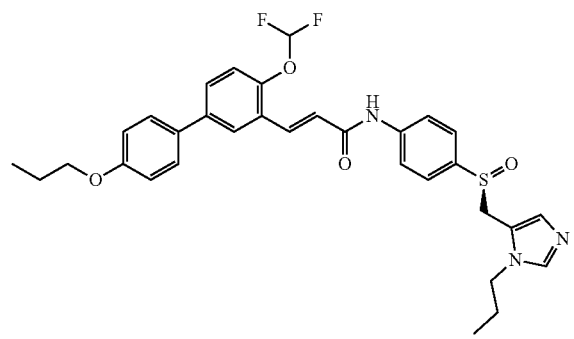 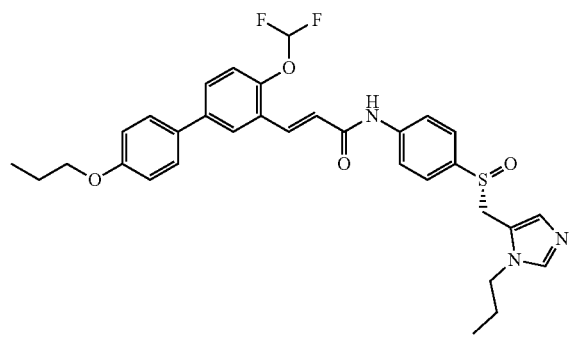

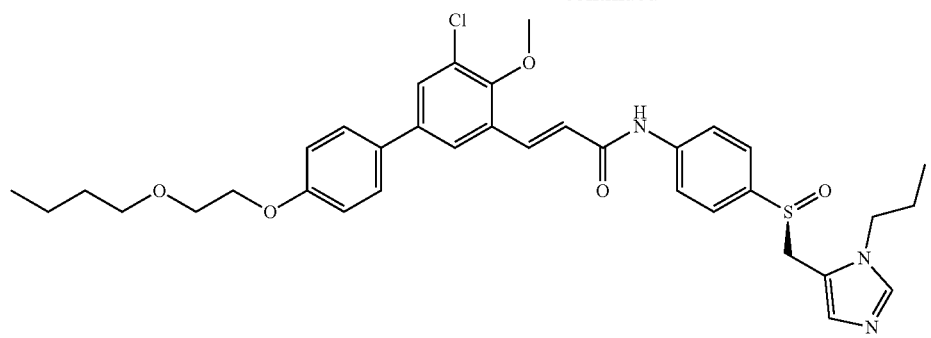
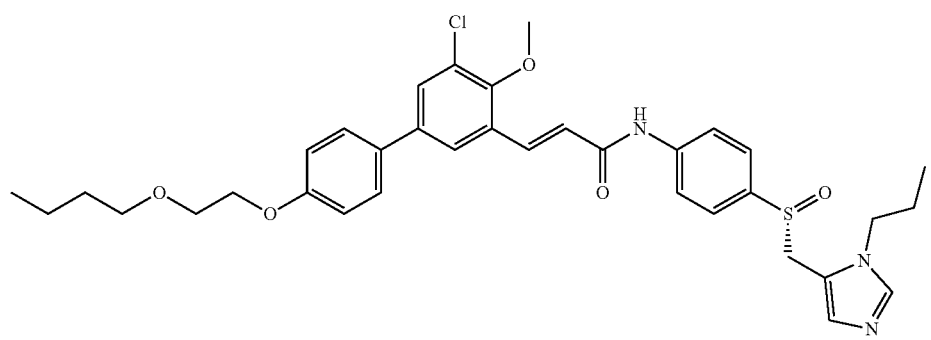
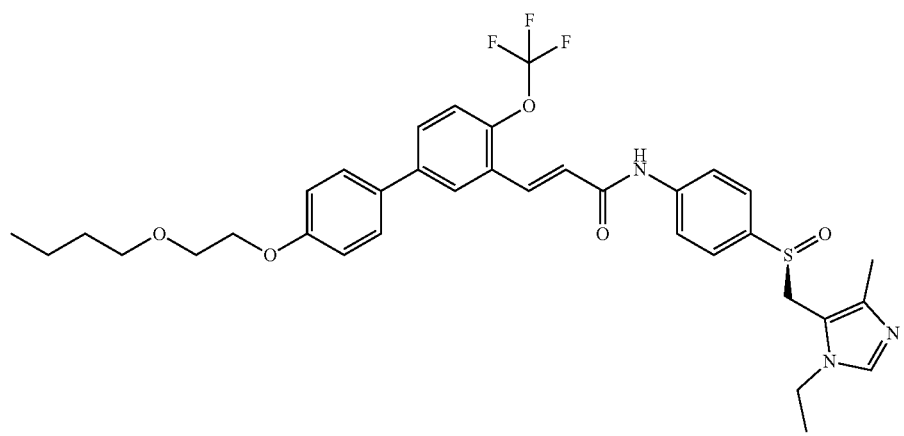
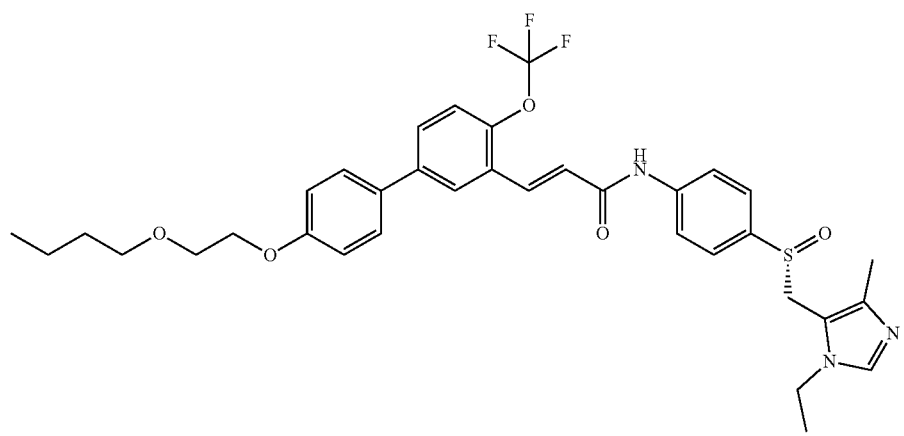

-continued
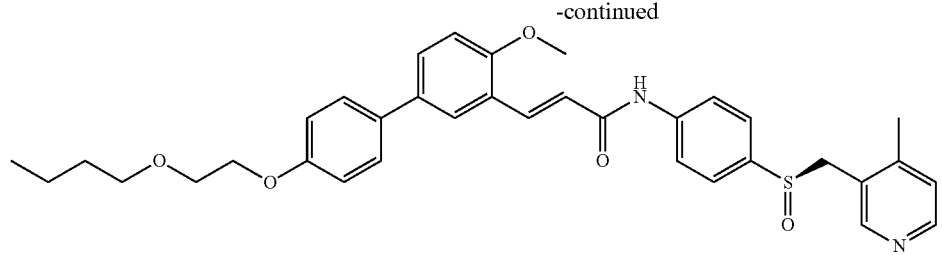
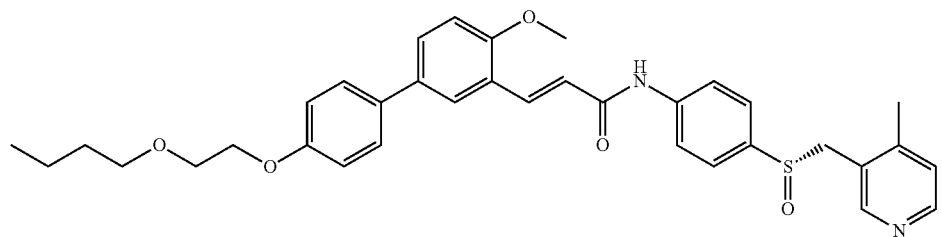
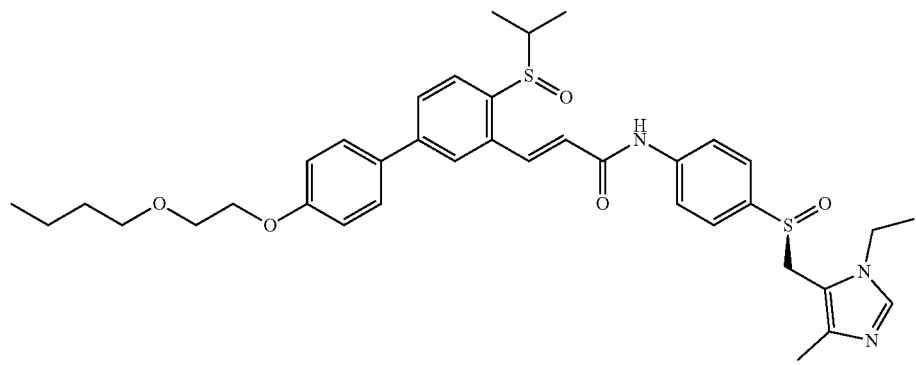
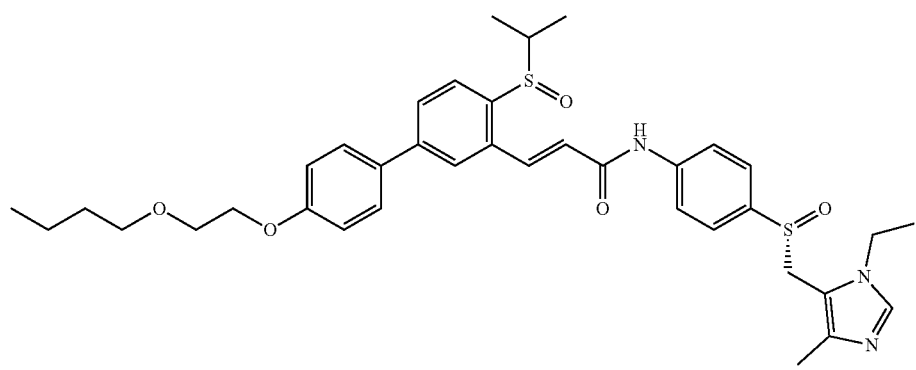
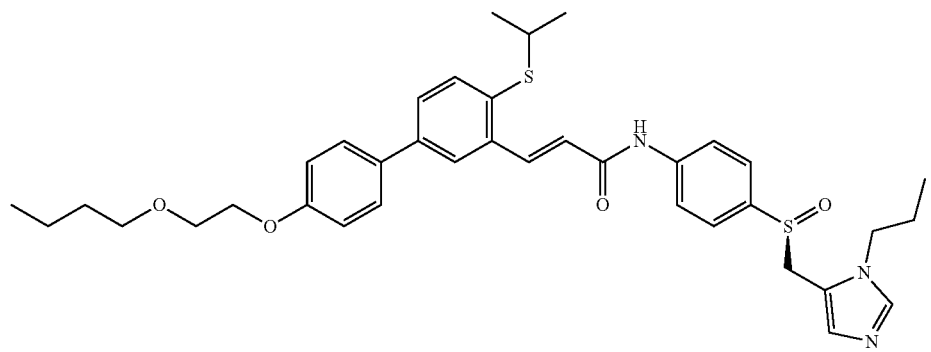

-continued
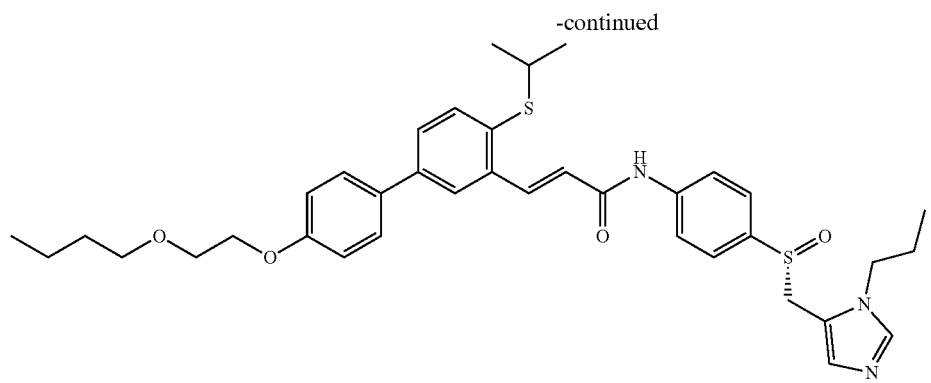
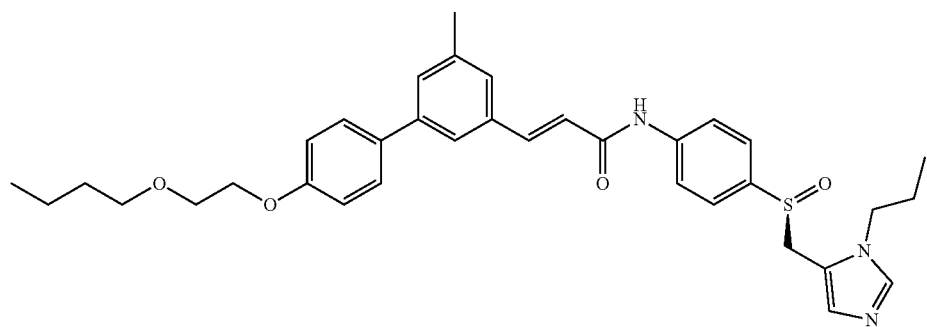
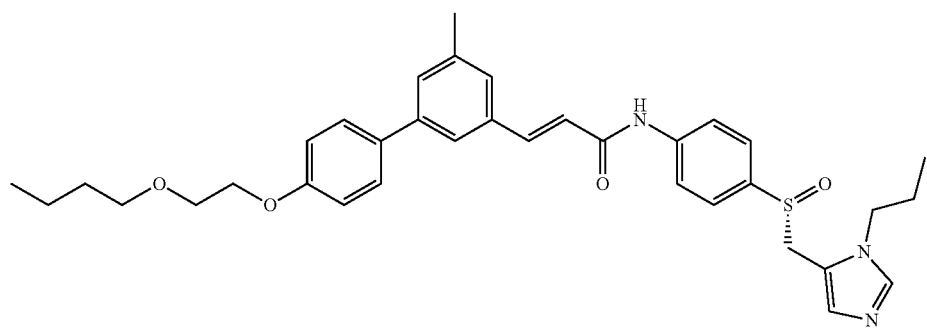
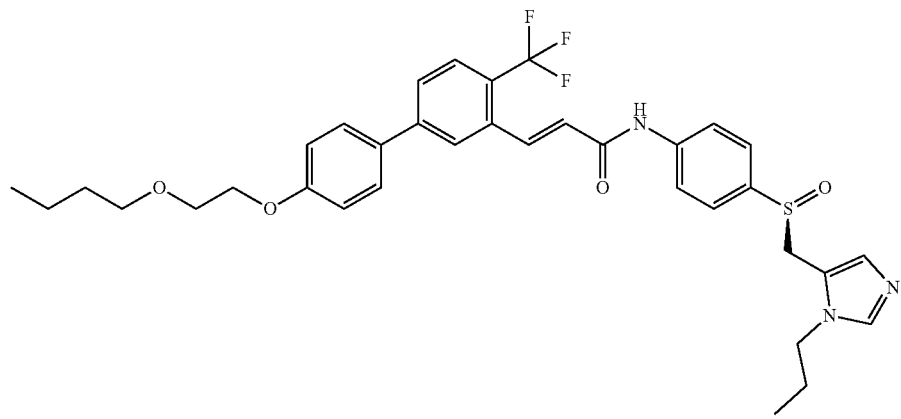

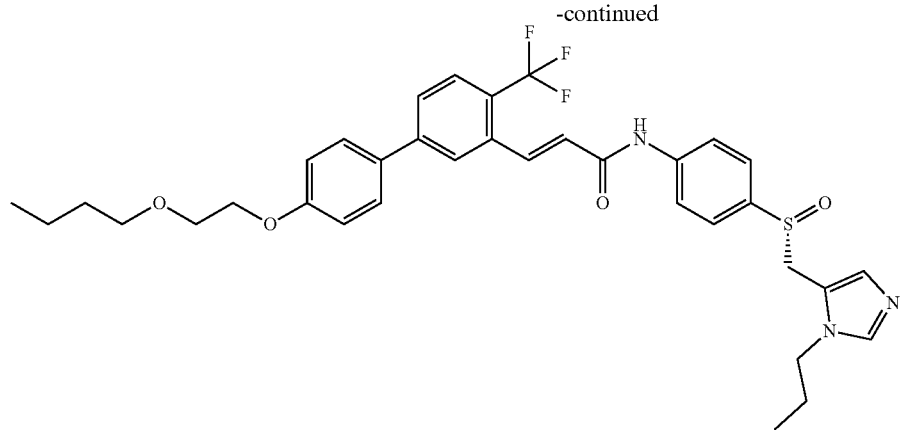
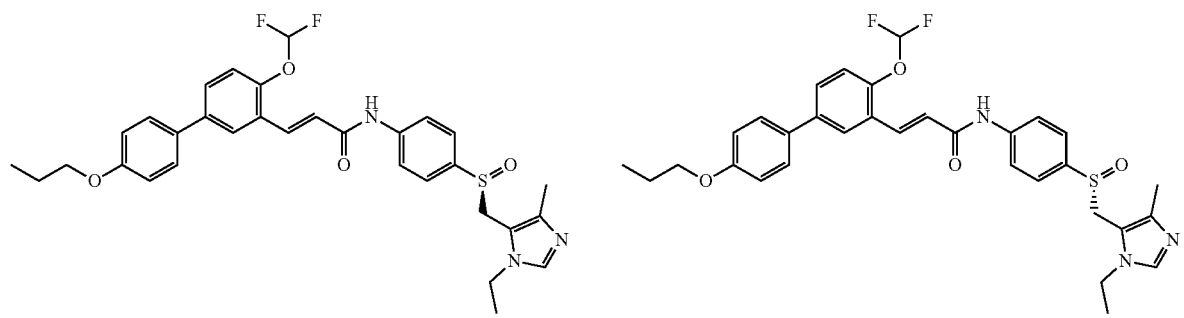
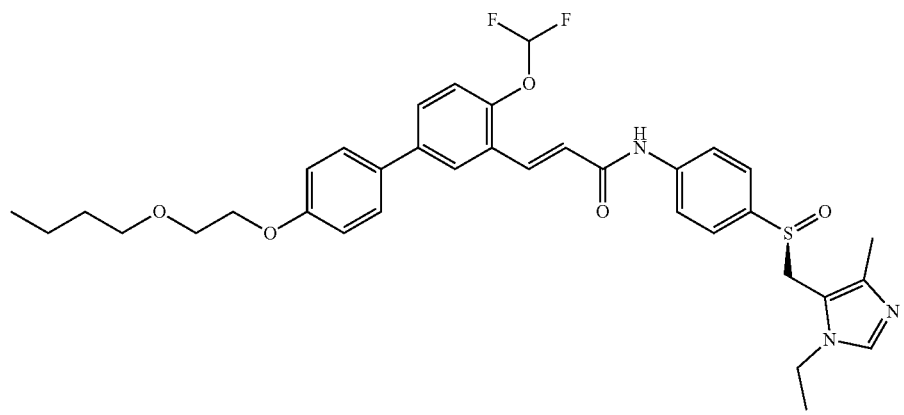
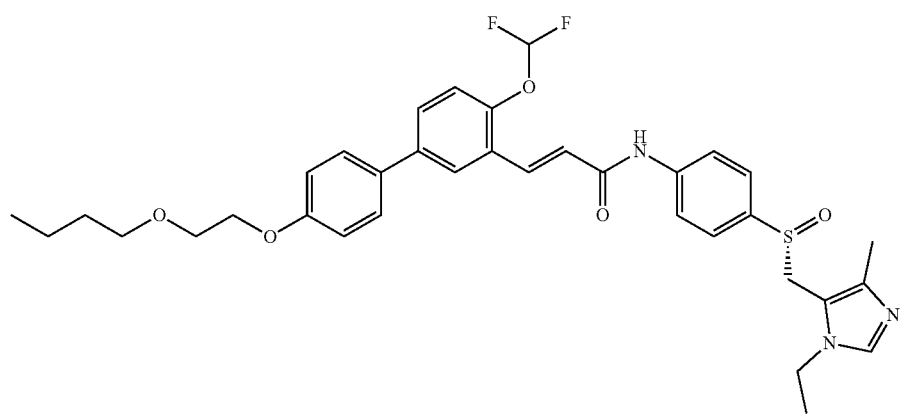

-continued
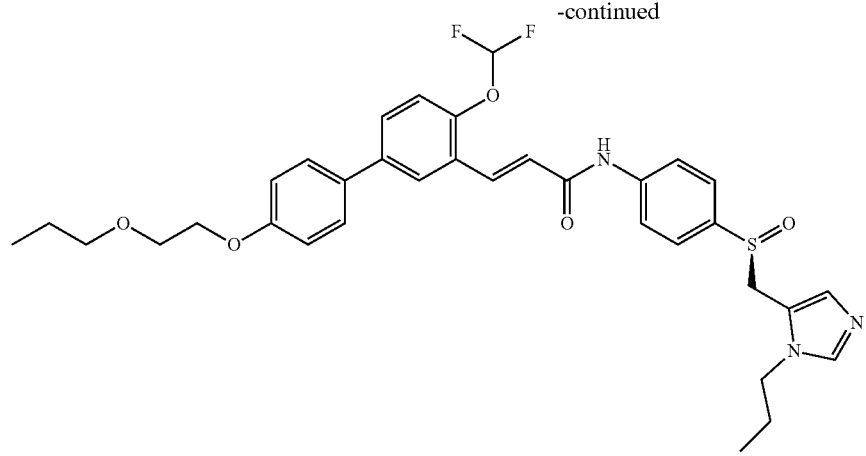
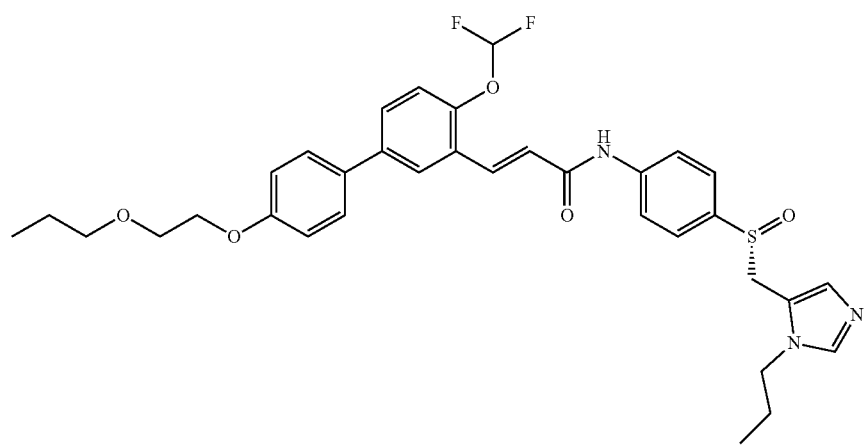
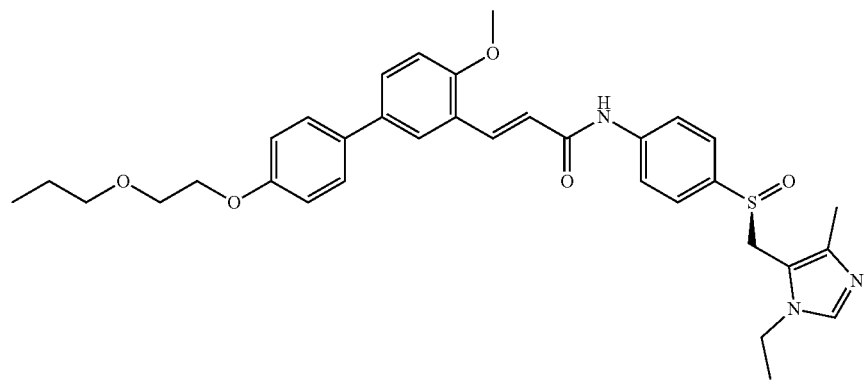
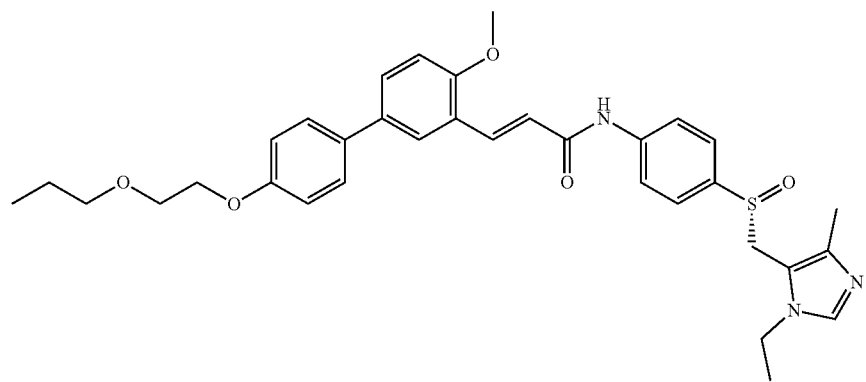

-continued
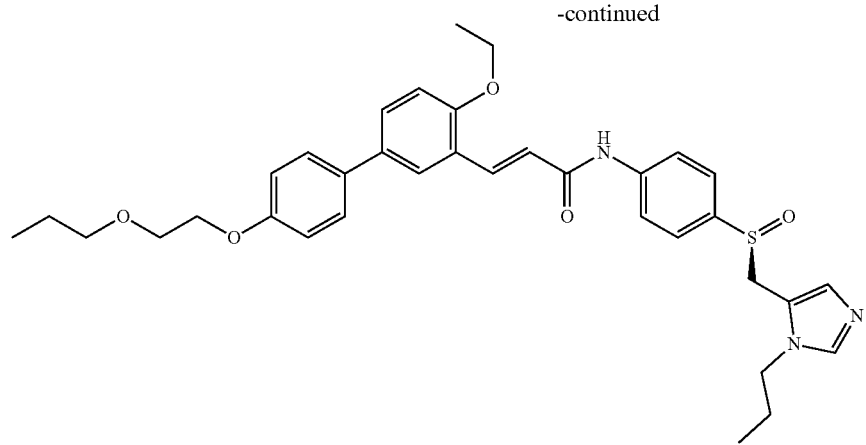
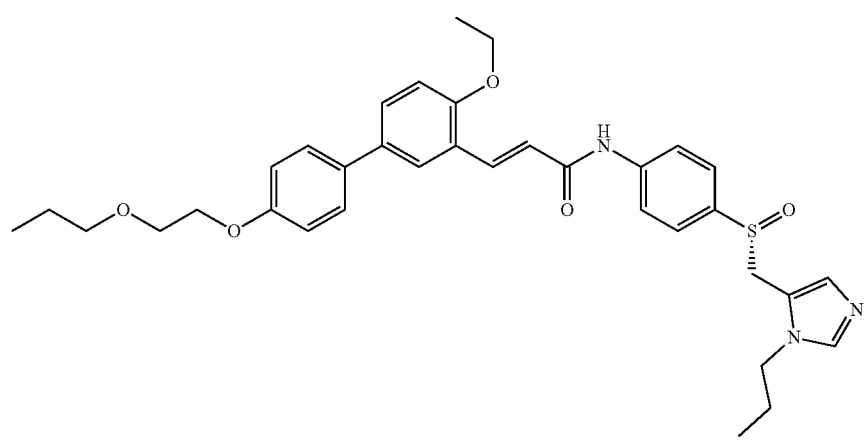
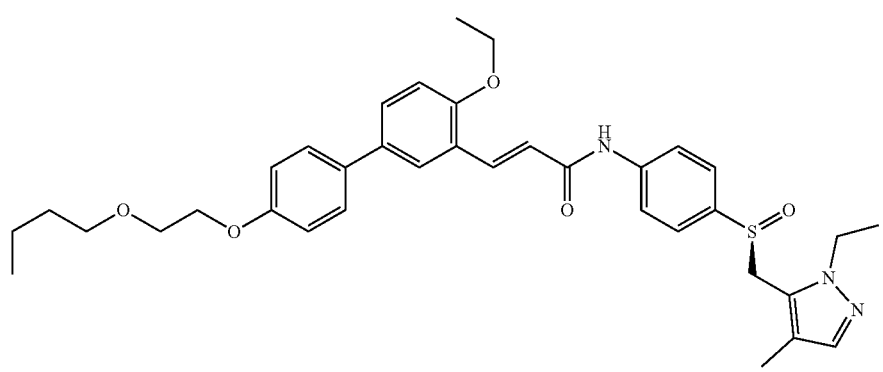
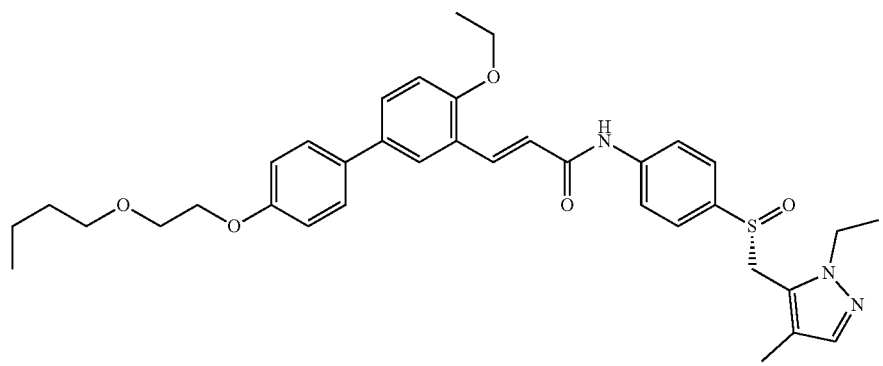

-continued
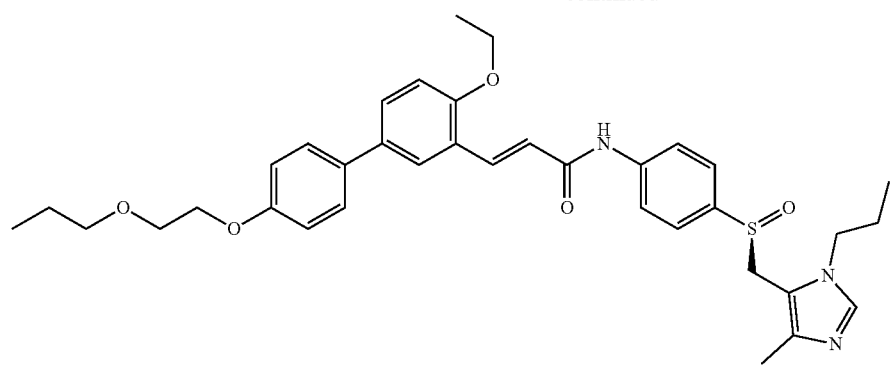
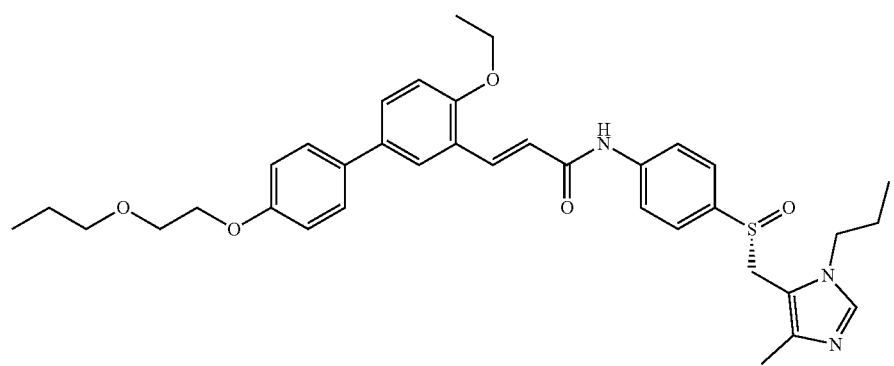
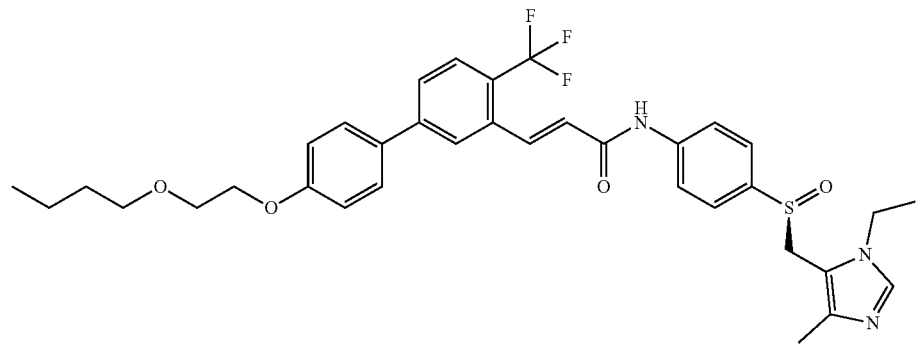
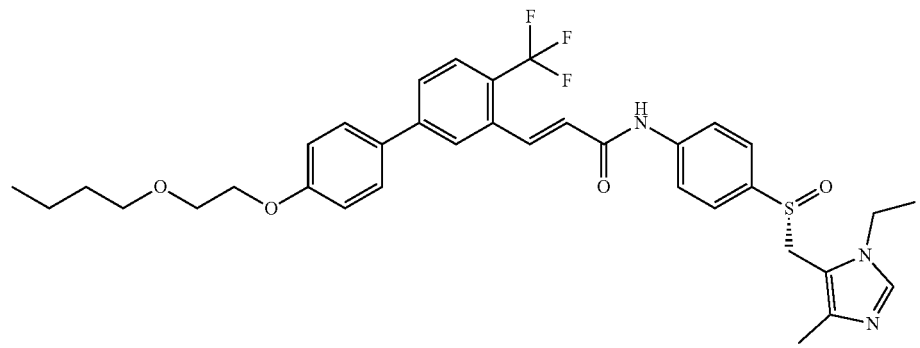

-continued
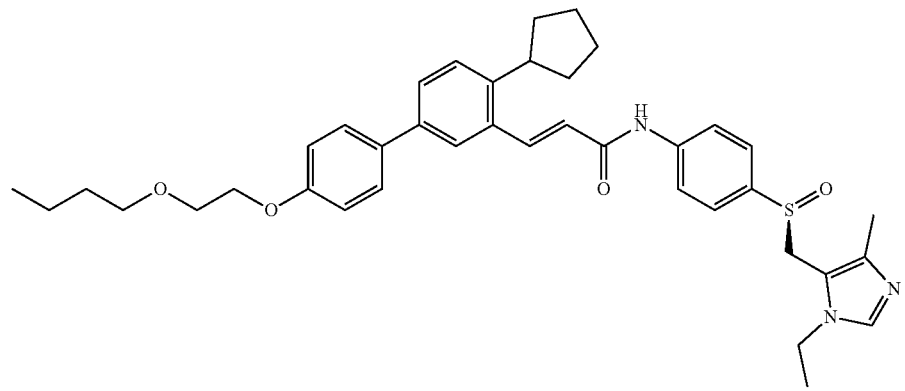
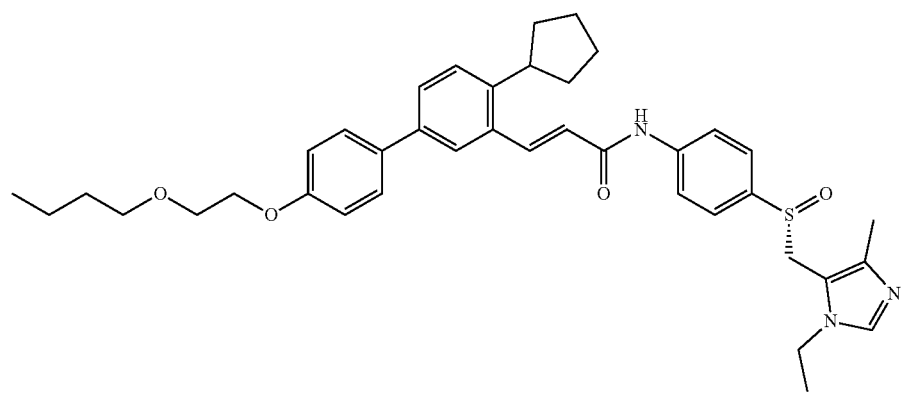
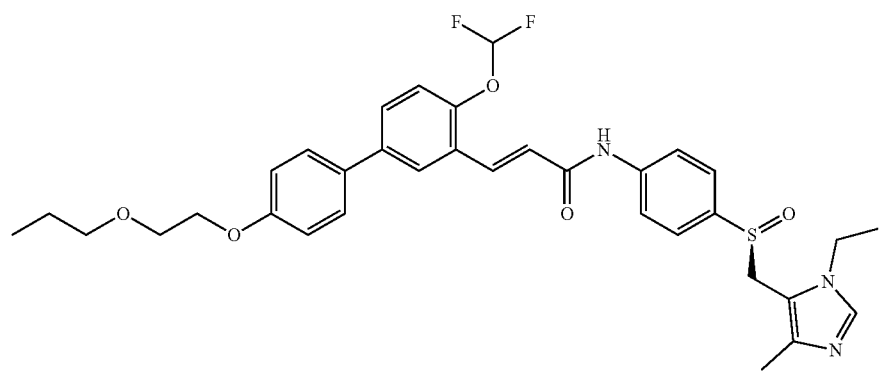
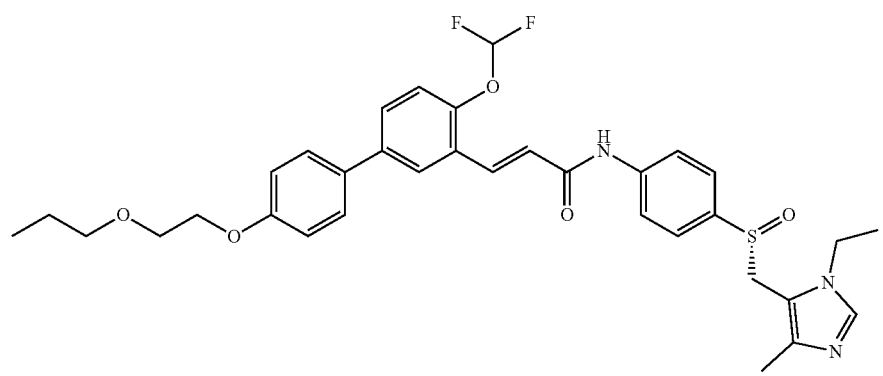

-continued
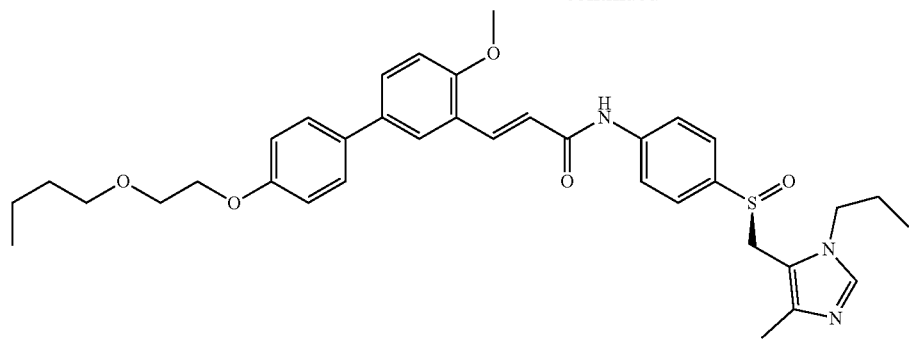
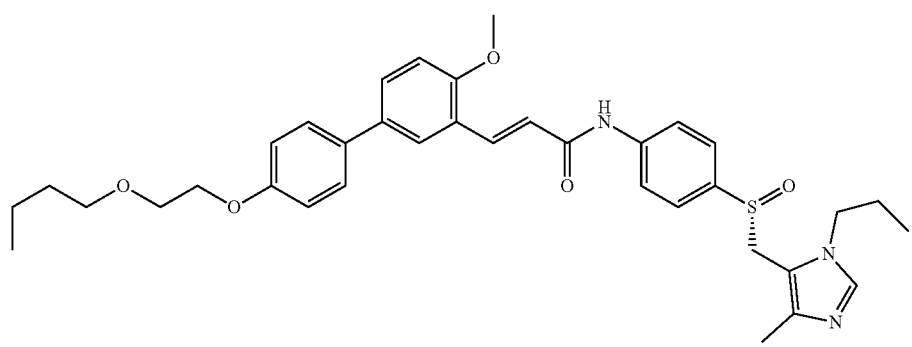
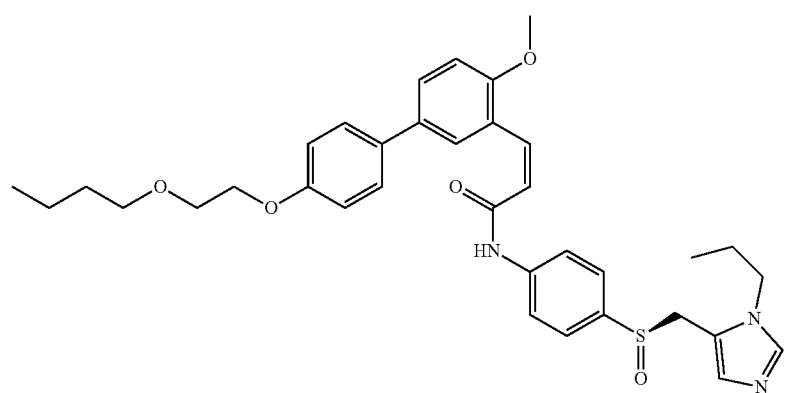
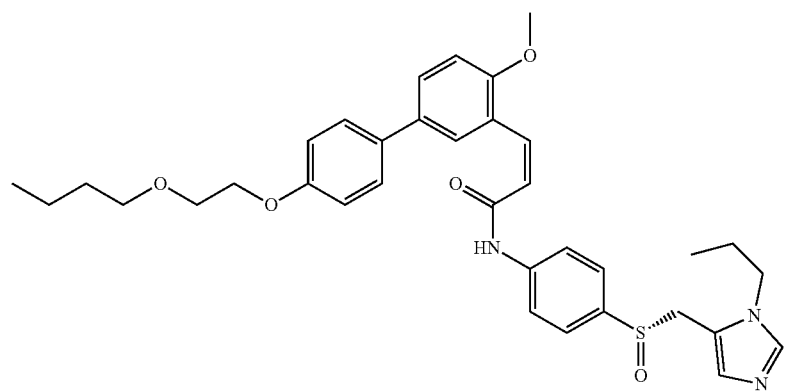

-continued
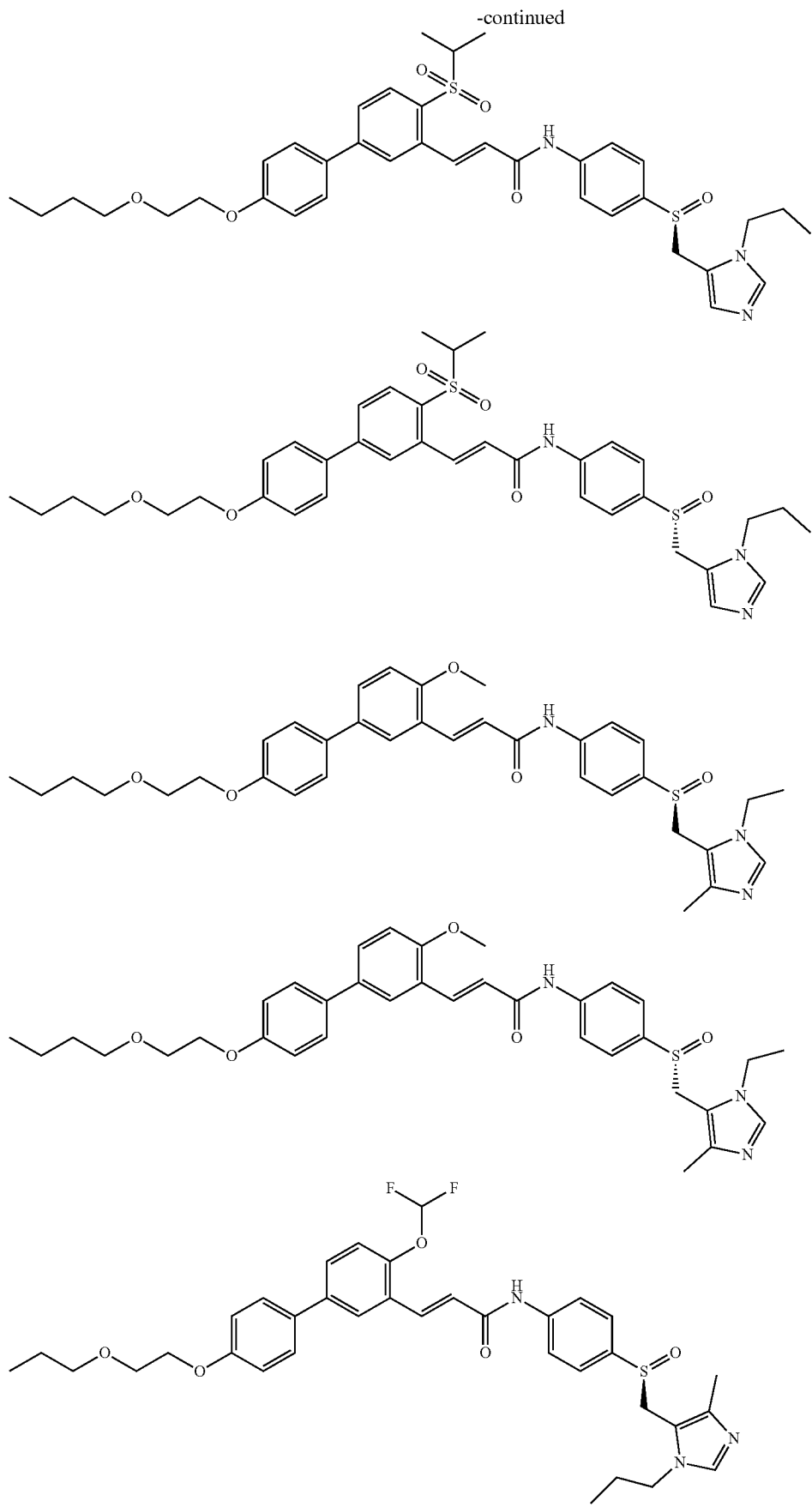

-continued
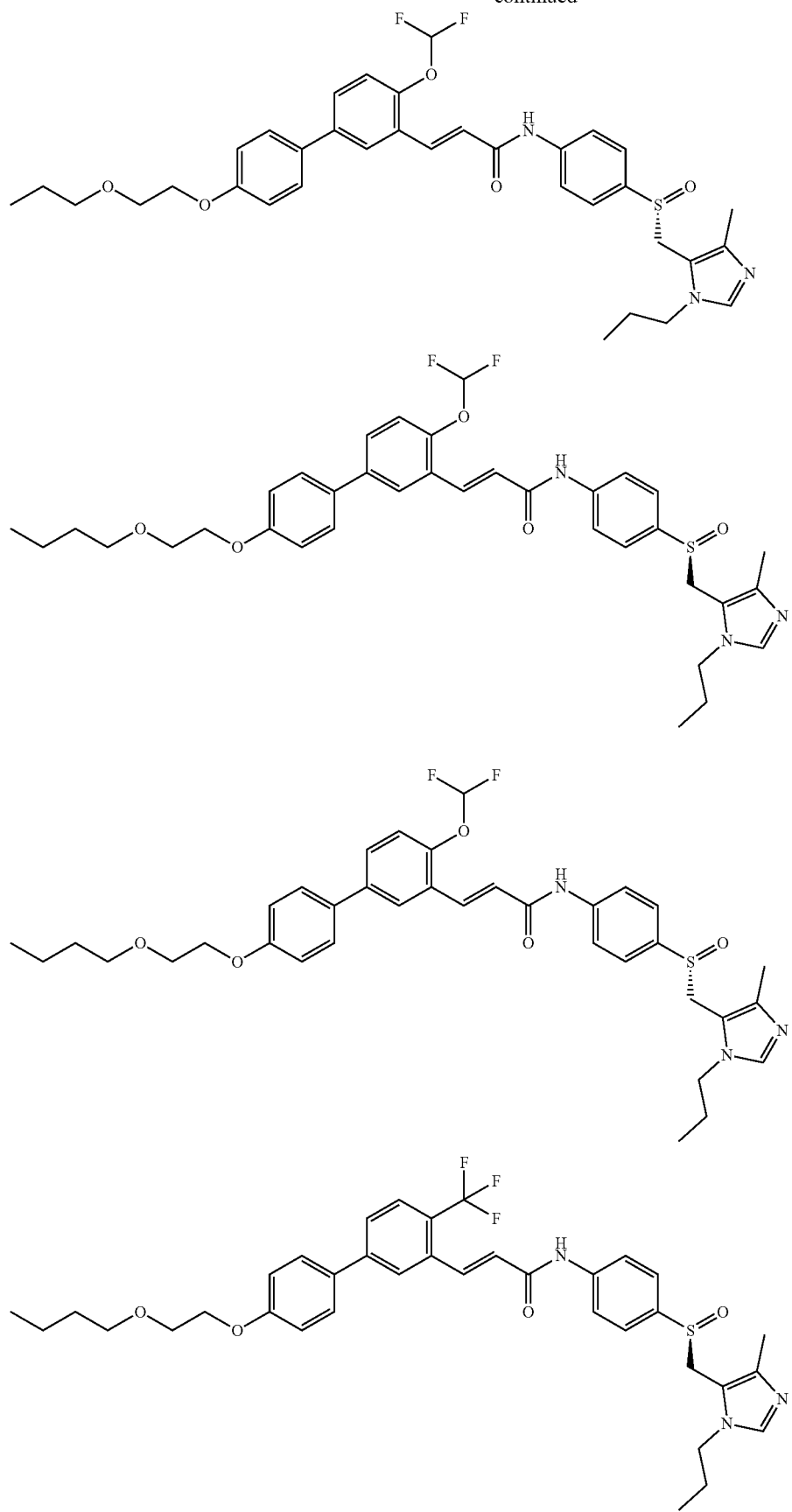

-continued
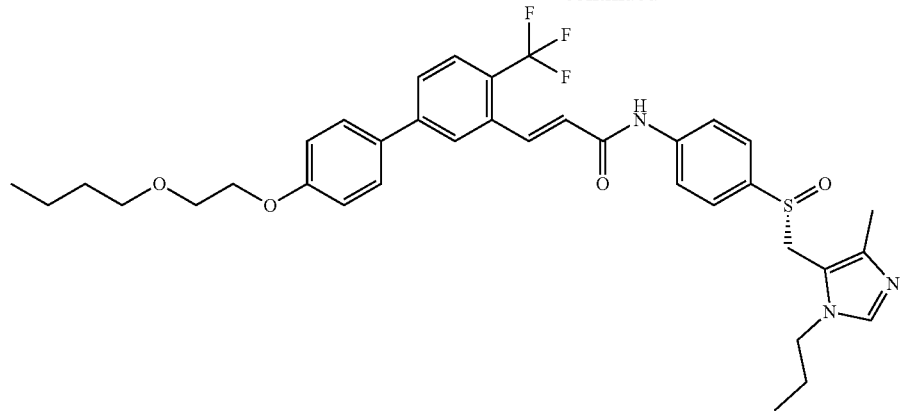
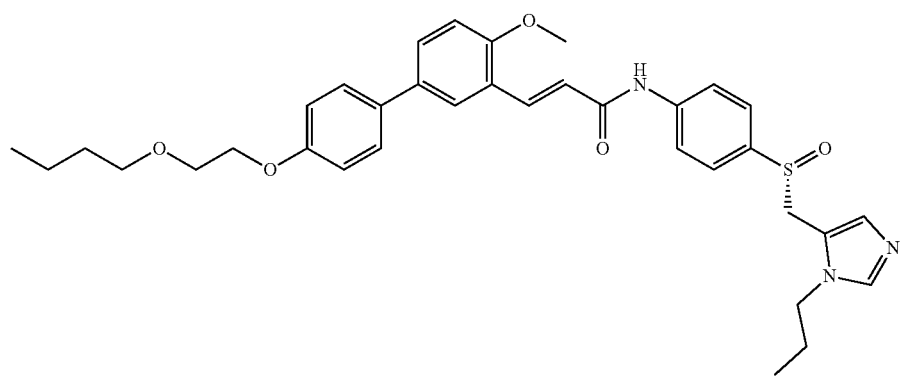
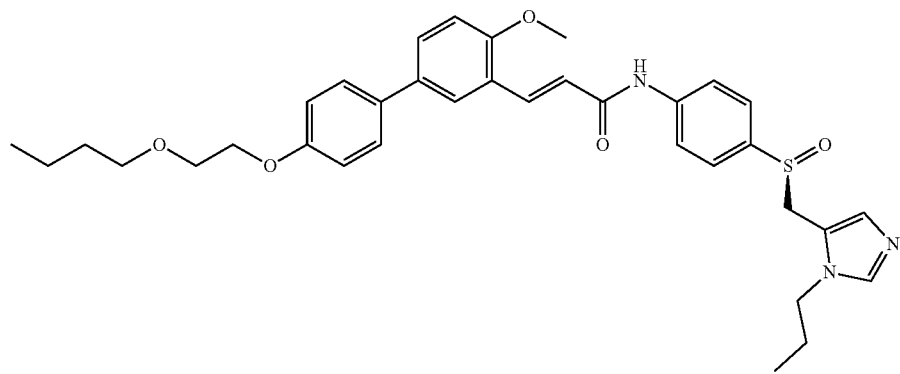
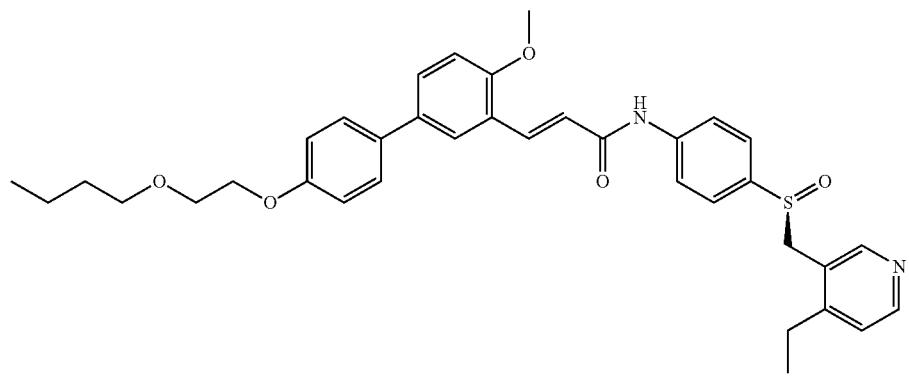

-continued
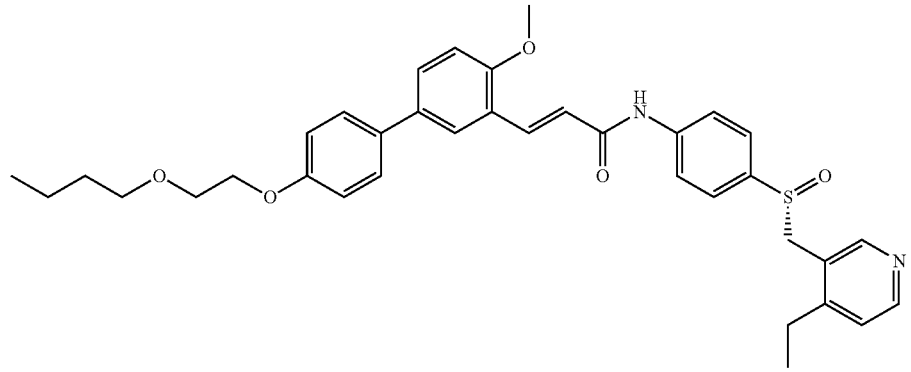
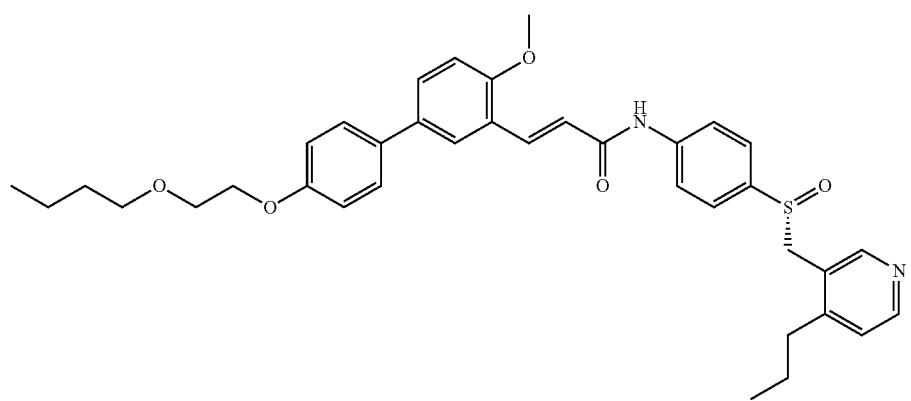
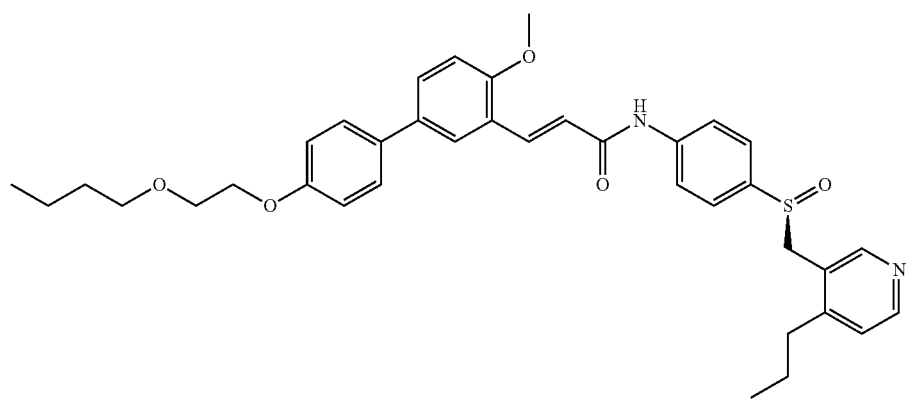
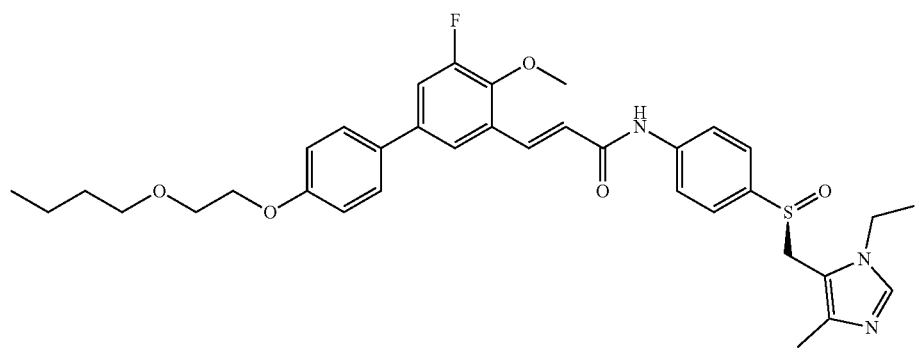

-continued
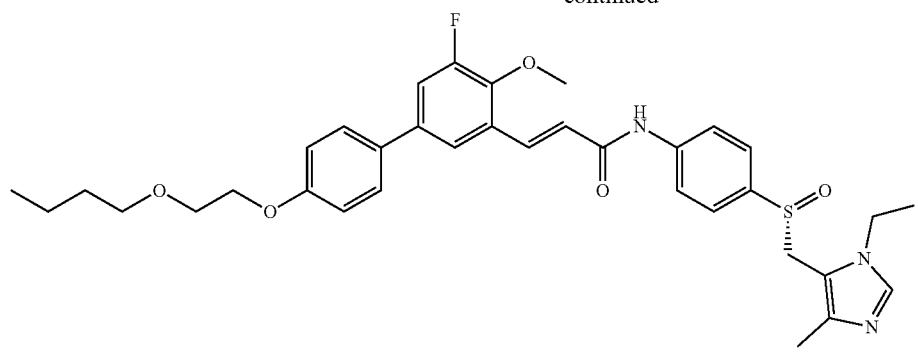
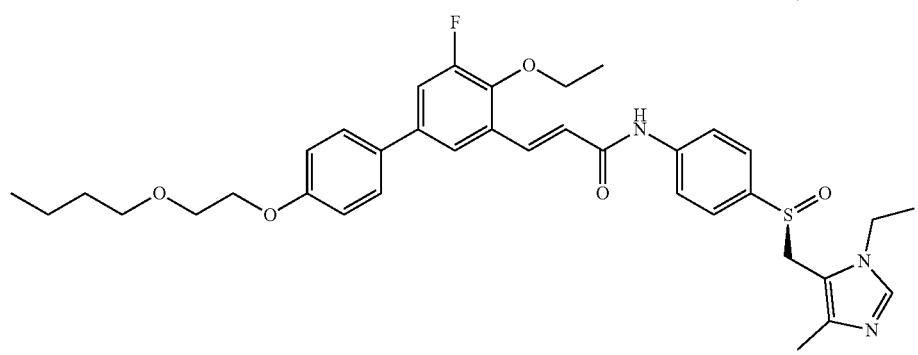
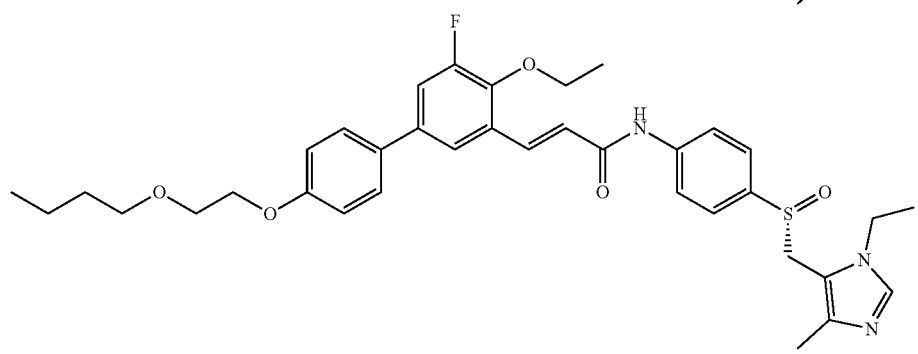
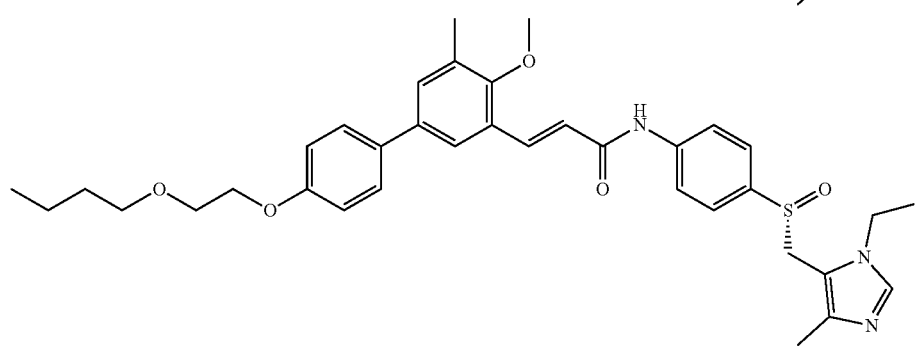
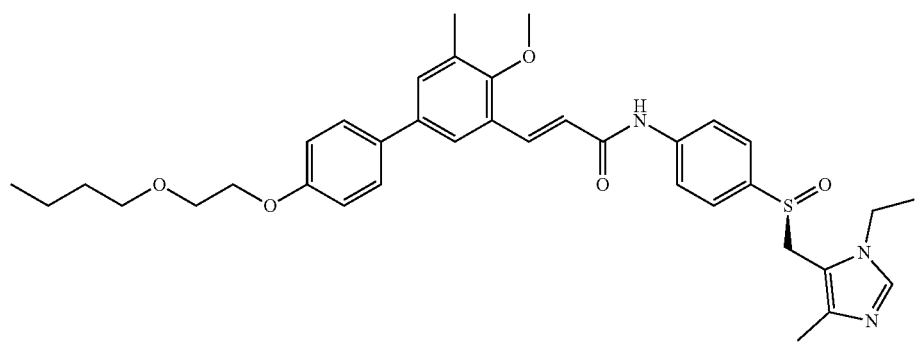

-continued

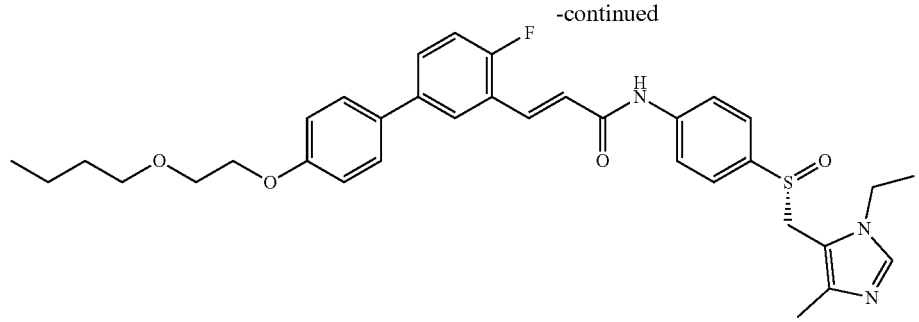

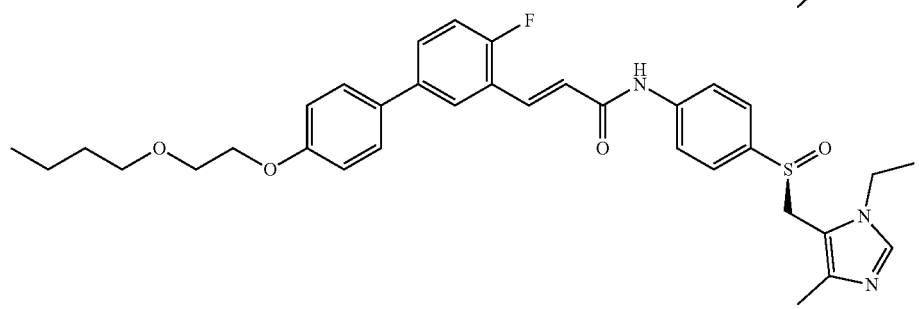

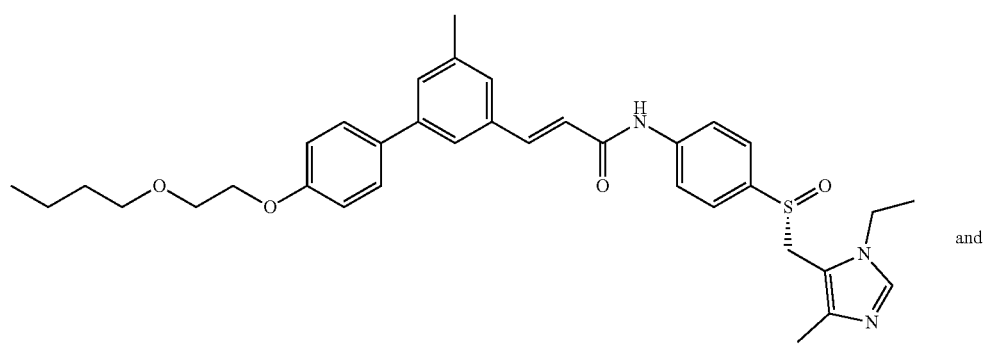

and

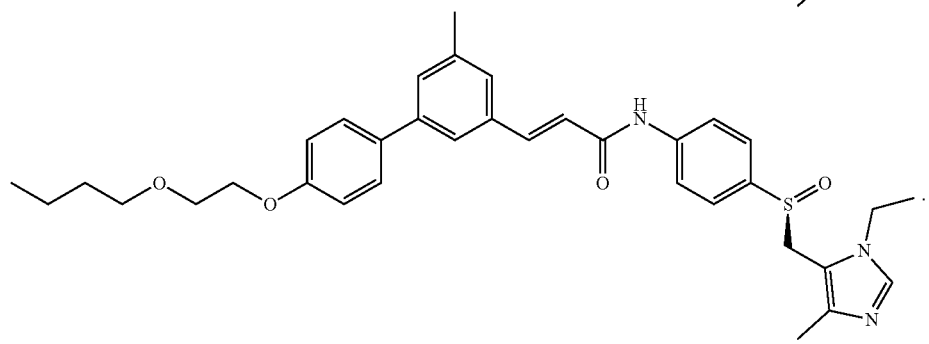

The present invention also provides a pharmaceutical composition, comprising a therapeutically effective amount of the above compound or the pharmaceutically acceptable salt thereof, and a pharmaceutically acceptable carrier.

The present invention also provides a use of the above compound or the pharmaceutically acceptable salt thereof in manufacturing a medicament for treating CCR2 and/or CCR5 related diseases.

The present invention also provides a use of the above compound or the pharmaceutically acceptable salt thereof in manufacturing a medicament for treating inflammation, autoimmune diseases and cancers.

In some embodiments of the present invention, the above $R_1$ is selected from the group consisting of $C_{1-4}$ alkoxy and pyrrolidinyl, each of which is optionally substituted by 1, 2 or 3 R, and other variables are as defined above.

In some embodiments of the present invention, the above $R_1$ is selected from the group consisting of

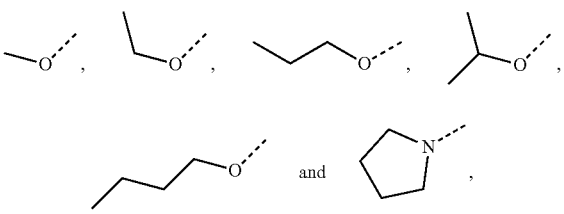

each of which is optionally substituted by 1, 2 or 3 R, and other variables are as defined above.

In some embodiments of the present invention, the above $R_1$ is

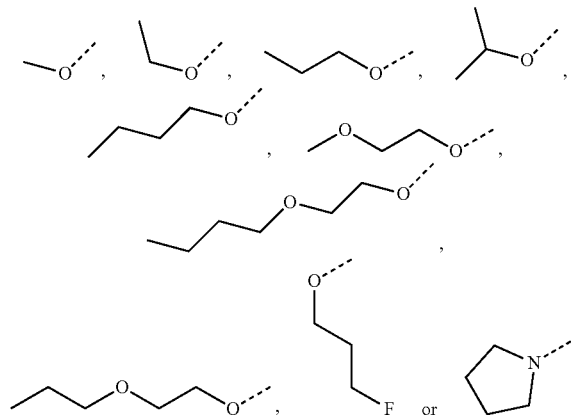

and other variables are as defined above.

In some embodiments of the present invention, each of the above $R_2$, $R_3$ and $R_4$ is independently H, halogen, OH, CN, or selected from the group consisting of $C_{1-3}$ alkyl, $C_{1-3}$ alkoxy, $C_{1-3}$ alkylthio, $C_{1-3}$ alkyl-S(=O)—, $C_{1-3}$ alkyl-S(=O)$_2$— and $C_{4-5}$ cycloalkyl, each of which is optionally substituted by 1, 2 or 3 R, and other variables are as defined by the present invention.

In some embodiments of the present invention, each of the above $R_2$, $R_3$ and $R_4$ is independently H, F, Cl, Br, I, OH, CN, or selected from the group consisting of Me,

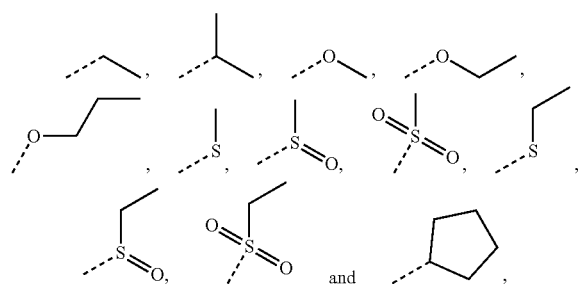

each of which is optionally substituted by 1, 2 or 3 R, and other variables are as defined by the present invention.

In some embodiments of the present invention, each of the above $R_2$, $R_3$ and $R_4$ is independently H, F, Cl, OH, CN, Me,

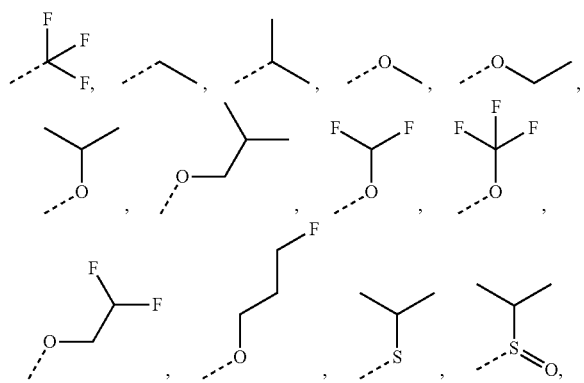

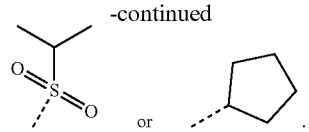

and other variables are as defined by the present invention.

In some embodiments of the present invention, the above $R_2$ is H, F, Cl, OH, CN, Me,

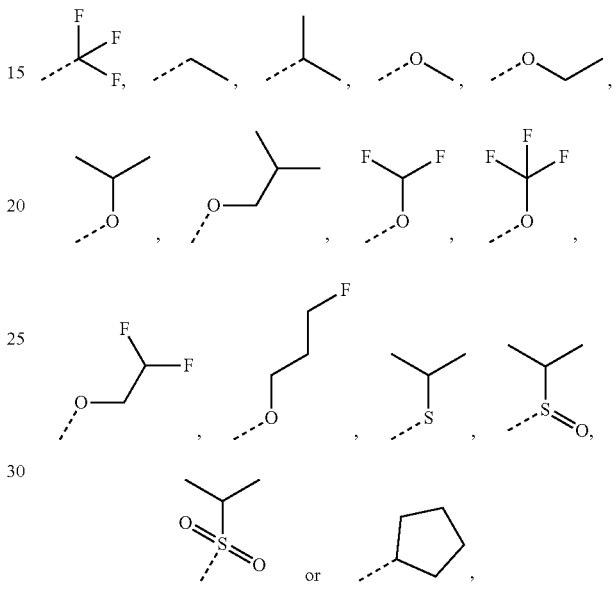

and other variables are as defined by the present invention.

In some embodiments of the present invention, the above $R_3$ is H, F, Cl, Me or

and other variables are as defined by the present invention.

In some embodiments of the present invention, the above $R_4$ is H or Cl, and other variables are as defined by the present invention.

In some embodiments of the present invention, each of the above $R_5$ and $R_6$ is independently H or Me, and other variables are as defined by the present invention.

In some embodiments of the present invention, the above $R_7$ is selected from the group consisting of Me,

each of which is optionally substituted by 1, 2 or 3 R, and other variables are as defined by the present invention.

In some embodiments of the present invention, the above $R_7$ is Me,

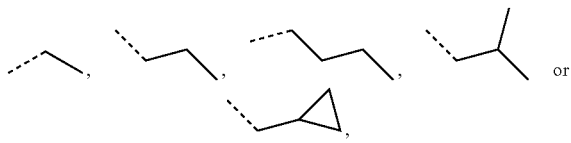

and other variables are as defined by the present invention.

In some embodiments of the present invention, the above RR is H, or selected from the group consisting of Me and

each of which is optionally substituted by 1, 2 or 3 R, and other variables are as defined by the present invention.

In some embodiments of the present invention, the above $R_8$ is H, Me or

and other variables are as defined by the present invention.

In some embodiments of the present invention, the above ring A

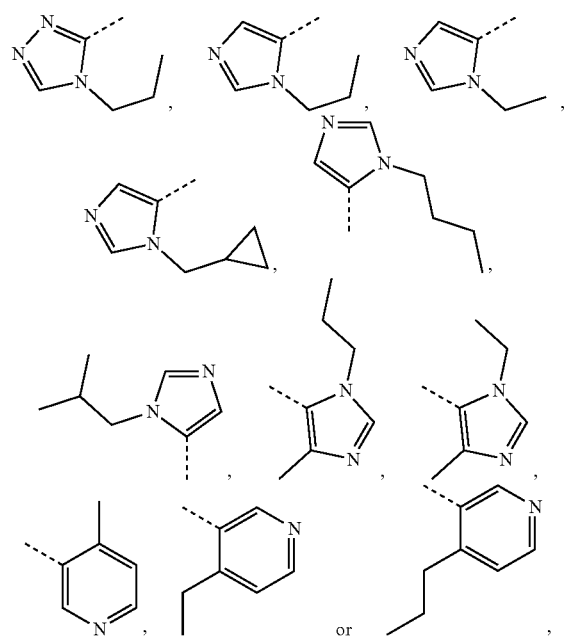

and other variables are as defined by the present invention.

Other embodiments of the present invention can be obtained by the arbitrary combination of the above variables.

Technical Effect

The compound of the present invention has significant antagonism effect on CCR2 and CCR5, lower plasma clearance, higher oral bioavailability, obvious advantages in oral plasma system exposure and excellent pharmacokinetic properties.

Definition and Description

Unless otherwise indicated, the following terms when used in the descriptions and the claims of the present invention have the following meanings. A specific term or phrase should not be considered indefinite or unclear in the absence of a particular definition, but should be understood in the ordinary sense. When a trade name appears herein, it is intended to refer to its corresponding commodity or active ingredient thereof. The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present invention that is prepared by reacting the compound having a specific substituent of the present invention with a relatively non-toxic acid or base. When the compound of the present invention contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the present invention contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like (refer to Berge et al., "*Pharmaceutical Salts*", *Journal of Pharmaceutical Science* 66: 1-19 (1977)). Certain specific compounds of the present invention that contain both basic and acidic functional groups can be converted to any base or acid addition salt.

Preferably, through bringing the salt into contact with a base or an acid in a conventional manner, then separating the parent compound, the neutral form of the compound is thereby regenerated. The difference between the parent form of the compound and its various salt forms lies in specific physical properties, such as different solubility in a polar solvent.

"Pharmaceutically acceptable salt" used herein belongs to a derivative of the compound of the present invention, wherein, the parent compound is modified by forming a salt with an acid or a base. Examples of the pharmaceutically acceptable salt include but are not limited to an inorganic acid or organic acid salt of a basic moiety such as amine, an alkali metal salt or an organic salt of an acidic moiety such as carboxylic acid, and the like. The pharmaceutically acceptable salt includes conventional non-toxic salt or quaternary ammonium salt of the parent compound, such as a salt formed by a non-toxic inorganic acid or an organic acid. The conventional non-toxic salt includes but is not limited to the salt derived from an inorganic acid and an organic acid, wherein the inorganic acid or organic acid is selected from the group consisting of 2-acetoxybenzoic acid, 2-hydroxyethanesulfonic acid, acetic acid, ascorbic acid, benzenesulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydroiodide, hydroxyl, hydroxynaphthalene, isethionic acid, lactic acid, lactose, dodecyl sulfonic acid, maleic acid, malic acid, mandelic acid, methanesulfonic acid, nitric acid, oxalic acid, pamoic acid, pantothenic acid, phenylacetic acid, phosphoric acid, polygalactanal acid, propionic acid, salicylic acid, stearic acid, subacetic acid, succinic acid, sulfamic acid, sulfanilic acid, sulfuric acid, tannin, tartaric acid and p-toluenesulfonic acid.

The pharmaceutically acceptable salt of the present invention can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof. Generally, non-aqueous media such as ether, ethyl acetate, ethanol, isopropanol or acetonitrile are preferred.

In addition to the salt form, the compound provided by the present invention also exists in prodrug form. The prodrug of the compound described herein is the compound that readily undergoes chemical change under physiological condition to be converted into the compound of the present invention. Additionally, the prodrug can be converted to the compound of the present invention by a chemical or biochemical method in vivo environment.

Certain compounds of the present invention can exist in an nonsolvated form or a solvated form, including hydrated form. Generally, the solvated form is equivalent to the nonsolvated form, and both are encompassed within the scope of the present invention.

Certain compounds of the present invention can have an asymmetric carbon atom (optical center) or a double bond. The racemate, diastereomer, geometric isomer and individual isomer are all encompassed within the scope of the present invention.

Unless otherwise specified, the absolute configuration of a stereogenic center is represented by a wedged solid bond () and a wedged dashed bond (), and the relative configuration of a stereogenic center is represented by a straight solid bond () and a straight dashed bond () When the compound described herein contains an olefinic double bond or other geometric asymmetric centers, E and Z geometric isomers are included unless otherwise specified. Likewise, all tautomeric forms are encompassed within the scope of the present invention.

The compound of the present invention may have a specific geometric or stereoisomeric form. The present invention contemplates all such compounds, including cis and trans isomer, (−)- and (+)-enantiomer, (R)- and (S)- enantiomer, diastereoisomer, (D)-isomer, (L)-isomer, and racemic mixture and other mixtures, for example, an enantiomer or diastereoisomer enriched mixture, all of which are encompassed within the scope of the present invention. The substituent such as alkyl may have an additional asymmetric carbon atom. All these isomers and mixtures thereof are encompassed within the scope of the present invention.

Optically active (R)- and (S)-isomer, or D and L isomer can be prepared using chiral synthesis or chiral reagents or other conventional techniques. If one kind of enantiomer of certain compound of the present invention is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to obtain the pure enantiomer. In addition, the enantiomer and the diastereoisomer are generally isolated through chromatography which uses a chiral stationary phase and optionally combines with a chemical derivative method (such as carbamate generated from amine).

The compound of the present invention may contain an unnatural proportion of atomic isotope at one or more than one atom(s) that constitute the compound. For example, the compound can be radiolabeled with a radioactive isotope, such as tritium ($^3$H), iodine-125 ($^{125}$I) or C-14 ($^{14}$C). For another example, hydrogen can be replaced by heavy hydrogen to form a deuterated drug, and the bond composed of barium and carbon is stronger than the bond composed of common hydrogen and carbon. Compared with undeuterated drugs, deuterated drugs have reduced side effects and increased drug stability, enhanced the efficacy and prolonged the biological half-life of the drug. All isotopic variations of the compound of the present invention, whether radioactive or not, are encompassed within the scope of the present invention.

The term "pharmaceutically acceptable carrier" refers to any agent or carrier medium which is capable of delivering an effective amount of the active substance of the present invention, does not interfere with the biological activity of the active substance and has no toxic side effect on the host or patient. The representative carrier includes water, oil, vegetable and mineral, cream base, lotion base, ointment base and the like. The base includes a suspending agent, a thickener, a penetration enhancer and the like. Their formulations are well known to the skilled in the cosmetic field or the topical pharmaceutical field.

The term "excipient" generally refers to the carrier, diluent and/or vehicle required to formulate an effective pharmaceutical composition.

For a medicament or a pharmacologically active agent, the term "effective amount" or "therapeutically effective amount" refers to a nontoxic but sufficient amount to achieve a desired effect of the medicament or the agent. For the oral dosage form of the present invention, an "effective amount" of the active substance in the composition refers to an amount required for achieving a desired effect when combining with another active substance in the composition. The effective amount varies from person to person and is determined depending on the age and general condition of the recipient as well as the specific active substance. The appropriate effective amount in an individual case can be determined by the skilled in the art based on routine experiment.

The term "active ingredient", "therapeutic agent", "active substance" or "active agent" refers to a chemical entity which can effectively treat the target disorder, disease or condition.

"Optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variants, as long as the valence of the specific atom is normal and the substituted compound is stable. When the substituent is an oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist. For example, when x is vacant in A-X, the structure of A-X is actually A. When a bond of a substituent can be cross-linked to more than one atom on a ring, such substituent can be bonded to any atom of the ring. When an enumerative substituent does not indicate by which atom it is attached to a compound included in the general chemical formula but not specifically mentioned, such substituent can be bonded by any of its atoms. For example, the structural unit

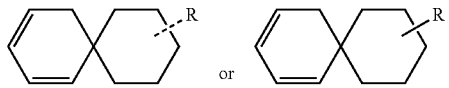

means that the substituent R can be located at any position on cyclohexyl or cyclohexadiene. When the enumerative linking group does not indicate the direction for linking, the direction for linking is arbitrary, for example, the linking group L contained in

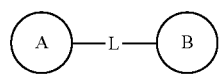

is -M-W—, then -M-W— can link ring A and ring B to form

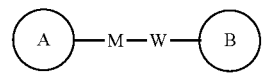

in the direction same as left-to-right reading order, and form

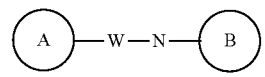

in the direction contrary to left-to-right reading order. A combination of substituents and/or variants thereof is allowed only when such combination can result in a stable compound.

Unless otherwise specified, the term "hetero" represents a heteroatom or a heteroatom group (e.g., an atom group containing a heteroatom), including the atom except carbon (C) and hydrogen (H) and the atom group containing the above heteroatom, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and the group consisting of —C(=O)N(H)—, —N(H)—, —C(=NH)—, —S(=O)$_2$N(H)— and —S(=O)N(H)—, each of which is optionally substituted.

Unless otherwise specified, the term "ring" refers to a substituted or unsubstituted cycloalkyl, heterocycloalkyl, cycloalkenyl, heterocycloalkenyl, cycloalkynyl, heterocycloalkynyl, aryl or heteroaryl. The so-called ring includes a single ring, a ring assembly, a spiral ring, a fused ring or a bridged ring. The number of the atom on the ring is usually defined as the member number of the ring, for example, a "5-7 membered ring" means that 5 to 7 atoms are arranged on a ring. Unless otherwise specified, the ring optionally contains 1 to 3 heteroatoms. Therefore, a "5-7 membered ring" includes, for example, phenyl, pyridinyl and piperidinyl; on the other hand, the term "5-7 membered heterocycloalkyl ring" includes pyridyl and piperidinyl, but excluding phenyl. The term "ring" also includes a ring system containing at least one ring, wherein each ring independently meets the above definition.

Unless otherwise specified, the term "heterocycle" or "heterocyclo" refers to a stable monocyclic, bicyclic or tricyclic ring containing a heteroatom or a heteroatom group, which can be saturated, partially unsaturated or unsaturated (aromatic) and can contain carbon atoms and 1, 2, 3 or 4 ring heteroatoms independently selected from N, O and S, wherein any of the above heterocycle can be fused to a benzene ring to form a bicyclic ring. Nitrogen and sulfur heteroatoms can optionally be oxidized (i.e., NO and S(O)p, p is 1 or 2). Nitrogen atom can be substituted or unsubstituted (i.e., N or NR, wherein R is H or other substituents already defined herein). The heterocycle can be attached to the pendant group of any heteroatom or carbon atom to form a stable structure. If the resulting compound is stable, the heterocycle described herein may have a substitution at a carbon or nitrogen position. Nitrogen atom on the heterocycle is optionally quaternized. In a preferred embodiment, when the total number of S and O atom of the heterocycle is more than 1, the heteroatom is not adjacent to each other. In another preferred embodiment, the total number of S and O atom of the heterocycle is not more than 1. As used herein, the term "aromatic heterocyclic group" or "heteroaryl"

refers to a stable 5-, 6- or 7-membered monocyclic or bicyclic or 7-, 8-, 9- or 10-membered bicyclic heterocyclic aromatic ring which contains carbon atoms and 1, 2, 3 or 4 ring heteroatoms independently selected from N, O and S. Nitrogen atom can be substituted or unsubstituted (i.e., N or NR, wherein R is H or other substituents already defined herein). Nitrogen and sulfur heteroatoms may optionally be oxidized (i.e., NO and $S(O)_p$, p is 1 or 2). It is worth noting that the total number of S and O atom of an aromatic heterocycle is not more than one. The bridged ring is also included in the definition of the heterocycle. A bridged ring is formed when one or more than one atom (i.e, C, O, N or S) link two non-adjacent carbon or nitrogen atoms. A preferred bridged ring includes, but not limited to one carbon atom, two carbon atoms, one nitrogen atom, two nitrogen atoms and one carbon-nitrogen group. It is worth noting that a bridge always converts a monocyclic ring to a tricyclic ring. In a bridged ring, the substituent on the ring may also be present on the bridge.

Examples of the heterocyclic compound include, but are not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolinyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isoindolyl, isoindolinyl, isoquinolinyl, isothiazolyl, isoxazolyl, methylenedioxyphenyl, morpholinyl, naphthyridinyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxindolyl, pyrimidinyl, phenanthridinyl, phenanthrolinyl, phenazine, phenothiazine, benzoxanthinyl, phenoloxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyrido-oxazolyl, pyrido-imidazolyl, pyrido-thiazolyl, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthienyl, thieno-oxazolyl, thieno-thiazolyl, thieno-imidazolyl, thienyl, triazinyl, 1,2,3-triazolyl, 1,2,4-triazolyl, 1,2,5-triazolyl, 1,3,4-triazolyl and xanthenyl. Also included are fused-ring compounds and spiro compounds.

Unless otherwise specified, the term "hydrocarbyl" or its hyponyms (e.g., alkyl, alkenyl, alkynyl, and aryl, etc.), by itself or as part of another substituent, refers to a linear, branched chain or cyclic hydrocarbon radical or any combination thereof. They can be fully saturated (e.g., alkyl), mono- or polyunsaturated (e.g., alkenyl, alkynyl, and aryl), can be mono-, di- or poly-substituted, can be monovalent (e.g., methyl), divalent (e.g., methylene) or multivalent (e.g., methenyl), can also include a divalent or multivalent group, have a specified number of carbon atom (for example, $C_1$-$C_{12}$ indicates 1 to 12 carbon atoms, $C_{1-12}$ is selected from $C_1$, $C_2$, $C_3$, $C_4$, $C_5$, $C_6$, $C_7$, $C_8$, $C_9$, $C_{10}$, $C_{11}$ and Cu; $C_{3-12}$ is selected from $C_3$, $C_4$, $C_5$, $C_6$, $C_7$, $C_8$, $C_9$, $C_{10}$, $C_{11}$ and $C_{12}$). The term "hydrocarbyl" includes, but is not limited to aliphatic hydrocarbyl and aromatic hydrocarbyl. The aliphatic hydrocarbyl includes linear and cyclic hydrocarbyl, specifically includes but not limited to alkyl, alkenyl, and alkynyl. The aromatic hydrocarbyl includes but is not limited to 6-12 membered aromatic hydrocarbyl such as phenyl, naphthyl and the like. In some embodiments, the term "hydrocarbyl" refers to a linear or branched group or a combination thereof which can be fully saturated, mono- or polyunsaturated, and can include a divalent or multivalent group. Examples of the saturated hydrocarbyl group include, but are not limited to, methyl, ethyl, n-propyl, isopropyl, n-butyl, tert-butyl, isobutyl, sec-butyl, cyclohexyl, (cyclohexyl)methyl, cyclopropylmethyl, and the homolog or isomer of n-amyl, n-hexyl, n-heptyl, n-octyl and other atom groups. The unsaturated hydrocarbyl has one or more than one double or triple bonds. Examples of the unsaturated alkyl include but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and more higher homologs and isomers.

Unless otherwise specified, the term "heterohydrocarbyl" or its hyponyms (such as heteroalkyl, heteroalkenyl, heteroalkynyl, and heteroaryl, etc.), by itself or as part of another substituent, refers to a stable linear, branched or cyclic hydrocarbon group or any combination thereof, which has a specified number of carbon atoms and at least one heteroatom. In some embodiments, the term "heteroalkyl" by itself or in combination with another term refers to a stable linear chain, branched hydrocarbon radical or a combination thereof which has a specified number of carbon atoms and at least one heteroatom. In a specific embodiment, a heteroatom is selected from B, O, N and S, wherein nitrogen and sulfur atoms are optionally oxidized and the nitrogen atom is optionally quaternized. The heteroatom or heteroatom group can be located at any interior position of a heterohydrocarbyl, including the position where the hydrocarbyl attaches to the rest part of the molecule. But the terms "alkoxy", "alkylamino" and "alkylthio" (or thioalkyl) are used by the conventional meaning and refer to an alkyl group connected to the rest part of the molecule via an oxygen atom, an amino or a sulfur atom respectively. Examples include, but are not limited to, $-CH_2-CH_2-O-CH_3$, $-CH_2-CH_2-NH-CH_3$, $-CH_2-CH_2-N(CH_3)-CH_3$, $-CH_2-S-CH_2-CH_3$, $-CH_2-CH_2$, $-S(O)-CH_3$, $-CH_2-CH_2-S(O)_2-CH_3$, $-CH=CH-O-CH_3$, $-CH_2-CH=N-OCH_3$ and $-CH=CH-N(CH_3)-CH_3$. Up to two consecutive heteroatoms can be present, such as, $-CH_2-NH-OCH_3$.

Unless otherwise specified, the term "cyclohydrocarbyl", "heterocyclohydrocarbyl" or its hyponyms (such as aryl, heteroaryl, cycloalkyl, heterocycloalkyl, cycloalkenyl, heterocycloalkenyl, cycloalkynyl, heterocycloalkynyl, etc.) by itself or in combination with another term refers to cyclized "hydrocarbyl" or "heterohydrocarbyl". Furthermore, for heterohydrocarbyl or heterocyclohydrocarbyl (e.g., heteroalkyl, and heterocycloalkyl), one heteroatom can occupy the position where the heterocycle attaches to the remainder position of the molecule. Examples of the cycloalkyl include, but are not limited to, cyclopentyl, cyclohexyl, 1-cyclohexenyl, 3-cyclohexenyl, cycloheptyl and the like. Non-limiting examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydro-thiophen-2-yl, tetrahydro-thiophen-3-yl, 1-piperazinyl and 2-piperazinyl.

Unless otherwise specified, the term "alkyl" refers to a linear chain or branched saturated hydrocarbon group, can be mono-substituted (e.g., $-CH_2F$) or poly-substituted (e.g., $-CF_3$), can be monovalent (e.g. methyl), divalent (e.g., methylene) or multivalent (e.g., methenyl). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl) and the like.

Unless otherwise specified, the term "alkenyl" refers to an alkyl group having one or more than one carbon-carbon double bonds at any position on the chain, can be mono-substituted or poly-substituted, and can be monovalent, divalent or multivalent. Examples of alkenyl include ethenyl, propenyl, butenyl, pentenyl, hexenyl, butadienyl, pentadienyl, hexadienyl, and the like.

Unless otherwise specified, the term "alkynyl" refers to an alkyl group having one or more than one carbon-carbon triple bonds at any position on the chain, can be mono-substituted or poly-substituted, and can be monovalent, divalent or multivalent. Examples of alkynyl include ethynyl, propynyl, butynyl, pentynyl, and the like.

Unless otherwise specified, cycloalkyl includes any stable cyclic or polycyclic hydrocarbyl, and any carbon atom is saturated, can be mono-substituted or poly-substituted, and can be monovalent, divalent or multivalent. Examples of cycloalkyl include, but are not limited to, cyclopropyl, norbornanyl, [2.2.2]bicyclooctane, [4.4.0]bicyclodecanyl and the like.

Unless otherwise specified, cycloalkenyl includes any stable cyclic or polycyclic hydrocarbyl having one or more than one unsaturated carbon-carbon single bonds at any position on the ring, can be mono-substituted or poly-substituted, and can be monovalent, divalent or multivalent. Examples of the cycloalkenyl include, but are not limited to, cyclopentenyl, cyclohexenyl and the like.

Unless otherwise specified, cycloalkynyl includes any stable cyclic or polycyclic hydrocarbyl having one or more carbon-carbon triple bonds at any position on the ring, can be mono-substituted or poly-substituted, and can be monovalent, divalent or multivalent.

Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo($C_1$-$C_4$)alkyl" is meant to include, but not limited to, trifluoromethyl, 2,2,2-trifluoroethyl, 4-chlorobutyl, 3-bromopropyl and the like. Examples of haloalkyl include, but not limited to trifluoromethyl, trichloromethyl, pentafluoroethyl and pentachloroethyl.

The term "alkoxy" represents any alkyl defined above having a specified number of carbon atoms attached by an oxygen bridge. Unless otherwise specified, $C_{1-6}$ alkoxy includes $C_1$, $C_2$, $C_3$, $C_4$, $C_5$ and $C_6$ alkoxy. Examples of alkoxy include, but not limited to methoxy, ethoxy, n-propoxy, isopropoxy, n-butoxy, sec-butoxy, tert-butoxy, n-pentyloxy and S-pentoxy. Unless otherwise specified, the term "aryl" refers to a polyunsaturated aromatic substituent, can be mono-, di- or poly-substituted, can be a monovalent, divalent or multivalent, can be a single ring or a multiple ring (e.g. one to three rings; wherein at least one ring is aromatic), which are fused together or connected covalently. The term "heteroaryl" refers to an aryl (or ring) containing one to four heteroatoms. In an illustrative example, the heteroatom is selected from B, O, N and S, wherein nitrogen and sulfur atoms are optionally oxidized and nitrogen atom is optionally quaternized. A heteroaryl may attach to the rest part of a molecule via a heteroatom. Non-limiting examples of aryl or heteroaryl include phenyl, naphthyl, biphenyl, pyrrolyl, pyrazolyl, imidazolyl, pyrazinyl, oxazolyl, phenyloxazolyl, isoxazolyl, thiazolyl, furanyl, thienyl, pyridyl, pyrimidinyl benzothiazolyl, purinyl, benzimidazolyl, indolyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituent of any of the above aryl and heteroaryl ring system is selected from the acceptable substituent described below.

Unless otherwise specified, when aryl combines with other terms (such as aryloxy, arylthio, arylalkyl), the aryl includes the aryl and heteroaryl ring as defined above. Thus, the term "aralkyl" is meant to include the group (e.g., benzyl, phenethyl, pyridylmethyl, etc.) where an aryl is attached to an alkyl, including an alkyl where the carbon atom (e.g, methylene) has been replaced by an atom such as oxygen, for example, phenoxymethyl, 2-pyridyloxy, 3-(1-naphthyloxy)propyl, and the like.

The term "leaving group" refers to a functional group or atom which can be replaced by another functional group or atom through a substitution reaction (such as affinity substitution reaction). For example, representative leaving groups include triflate; chlorine, bromine and iodine; sulfonate group, such as mesylate, tosylate, p-bromobenzenesulfonate, p-toluenesulfonates and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g, acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl) methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl and tert-butyl; acyl such as alkanoyl (e.g, acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

The compound of the present invention can be prepared by a variety of synthetic methods well known to the skilled in the art, including the following enumerative embodiment, the embodiment formed by the following enumerative embodiment in combination with other chemical synthesis methods and the equivalent replacement well known to the skilled in the art. The preferred embodiment includes, but is not limited to the embodiment of the present invention.

All of the solvents used in the present invention are commercially available. The present invention adopts the abbreviating words as followed: aq refers to water; "HATU" refers to O-(7-azabenzotriazol-1-yl)-N,N,N',N'-tetramethyluronium hexafluorophosphate; EDC refers to N-(3-dimethylaminopropyl)-N'-ethylcarbodiimide hydrochloride; m-CPBA refers to 3-chloroperoxybenzoic acid; eq refers to equivalent; CDI refers to carbonyldiimidazole; DCM refers to dichloromethane; PE refers to petroleum ether; DIAD refers to diisopropyl azodicarboxylate; DMF refers to N,N-dimethylformamide; DMSO refers to dimethyl sulfoxide; EtOAc refers to ethyl acetate; EtOH refers to ethanol; MeOH refers to methanol; CBz refers to benzyloxycarbonyl, which is an amine protecting group; BOC refers to t-butylcarbonyl which is an amine protecting group; HOAc refers to acetic acid; NaCNBH₃ refers to sodium cyanoborohydride; r.t. refers to room temperature; O/N refers to overnight; THF refers to tetrahydrofuran; Boc₂O refers to di-tert-butyldicarbonate; TFA refers to trifluoroacetic acid; DIPEA refers to diisopropylethylamine; SOCl₂ refers to thionyl chloride; CS₂ refers to carbon disulfide; TsOH refers to p-toluenesulfonic acid; NFSI refers to N-fluoro-N-(phenylsulfonyl)benzenesulfonamide; NCS refers to 1-chloropyrrolidine-2,5-dione; n-Bu₄NF refers to tetrabutylammonium fluoride; iPrOH Table 2-propanol; mp refers to melting point; LDA refers to lithium diisopropylamide.

Compounds are named manually or by ChemDraw® software, the commercially available compounds use their vendor directory names.

DETAILED DESCRIPTION OF THE PREFERRED EMBODIMENT

Reference Example 1: Fragment BB-1A

BB-1A

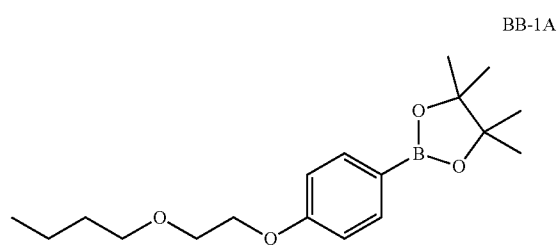 [SMILES: CCCCOCCOc1ccc(B2OC(C)(C)C(C)(C)O2)cc1]

Synthesis Pathway:

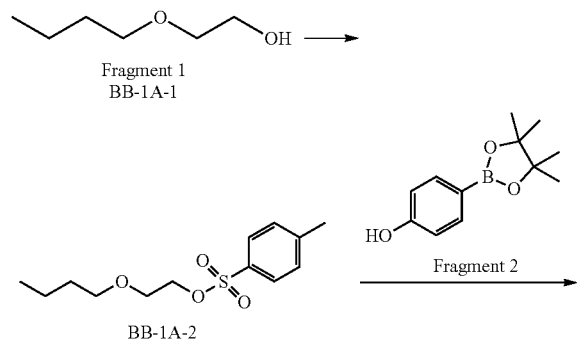

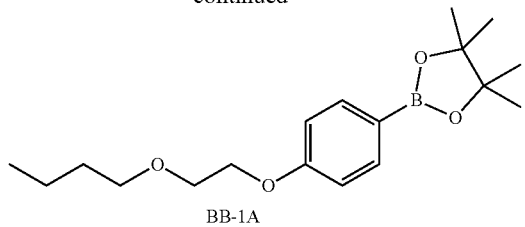

BB-1A

Step 1: Synthesis of Compound BB-1A-2

Compound BB-1A-1 (100 g, 0.846 mol), p-toluenesulfonyl chloride (146.67 g, 769.31 mmol) and triethylamine (233.54 g, 2.31 mol) were dissolved in dichloromethane (0.5 L), and stirred at room temperature for 12 hours. The reaction solution was cooled to room temperature, and the solvent was removed under reduced pressure, followed by addition of water (400 mL) to dissolve the residue. The aqueous phase was extracted with ethyl acetate three times (1.5 L). The combined organic phase was washed with saturated brine twice (400 mL), and dried over anhydrous sodium sulfate. After the desiccant was filtered off, the solvent was removed under reduced pressure to obtain a brown oil BB-1A-2 (170.10 g, 624.54 mmol, yield 81.18%). ¹H NMR (400 MHz, CDCl₃) δ ppm 0.81 (t, J=7.40 Hz, 3H) 1.16-1.27 (m, 3H) 1.35-1.44 (m, 2H) 2.37 (s, 3H) 3.30 (t, J=6.53 Hz, 2H) 3.50-3.55 (m, 2H) 4.05-4.10 (m, 2H) 7.27 (d, J=8.03 Hz, 2H) 7.73 (d, J=8.28 Hz, 2H). MS m/z: 273.9 [M+H]⁺.

Step 2: Synthesis of Compound BB-1A

Compound BB-1A-2 (170.10 g, 624.54 mmol), p-hydroxyphenyl borate (137.44 g, 624.54 mmol) was dissolved in acetonitrile (1.6 L), followed by addition of potassium carbonate (86.32 g, 624.54 mmol) and potassium iodide (10.37 g, 62.45 mmol) at room temperature. The resulting solution was heated to reflux and reacted with stirring for 12 hours at 60° C. under nitrogen protection. After cooling to room temperature, the solvent was removed under reduced pressure, followed by addition of water (500 mL) to dissolve the residue. The aqueous phase was extracted with ethyl acetate three times (2 L). After combining, the solvent was removed under reduced pressure. Other impurities were removed by column chromatography to obtain a yellow oil Compound BB-1A (99.30 g, 310.09 mmol, 49.65% yield). ¹H NMR (400 MHz, CDCl₃-d) δ ppm 0.93 (t, J=7.40 Hz, 4H) 1.28-1.36 (m, 13H) 1.39 (dd, J=15.18, 7.40 Hz, 1H) 1.51-1.65 (m, 3H) 3.54 (t, J=6.65 Hz, 2H) 3.75-3.88 (m, 2H) 4.06-4.25 (m, 2H) 6.92 (d, J=8.53 Hz, 2H) 7.75 (d, J=8.53 Hz, 2H).

The reference examples in the following table were synthesized according to the synthesis method of the steps 1-2 in Reference Example 1.

| Reference Example | Fragment 1 | Fragment 2 | Structure |
|---|---|---|---|
| 2 | 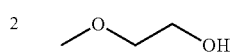 | 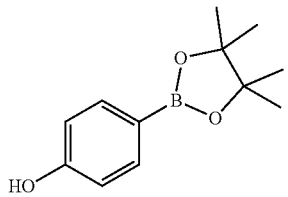 [SMILES: CC1(C)OB(c2ccc(O)cc2)OC1(C)C] | 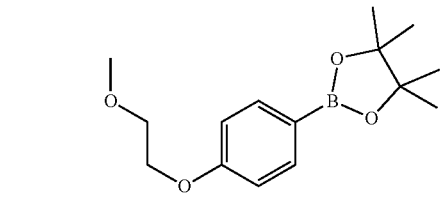 BB-1F |

| Reference Example | Fragment 1 | Fragment 2 | Structure |
|---|---|---|---|
| 3 | F-CH2CH2CH2-OH | HO-C6H4-Bpin | F-CH2CH2CH2-O-C6H4-Bpin  BB-1G |
| 4 | Bu-O-CH2CH2-OH | HO-C6H3(Me)-Bpin | Bu-O-CH2CH2-O-C6H3(Me)-Bpin  BB-1H |
| 41 | Pr-O-CH2CH2-OH | HO-C6H4-Bpin | Pr-O-CH2CH2-O-C6H4-Bpin  BB-1I |

Reference Example 5: Fragment BB-1B

BB-1B

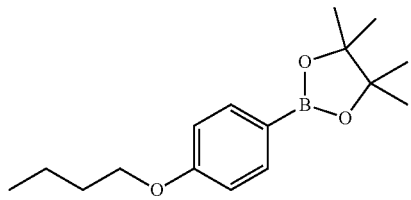

Synthesis Pathway:

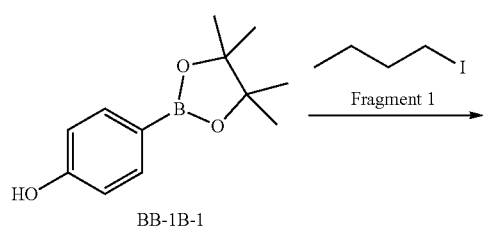

Step 1: Synthesis of Compound BB-1B

Compound BB-1A-1 (6 g, 27.26 mmol), n-bromobutane (5.6 g, 40.89 mmol) was dissolved in acetonitrile (50 mL), followed by addition of potassium carbonate (11.3 g, 81.78 mmol) at room temperature. The resulting solution was heated to reflux and reacted with stirring for 6 hours at 80° C. under nitrogen protection. After cooling to room temperature, the solvent was removed under reduced pressure. The aqueous phase was extracted with ethyl acetate three times (600 mL). After combining, the solvent was removed under reduced pressure to obtain a red oil Compound BB-1B (7.05 g, 25.53 mmol, yield 93.64%). $^1$H NMR (400 MHz, CDCl$_3$-d) δ=7.76 (d, J=8.5 Hz, 2H), 7.11-6.70 (m, 2H), 4.00 (t, J=6.5 Hz, 2H), 1.82-1.74 (m, 2H), 1.56-1.47 (m, 2H), 1.38-1.32 (m, 11H), 0.99 (t, J=7.4 Hz, 3H); MS m/z: 279.1 [M+H]$^+$.

The reference examples in the following table were synthesized according to the synthesis method of the step 1 in Reference Example 5

| Reference Example | Fragment 1 | Structure |
|---|---|---|
| 6 | Et-I | Et-O-C6H4-Bpin  BB-1C |

-continued

| Reference Example | Fragment 1 | Structure |
|---|---|---|
| 7 | 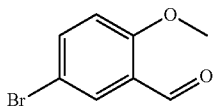 | BB-1D |
| 8 | | BB-1E |

| Reference Example | Fragment 1 | Structure |
|---|---|---|
| 10 | | BB-2C |
| 11 | | BB-2D |
| 12 | | BB-2E |
| 13 | | BB-2F |
| 14 | | BB-2G |

Reference Example 9: Fragment BB-2A

BB-2A

Step 1: Synthesis of Compound BB-1B

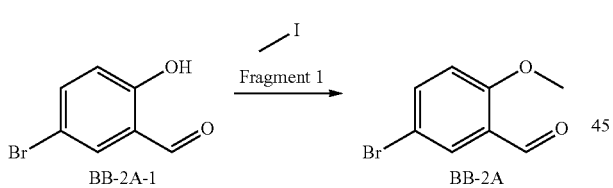

Compound BB-2A-1 (10.00 g, 49.75 mmol) was dissolved in N,N-dimethylformamide (30.00 mL) at room temperature, followed by addition of potassium carbonate (20.63 g, 149.25 mmol) and methyl iodide (25.80 g, 181.77 mmol). The reaction mixture was stirred at room temperature for 15 hours. After completion of the reaction, 100 mL of ice water was added to the reaction solution, and extracted with ethyl acetate (100 mL*3). The organic phases were combined, washed with saturated brine (300 mL×2), and dried over anhydrous sodium sulfate, filtered to remove the desiccant, and concentrated under reduced pressure to obtain the product BB-2A (10.50 g, yield 98.15%). $^1$H NMR (400 MHz, CDCl$_3$) δ=10.38 (s, 1H), 7.91 (d, J=2.8 Hz, 1H), 7.63 (dd, J=2.6, 8.9 Hz, 1H), 6.89 (d, J=8.8 Hz, 1H), 3.92 (s, 3H).

The reference examples in the following table were synthesized according to the synthesis method of the step 1 in Reference Example 9.

Reference Example 15: Fragment BB-2B

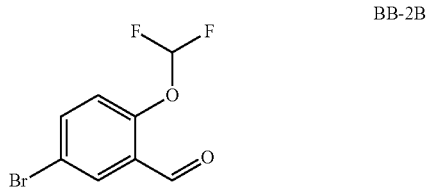 [SMILES: O=Cc1cc(Br)ccc1OC(F)F]

Step 1: Synthesis of Compound BB-2B

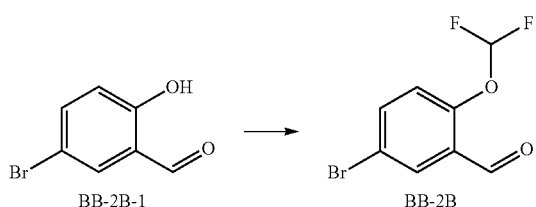

Compound 1 (1.51 g, 7.49 mmol), diethyl bromofluoromethyl phosphate (3.00 g, 11.24 mmol) and potassium carbonate (2.07 g, 14.99 mmol) were sequentially added to a mixture of acetonitrile (10.00 mL) and water (1.00 mL) at 0° C. under a nitrogen atmosphere. The mixture was stirred for 0.5 hour at 0° C. under nitrogen protection. After completion of the reaction, water (50 mL) was added to the mixture, and extracted with ethyl acetate (50 mL×3). The organic phase was washed with saturated brine (50 mL×2), dried over anhydrous sodium sulfate, filtered, and concentrated under reduced pressure to obtain the title compound BB-2B (2.11 g). $^1$H NMR (400 MHz, CDCl$_3$) δ: 10.26 (s, 1H), 7.97 (d, J=2.5 Hz, 1H), 7.65 (dd, J=9.0, 2.5 Hz, 1H), 7.09 (d, J=8.53 Hz, 1H), 7.09 (d, J=8.53 Hz, 1H), 6.77-6.40 (t, J=72.4 Hz, 1H).

Reference Example 16: Fragment BB-2H

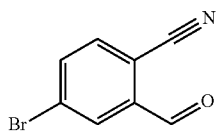

Synthesis Pathway:

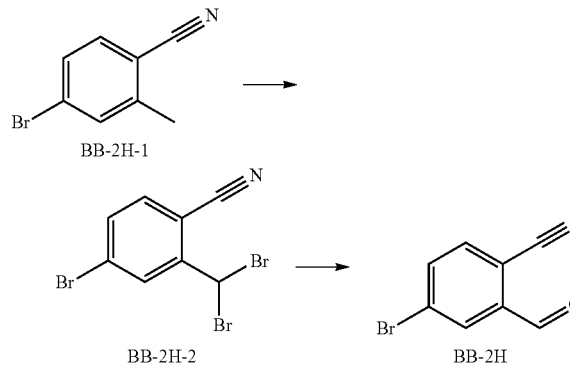

Step 1: Synthesis of Compound BB-2H-2

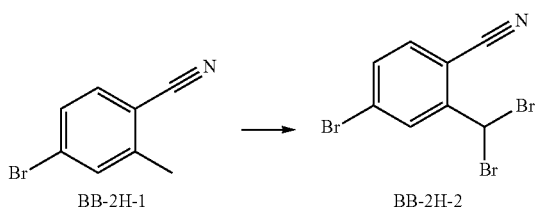

Compound BB-2H-1 (11.50 g, 58.66 mmol) was dissolved in carbon tetrachloride (150 mL) at room temperature, followed by addition of N-bromobutanimide (31.32 g, 175.98 mmol) and benzoyl peroxide (1.42 g, 5.87 mmol). After completion of the addition, the reaction mixture was heated to 85° C. and stirred for 10 hours. After completion of the reaction, the mixture was cooled to room temperature, followed by filtration. The filter cake was wash with ethyl acetate (50 mL). The filtrate was combined and concentrated under reduced pressure. The obtained residue was dissolved in ethyl acetate (50 mL), washed with saturated brine (100 mL×2), dried over anhydrous sodium sulfate, filtered to remove the desiccant, and concentrated under reduced pressure to obtain the title compound BB-2H-2 (pale-yellow solid, 20.00 g). The crude product was used directly in the next step without purification. $^1$H NMR (400 MHz, CDCl$_3$) δ: 8.18 (d, J=1.8 Hz, 1H), 7.60 (dd, J=1.8, 8.3 Hz, 1H), 7.48 (d, J=8.3 Hz, 1H), 6.92 (s, 1H).

Step 2: Synthesis of Compound BB-2H

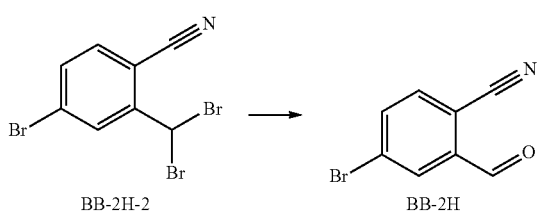

Compound BB-2H-2 (5.00 g, 14.13 mmol) was dissolved in acetonitrile (20 mL) at room temperature, followed by addition of a solution prepared by silver nitrate (6.72 g, 39.56 mmol) and water (10 mL). After completion of the addition, the reaction mixture was heated to 80° C. and stirred for 6 hours. After completion of the reaction, the mixture was cooled to room temperature, and filtered to remove the yellow silver bromide precipitate. The filtrate was concentrated under reduced pressure. The obtained residue was purified by silica gel column chromatography (eluent: ethyl acetate/petroleum ether=1/20-1/5) to obtain the title compound BB-2H (1.20 g, yield: 40.44%). $^1$H NMR (400 MHz, CDCl$_3$) δ: 10.31 (s, 1H), 8.19 (d, J=2.0 Hz, 1H), 7.90 (dd, J=1.9, 8.2 Hz, 1H), 7.71 (d, J=8.3 Hz, 1H).

Reference Example 42: Fragment BB-2I

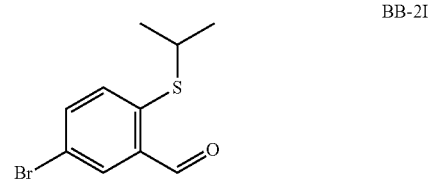

Step 1: Synthesis of Compound BB-2I

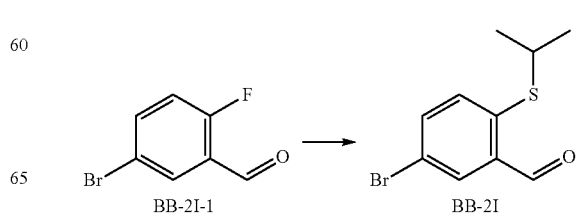

Compound BB-2I-1(20.00 g, 98.52 mmol) and isopropyl mercaptan (11.25 g, 147.78 mmol, 13.72 mL) were dissolved in N,N-dimethylformamide (200 mL) at room temperature, followed by addition of potassium carbonate (40.85 g, 295.56 mmol). After completion of the addition, the reaction mixture was heated to 60° C. and stirred for 12 hours. After completion of the reaction, the reaction miture was cooled to room temperature, followed by addition of 1000 mL of saturated sodium carbonate solution, and extraction with ethyl acetate (800 mL). The organic phases were combined, washed with saturated brine (500 mL), dried over anhydrous sodium sulfate, filtered to remove the desiccant, and concentrated under reduced pressure to obtain the product BB-2I (10.50 g, yield 98.15%). $^1$H NMR (400 MHz, CHLOROFORM-d) 6=10.47 (s, 1H), 7.99 (d, J=1.5 Hz, 1H), 7.70-7.58 (m, 1H), 7.39 (d, J=8.3 Hz, 1H), 4.11 (q, J=7.0 Hz, 1H), 3.44-3.26 (m, 1H), 3.47-3.22 (m, 1H), 1.32 (d, J=6.8 Hz, 7H), 1.28-1.23 (m, 1H); MS m/z: 260.9 [M+H]$^+$.

Reference Example 43: Fragment BB-2J

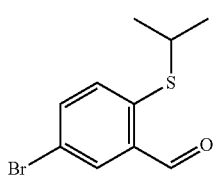

BB-2I

Step 1: Synthesis of Compound BB-2J

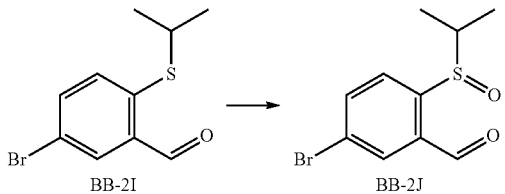

Compound BB-2I (5.00 g, 19.29 mmol) was dissolved in dichloromethane (30.00 mL), followed by dropwise addition of a solution prepared by potassium hydrogencarbonate (5.79 g, 57.87 mmol) and water (10.00 mL) at 0° C. After stirring for 10 minutes, liquid bromine (4.62 g, 28.93 mmol, 1.49 mL) was added dropwise to the reaction mixture at 0° C. The reaction was carried out for 50 minutes at room temperature. The reaction was quenched with saturated sodium sulfite solution (40 mL). 100 mL of water was added to the reaction solution, and extracted with dichloromethane (00 mL). The organic phase was combined, washed with brine (500 mL), dried over anhydrous sodium sulfate, filtered to remove the desiccant, concentrated under reduced pressure, and purified by silica gel column chromatography (eluent: petroleum ether/ethyl acetate=50/1, 5/1) to obtain the product BB-2J (2.00 g, yield 37.68%). $^1$H NMR (400 MHz, CHLOROFORM-d) 6=10.00 (s, 1H), 8.07 (d, J=2.0 Hz, 1H), 8.05 (s, 1H), 8.06-8.04 (m, 1H), 7.98-7.94 (m, 1H), 3.02 (quin, J=7.0 Hz, 1H), 1.54 (d, J=7.0 Hz, 3H), 0.93 (d, J=6.8 Hz, 3H); MS m/z: 276.7 [M+H]$^+$.

Reference Example 17: Fragment BB-3A

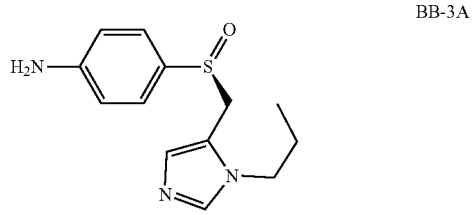 [SMILES: CCCn1cncc1C[S@](=O)c1ccc(N)cc1]

BB-3A

Synthesis Pathway:

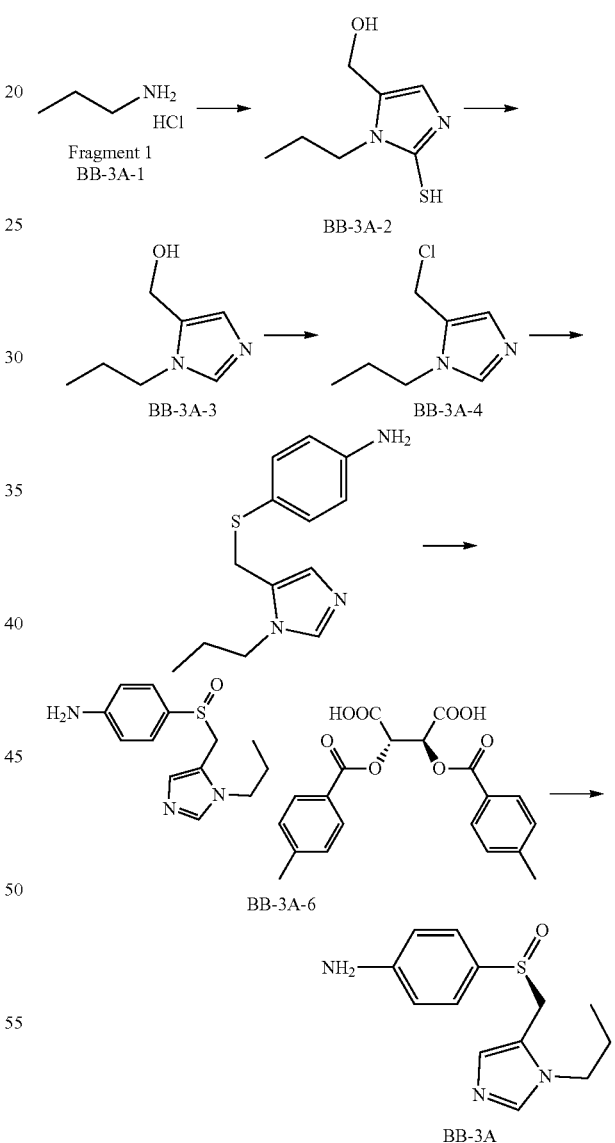

Step 1: Synthesis of Compound BB-3A-2

Compound BB-3A-1 (150 g, 1.57 mol), 1,3-dihydroxyacetone (110.28 g, 1.22 mol) and potassium thiocyanate (178.46 g, 1.84 mol) were dissolved in n-butanol (2 L), followed by addition of acetic acid (133.74 mL, 2.34 mol) at room temperature, and stirred for 16 hours at room temperature. 60 mL of water was added to the reaction solution, and stirred for 30 minutes at room temperature, followed by filtration. The filter cake was washed with water and dried to obtain a white powdery compound BB-3A-2 (210 g, yield 77.7%). MS m/z: 173.0 [M+H]$^+$.

Step 2: Synthesis of Compound BB-3A-3

BB-3A-2 (210.00 g, 1.22 mol, 1.00 eq) was suspended in n-butanol (2.00 L) at 20° C., and hydrogen peroxide (207.32 g, 1.83 mol, 175.69 mL, 1.50 eq, purity 30%) was added dropwise to the suspension at 0° C. The reaction solution was naturally warmed to 20° C. and stirred for 16 hours. The reaction solution was quenched with 100 mL of saturated sodium sulfite, and concentrated obtain a crude product. The crude product was purified by column chromatography (dichloromethane:methanol=40:1 to 20:1) to obtain compound BB-3A-3 (70.00 g, yield 40.93%). MS m/z: 141.0 [M+H]$^+$.

Step 3: Synthesis of Compound BB-3A-4

BB-3A-3 (40.00 g, 285.35 mmol, 1.00 eq) was dissolved in dichloromethane (150 mL), and dichlorosulfoxide (82.15 g, 690.55 mmol, 50.09 mL, 2.42 eq) was added dropwise to the solution at room temperature. The reaction solution was heated to 40° C. and stirred for 30 minutes. The reaction solution was filtered, and the filtrate was concentrated under reduced pressure to obtain a crude product. 300 mL of ethyl acetate was added to the crude product, followed by filtration. The filter cake was collected to obtain compound BB-3A-4 (33.00 g, 169.15 mmol, hydrochloride, yield: 59.3%). $^1$H NMR (400 MHz, DMSO-d6): 9.31 (d, J=1.5 Hz, 1H), 7.82 (d, J=1.5 Hz, 1H), 5.03 (s, 2H), 4.29-4.12 (m, 2H), 1.93-1.82 (m, 2H), 0.90 (t, J=7.4 Hz, 3H).

Step 4: Synthesis of Compound BB-3A-5

4-Aminothiophenol (52.94 g, 422.88 mmol, 2.5 eq) and triethylamine (51.35 g, 507.45 mmol, 70.34 mL, 3.00 eq) were dissolved in isopropanol (1.00 L), followed by addition of a solution of BB-3A-4 (33.00 g, 169.15 mmol, 1.00 eq, hydrochloride) in water (100 mL) at room temperature, and stirred for 16 hours at room temperature. The mixture was diluted with water (100 mL) and extracted with (200 mL). The organic phase was washed with saturated brine (100 mL), dried over anhydrous sodium sulfate, filtered and concentrated to obtain a crude material. The crude product was purified by column chromatography (petroleum ether: ethyl acetate=50:1-10:1) to obtain BB-3A-5 (15.00 g, 60.64 mmol, yield 35.85%). $^1$H NMR (400 MHz, CHLOROFORM-d) □=7.41 (s, 1H), 7.10-7.03 (m, 2H), 6.62 (s, 1H), 6.57-6.52 (m, 2H), 3.91-3.83 (m, 4H), 1.80 (sxt, J=7.4 Hz, 2H), 0.93 (t, J=7.4 Hz, 3H).

Step 5: Synthesis of Compound BB-3A-6

BB-3A-5 (10.00 g, 40.43 mmol, 1.00 eq) was dissolved in methyl isobutyl ketone (600 mL) and toluene (1.2 L), followed by addition of p-dimethylbenzoyl-D-tartaric acid (15.62 g, 40.43 mmol, 1.00 eq) at room temperature. The mixture was stirred for 10 hours at room temperature, and cooled to 0° C., followed by dropwise addition of H$_2$O$_2$ (13.75 g, 121.29 mmol, 11.65 mL, 30% purity, 3.00 eq) at room temperature. The mixture was stirred for 96 hours at room temperature. The mixture was quenched with saturated aqueous solution of sodium sulfite, followed by addition of water (200 mL), sodium hydroxide (3.08 g, 76.96 mmol, 1.00 eq) and ethyl acetate (500 mL), and stirred for 30 minutes at room temperature. The organic phase was separated, dried over anhydrous sodium sulfate, filtered and concentrated to obtain a crude product. The crude material was dissolved in water (100 mL) and ethylene glycol dimethyl ether (100 mL), and concentrated after stirring for 14 hours at room temperature. The crude product was washed with acetonitrile:water=1:1 (80 mL) and filtered to obtain BB-3A-6 (8.00 g, 12.31 mmol, yield 40.53%).

Step 6: Synthesis of Compound BB-3A

BB-3A-6 (8.00 g, 12.31 mmol, 1.00 eq) was dissolved in water (100 mL) and ethyl acetate (100 mL), and adjusted to pH=3 with 1N hydrochloric acid. The mixture was stirred for 30 minutes at room temperature. The aqueous phase was collected, and adjusted to pH=10 with a saturated aqueous solution of sodium carbonate. The mixture was extracted with dichloromethane: isopropyl alcohol=10:1 (3*200 mL), and the organic phase was concentrated under reduced pressure to obtain BB-3A (2.80 g, 10.63 mmol, yield 86.37%). $^1$H NMR (400 MHz, METHANOL-d4) □=7.66 (s, 1H), 7.22-7.17 (m, 2H), 6.77-6.70 (m, 3H), 4.24 (s, 2H), 3.75 (dt, J=1.5, 7.3 Hz, 2H), 1.72 (sxt, J=7.3 Hz, 2H), 0.90 (t, J=7.5 Hz, 3H).

The reference examples in the following table were synthesized according to the synthesis method of the steps 1-4 in Reference Example 17.

| Reference Example | Fragment 1 | Compound structure |
|---|---|---|
| 18 | (structure with NH$_2$·HCl) | BB-3C-1 |
| 19 | (cyclopropylmethyl-NH$_2$·HCl) | BB-3D-1 |
| 20 | (propyl-NH$_2$·HCl) | BB-3E-1 |

| Reference Example | Fragment 1 | Compound structure |
|---|---|---|
| 21 | 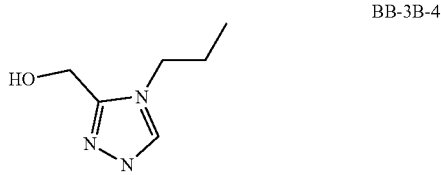 | 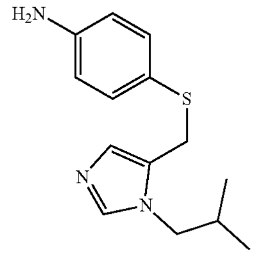 |

BB-3F-1

Reference Example 22: Fragment BB-3B-4

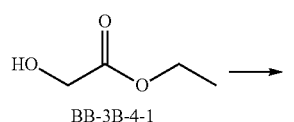

BB-3B-4

Synthesis Pathway:

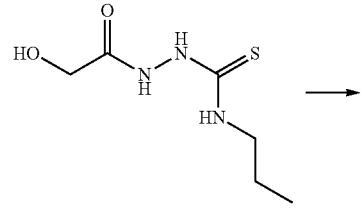

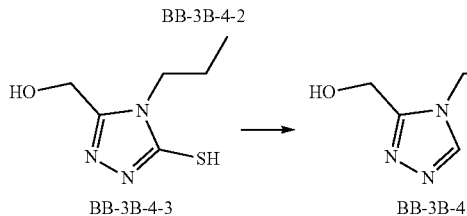

Step 1: Synthesis of Compound BB-3B-4-2

BB-3B-4-1 (4.50 g, 43.23 mmol) was added dropwise to a solution of hydrazine hydrate (2.80 g, 47.55 mmol) in ethanol (20.00 mL) at 0° C. After the reaction mixture was stirred at room temperature for 15 hours, 1-propyl isocyanate (4.37 g, 43.18 mmol) was added dropwise to the reaction system. The system was raised to 40° C. and reacted for 15 hours. After completion of the reaction, the mixture was cooled to room temperature and concentrated under reduced pressure to obtain a crude compound BB-3B-4-2 (9.5 g, yield: 82.69%). $^1$H NMR (400 MHz, DMSO-d6) δ=9.63 (s, 1H), 9.08 (br s, 1H), 7.77 (br s, 1H), 5.27 (br s, 1H), 3.93 (d, J=5.8 Hz, 2H), 3.42-3.36 (m, 2H), 1.54-1.45 (m, 2H), 0.88-0.78 (m, 3H).

Step 2: Synthesis of Compound BB-3B-4-3

Compound BB-3B-4-2 (9.50 g, 35.76 mmol) was dissolved in n-butanol (40.00 mL). The reaction solution was heated to 80° C. and stirred for 15 hours. After completion of the reaction, the temperature was cooled to 25° C., and the product BB-3B-4-3 was stored in n-butanol for direct use in the next reaction. MS-ESI (m/z): 173.8 (M+H)$^+$.

Step 3: Synthesis of Compound BB-3B-4

A solution of compound BB-3B-4-3 (35.70 mmol) in n-butanol (30.00 mL) was added dropwise to 30% hydrogen peroxide (12.14 g, 107.10 mmol) at 0° C. The reaction solution was stirred for 15 hours at room temperature. After completion of the reaction, the reaction was quenched with a saturated solution of sodium sulfite (15 mL). After separation, the aqueous phase was extracted with dichloromethane (20 mL×5). The organic phases were combined, washed with saturated brine (10 mL×2), dried over anhydrous sodium sulfate, filtrate to remove the desiccant, and concentrated under reduced pressure to obtain the title compound BB-3B-4 (3 g, crude).

Reference Example 23: Fragment BB-3B-3

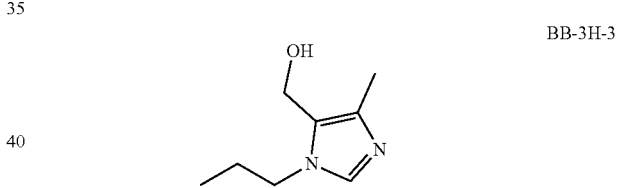

BB-3H-3

Synthesis Pathway:

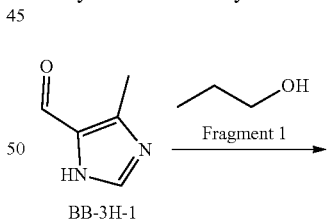

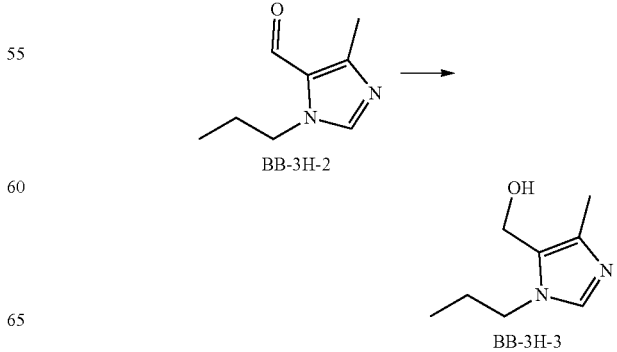

Step 1: Synthesis of Compound BB-3B-2

Triphenylphosphine (47.64 g, 181.64 mmol) and diisopropyl azodicarboxylate (36.73 g, 181.64 mmol) were dissolved in tetrahydrofuran (120.00 mL) at 0° C. under a nitrogen atmosphere, followed by sequential addition of compound 1 (10.00 g, 90.82 mmol) and n-propanol (10.91 g, 181.64 mmol). The mixture was warmed to 25° C. and stirred for 12 hours under a nitrogen atmosphere. After completion of the reaction, dilute hydrochloric acid (1 M) was added to the mixture to adjust to pH=1 and extracted with ethyl acetate (50 mL×3). The aqueous phase was adjusted to pH=13 with sodium hydroxide (1M) and extracted with ethyl acetate (50 mL×4). The organic phases were combined, washed with saturated brine (50 mL*2), dried over anhydrous sodium sulfate, filtered and concentrated under reduced pressure. The obtained residue was purified by column chromatography (petroleum ether: ethyl acetate=20:1-5:1) to obtain the title compound BB-3H-2 ((12.00 g, pale-yellow oily liquid, yield: 27.60%). $^1$H NMR (400 MHz, CDCl$_3$) δ: 9.81 (s, 1H), 7.50 (s, 1H), 4.19 (t, J=7.1 Hz, 2H), 2.49 (s, 3H), 1.98-1.74 (m, 2H), 0.89 (t, J=7.5 Hz, 3H).

Step 2: Synthesis of Compound BB-3B-3

Sodium borohydride (3.28 g, 86.74 mmol) was added to a solution of compound 2 (11.00 g, 72.28 mmol) in ethanol (30.00 mL) at 0° C. under a nitrogen atmosphere, and then the mixture was warmed to 25° C. and stirred for 2 hours under nitrogen protection. After completion of the reaction, the mixture was quenched with concentrated hydrochloric acid (12.5 mL), and then adjusted to pH=12-13 with sodium hydroxide solid. Dichloromethane (20 mL) was added to the mixture, filtered and concentrated under reduced pressure. The obtained residue was purified by HPLC to obtain the title compound BB-3H-3 (7.50 g, yield: 67.22%). MS-ESI m/z: 155 [M+H]$^+$; $^1$H NMR (400 MHz, CDCl$_3$) δ: 7.26 (s, 1H), 4.54 (s, 2H), 3.91-3.87 (m, 2H), 2.06 (s, 3H), 1.81-1.76 (m, 2H), 0.92 (t, J=7.4 Hz, 3H).

The reference examples in the following table were synthesized according to the synthesis method of the steps 1-2 in Reference Example 23.

| Reference Example | Fragment 1 | Compound structure |
|---|---|---|
| 24 | ⌃⌄OH | BB-3I-3 |

The reference examples in the following table were synthesized according to the synthesis method of the steps 2-4 in Reference Example 17.

| Reference Example | Fragment 2 | Compound structure |
|---|---|---|
| 25 | BB-3B-4 | BB-3B-1 |
| 26 | BB-3H-3 | BB-3H-1 |

Reference Example 27: BB-3C

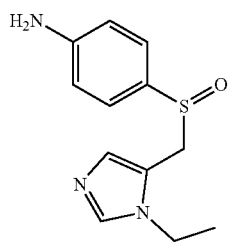 [SMILES: CCn1cncc1CS(=O)c1ccc(N)cc1]

Synthesis Pathway:

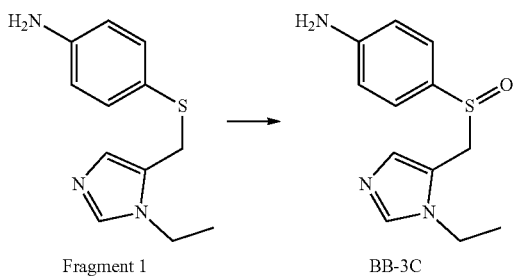

Fragment 1
BB-3C-1

BB-3C

Step 1: Synthesis of Compound BB-3C

Compound BB-3C-1 (450.00 mg, 1.93 mmol) was dissolved in 4-methyl-2-pentanone (5.00 mL), followed by dropwise addition of 30% hydrogen peroxide (555.86 μL, 5.79 mmol) at room temperature. The reaction mixture was stirred for 20 hours at room temperature. After completion of the reaction, the reaction mixture was cooled to 0-5° C., quenched with 2 mL of saturated sodium sulfite solution, and concentrated under reduced pressure to remove the solvent. The obtained crude was isolated by silica gel plate (developing agent: dichloromethane/methanol=10/1) to obtain the compound BB-3C (150.00 mg, yield 28.15% yield). $^{1}$H NMR (400 MHz, CHLOROFORM-d) δ=7.48 (s, 1H), 7.20-7.14 (m, 2H), 6.73-6.67 (m, 2H), 6.61 (s, 1H), 4.09-3.97 (m, 4H), 3.89-3.78 (m, 2H), 1.38 (t, J=7.4 Hz, 3H); MS-ESI (m/z): 250.0 (M+H)$^{+}$.

The reference examples in the following table were synthesized according to the synthesis method of the step 1 in Reference Example 27.

| Reference Example | Fragment 1 | Structure |
|---|---|---|
| 28 | 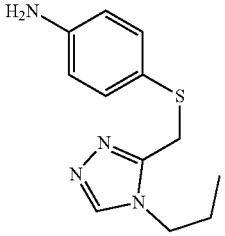 BB-3B-1 | BB-3B |
| 29 | 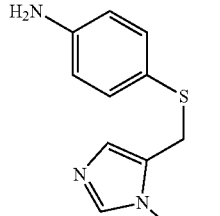 BB-3C-1 | BB-3C |
| 30 | 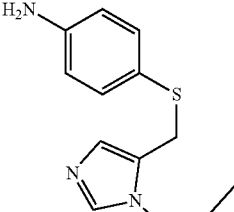 BB-3D-1 | BB-3D |
| 31 | 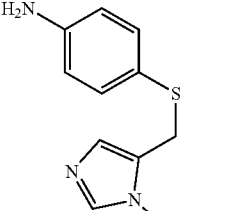 BB-3E-1 | BB-3E |
| 32 | 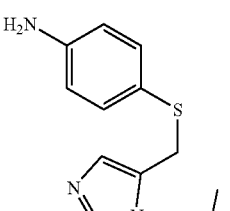 BB-3F-1 | BB-3F |

| Reference Example | Fragment 1 | Structure |
|---|---|---|
| 33 | BB-3H-1 | BB-3H |
| 34 | BB-3I-1 | BB-3I |
| 56 | BB-3A-5 | BB-3A'-1 |

Reference Example 57: BB-3A'

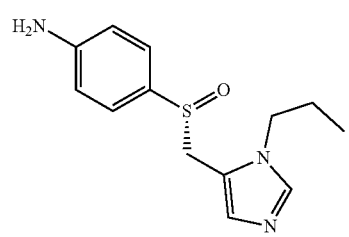 [SMILES: CCCn1cncc1C[S@@](=O)c1ccc(N)cc1]

Synthesis Pathway:

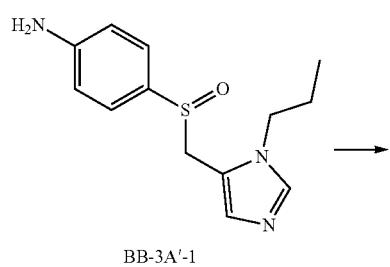

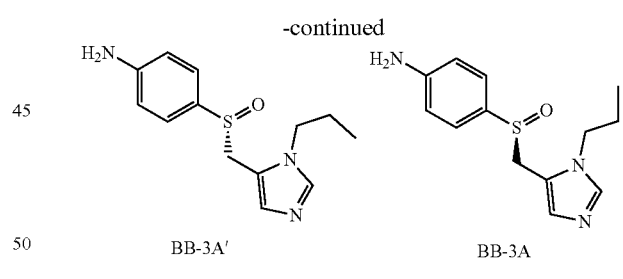

Step 1: Synthesis of Compound BB-3A'

Compound BB-3A'-1 was isolated by supercritical fluid chromatography (separation condition: Column: Chiralpak AS-3 150×4.6 mm I.D., 3 μm, mobile phase: A: $CO_2$ B: ethanol (0.05% DEA), gradient: 5%-40% B, 5 min, keeping 40% for 2.5 min, then keeping 5% B for 2.5 min, flow rate: 2.5 mL/min, column temperature: 35° C., wavelength: 220 nm) to obtain the isomers BB-3A' (retention time: 4.238 min) and BB-3A (retention time: 4.602 min). MS-ESI (m/z): 264.0 $(M+H)^+$.

Reference Example 35: BB-3G

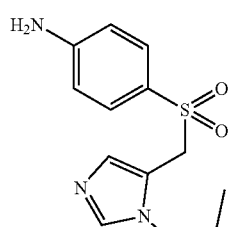

Synthesis Pathway:

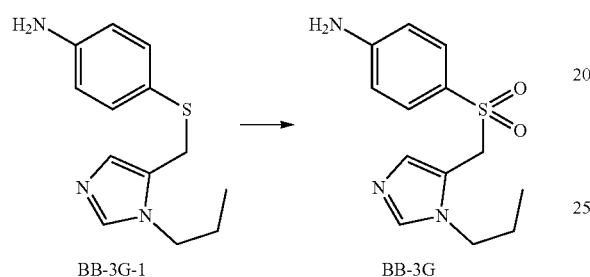

Step 1: Synthesis of Compound BB-3G

Compound BB-3G-1 (200.00 mg, 808.54 μmol) was dissolved in 4-methyl 2-pentanone (5.00 mL), followed by dropwise addition of 30% hydrogen peroxide (776.79 μL, 8.09 mmol) at room temperature. The reaction mixture was stirred for 96 hours at room temperature. After completion of the reaction, the temperature was decreased to 0 to 5° C., and the reaction was quenched by 2 mL of saturated sodium sulfite solution. The solvent was removed by concentration under reduced pressure. The obtained crude product was isolated by silica gel plate (developing agent: dichloromethane/methanol=10/1) to obtain compound BB-3G (30.00 mg, yield 13.28% yield). MS-ESI m/z: 279.9 (M+H)$^+$.

Reference Example 36: BB-3K, BB-3K'

Synthesis Pathway:

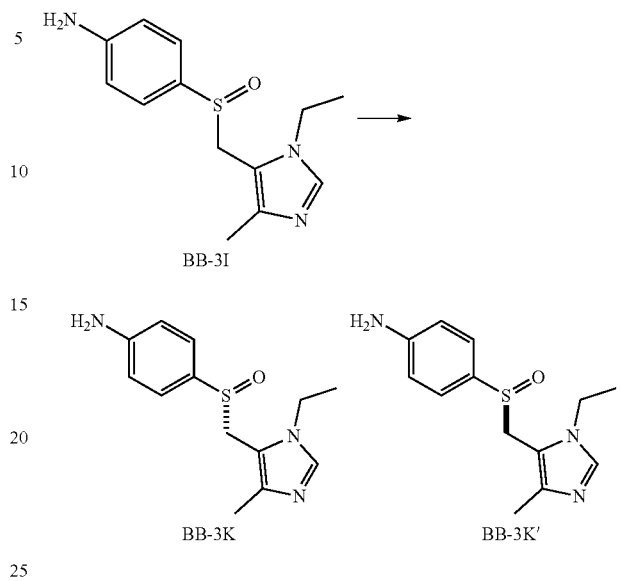

Step 1: Synthesis of Compound BB-3K, BB-3K'

Compound BB-3I was isolated by supercritical fluid chromatography (separation condition: Column: Chiralpak AS-3 150×4.6 mm I.D., 3 μm, mobile phase: A: $CO_2$ B: ethanol (0.05% DEA), gradient: 5%-40% B, 5.5 min, keeping 40% for 3 min, then keeping 5% B for 1.5 min, flow rate: 2.5 mL/min, column temperature: 40° C., wavelength: 220 nm) to obtain the isomers BB-3K (retention time: 5.828 min) and BB-3K' (retention time: 6.163 min). MS-ESI (m/z): 264.0 (M+H)$^+$; $^1$H NMR (400 MHz, $CDCl_3$) δ: 7.43 (s, 1H), 7.15-7.10 (m, 2H), 6.71-6.66 (m, 2H), 4.07-3.95 (m, 4H), 3.85 (dq, J=1.9, 7.3 Hz, 2H), 1.70 (s, 3H), 1.39 (t, J=7.3 Hz, 3H).

Reference Example 45: BB-3J, BB-3J'

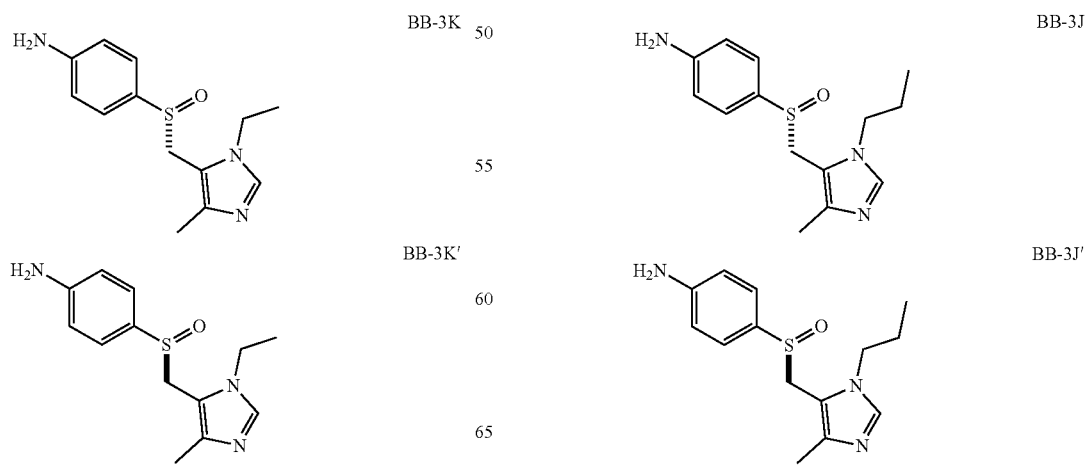

Synthesis Pathway:

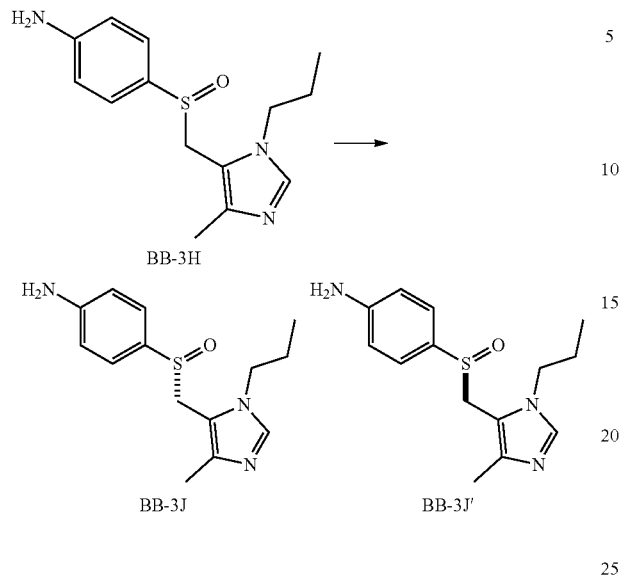

Step 1: Synthesis of Compound BB-3J, BB-3J'

Compound BB-3H was isolated by supercritical fluid chromatography (separation condition: Column: Chiralpak AS-3 150×4.6 mm I.D., 3 μm, mobile phase: A: $CO_2$ B: ethanol (0.05% DEA), gradient: 5%-40% B, 5.5 min, keeping 40% for 3 min, then keeping 5% B for 1.5 min, flow rate: 2.5 mL/min, column temperature: 40° C., wavelength: 220 nm) to obtain the isomers BB-3J (retention time: 4.775 min) and BB-3J' (retention time: 4.521 min). MS-ESI m/z: 277.9 (M+H)+; $^1$H NMR (400 MHz, $CDCl_3$) δ: 0.56 (br s, 3H) 1.27-1.37 (m, 8H) 1.39 (br d, J=7.03 Hz, 3H) 3.41 (br s, 2H) 3.59-3.76 (m, 5H) 6.35 (br d, J=6.53 Hz, 4H) 6.70-6.80 (m, 4H) 7.05 (s, 2H).

Reference Example 46: BB-3L

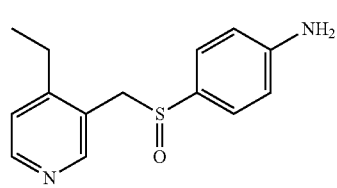 [SMILES: CCc1ccncc1CS(=O)c1ccc(N)cc1]

Synthesis Pathway:

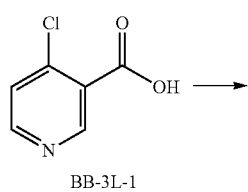

Step 1: Synthesis of Compound BB-3L-2

Compound BB-3L-1 (5.00 g, 31.74 mmol) and N,N-dimethylformamide (1.07 g, 14.60 mmol, 1.12 mL) were dissolved in dichloromethane (50 ml), followed by addition of oxalyl chloride (10.07 g, 79.35 mmol, 6.94 mL) at room temperature. The reaction solution was stirred at room temperature for 3 hours under nitrogen atmosphere, followed by addition of methanol (10 mL). The reaction mixture was concentrated to obtain compound BB-3L-2

(5.40 g, yield: 99.16%). $^1$H NMR (400 MHz, CDCl$_3$) δ:9.32 (s, 1H), 9.09 (d, J=6.0 Hz, 1H), 8.07 (d, J=6.0 Hz, 1H), 4.05 (s, 3H).

Step 2: Synthesis of Compound BB-3L-3

Compound BB-3L-2 (5.00 g, 29.14 mmol) and potassium vinyl fluoroborate (3.90 g, 29.14 m mol) were dissolved in dioxane (45 mL) and water (15 mL), followed by addition of (1,1'-bis(diphenylphosphino)ferrocene)palladium dichloride dichloromethane complex (213.22 mg, 291.40 u mol) and potassium carbonate (8.06 g, 58.28 mmol) at room temperature. The reaction mixture was heated to 100° C. and stirred for 12 hours under nitrogen atmosphere. After completion of the reaction, the mixture was cooled to room temperature, and water (10 mL) was added to the mixture, and the mixture was extracted with dichloromethane (10 mL×3). The organic phases were combined, dried over anhydrous sodium sulfate, filtered to remove the desiccant and concentrated under reduced pressure. The insoluble material was removed by filtration, and the obtained residue was purified by silica gel column chromatography (eluent: ethyl acetate/petroleum ether=1/10) to obtain the title compound BB-3L-3 (2.50 g, yield 52.58%). $^1$H NMR (400 MHz, CDCl$_3$) δ: 9.00 (s, 1H), 8.57 (d, J=5.5 Hz, 1H), 7.48-7.39 (m, 1H), 7.37 (d, J=5.3 Hz, 1H), 5.79 (d, J=17.6 Hz, 1H), 5.50-5.44 (m, 1H), 3.85 (s, 3H).

Step 3: Synthesis of Compound BB-3L-4

Compound BB-3L-3 (1.00 g, 6.13 mmol) was dissolved in tetrahydrofuran (10.00 mL), and wet palladium on carbon catalyst (1.8 g, palladium content 10%, water content 50%) was added thereto at room temperature. The reaction system was displaced with argon three times, followed by displacing with hydrogen three times. The reaction mixture was stirred for 3 hours at room temperature under hydrogen atmosphere (15 psi), followed by filtration to remove the catalyst. The filtrate was concentrated under reduced pressure to obtain the title compound BB-3L-4 (880.00 mg, yield: 86.95%). $^1$H NMR (400 MHz, CDCl$_3$) δ: 8.94 (s, 1H), 8.50 (d, J=5.0 Hz, 1H), 7.12 (d, J=5.0 Hz, 1H), 3.83 (s, 3H), 2.91 (q, J=7.5 Hz, 2H), 1.15 (t, J=7.5 Hz, 3H).

Step 4: Synthesis of Compound BB-3L-5

Compound BB-3L-4 (880.00 mg, 5.33 mmol) was dissolved in tetrahydrofuran (10.00 mL), followed by slow addition of lithium tetrahydroaluminum (303.25 mg, 7.99 mmol) at room temperature. The reaction mixture was stirred for 1 hour at room temperature. The reaction was quenched with sodium sulfate decahydrate (10 g), followed by addition of water (10 mL) and extraction with dichloromethane (10 mL×3). The organic phases were combined, dried over anhydrous sodium sulfate and filtered to remove desiccant. The filtrate was concentrated under reduced pressure to obtain the compound BB-3L-5 (470.00 mg, yield: 64.39%). $^1$H NMR (400 MHz, CDCl$_3$) δ: 8.36 (s, 1H), 8.32 (d, J=5.0 Hz, 1H), 7.06 (d, J=5.0 Hz, 1H), 4.66 (s, 2H), 2.67 (q, J=7.5 Hz, 2H), 2.26-2.14 (m, 1H), 1.18 (t, J=7.5 Hz, 3H).

Step 5: Synthesis of Compound BB-3L-6

Compound BB-3L-5 (470.00 mg, 3.43 mmol) was dissolved in dichloromethane (5.00 mL), followed by addition of thionyl chloride (2.04 g, 17.13 mmol, 1.24 mL, 5.00 eq) at room temperature. The mixture was stirred for 2 hours at room temperature under nitrogen atmosphere. The reaction solution was concentrated under reduced pressure to obtain the hydrochloride salt of compound BB-3L-6 (670.00 mg, hydrochloride, yield 96.81%). MS-ESI m/z: 156.0 (M+H)$^+$.

Step 6: Synthesis of Compound BB-3L-7

Compound BB-3L-6 (670.00 mg, 3.49 mmol, hydrochloride) and p-aminothiophenol (1.31 g, 10.47 mmol) were dissolved in dichloromethane (5.00 mL) and followed by addition of triethylamine (1.06 g, 10.47 mmol, 1.45 mL) at room temperature. The mixture was stirred for 4 hours at room temperature under nitrogen atmosphere. The solvent was removed under reduced pressure and the crude product was purified by silica gel column chromatograph (eluent: ethyl acetate/petroleum ether=1/4-1/0) to obtain the title compound BB-3L-7 (630.00 mg, yield 48.54%). MS-ESI m/z: 245.0 (M+H)$^+$.

Step 7: Synthesis of Compound BB-3L

Compound BB-3L-7 (630.00 mg, 2.58 mmol) was dissolved in dichloromethane (10.00 m L), followed by dropwise addition of hydrogen peroxide (2.92 g, 25.78 mmol, 2.48 mL, 30% purity) at room temperature. The reaction solution was heated to 40° C. and stirred for 18 hours under nitrogen atmosphere. After cooling to room temperature, sodium sulfite (10 g) was added to the reaction solution, and stirred for 0.5 hour, followed by filtration. The filtrate was concentrated under reduced pressure, and the obtained crude product was purified by silica gel plate to obtain the compound BB-3L (320.00 mg, yield 47.64% yield). MS-ESI m/z: 261.1 (M+H)$^+$.

The reference examples in the following table were synthesized according to the synthesis method of the steps 2-7 in Reference Example 46.

| Reference Example | Fragment 1 | Structure |
|---|---|---|
| 47 | (allyl-Bpin) | BB-3M |

The reference examples in the following table were synthesized according to the synthesis method of the steps 5-7 in Reference Example 46.

| Reference Example | Fragment 2 | Structure |
|---|---|---|
| 48 | (4-methylpyridin-3-yl)methanol | BB-3N |

Reference Example 37: BB-4A

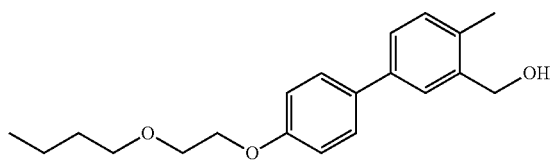 [SMILES: CCCCOCCOc1ccc(-c2ccc(C)c(CO)c2)cc1]

Synthesis Pathway:

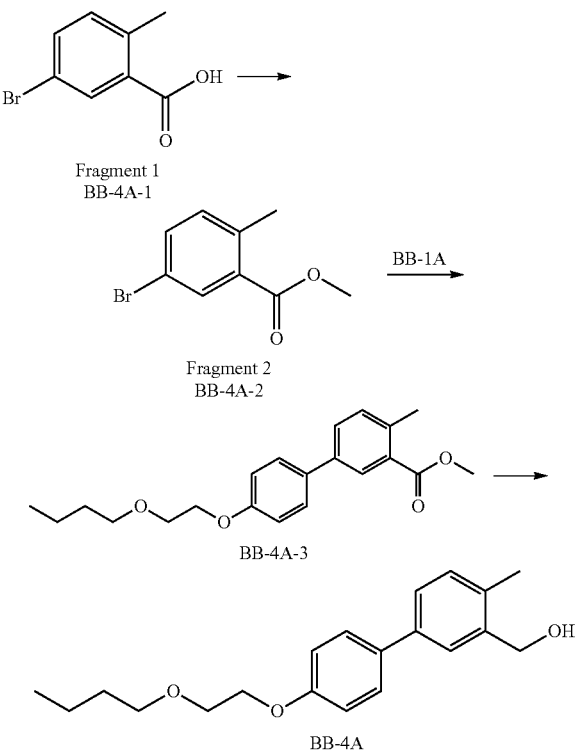

Step 1: Synthesis of Compound BB-4A-2

Compound BB-4A-1 (1.00 g, 4.65 mmol) and N,N-dimethylformamide (33.99 mg, 465.00 μmol) were dissolved in dichloromethane (10.00 mL) under nitrogen atmosphere, followed by dropwise addition of oxalyl chloride (1.48 g, 11.63 mmol) at 0° C. The reaction mixture was stirred for 1 hour at room temperature under nitrogen atmosphere. Methanol (1.49 g, 46.50 mmol) was added dropwise to the reaction solution. The reaction solution was concentrated under reduced pressure to remove solvent to give the crude compound BB-4A-2 (1.00 g, yield 93.88%).

Step 2: Synthesis of Compound BB-4A-3

Compound BB-4A-2 (1.00 g, 4.37 mmol), compound BB-1A (1.40 g, 4.37 mmol) and potassium carbonate (1.81 g, 13.10 mmol) were dissolved in 1,4-dioxane (10 mL) and water (3 mL) under nitrogen atmosphere, followed by addition of (1,1'-bis(diphenylphosphino)ferrocene)palladium dichloride dichloromethane complex (356.50 mg, 436.55 μmol). The reaction mixture was stirred for 10 hours at 90° C. under nitrogen atmosphere. After completion of the reaction, the reaction solution was cooled to room temperature and concentrated under reduced pressure, followed by addition of water (10 mL) and extraction with ethyl acetate (10 mL×3). The organic phases were combined, washed with saturated brine (30 mL), dried over anhydrous sodium sulfate, filtered to remove the desiccant and concentrated under reduced pressure. The insoluble material was removed by filtration, and the obtained residue was purified by column chromatography (eluent: petroleum ether/ethyl acetate=100/1, 9/1) to obtain the title compound BB-4A-3 (yellow solid, 1.00 g, yield 59.74%). $^1$H NMR (400 MHz, CDCl$_3$) δ: 8.03 (d, J=2.0 Hz, 1H), 7.51 (dd, J=1.9, 7.9 Hz, 1H), 7.45 (d, J=8.8 Hz, 2H), 7.21-7.17 (m, 1H), 6.93 (d, J=8.8 Hz, 2H), 4.11-4.08 (m, 2H), 3.84 (s, 3H), 3.74 (t, J=4.9 Hz, 2H), 3.48 (t, J=6.7 Hz, 2H), 2.55 (s, 3H), 1.55-1.50 (m, 2H), 1.36-1.28 (m, 2H), 0.86 (t, J=7.4 Hz, 3H).

Step 3: Synthesis of Compound BB-4A

Compound BB-4A-3 was dissolved in tetrahydrofuran (10 mL) under nitrogen atmosphere, and lithium tetrahydroaluminum (299.23 mg, 7.89 mmol) was added portionwise to the reaction solution at 0-5° C. The reaction mixture was stirred for 15 hours at room temperature under nitrogen protection. After completion of the reaction, the reaction was quenched by the addition of 0.5 mL of water and 0.5 mL of saturated sodium carbonate solution, followed by filtration. The filtrate was added to water (10 ml), and extracted with ethyl acetate (20 mL*3). The organic phases were combined washed with saturated brine (30 mL), dried over anhydrous sodium sulfate, filtered and concentrated under reduced pressure. The obtained crude product was isolated by silica gel column (eluent: petroleum ether/ethyl acetate=50/1, 10/1) to obtain the compound BB-4A (695.00 mg, yield 79.84%). $^1$H NMR (400 MHz, DMSO-d6) δ=7.58 (br s, 1H), 7.54 (br d, J=8.5 Hz, 2H), 7.37 (br d, J=7.5 Hz, 1H), 7.16 (br d, J=7.8 Hz, 1H), 7.00 (br d, J=8.5 Hz, 2H), 5.10 (br t, J=5.3 Hz, 1H), 4.52 (br d, J=4.8 Hz, 2H), 4.13-4.06 (m, 2H), 3.74-3.65 (m, 2H), 3.44 (br t, J=6.5 Hz, 2H), 2.24 (s, 3H), 1.53-1.45 (m, 2H), 1.31 (qd, J=7.3, 14.7 Hz, 2H), 0.87 (br t, J=7.3 Hz, 3H).

The reference examples in the following table were synthesized according to the synthesis method of the steps 1-3 in Reference Example 37.

| Reference Example | Fragment 2 | Structure |
|---|---|---|
| 38 | ![Fragment 2 structure] | ![BB-4B structure] BB-4B |

-continued

| Reference Example | Fragment 2 | Structure |
|---|---|---|
| 39 | | 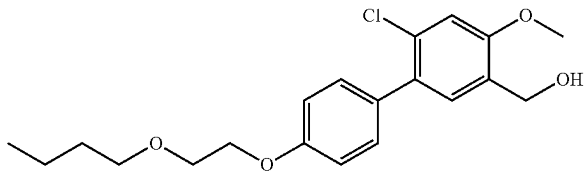 |
| 49 | | 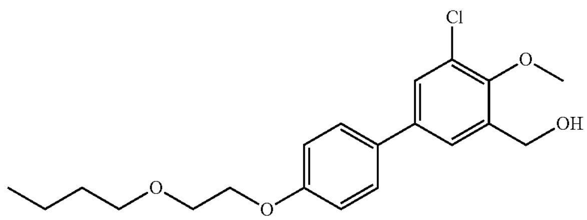 |
| 50 | | 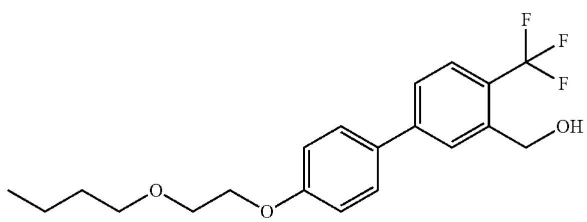 |
| 51 | | 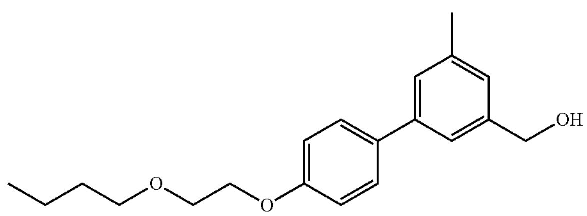 |

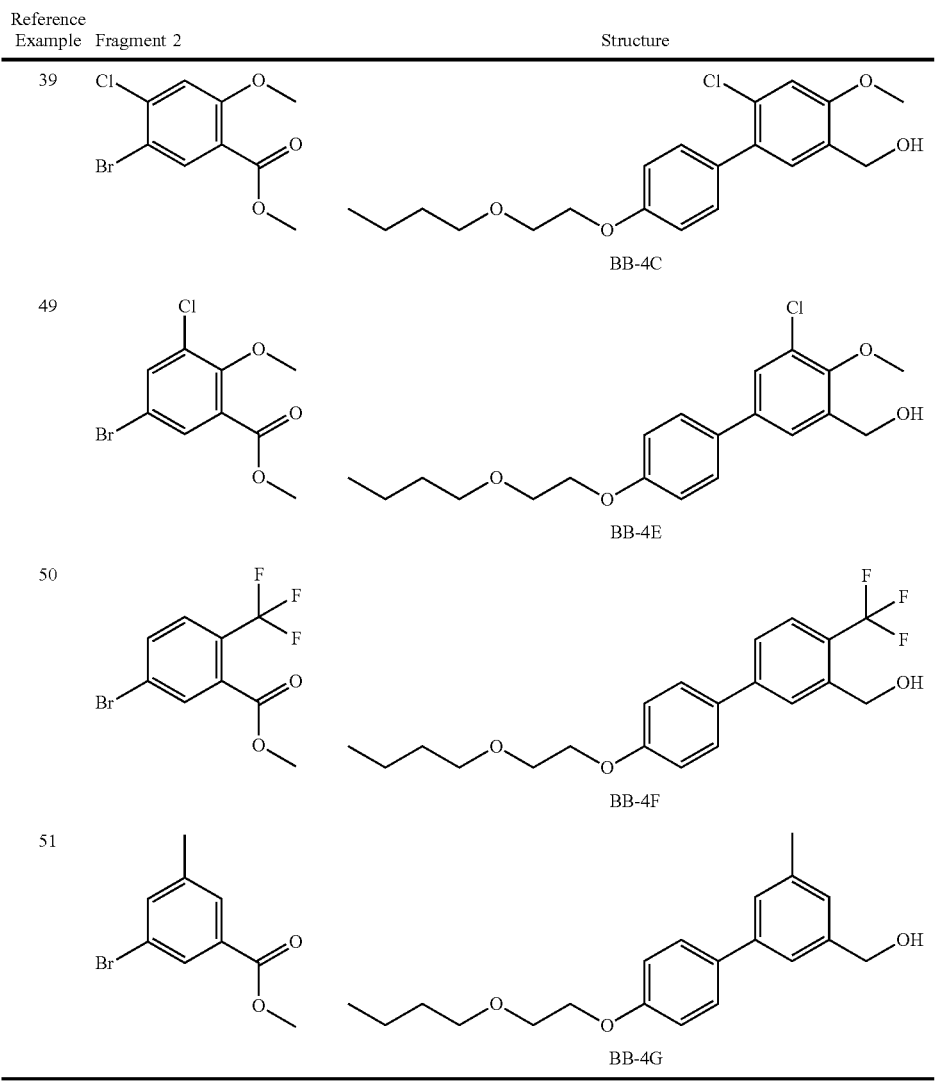

Reference Example 40: BB-4D

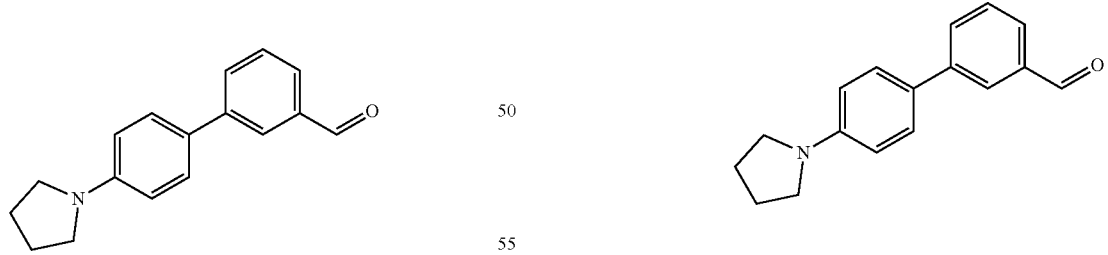

Step 1: Synthesis of Compound BB-4D-2

Compound BB-4D-1 (10.00 g, 35.35 mmol) and pyrrolidine (2.77 g, 38.89 mmol) were dissolved in N,N-dimethylformamide (100 mL) at room temperature under nitrogen atmosphere, followed by addition of cuprous iodide (673.24 mg, 3.54 mmol), L-proline (813.97 mg, 7.07 mmol) and cesium carbonate (13.82 g, 42.42 mmol). After completion of the addition, the reaction mixture was heated to 120° C. and stirred for 10 hours under nitrogen atmosphere. After completion of the reaction, the mixture was cooled to room Synthesis Pathway:

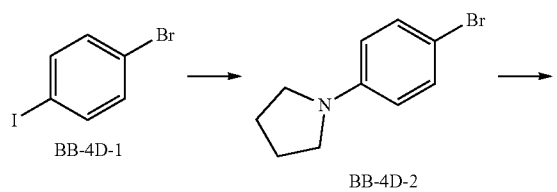

temperature, quenched with saturated brine (200 mL), and extracted with ethyl acetate (500 mL×3). The organic phases were combined, washed with water (200 mL), dried over anhydrous sodium sulfate, filtered to remove the desiccant and concentrated under reduced pressure. The insoluble material was removed by filtration, and the obtained residue was purified by silica gel column chromatography (eluent: petroleum ether) to obtain the title compound BB-4D-2 (white solid, 4.01 g, yield: 50.17%). $^1$H NMR (400 MHz, CDCl$_3$) δ: 7.29 (d, J=9.0 Hz, 2H), 6.43 (d, J=9.0 Hz, 2H), 3.25 (t, J=6.7 Hz, 4H), 2.01 (td, J=3.4, 6.6 Hz, 4H).

Step 2: Synthesis of Compound BB-4D

Compound BB-4D-2 (1.00 g, 4.42 mmol) and 3-formyl-benzeneboronic acid (663.13 mg, 4.42 mmol) were dissolved in 1,4-dioxane (10 mL) under nitrogen atmosphere, followed by addition of (1,1'-bis(diphenylphosphino)ferrocene)palladium dichloride dichloromethane complex (360.95 mg, 4.42 mmol), potassium carbonate (916.33 mg, 6.63 mmol) and water (3 mL). The reaction mixture was heated to 80° C. and stirred for 12 hours under nitrogen atmosphere. After completion of the reaction, the mixture is cooled to room temperature and concentrated under reduced pressure. The obtained residue was purified by column chromatography (eluent: ethyl acetate/petroleum ether=1/100-1/20) to obtain the title compound BB-4D (yellow liquid, 489.00 mg, yield: 44.02%). $^1$H NMR (400 MHz, CDCl$_3$) δ: 10.08 (s, 1H), 8.07 (s, 1H), 7.83 (d, J=7.8 Hz, 1H), 7.75 (d, J=7.8 Hz, 1H), 7.58-7.52 (m, 3H), 6.66 (d, J=8.8 Hz, 2H), 3.39-3.32 (m, 4H), 2.05 (td, J=3.4, 6.5 Hz, 4H).

Reference Example 52: BB-4H

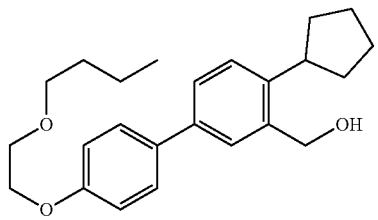 [SMILES: CCCCOCCOc1ccc(-c2ccc(C3CCCC3)c(CO)c2)cc1]

Synthesis Pathway:

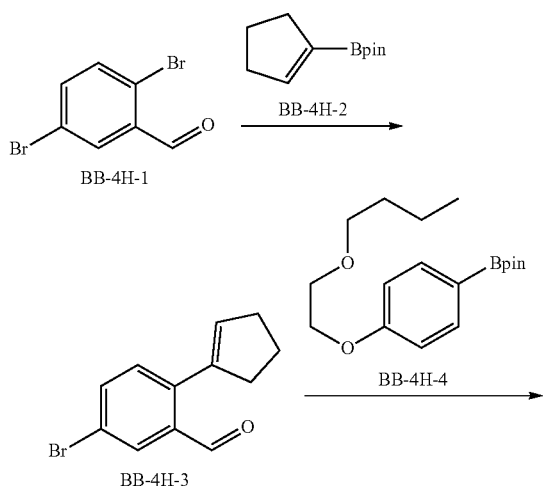

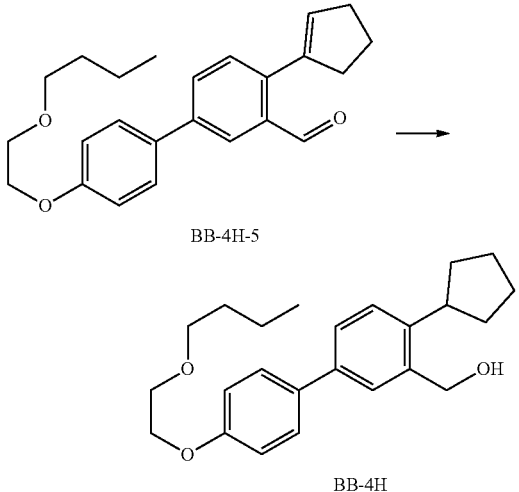

Step 1: Synthesis of Compound BB-4H-3

Compound BB-4H-1 (4.00 g, 15.16 mmol) and compound BB-4H-2 (2.80 g, 14.40 mmol) were dissolved in 1,4-dioxane (50 mL) under nitrogen atmosphere, followed by addition of (1,1'-bis(diphenylphosphino)ferrocene)palladium dichloride dichloromethane complex (1.24 g, 1.52 mmol), potassium carbonate (3.14 g, 22.74 mmol) and water (15 mL). The reaction mixture was stirred for 12 hours at room temperature under nitrogen protection. After completion of the reaction, saturated brine (50 mL) was added to the reaction mixture to quench the reaction, followed by extraction with ethyl acetate (30 mL×3). The organic phases were combined, washed with saturated brine (100 mL), dried over anhydrous sodium sulfate, filtered to remove the desiccant and concentrated under reduced pressure. The insoluble material was removed by filtration, and the obtained residue was purified by column chromatography (eluent: ethyl acetate/petroleum ether=0/10-1/10) to obtain the title compound BB-4H-3 (3.40 g, yield: 89.31%). $^1$H NMR (400 MHz, CDCl$_3$) δ: 10.04 (s, 1H), 7.95 (d, J=2.3 Hz, 1H), 7.57 (dd, J=2.1, 8.4 Hz, 1H), 7.18 (d, J=8.4 Hz, 1H), 5.69 (quin, J=2.2 Hz, 1H), 2.68 (qt, J=2.3, 7.4 Hz, 2H), 2.53 (qt, J=2.4, 7.5 Hz, 2H), 2.02 (quin, J=7.5 Hz, 2H).

Step 2: Synthesis of Compound BB-4H-5

Compound BB-4H-3 (2.00 g, 7.96 mmol) and compound BB-4H-5 (2.68 g, 8.36 mmol) were dissolved in 1,4-dioxane (45 mL) under nitrogen atmosphere, followed by addition of (1,1'-bis(diphenylphosphino)ferrocene)palladium dichloride dichloromethane complex (650.05 mg, 796.00 μmol), potassium carbonate (1.65 g, 11.94 mmol) and water (15 mL). The reaction mixture was heated to 80° C. u and stirred for 10 hours under nitrogen atmosphere. After completion of the reaction, saturated brine (100 mL) was added to the reaction mixture to quench the reaction, followed by extraction with ethyl acetate (30 mL×3). The organic phases were combined, washed with saturated brine (100 mL), dried over anhydrous sodium sulfate, filtered to remove the desiccant and concentrated under reduced pressure. The insoluble material was removed by filtration, and the obtained residue was purified by flash silica gel column chromatography (eluent: ethyl acetate/petroleum ether=0/10-1/10) to obtain the title compound BB-4H-5 (1.89 g, yield: 65.14%). $^1$H NMR (400 MHz, CDCl$_3$) δ: 10.25 (s, 1H), 8.11 (d, J=1.8 Hz, 1H), 7.75 (dd, J=2.0, 8.0 Hz, 1H), 7.57 (d, J=8.8 Hz, 2H), 7.43 (d, J=8.0 Hz, 1H), 7.02 (d, J=8.8 Hz, 2H), 5.86-5.72 (m, 1H), 4.29-4.10 (m, 2H), 3.86-3.79 (m, 2H), 3.56 (t, J=6.7

Hz, 2H), 2.80 (dt, J=2.0, 7.5 Hz, 2H), 2.63 (dt, J=2.4, 7.3 Hz, 2H), 2.12 (quin, J=7.5 Hz, 2H), 1.66-1.59 (m, 2H), 1.46-1.37 (m, 2H), 0.94 (t, J=7.3 Hz, 3H).

Step 3: Synthesis of Compound BB-4H

Compound BB-4H-5 (1.89 g, 5.19 mmol) was dissolved in methanol (100 mL) at room temperature, and wet palladium on carbon catalyst (70.00 mg, palladium content 10%, water content 50%) was added thereto. The system was displaced with argon three times, followed by displacing with hydrogen three times. The reaction mixture was stirred for 24 hours at room temperature under hydrogen atmosphere (30 psi). The catalyst was removed by filtration, and the filtrate was concentrated under reduced pressure to obtain the crude product BB-4H (white solid, 1.70 g, yield 88.89%). The crude product was used directly in the next reaction without purification. $^1$H NMR (400 MHz, CDCl$_3$) δ: 7.55 (d, J=2.0 Hz, 1H), 7.54-7.51 (m, 2H), 7.49 (dd, J=2.0, 8.0 Hz, 1H), 7.38 (d, J=8.0 Hz, 1H), 6.99 (d, J=8.5 Hz, 2H), 4.82 (d, J=5.8 Hz, 2H), 4.19-4.15 (m, 2H), 3.84-3.80 (m, 2H), 3.56 (t, J=6.7 Hz, 2H), 3.38-3.27 (m, 1H), 2.13-2.06 (m, 2H), 1.92-1.83 (m, 2H), 1.79-1.70 (m, 2H), 1.67-1.63 (m, 2H), 1.61 (br d, J=8.0 Hz, 2H), 1.40 (qd, J=7.4, 14.9 Hz, 2H), 0.94 (t, J=7.4 Hz, 3H).

Reference Example 53: BB-5A

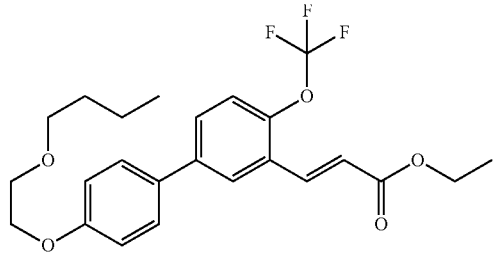 [SMILES: CCCCOCCOc1ccc(-c2ccc(OC(F)(F)F)c(/C=C/C(=O)OCC)c2)cc1]

Synthesis Pathway:

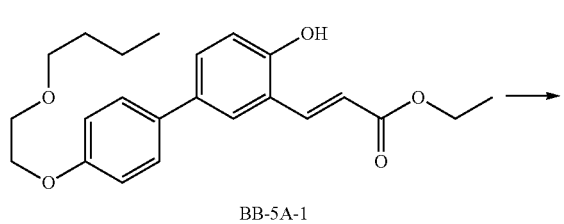

BB-5A-1

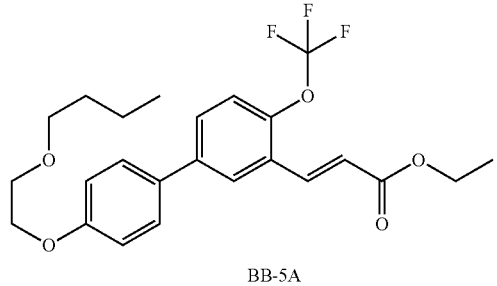

BB-5A

Step 1: Synthesis of Compound BB-5A

Compound BB-5A-1 (800.00 mg, 2.08 mmol) and trimethyltrifluoromethylsilane (887.62 mg, 6.24 mmol) were dissolved in toluene (10 mL) under nitrogen atmosphere, followed by addition of silver trifluoromethanesulfonate (2.67 g, 10.40 mmol), 1-chloromethyl-4-fluoro-1,4-diazabicyclo[2.2.2]octane bis(tetrafluoroborate) (1.47 g, 4.16 mmol), cesium fluoride (948.24 mg, 6.24 mmol) and 2-fluoropyridine (1.01 g, 10.40 mmol). The reaction mixture was stirred for 12 hours at room temperature under nitrogen protection. After completion of the reaction, saturated brine (20 mL) was added to the mixture to quench the reaction, followed by extraction with ethyl acetate (10 mL×3). The organic phases were combined, washed with saturated brine (30 mL×2), dried over anhydrous sodium sulfate, filtered to remove the desiccant and concentrated under reduced pressure. The insoluble material was removed by filtration, and the obtained residue was purified by column chromatography (eluent: ethyl acetate/petroleum ether=1/50-1/5) to obtain the title compound BB-5A (yellow oily liquid, 122.00 mg, yield: 12.96%). $^1$H NMR (400 MHz, CDCl$_3$) δ: 7.95 (d, J=16.1 Hz, 1H), 7.80 (d, J=2.3 Hz, 1H), 7.57 (dd, J=2.3, 8.8 Hz, 1H), 7.49 (d, J=8.8 Hz, 2H), 7.34 (dd, J=1.3, 8.5 Hz, 1H), 7.03 (d, J=8.8 Hz, 2H), 6.56 (d, J=16.1 Hz, 1H), 4.30 (q, J=7.3 Hz, 2H), 4.22-4.14 (m, 2H), 3.87-3.78 (m, 2H), 3.57 (t, J=6.7 Hz, 2H), 1.68-1.60 (m, 2H), 1.47-1.39 (m, 2H), 1.36 (t, J=7.2 Hz, 3H), 0.94 (t, J=7.4 Hz, 3H).

Reference Example 53: BB-5B

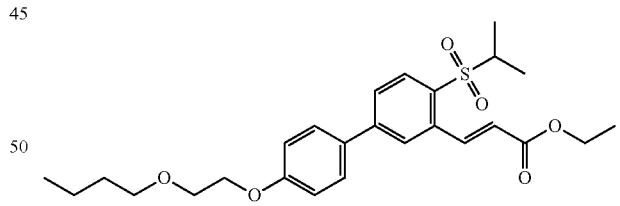

Synthesis Pathway:

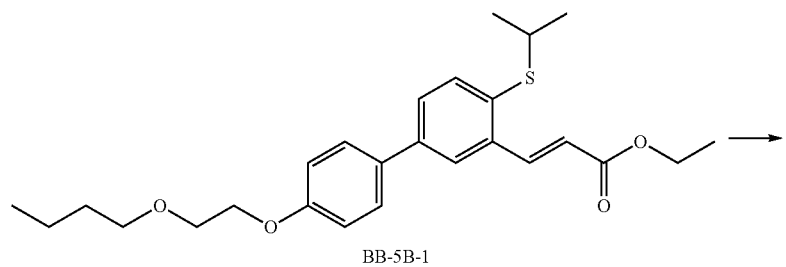

BB-5B-1

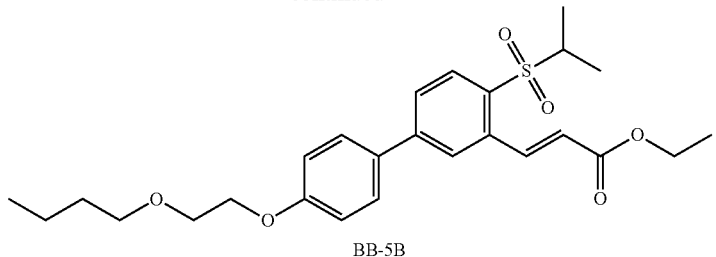

BB-5B

Step 1: Synthesis of Compound BB-5B

Compound BB-5B-1 (400.00 mg, 903.73 μmol, 1.00 eq) was dissolved in dichloromethane (5.00 mL), followed by addition of m-chloroperoxybenzoic acid at room temperature (779.78 mg, 3.61 mmol, 80% purity, 4.00 eq). The reaction was carried at room temperature for 3 hours, and quenched with 8 mL of saturated sodium sulfite, followed by addition of water (20 mL) and extraction with dichloromethane (50 mL×3). The organic phases were combined, washed with saturated brine (100 mL), dried over anhydrous sodium sulfate, filtered to remove the desiccant and concentrated under reduced pressure. The obtained residue was purified by column chromatography (eluent: petroleum ether/ethyl acetate=50/1, 3/1) to obtain the title compound BB-5B (400.00 mg, 842.80 μmol, 93.26% yield). MS-ESI m/z: 497.2[M+Na]$^+$; $^1$H NMR (400 MHz, CHLOROFORM-d) δ=8.64 (d, J=16.1 Hz, 1H), 8.08 (d, J=8.3 Hz, 1H), 7.85 (d, J=1.5 Hz, 1H), 7.72 (dd, J=1.8, 8.3 Hz, 1H), 7.63-7.51 (m, 2H), 7.10-6.99 (m, 2H), 6.46 (d, J=15.8 Hz, 1H), 4.31 (q, J=7.0 Hz, 2H), 4.22-4.17 (m, 2H), 3.86-3.80 (m, 2H), 3.57 (t, J=6.7 Hz, 2H), 3.25 (td, J=6.8, 13.7 Hz, 1H), 1.67-1.61 (m, 3H), 1.45-1.39 (m, 2H), 1.36 (t, J=7.2 Hz, 4H), 1.31 (d, J=7.0 Hz, 6H), 0.94 (t, J=7.3 Hz, 3H).

Reference Example 55: BB-5C

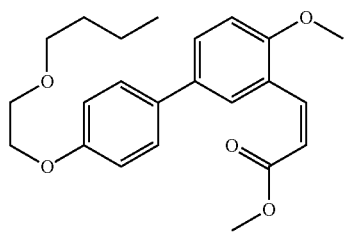 [SMILES: CCCCOCCOc1ccc(-c2ccc(OC)c(/C=C\C(=O)OC)c2)cc1]

Synthesis Pathway:

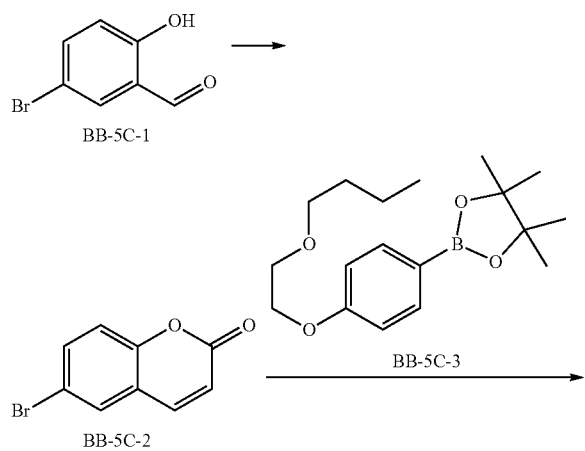

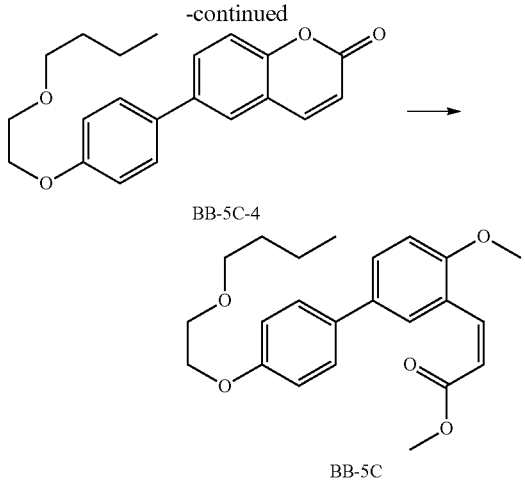

BB-5C

Step 1: Synthesis of Compound BB-5C-2

Phosphorus oxychloride (4.62 mL, 49.74 mmol) was carefully added to N,N-dimethylacetamide (6.91 mL, 74.61 mmol) at 0° C., and the mixture was stirred for 0.5 hour at 0° C., followed by addition of compound BB-5C-1 (5.00 g, 24.87 mmol) to the above mixture. After completion of the addition, the reaction mixture was heated to 70° C. and stirred for 3 hours. After completion of the reaction, the mixture was cooled to room temperature. After saturated sodium hydrogen carbonate solution (30 mL) was added thereto, the mixture was heated to 60° C. and stirred for 0.5 hour to quench the reaction. The mixture was then cooled again to room temperature, adjusted to pH=2 with concentrated hydrochloric acid, and extracted with dichloromethane (15 mL×3). The organic phases were combined, washed with water (50 mL), dried over anhydrous sodium sulfate, filtered to remove the desiccant and concentrated under reduced pressure. The obtained residue was purified by silica gel column chromatography (eluent: ethyl acetate/petroleum ether=1/50-1/5) to obtain the title compound BB-5C-2 (1.50 g, yield: 26.80%). $^1$H NMR (400 MHz, CDCl$_3$) δ: 7.71-7.61 (m, 3H), 7.27-7.22 (m, 1H), 6.48 (br d, J=9.5 Hz, 1H).

Step 2: Synthesis of Compound BB-5C-4

Compound BB-5C-2 (1.00 g, 4.44 mmol) and compound BB-5C-3 (1.56 g, 4.88 mmol) were dissolved in 1,4-dioxane (15 mL) under nitrogen atmosphere, followed by addition of (1,1'-bis(diphenylphosphino)ferrocene)palladium dichloride dichloromethane complex (362.59 mg, 444.00 μmol), potassium carbonate (920.48 mg, 6.66 mmol) and water (3.00 mL). After completion of the addition, the reaction mixture was heated to 80° C. and stirred for 4 hours. After completion of the reaction, saturated brine (40 mL) was added to the mixture to quench the reaction, and the mixture was extracted with ethyl acetate (15 mL×3). The organic phases were combined, washed with water (50 mL), dried over anhydrous sodium sulfate, filtered to remove the desiccant and concentrated under reduced pressure. The residue obtained was purified by silica gel column chromatography (eluent: ethyl acetate/petroleum ether=1/40-1/2) to obtain the title compound BB-5C-4 (1.25 g, yield: 83.19%). $^1$H NMR (400 MHz, CDCl$_3$) δ: 7.74 (br dd, J=9.2, 18.4 Hz, 2H), 7.63 (s, 1H), 7.51 (br d, J=7.8 Hz, 2H), 7.39 (br d, J=8.3 Hz, 1H), 7.03 (br d, J=7.5 Hz, 2H), 6.47 (br d, J=9.5 Hz, 1H), 4.18 (br s, 2H), 3.83 (br s, 2H), 3.57 (br t, J=6.4 Hz, 2H), 1.68-1.59 (m, 2H), 1.41 (qd, J=7.1, 14.5 Hz, 2H), 0.94 (br t, J=7.2 Hz, 3H).

Step 3: Synthesis of Compound BB-5C

Compound BB-5C-4 (150.00 mg, 443.26 μmol) was dissolved in dimethyl sulfoxide (1 mL) at room temperature, and then hydrazine hydroxide octahydrate (279.66 mg, 886.52 μmol) was added thereto. After completion of the addition, the reaction mixture was carefully heated to 40° C. and stirred for 3 hours, followed by addition of methyl iodide (251.67 mg, 1.77 mmol) to the above mixture. After completion of the addition, the reaction mixture was stirred for 0.5 hour at this temperature. After completion of the reaction, the reaction mixture was cooled to room temperature, and nitrogen was introduced thereto to remove the excess methyl iodide. Saturated brine (20 mL) was added to quench the reaction, and the mixture was extracted with ethyl acetate (5 mL×3). The organic phases were combined, washed with saturated brine (20 mL) dried over anhydrous sodium sulfate, filtered to remove the desiccant and concentrated under reduced pressure to obtain the title compound BB-5C (148.00 mg, yield: 86.85%). $^1$H NMR (400 MHz, CDCl$_3$) δ: 7.78 (d, J=2.3 Hz, 1H), 7.52-7.46 (m, 3H), 7.20 (d, J=12.5 Hz, 1H), 6.98 (d, J=8.8 Hz, 2H), 6.93 (d, J=8.8 Hz, 1H), 6.02 (d, J=12.5 Hz, 1H), 4.19-4.13 (m, 2H), 3.87 (s, 3H), 3.83-3.79 (m, 2H), 3.69 (s, 3H), 3.56 (t, J=6.7 Hz, 2H), 1.66-1.60 (m, 2H), 1.40 (qd, J=7.5, 14.9 Hz, 2H), 0.94 (t, J=7.3 Hz, 3H).

Example 1: WX017

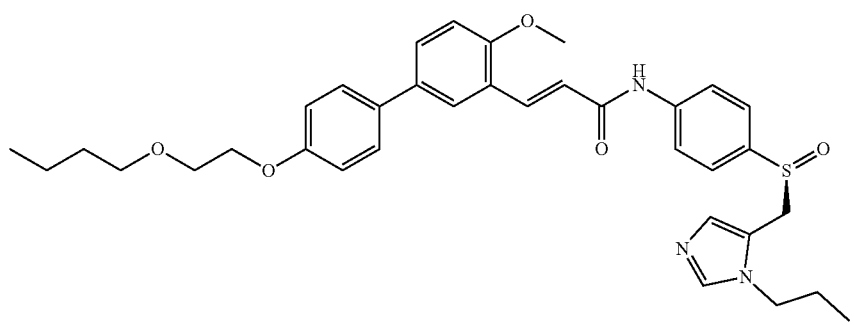

WX017

Synthesis Pathway:

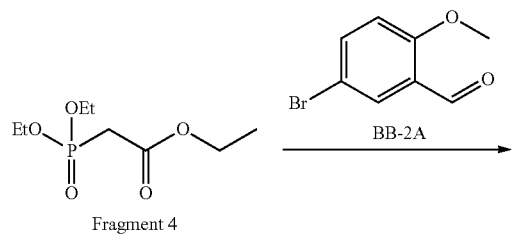

Fragment 4   BB-2A

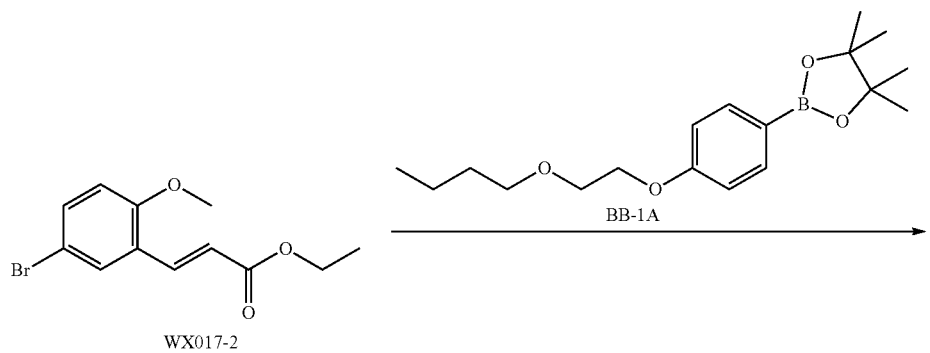

WX017-2

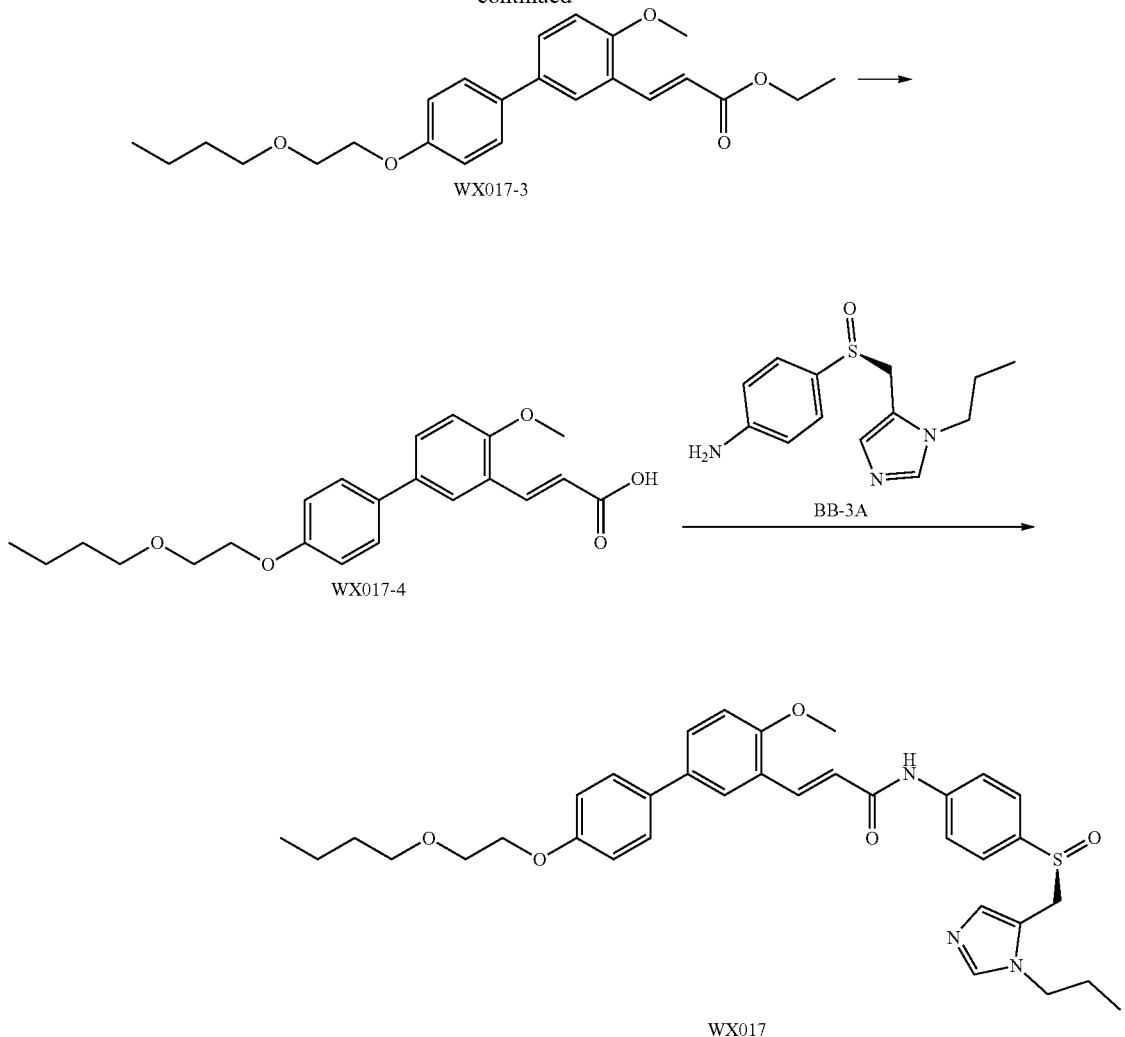

Step 1: Synthesis of Compound WX017-2

Triethylphosphorylacetate (25.02 g, 111.60 mmol) was dissolved in tetrahydrofuran under nitrogen atmosphere, followed by portionwise addition of sodium hydride (4.46 g, 111.60 mmol) of 60% purity at 0° C. The reaction mixture was stirred a for 0.5 hourt 0-5° C., followed by addition of a solution of compound BB-2A (16.00 g, 74.40 mmol) in tetrahydrofuran (20.00 mL). The reaction mixture was stirred for 1.5 hours at room temperature under nitrogen protection. After completion of the reaction, the reaction solution was slowly poured into 50 mL of saturated aqueous solution of ammonium chloride. The organic phase and the aqueous phase were separated, and the aqueous phase was extracted with ethyl acetate (40 mL*3). The organic phases were combined, washed with saturated brine (120 mL×2), dried over anhydrous sodium sulfate, filtered to remove the desiccant and concentrated under reduced pressure to obtain the product WX017-2 (21.00 g, yield 98.99%). $^1$H NMR (400 MHz, CDCl$_3$) δ=7.89 (d, J=16.3 Hz, 1H), 7.61 (d, J=2.5 Hz, 1H), 7.43 (dd, 8.8 Hz, 1H), 6.80 (d, J=9.0 Hz, 1H), 6.49 (d, J=16.1 Hz, 1H), 4.27 (q, J=7.3 Hz, 2H), 3.87 (s, 3H), 1.34-1.31 (m, 3H).

Step 2: Synthesis of Compound WX017-3

Compound WX017-2 (10.00 g, 35.07 mmol), compound BB-1A (10.11 g, 31.56 mmol) and potassium carbonate (14.54 g, 105.21 mmol) were dissolved in 1,4-dioxane (80.00 mL) and water (15.00 mL) under nitrogen atmosphere followed by addition of (1,1'-bis(diphenylphosphino)ferrocene)palladium dichloride dichloromethane complex (2.57 g, 3.51 mmol). The reaction mixture was heated to 80° C. and stirred for 5 hours under nitrogen atmosphere. After completion of the reaction, the mixture was cooled to room temperature, followed by addition of water (60 mL) and extraction with ethyl acetate (60 mL×2). The organic phases were combined, washed with saturated brine (120 mL×2), dried over anhydrous sodium sulfate, filtered to remove the desiccant and concentrated under reduced pressure. The insoluble material was removed by filtration and the obtained residue was purified by flash column chromatography (eluent: petroleum ether/ethyl acetate=100/1, 20/1) to obtain the title compound WX017-3 (8.60 g, yield 58.89%). MS-ESI m/z: 399.1 (M+H)+; $^1$H NMR (400 MHz, CHLOROFORM-d) δ=7.95 (d, J=16.3 Hz, 1H), 7.60 (d, J=2.3 Hz, 1H), 7.44 (dd, J=2.3, 8.5 Hz, 1H), 7.40-7.35 (m, 2H), 6.94-6.86 (m, 3H), 6.52 (d, J=16.1 Hz, 1H), 4.20 (q, J=7.0 Hz, 2H), 4.11-4.06 (m, 2H), 3.84 (s, 3H), 3.75-3.71 (m, 2H), 3.48 (t, J=6.8 Hz, 2H), 1.56-1.49 (m, 2H), 1.32 (dd, J=7.4, 15.2 Hz, 2H), 1.27 (t, J=7.2 Hz, 3H), 0.86 (t, J=7.4 Hz, 3H).

Step 3: Synthesis of Compound WX017-4

The compound WX017-3 was dissolved in methanol, tetrahydrofuran and water, followed by addition of sodium hydroxide at room temperature. The reaction mixture was stirred for 15 hours at room temperature. After completion of the reaction, the reaction mixture was concentrated under reduced pressure to remove the solvent. 10 mL of water and 4 M hydrochloric acid were added to adjust the pH to 4-5 by, and then extracted with ethyl acetate (15 mL×3). The organic phases were combined, washed with saturated brine (120 mL×2), dried over anhydrous sodium sulfate, filtered to remove the desiccant and concentrated under reduced pressure to obtain the compound WX017-4 (600.00 mg, yield 40.29%). $^1$H NMR (400 MHz, CHLOROFORM-d) δ=8.16 (d, J=16.3 Hz, 1H), 7.71 (d, J=2.3 Hz, 1H), 7.57 (dd, J=2.3, 8.5 Hz, 1H), 7.57-7.55 (m, 2H), 7.02-6.98 (m, 3H), 6.63 (d, J=16.1 Hz, 1H), 4.17 (q, J=7.0 Hz, 2H), 3.95 (s, 3H), 3.84-3.81 (m, 2H), 3.58-3.55 (m, 2H), 1.66-1.59 (m, 2H), 1.43-1.38 (m, 2H), 0.94 (t, J=7.4 Hz, 3H).

Step 4: Synthesis of Compound WX017

Compound WX017-4 (80.00 mg, 215.96 μmol) was dissolved in dichloromethane (5 mL) at room temperature. The solution was cooled to 0° C., and N,N-dimethylformamide (789.23 ug, 10.80 μmol) and oxalyl chloride (82.24 mg, 647.88 μmol) were added to the above solution. The reaction mixture was stirred for 0.5 hour at 0-5° C. under nitrogen atmosphere. After completion of the reaction, nitrogen was introduced to the mixture to remove the organic solvent. The mixture was mixed in 3 mL of tetrahydrofuran, and added dropwise to a mixture of compound BB-3A (56.21 mg, 213.43 μmol) and triethylamine (64.79 mg, 640.29 μmol) in tetrahydrofuran (5 mL) at 0° C. After completion of the addition, the reaction mixture was warmed to room temperature and stirred for 15 hours under nitrogen atmosphere. After completion of the reaction, methanol (5 mL) was added to the mixture to quench the reaction, and the mixture was concentrated under reduced pressure. The obtained residue was purified by preparative high performance liquid chromatography to give the compound WX017. MS-ESI m/z: 616.1; 617.1[M+H]$^+$; $^1$H NMR (400 MHz, CDCl$_3$) δ: 9.33 (s, 1H), 8.05 (d, J=15.6 Hz, 1H), 7.80 (d, J=8.8 Hz, 2H), 7.61 (d, J=2.3 Hz, 1H), 7.50 (br d, J=2.3 Hz, 1H), 7.48 (s, 1H), 7.44-7.39 (m, 2H), 7.29 (d, J=8.8 Hz, 2H), 6.98-6.93 (m, 3H), 6.88 (d, J=15.8 Hz, 1H), 6.55 (s, 1H), 4.15 (d, J=4.8 Hz, 2H), 4.14-4.13 (m, 1H), 4.13 (d, J=2.8 Hz, 1H), 3.97 (d, J=14.1 Hz, 1H), 3.86 (s, 3H), 3.83-3.79 (m, 1H), 3.79-3.79 (m, 1H), 3.76 (dt, J=4.0, 7.3 Hz, 2H), 3.56 (t, J=6.8 Hz, 2H), 1.73-1.66 (m, 2H), 1.65-1.57 (m, 2H), 1.45-1.35 (m, 2H), 0.93 (t, J=7.4 Hz, 2H), 0.87 (t, J=7.4 Hz, 3H).

The reference examples in the following table were synthesized according to the synthesis method of the steps 1-4 in Example 1.

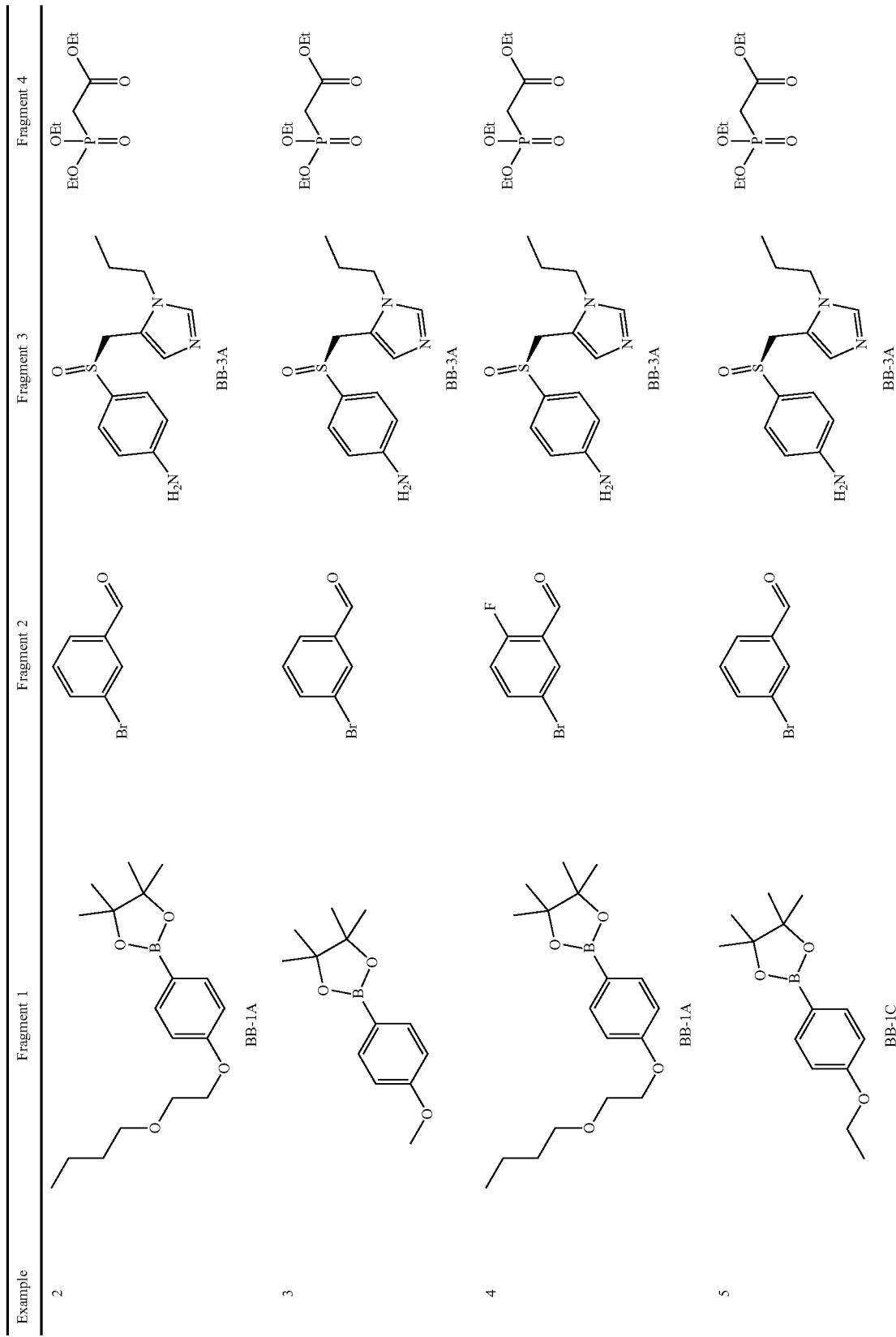

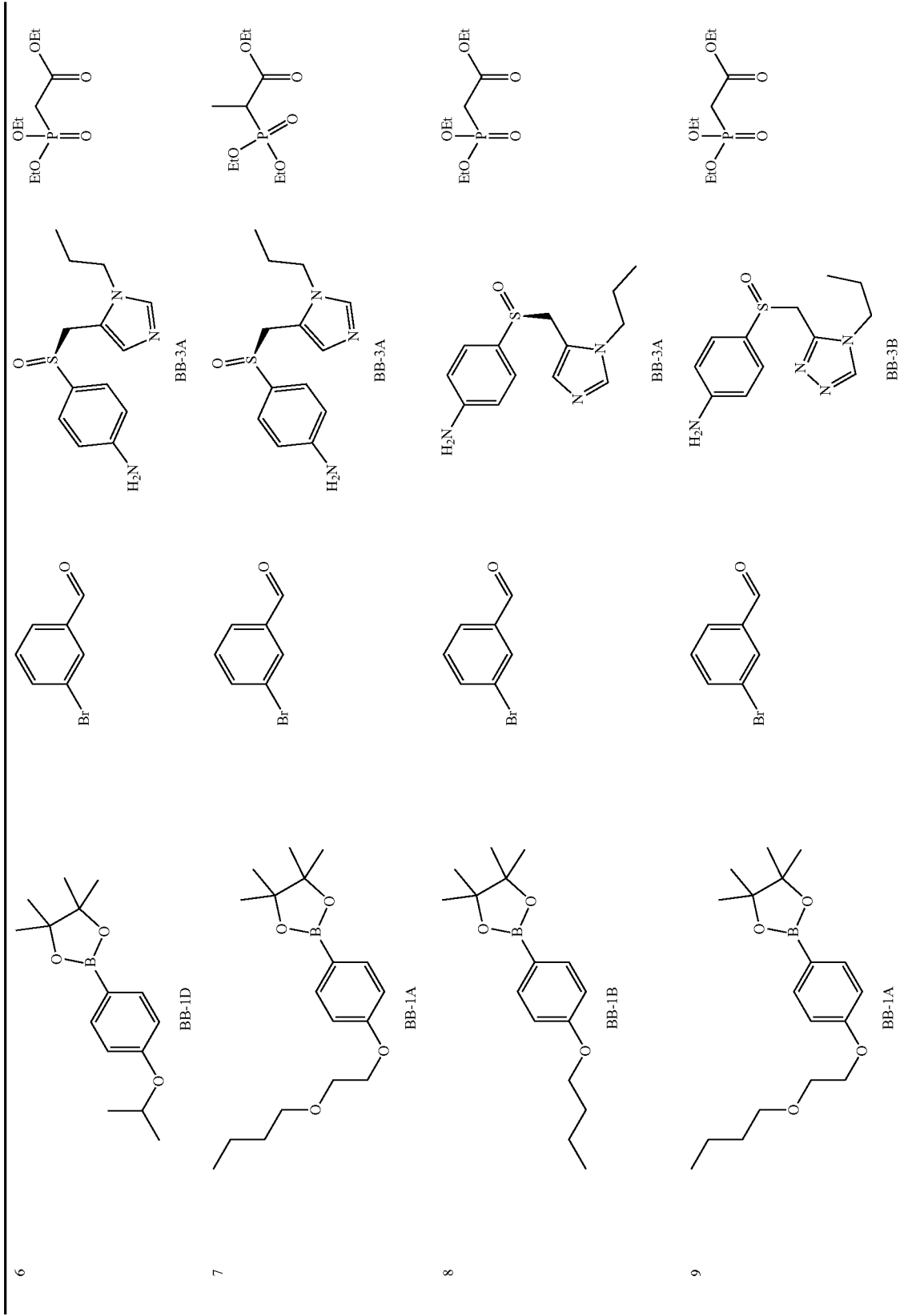

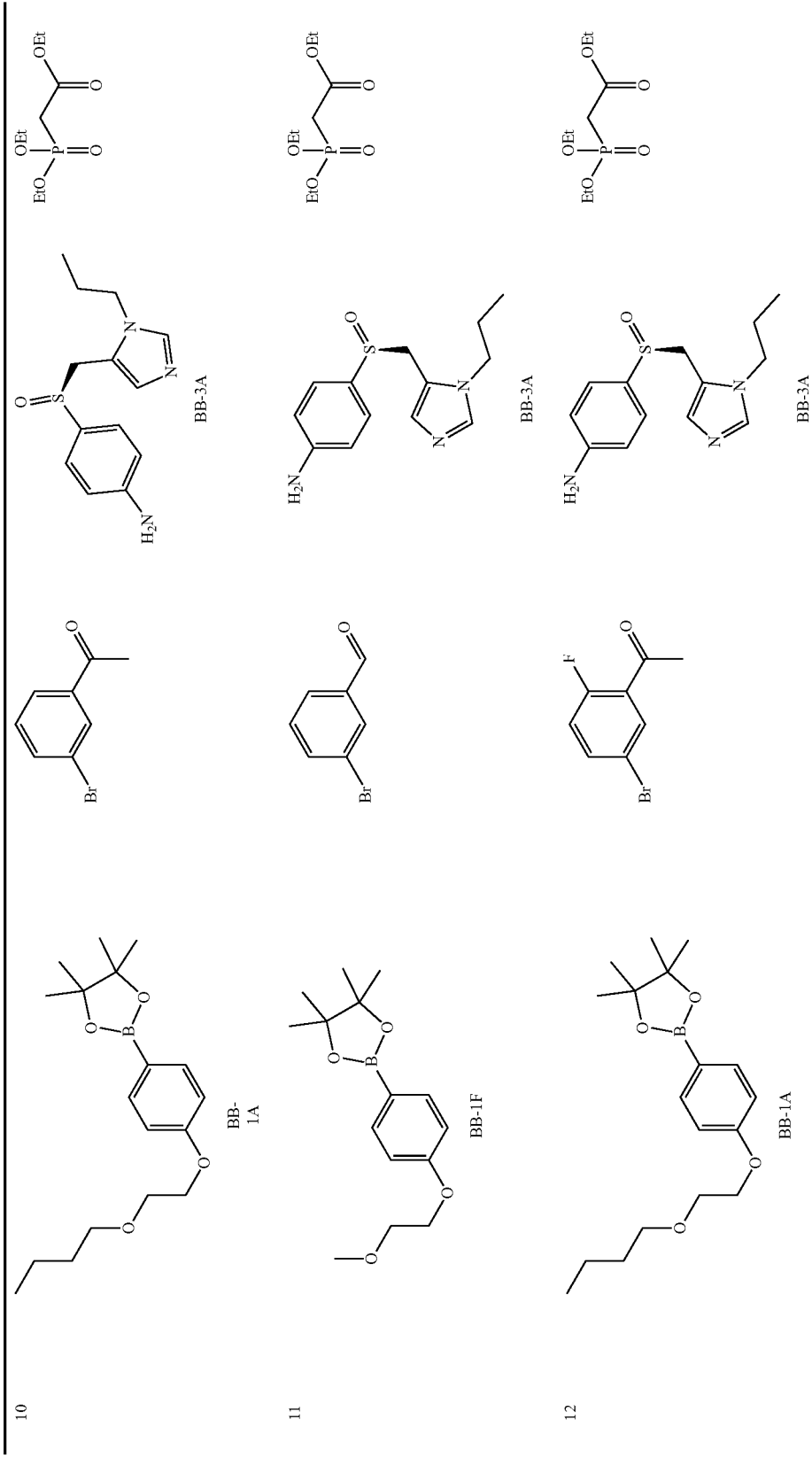

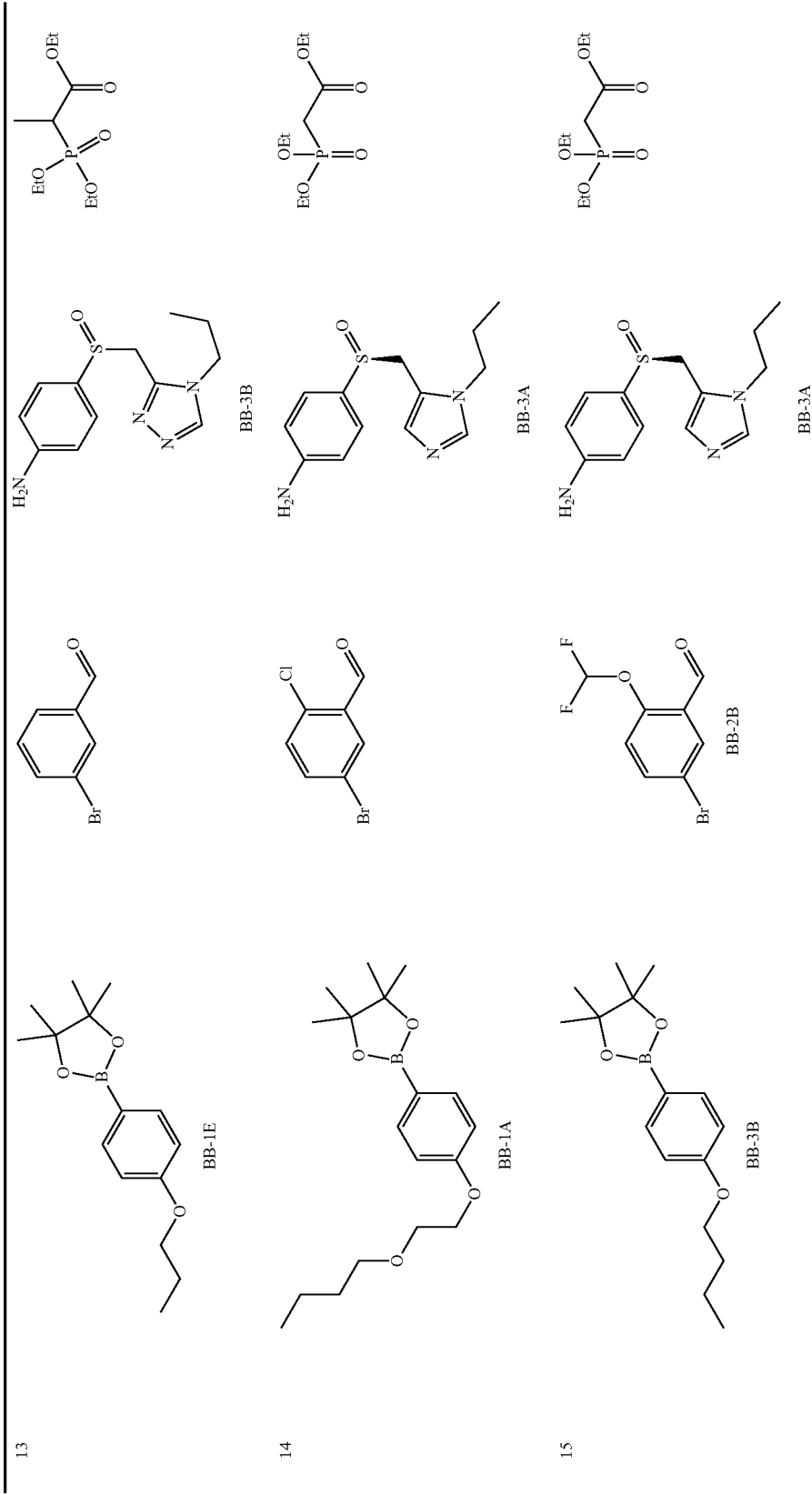

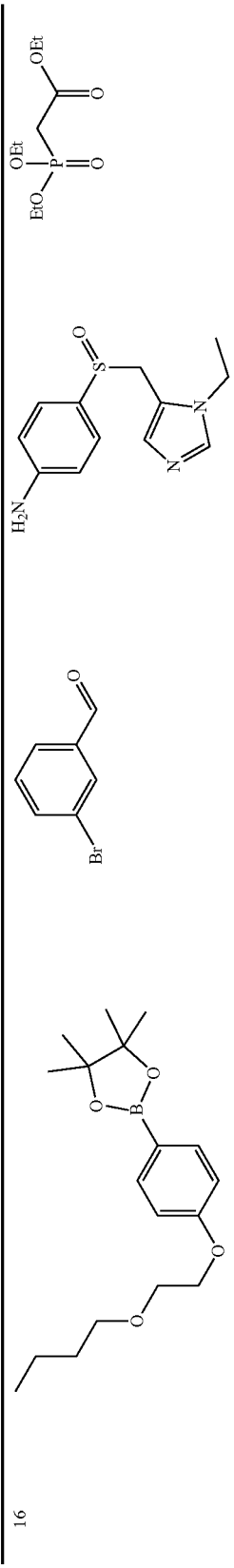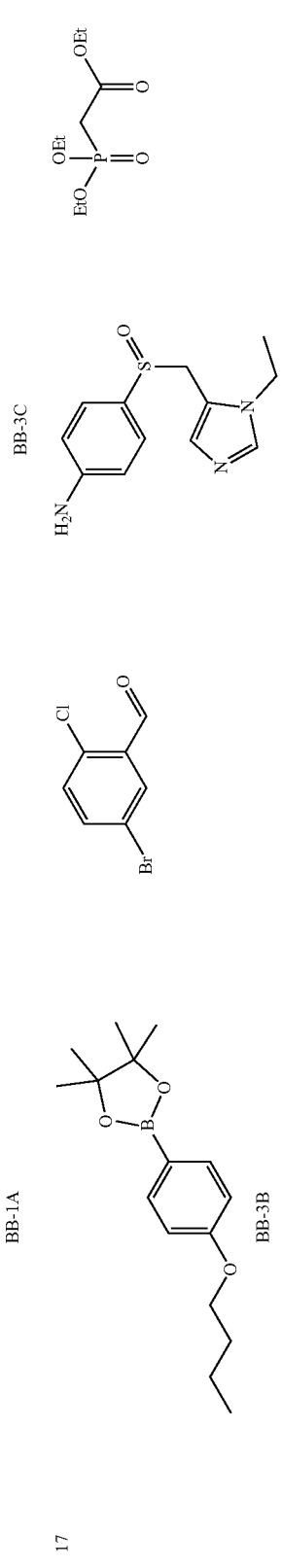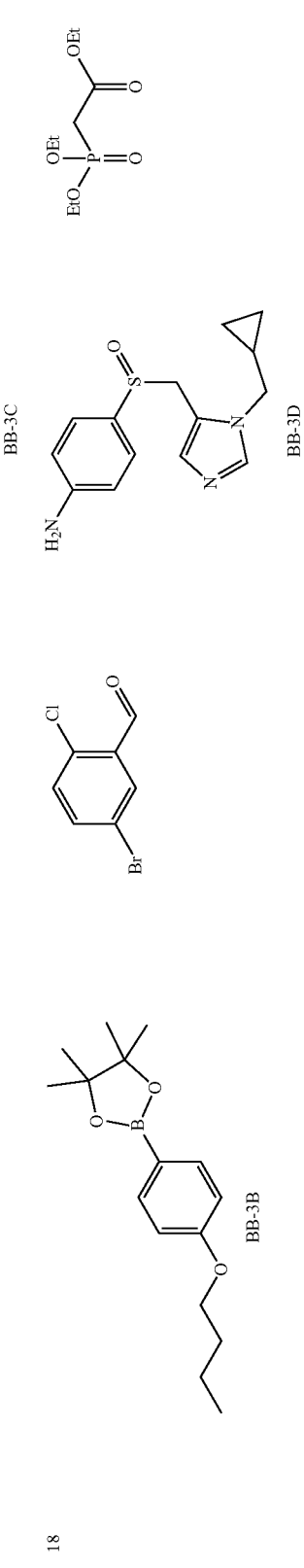

-continued

| | | | | |
|---|---|---|---|---|
| 19 | BB-3G | BB-2C (3-bromo-2-(3-fluoropropoxy)benzaldehyde) | BB-3A | triethyl phosphonoacetate |
| 20 | BB-1A | 3-bromobenzaldehyde | BB-3D | triethyl phosphonoacetate |
| 21 | BB-3B | BB-2C | BB-3A | triethyl phosphonoacetate |

-continued

| | | | | |
|---|---|---|---|---|
| 22 | BB-3B | Cl-C6H3(Br)-CHO | BB-3A | (EtO)2P(O)CH2C(O)OEt |
| 23 | BB-3B | F2CHCH2O-C6H3(Br)-CHO (BB-2D) | BB-3A | (EtO)2P(O)CH2C(O)OEt |
| 24 | BB-3B | Cl-C6H3(Br)-CHO | BB-3E | (EtO)2P(O)CH2C(O)OEt |

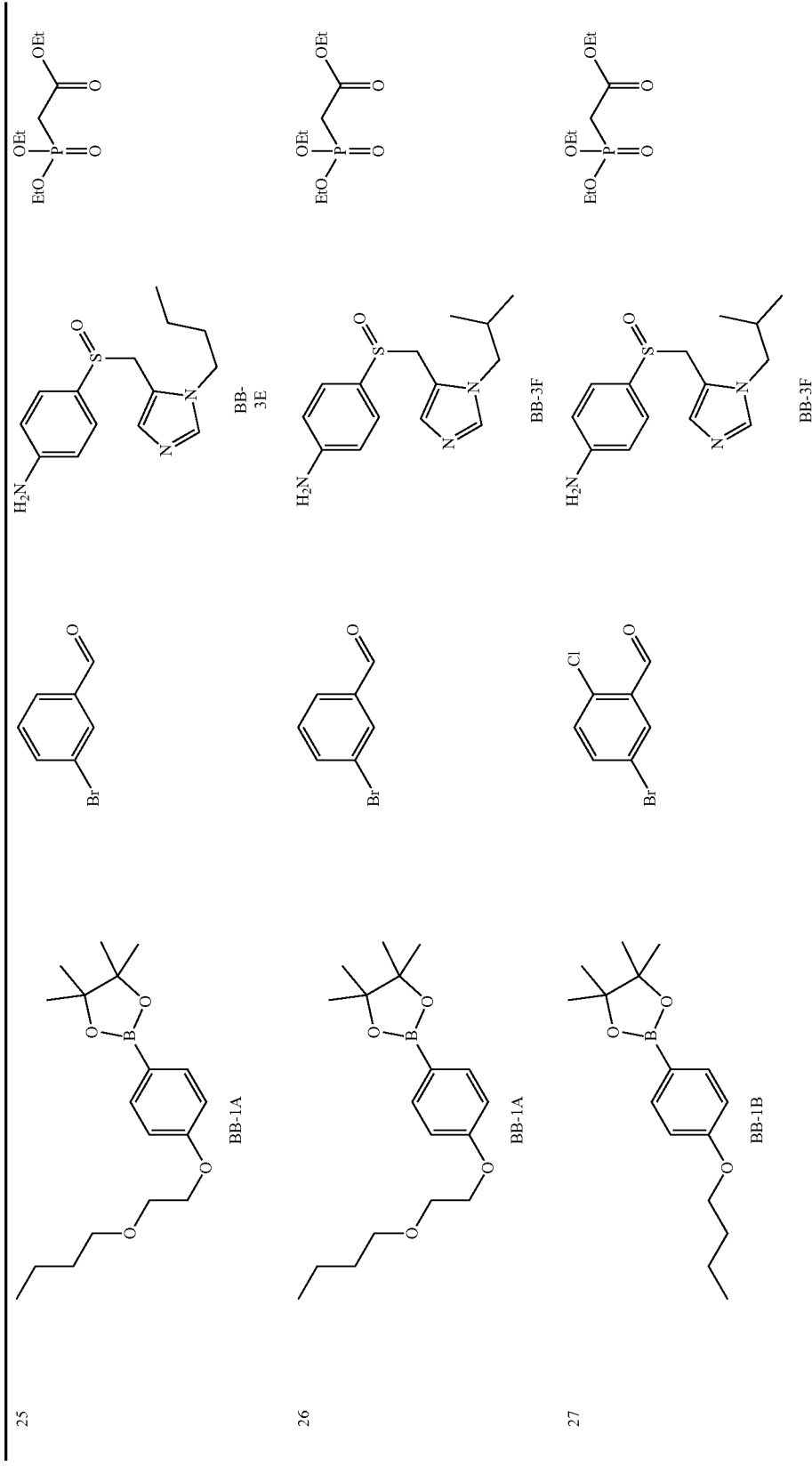

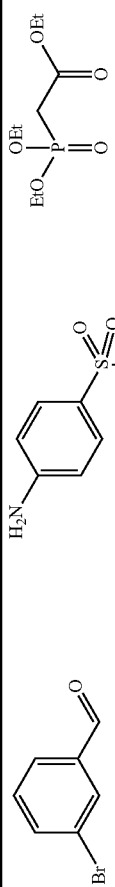
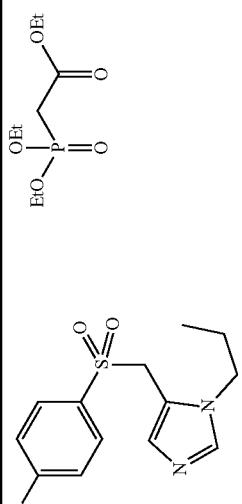
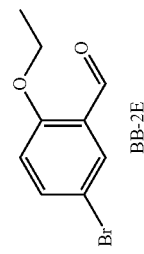
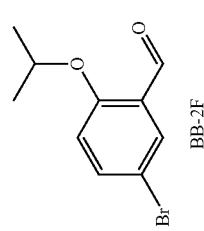
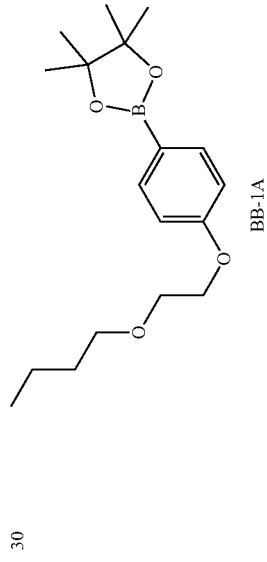
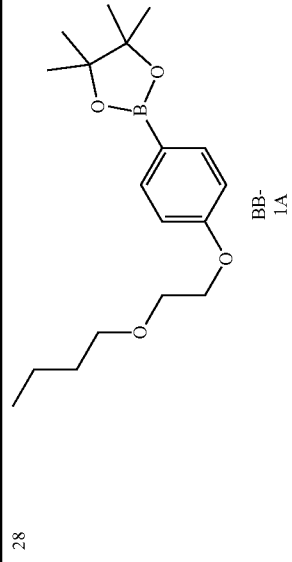
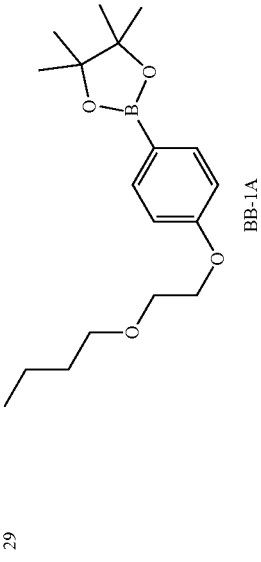

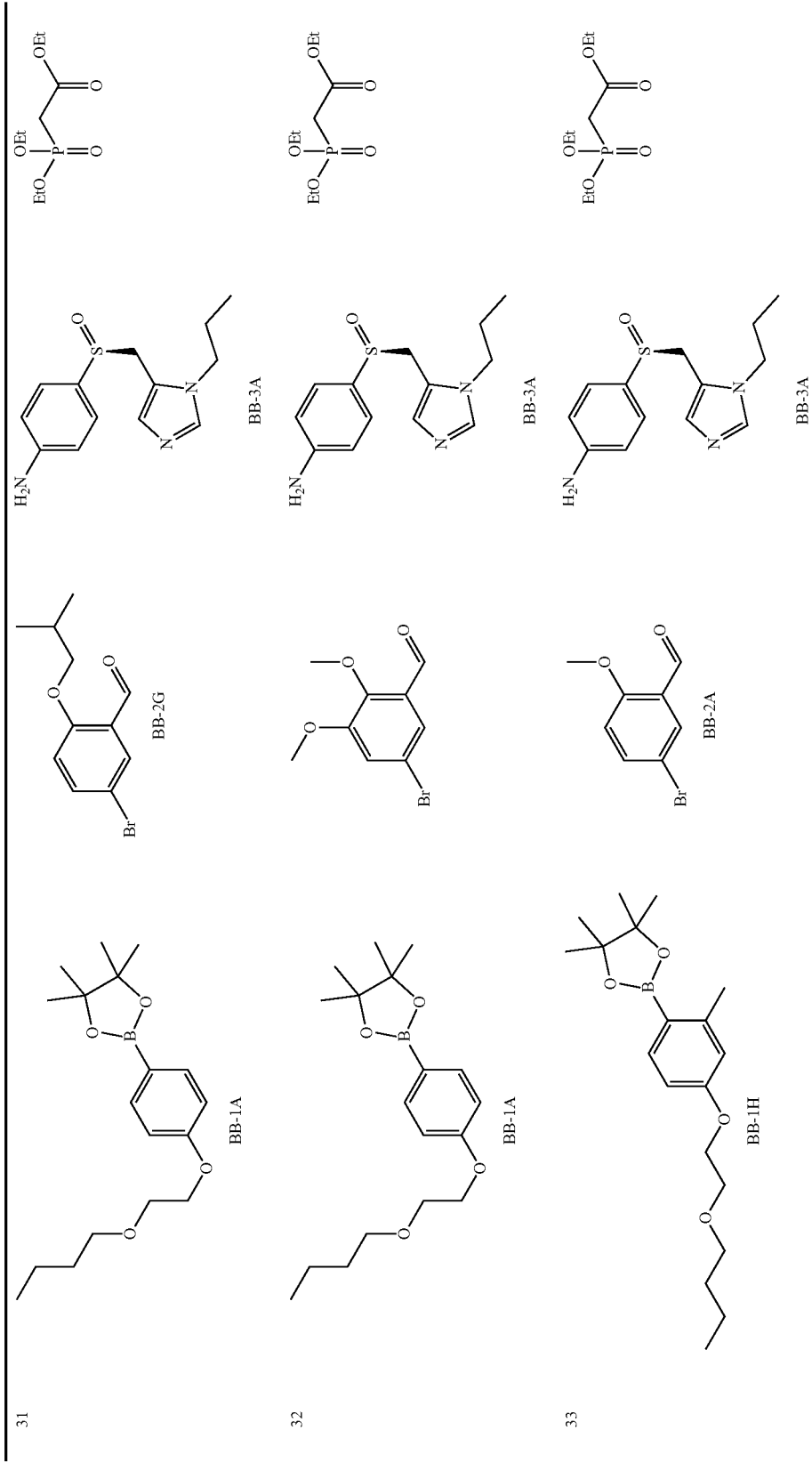

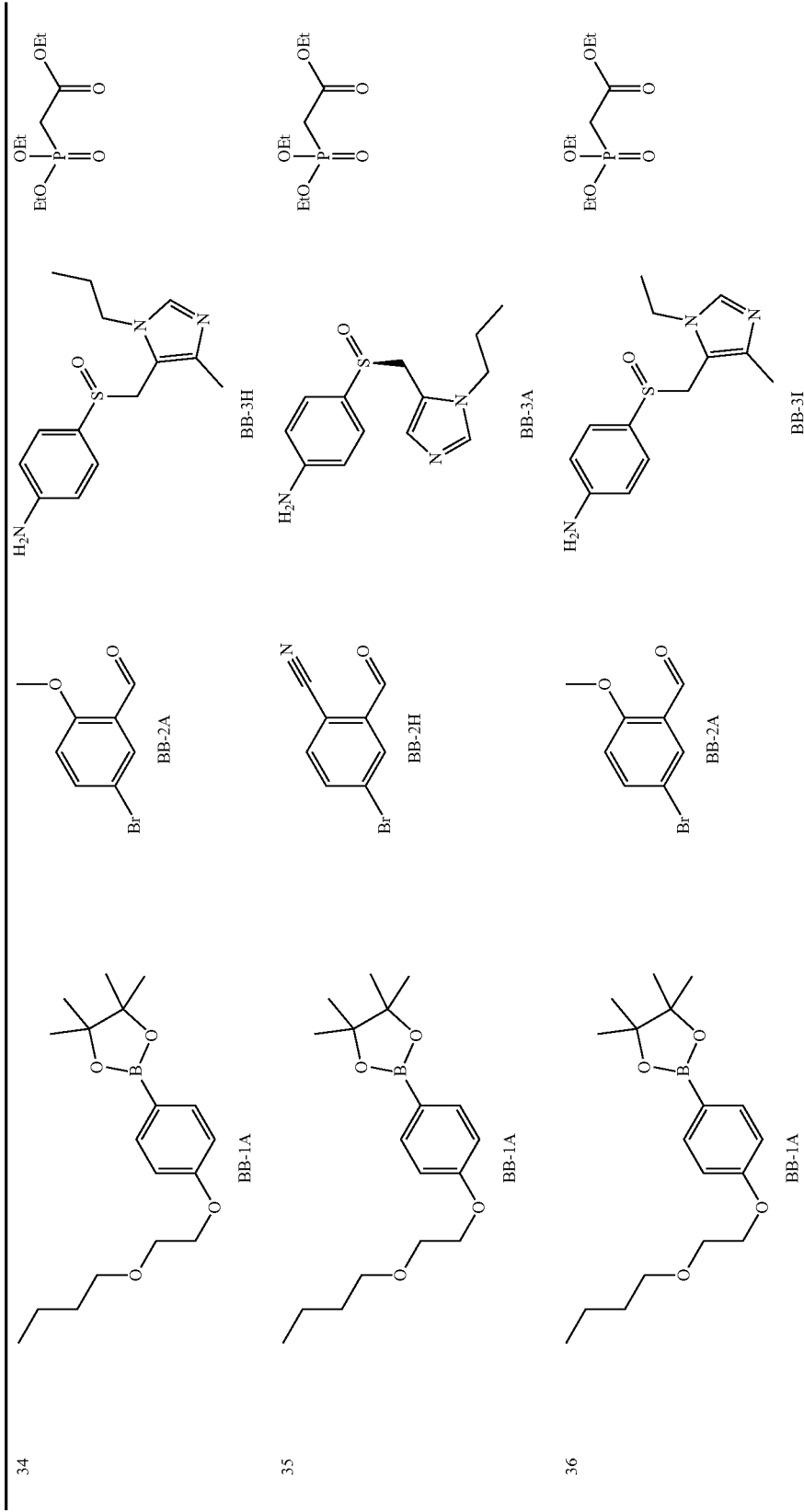

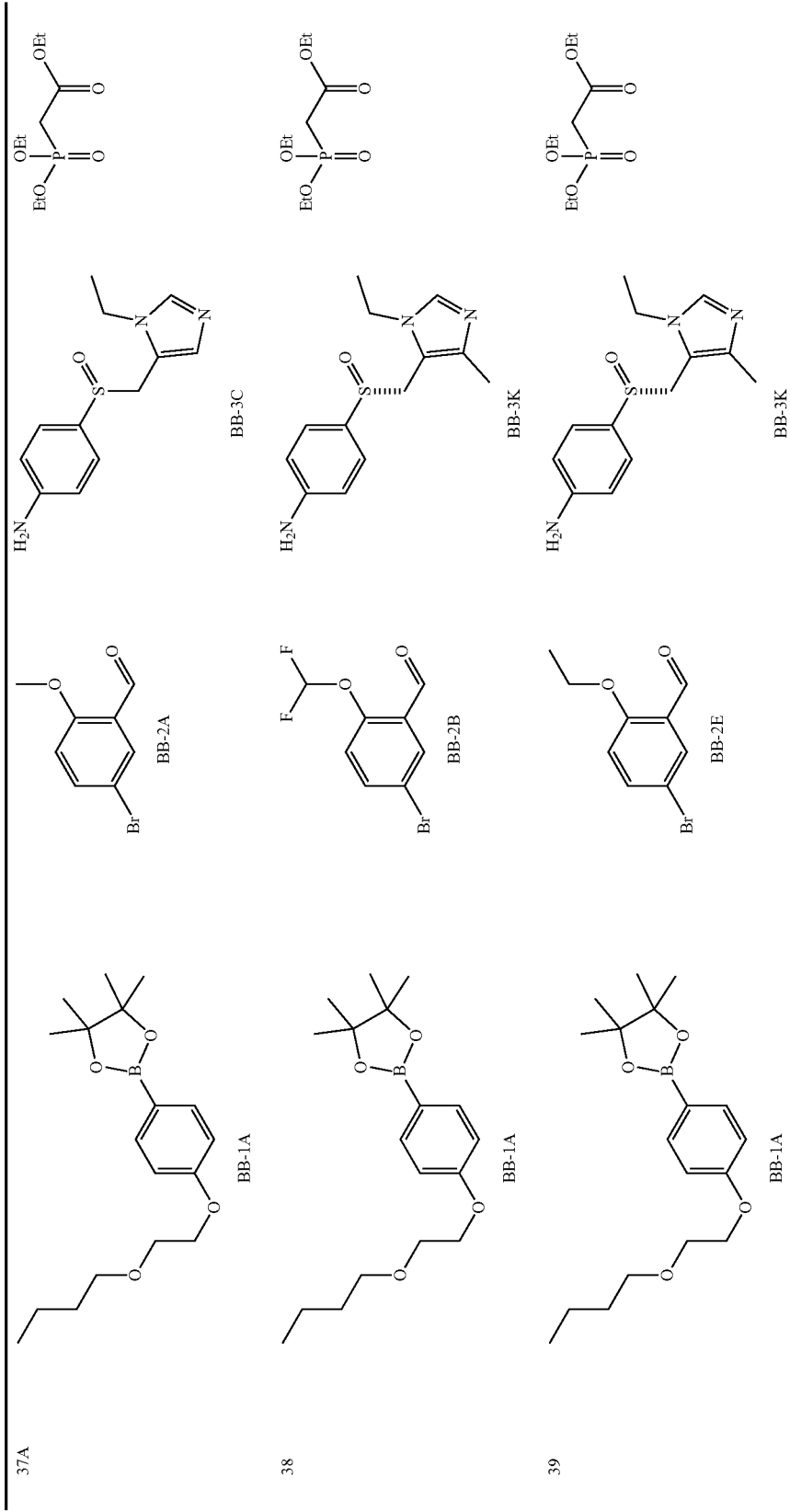

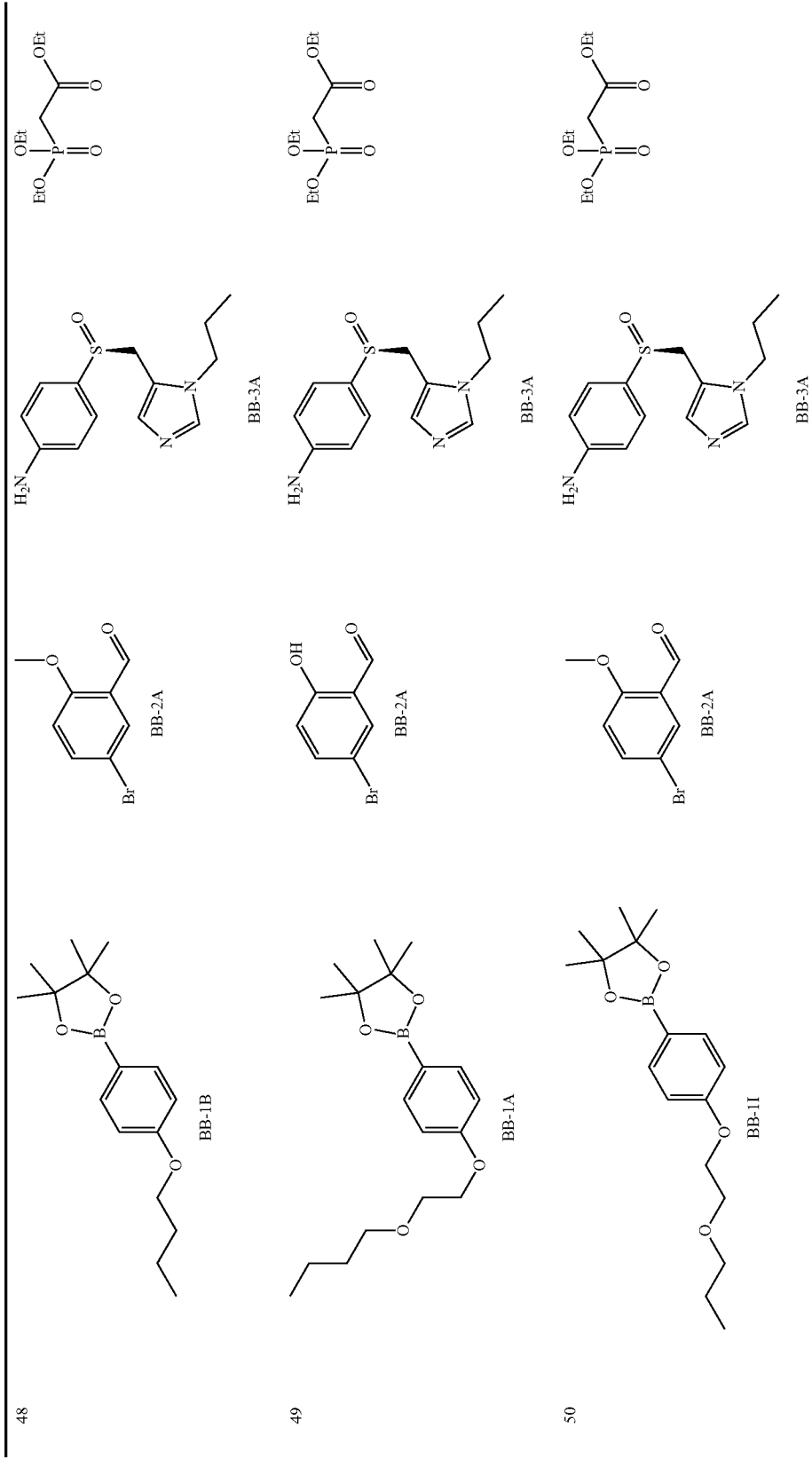

| | | | | |
|---|---|---|---|---|
| 51 | BB-1A | BB-2B | BB-3A | (EtO)₂P(O)CH₂C(O)OEt |
| 52 | BB-1E | BB-2B | BB-3A | (EtO)₂P(O)CH₂C(O)OEt |
| 56 | BB-1A | BB-2A | BB-3N | (EtO)₂P(O)CH₂C(O)OEt |

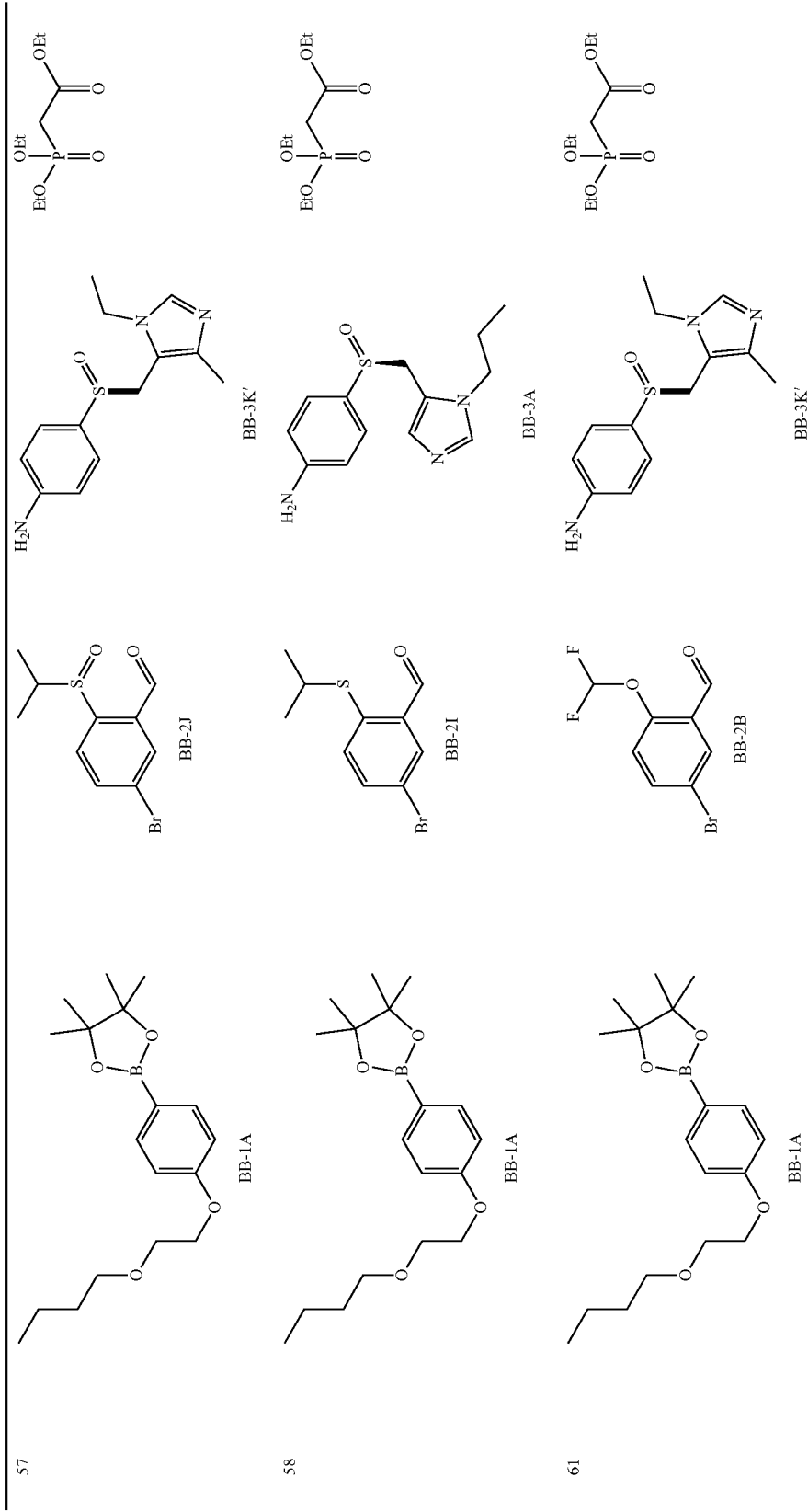

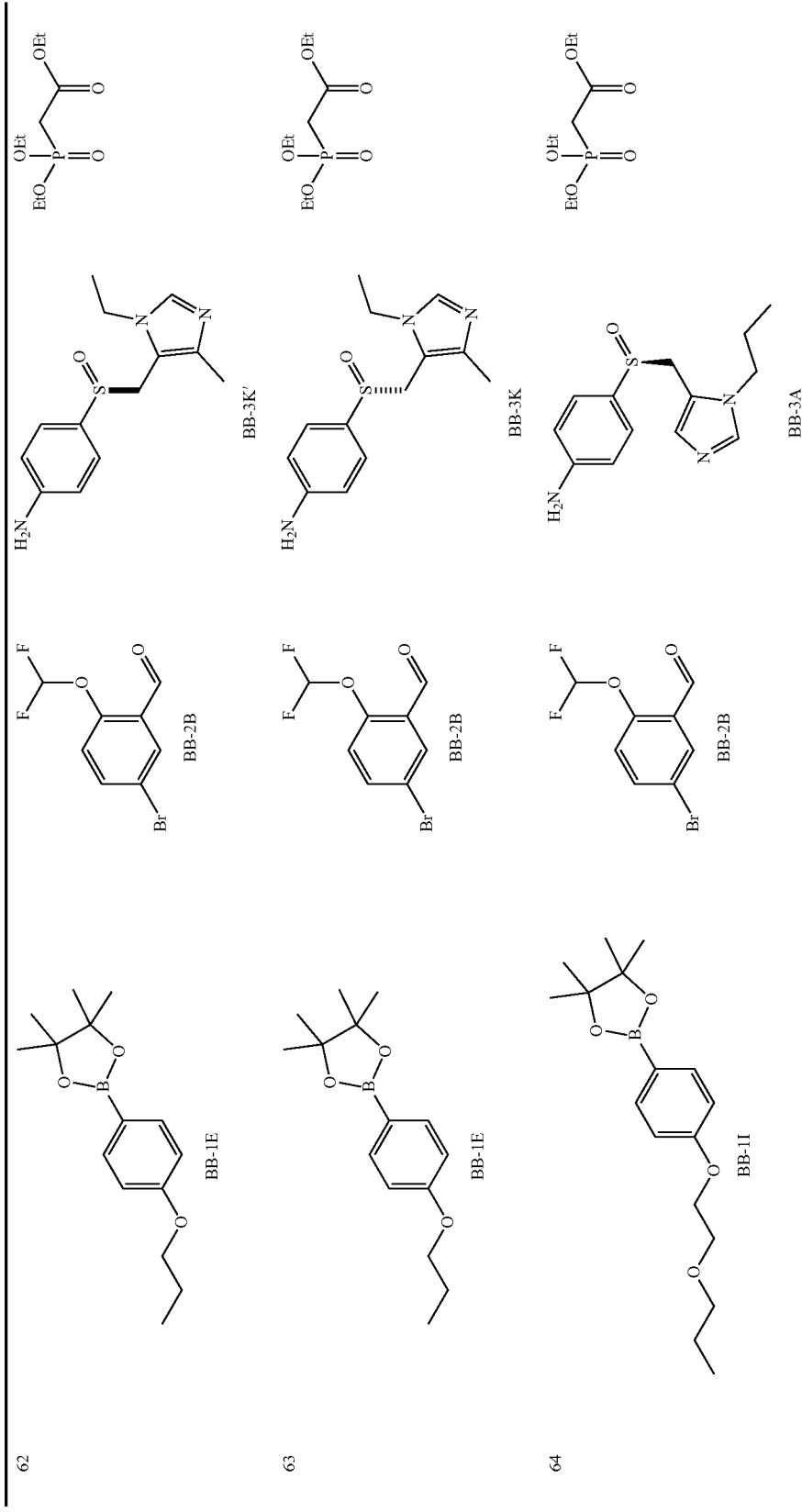

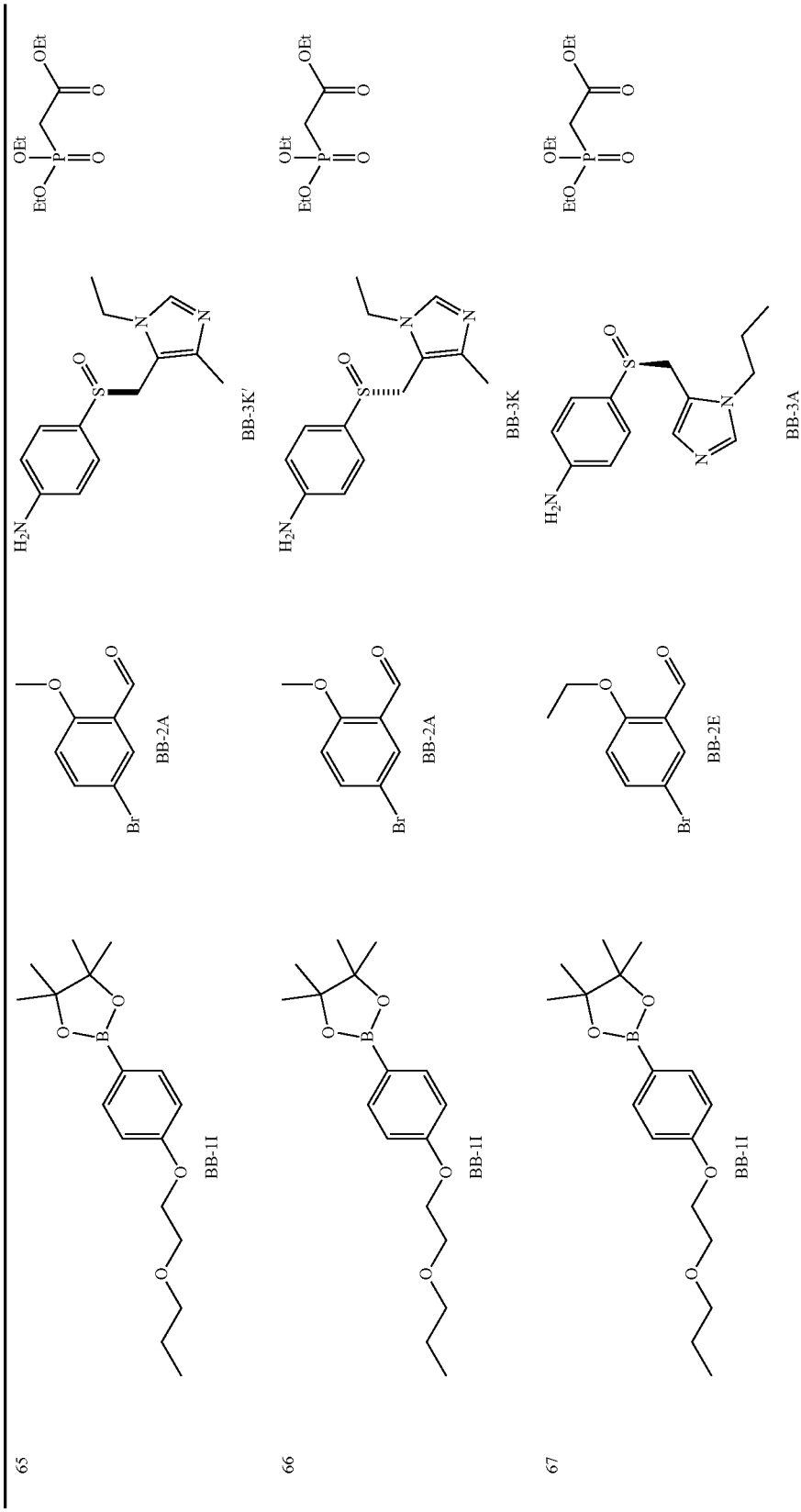

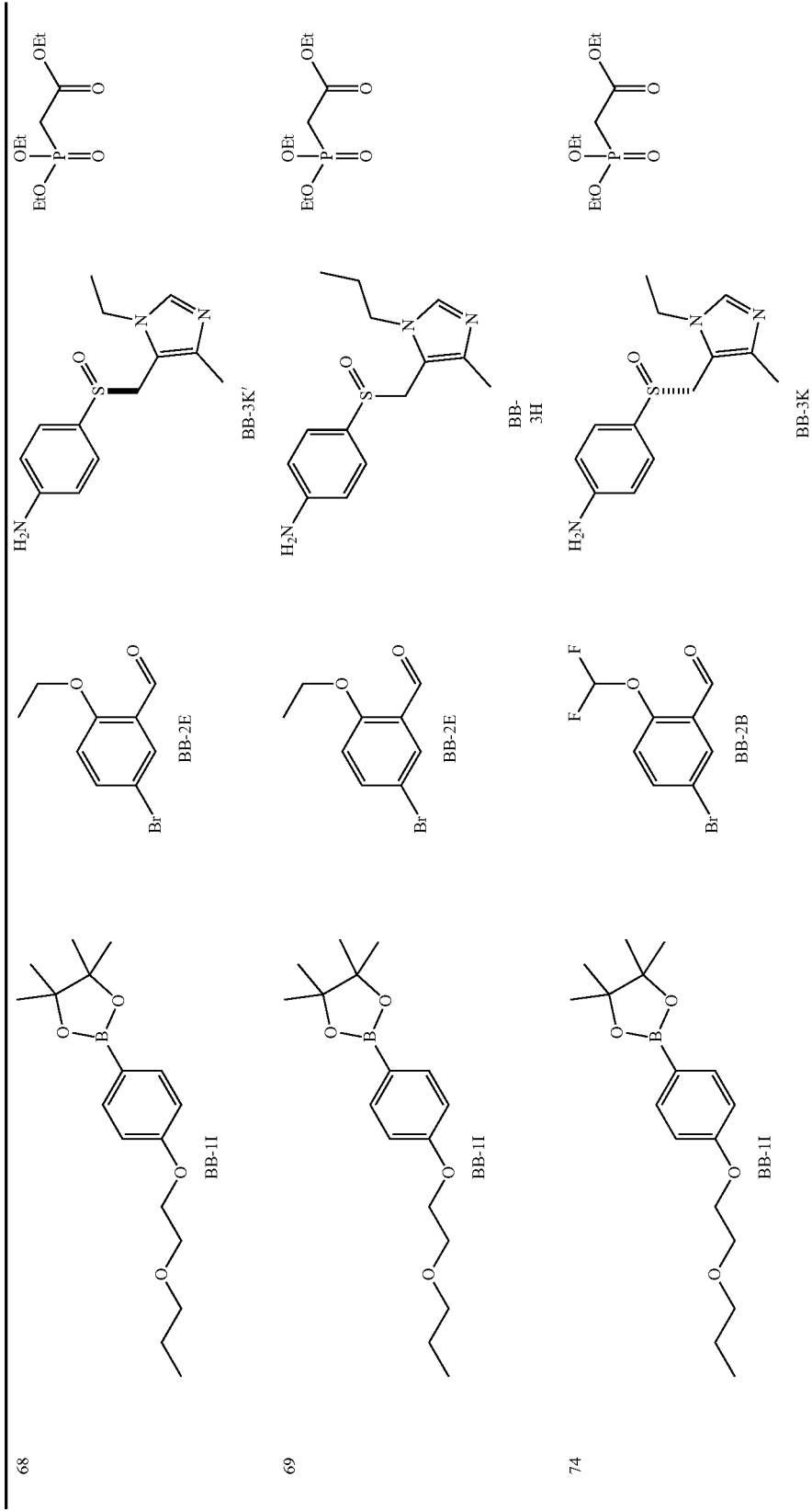

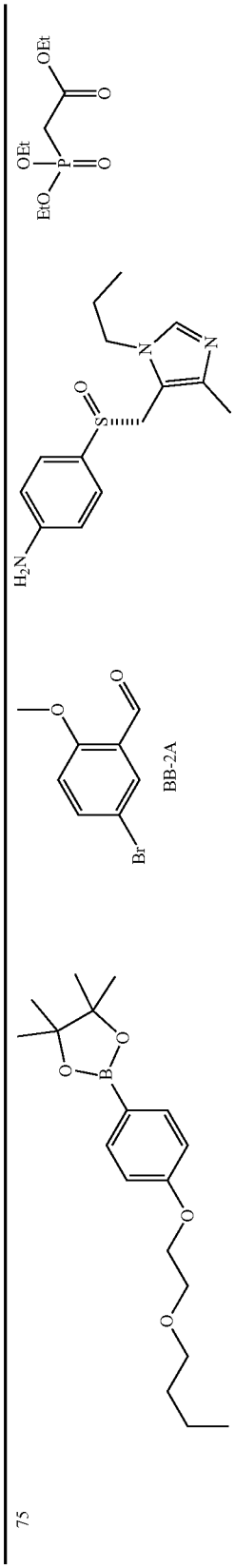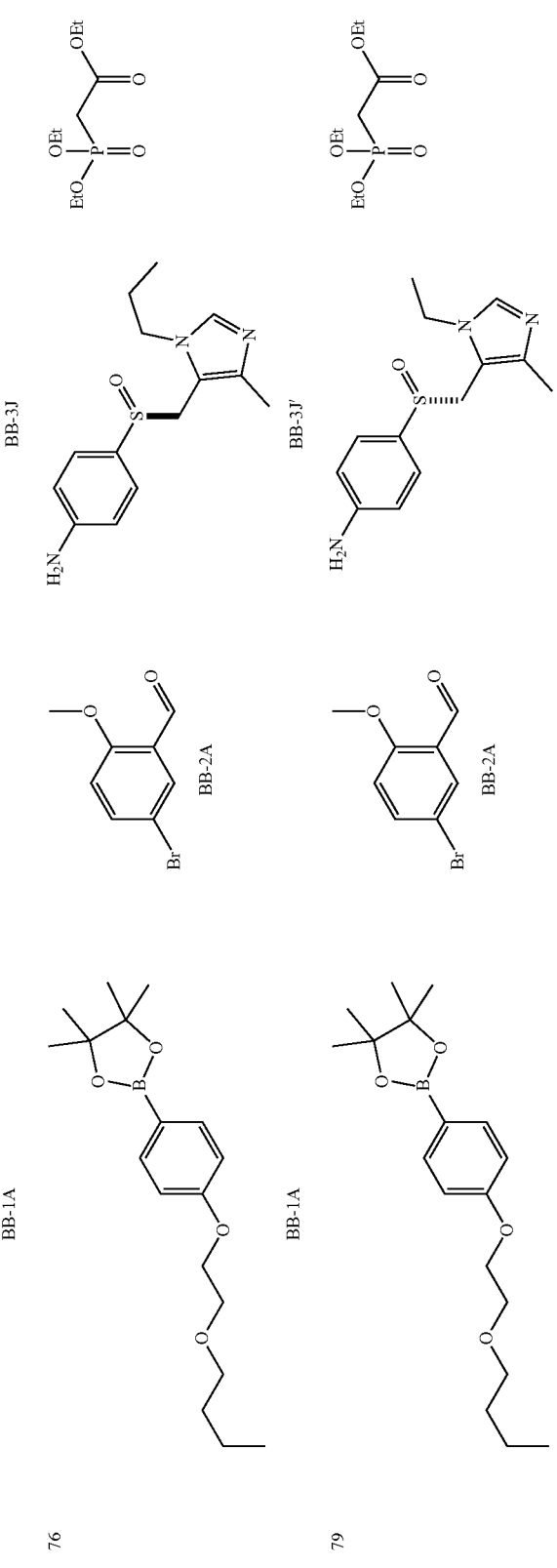

-continued

| | | | | |
|---|---|---|---|---|
| 80 | BB-1I | BB-2B | BB-3J | (EtO)₂P(O)CH₂C(O)OEt |
| 81 | BB-1A | BB-2B | BB-3J | (EtO)₂P(O)CH₂C(O)OEt |
| 82 | BB-1A | BB-2B | BB-3J' | (EtO)₂P(O)CH₂C(O)OEt |
| 85 | BB-1A | BB-2A | BB-3A' | (EtO)₂P(O)CH₂C(O)OEt |

-continued

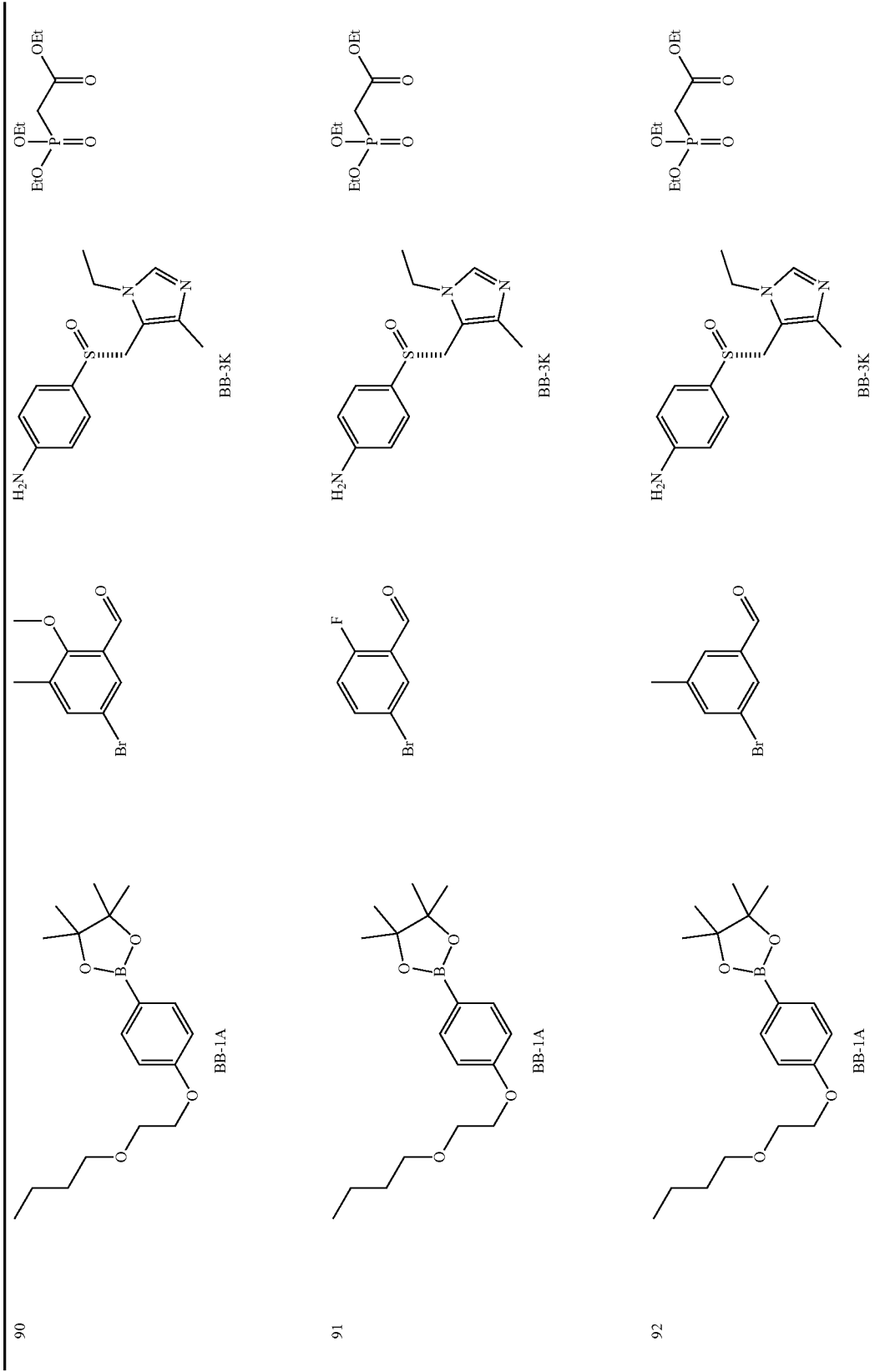

-continued
| Example | Structure | Compound |
|---|---|---|
| 2 | 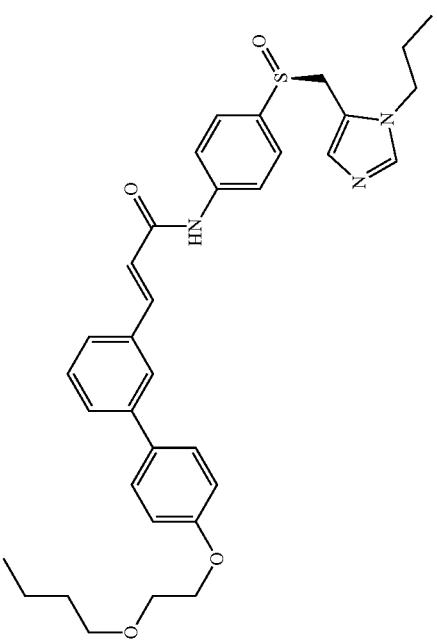 | WX001 |
| 3 | 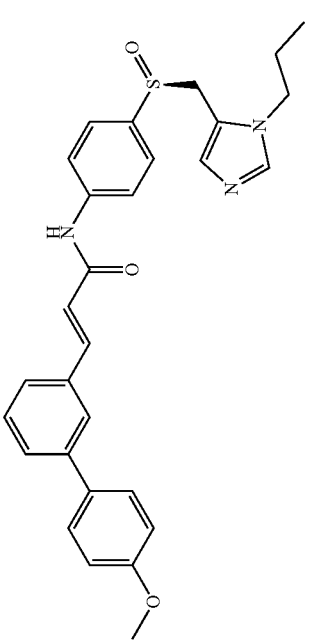 | WX002 |

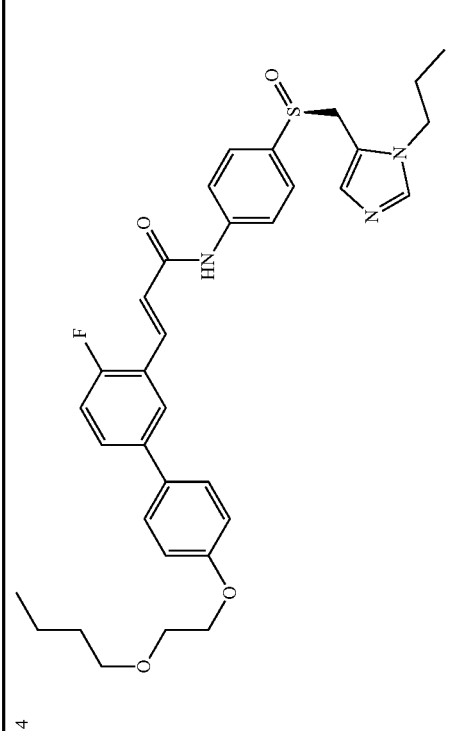
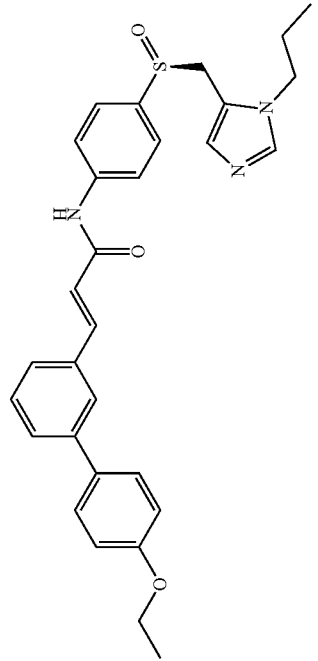
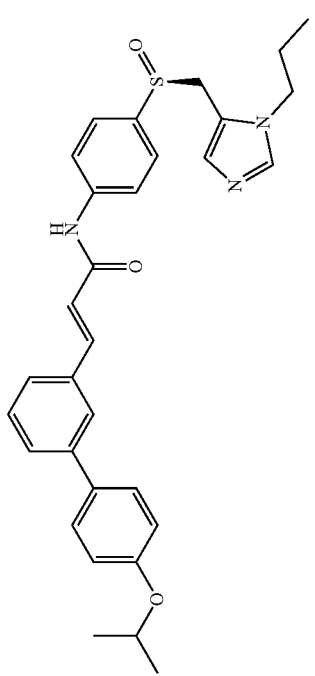

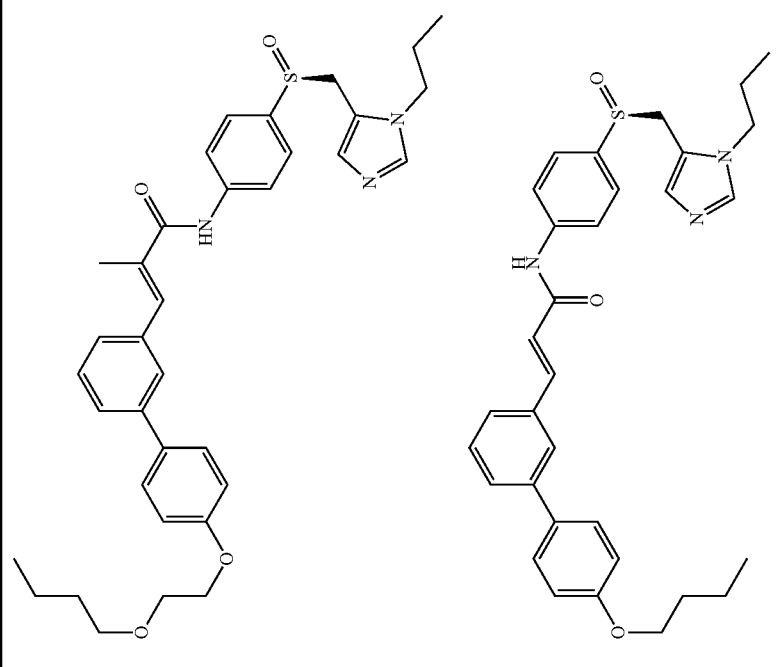

| | | |
|---|---|---|
| 9 | WX010 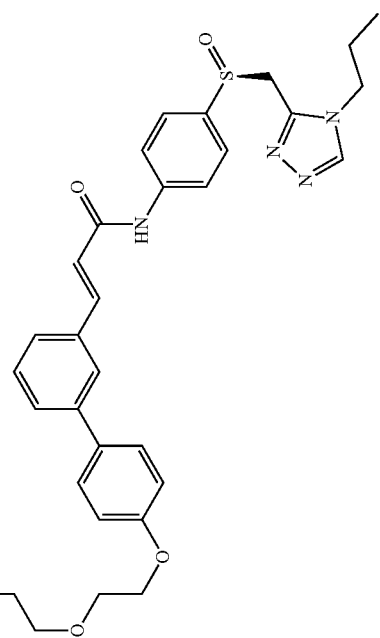 | 10 | WX012 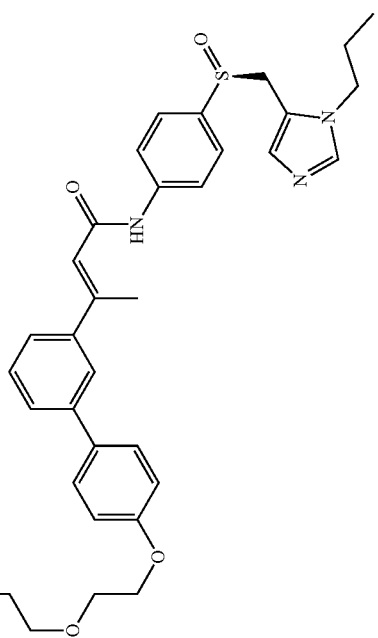 |

-continued
WX013
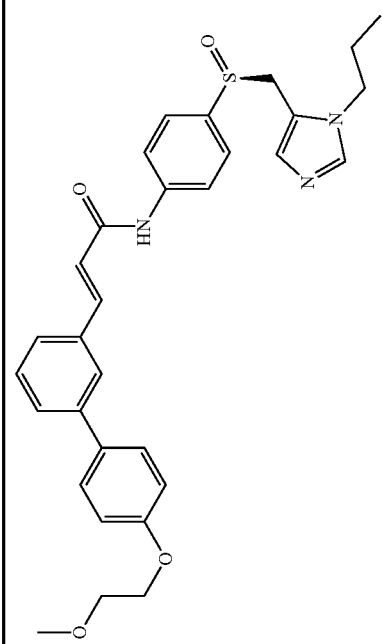
11
WX014
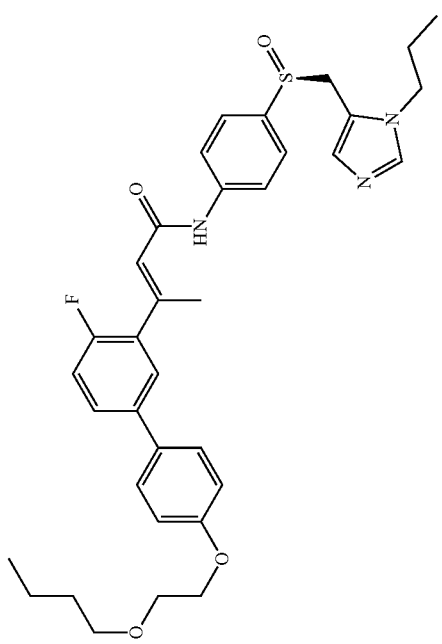
12

| 13 | WX015 | 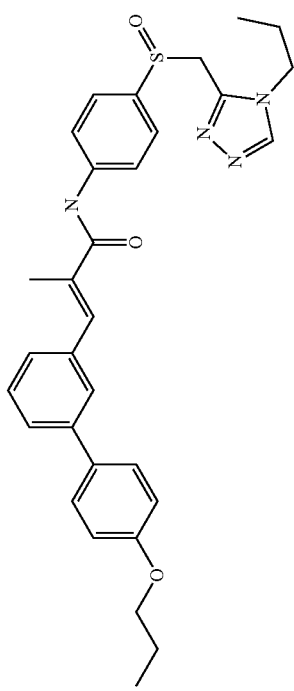 |
| 14 | WX016 | 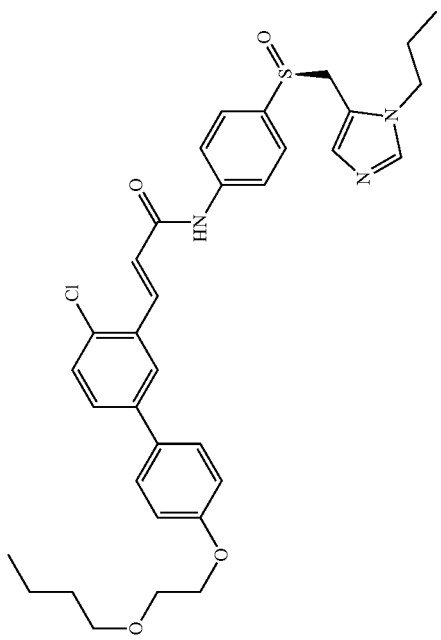 |

| 15 | WX018 | 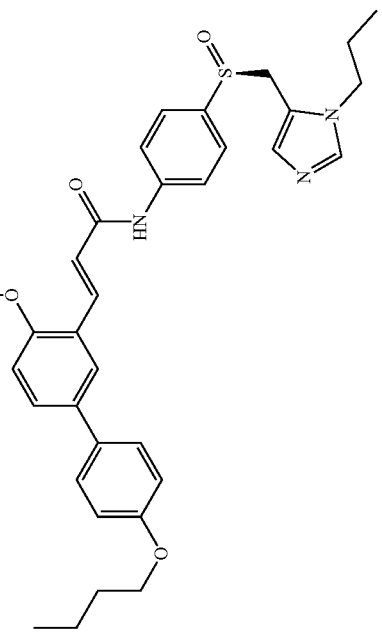 |
| 16 | WX019 | 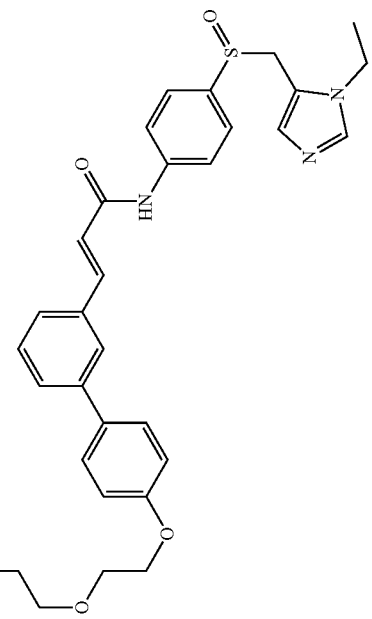 |

| 17 | WX020 | 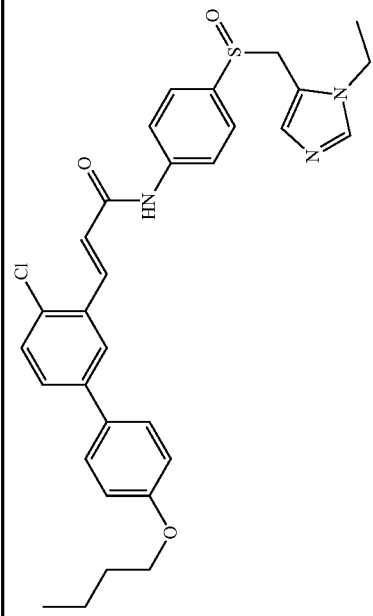 |
| 18 | WX021 | 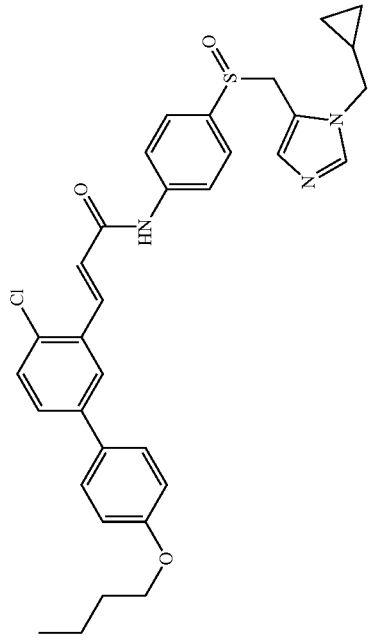 |
| 19 | WX022 | 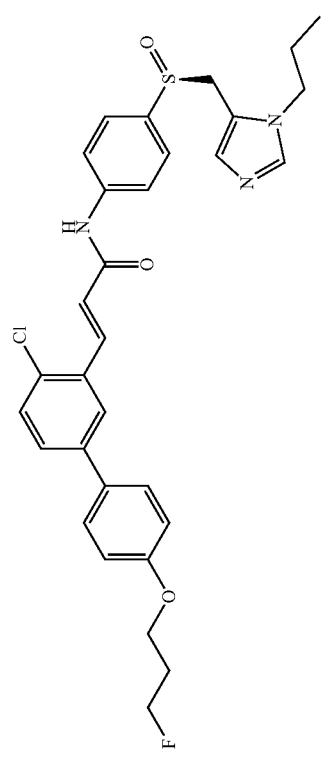 |

| 20 | WX023 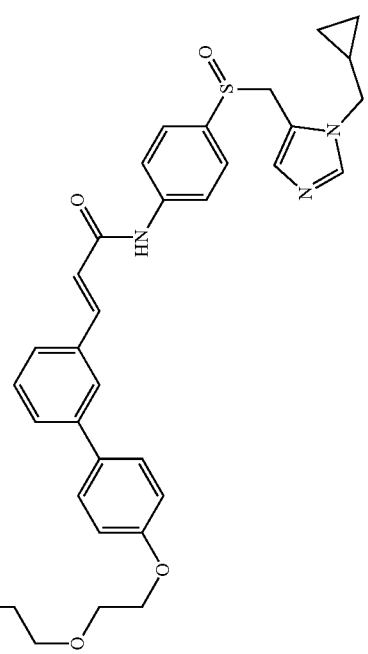 |
| 21 | WX024 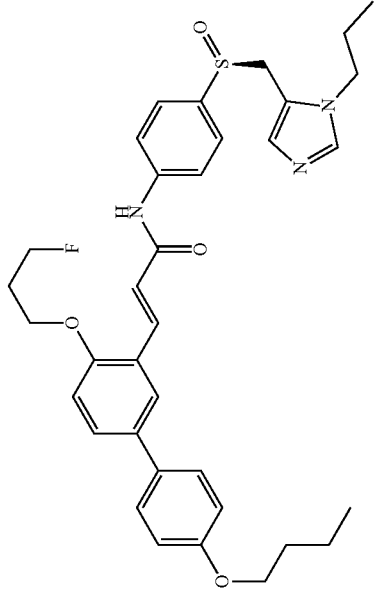 |

| | | |
|---|---|---|
| 22 | 23 | 24 |
| WX025 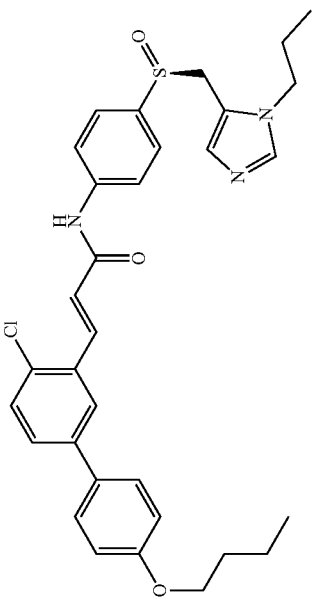 | WX026 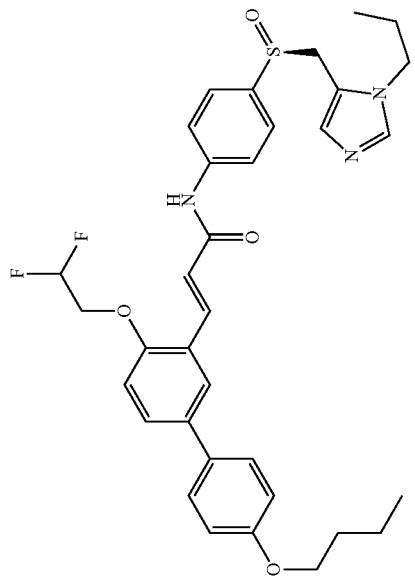 | WX027 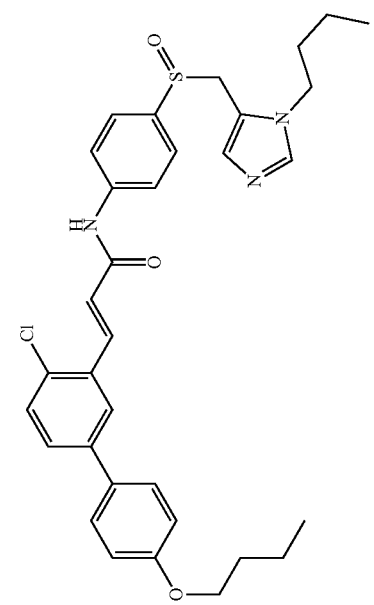 |

-continued
| | |
|---|---|
| 25 WX028 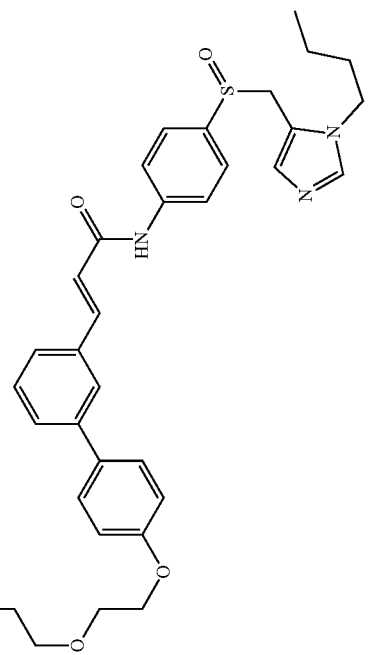 | 26 WX029 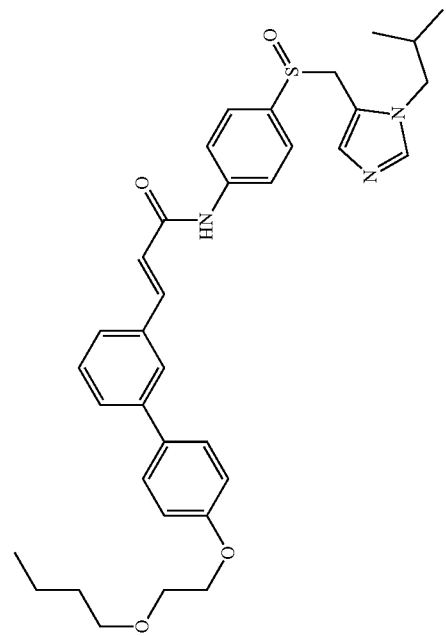 |

| | | |
|---|---|---|
| 27 | 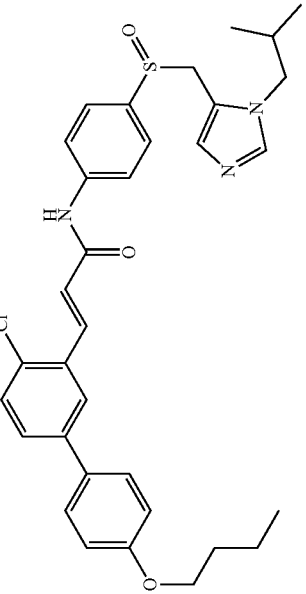 | WX030 |
| 28 | 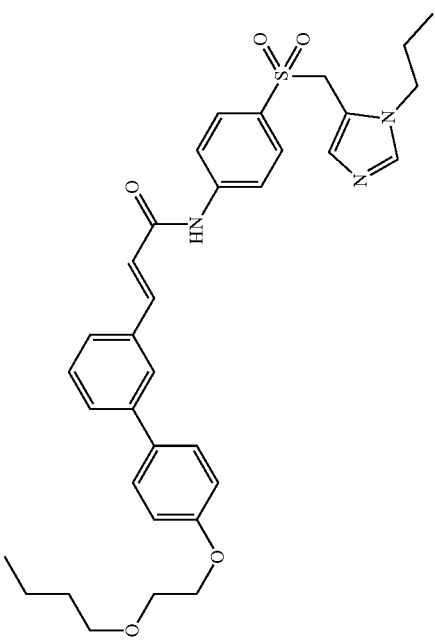 | WX031 |

| | | |
|---|---|---|
| 29 | WX032 | 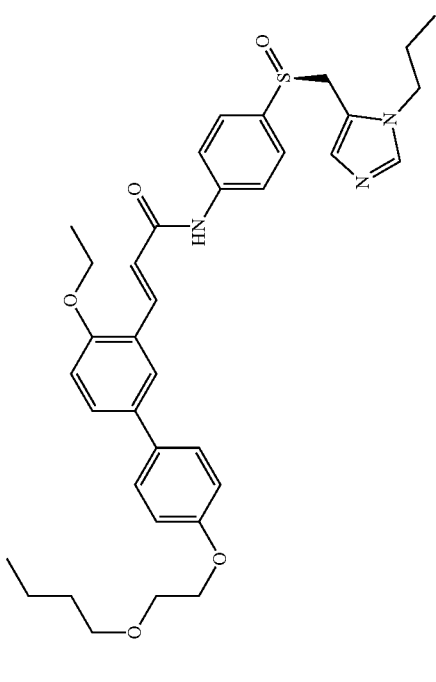 |
| 30 | WX033 | 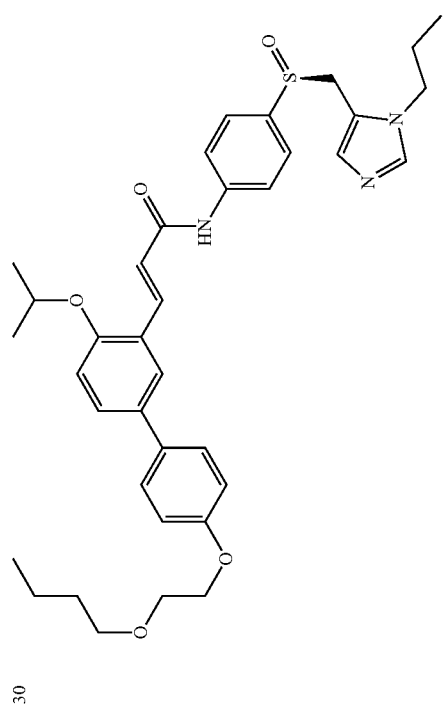 |

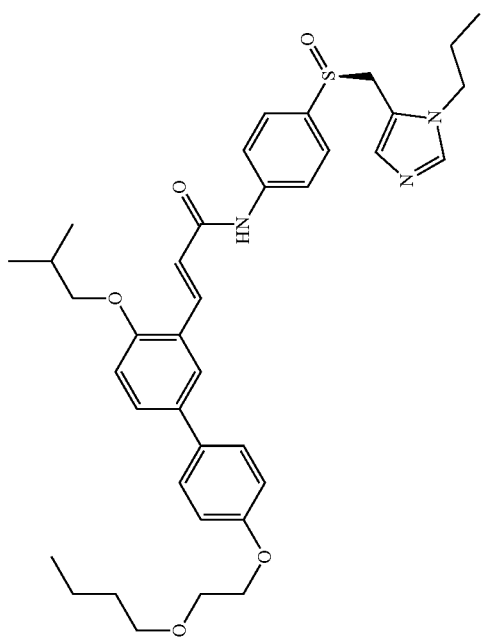
31 WX034
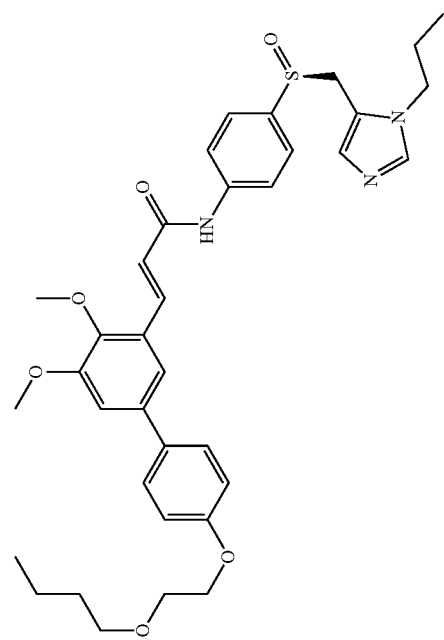
32 WX035

-continued
WX036
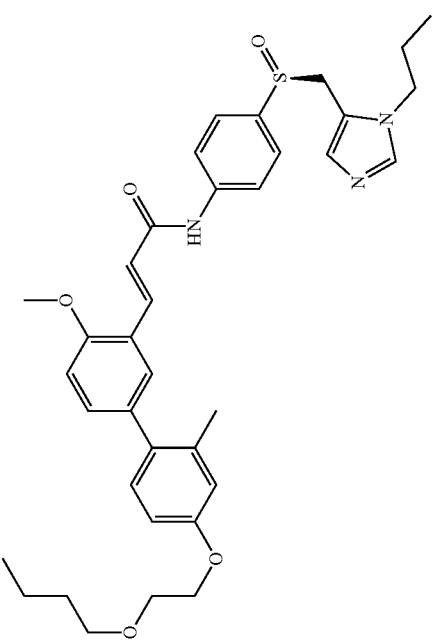
33
WX038
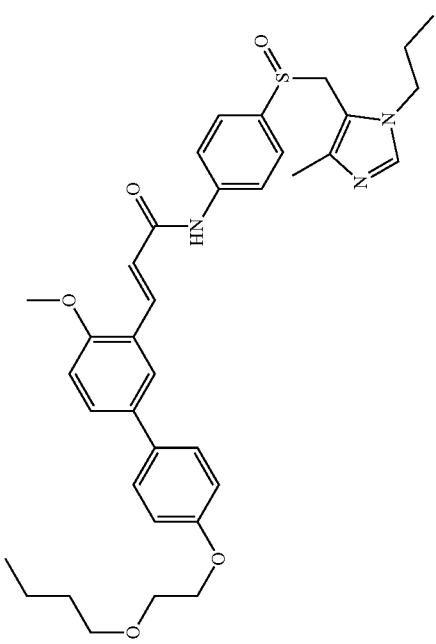
34

-continued
| 35 | WX044 | 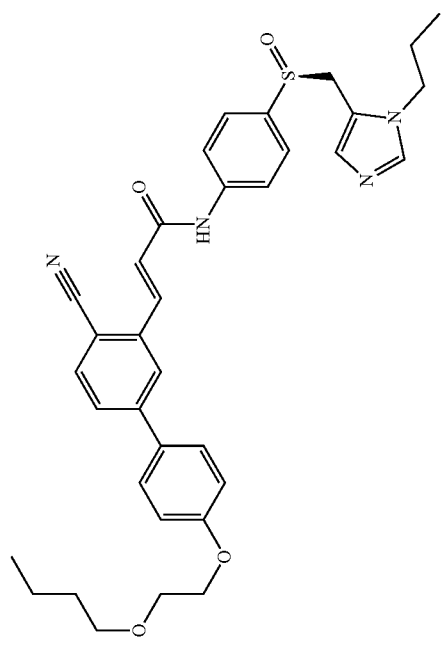 |
| 36 | WX045 | 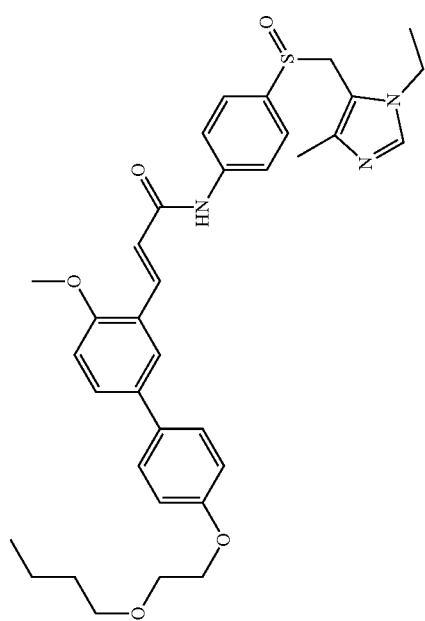 |

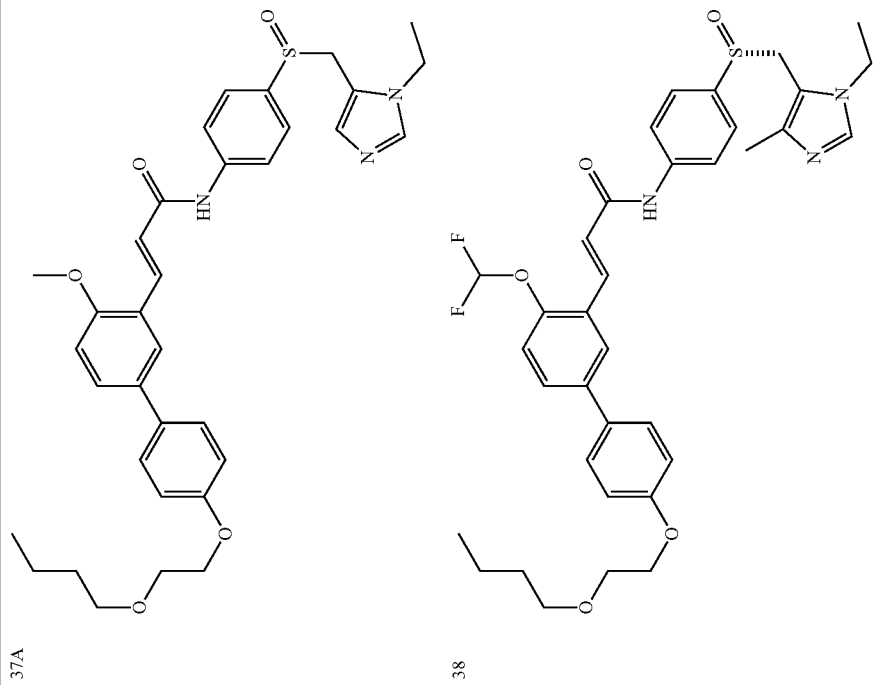

-continued
| WX047 | 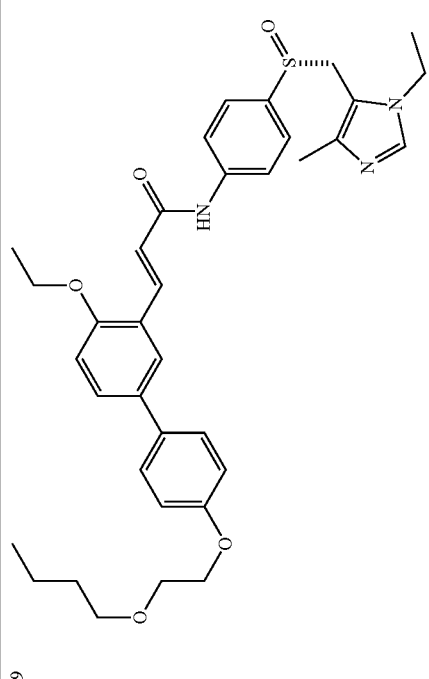 |
| 39 | |
| WX048 | 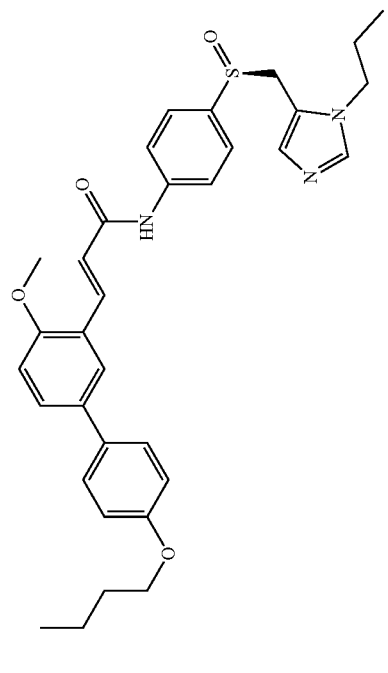 |
| 48 | |

| | WX049 | | WX050 |
|---|---|---|---|
| 49 | 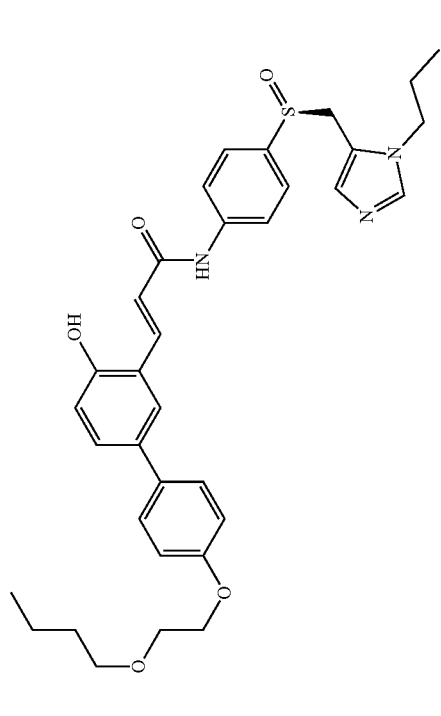 | 50 | 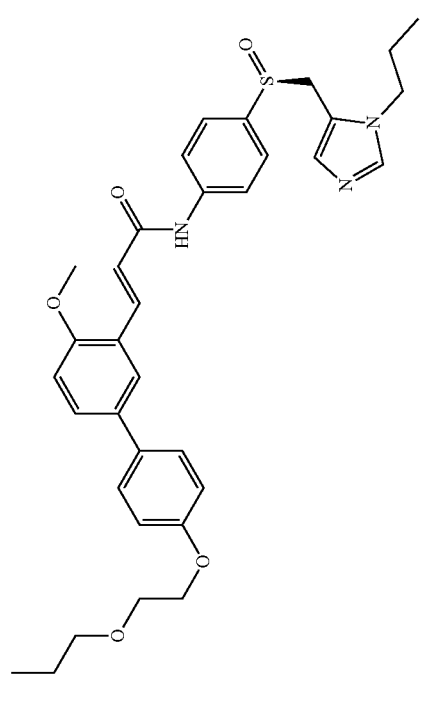 |

-continued
| WX051 | WX052 |
|---|---|
| 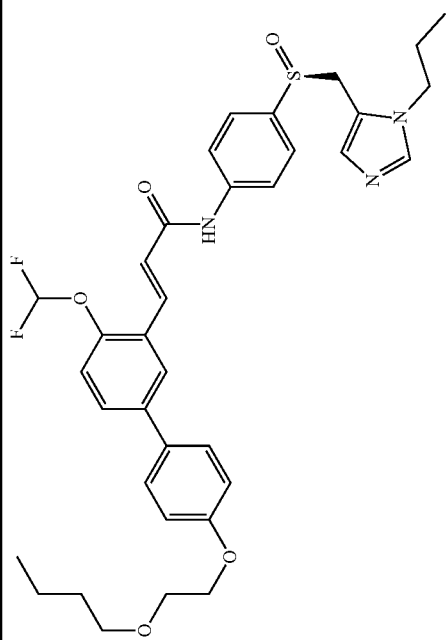 | 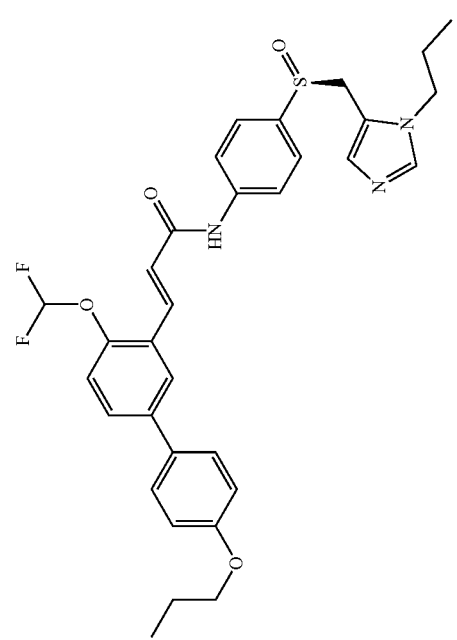 |
| 51 | 52 |

-continued
| WX056 | WX057 | WX058 |
|---|---|---|
| 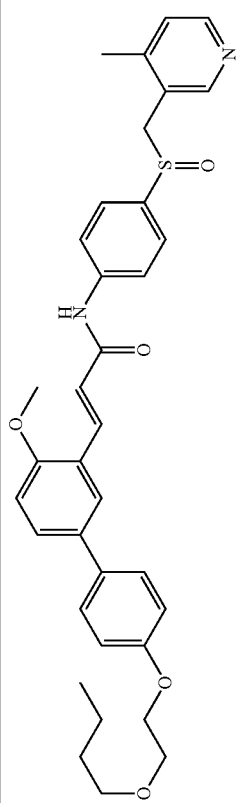 | 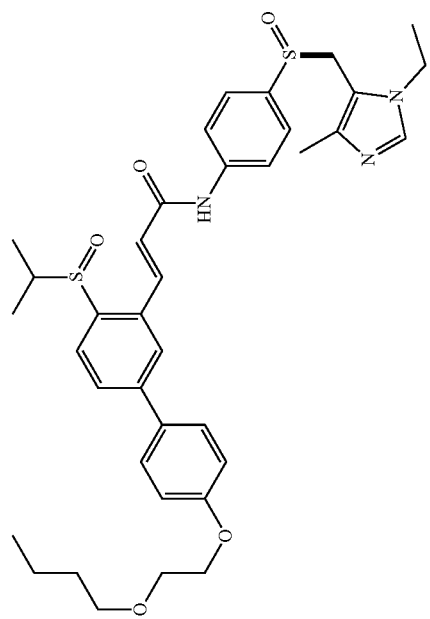 | 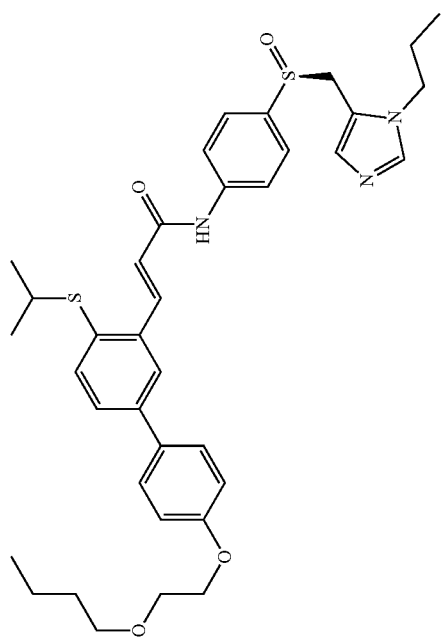 |
| 56 | 57 | 58 |

WX061
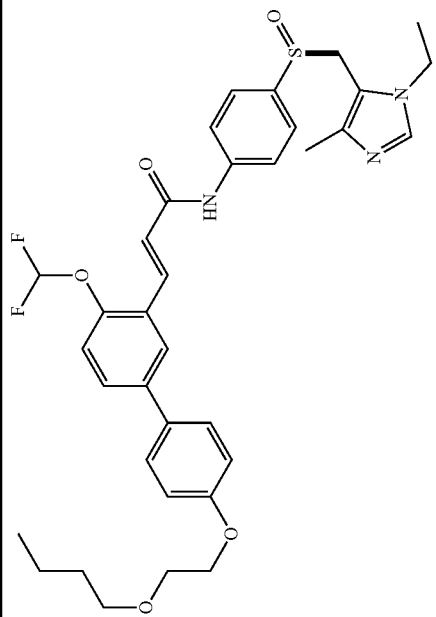
61
WX062
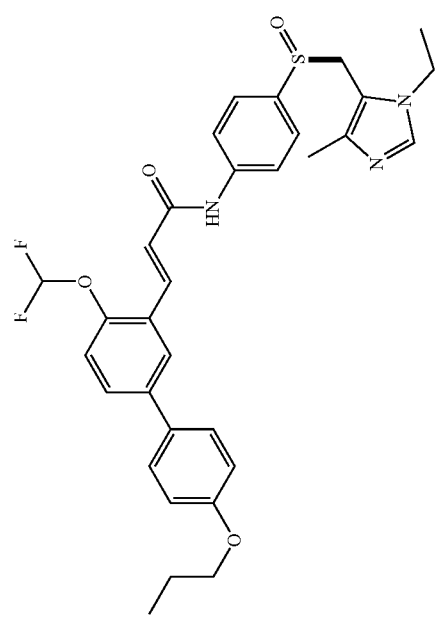
62

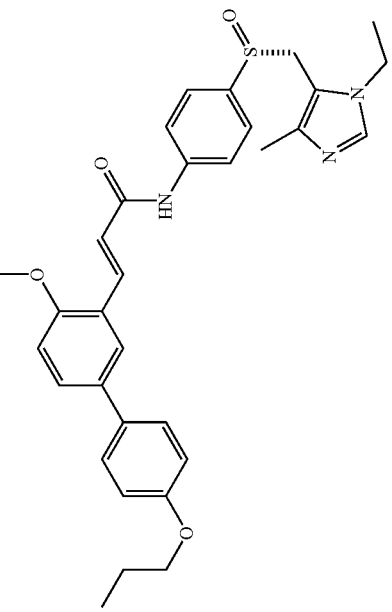
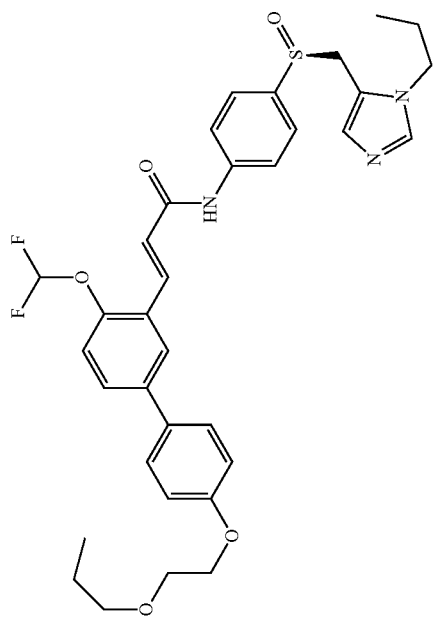

-continued
WX065
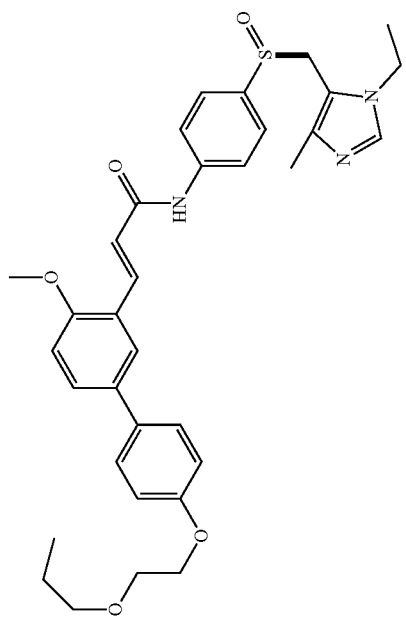
65
WX066
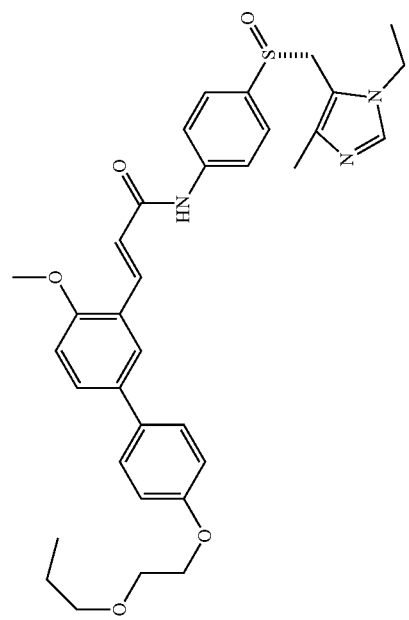
66

| 67 | WX067 | 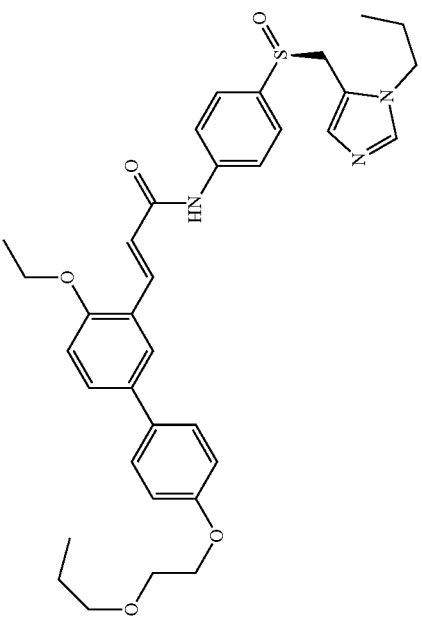 |
| 68 | WX068 | 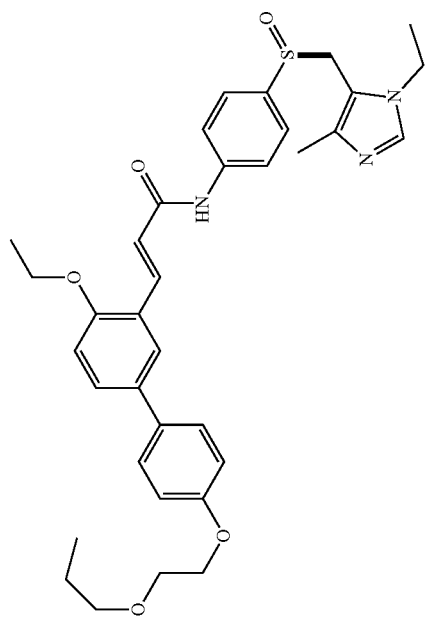 |

-continued
| WX069 | WX074 |
|---|---|
| 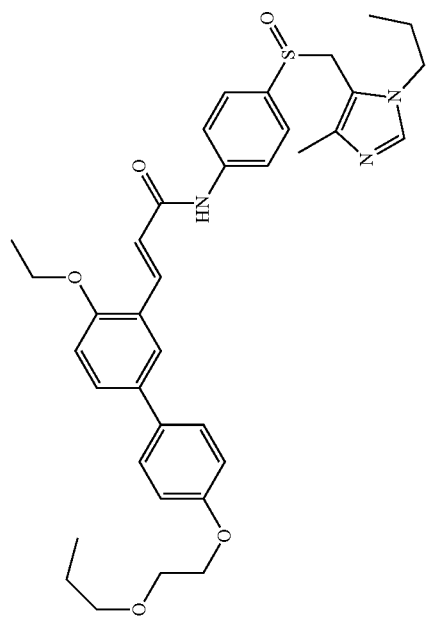 | 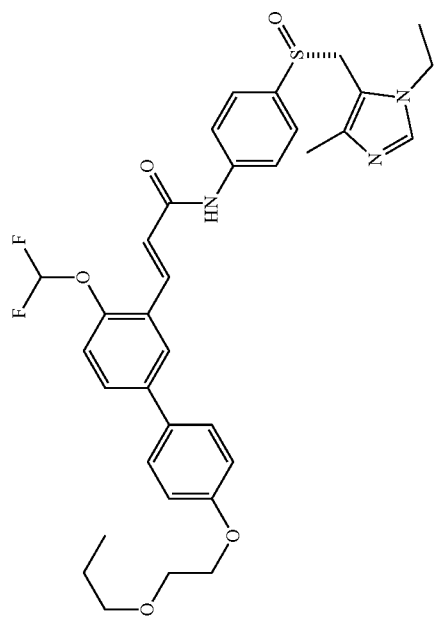 |
| 69 | 74 |

-continued
| WX075 | WX076 |
|---|---|
| 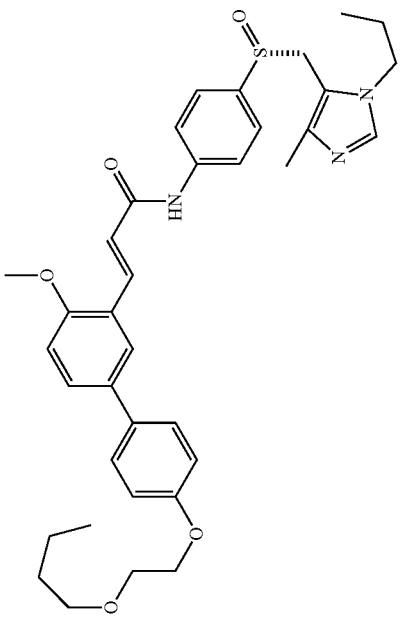 | 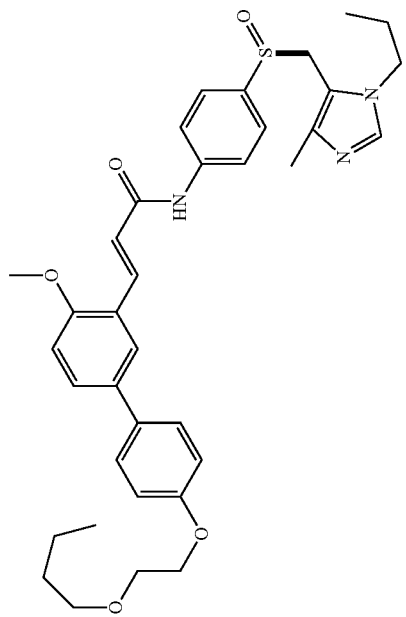 |
| 75 | 76 |

-continued
| | |
|---|---|
| WX079 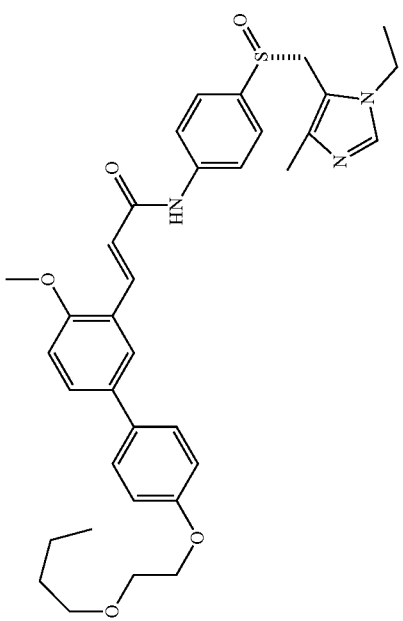 79 | WX080 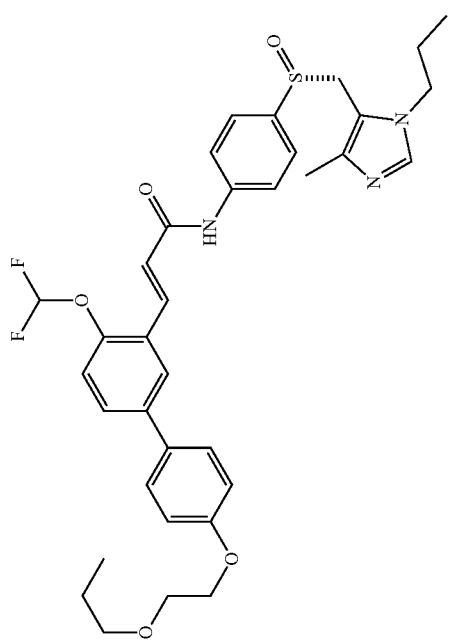 80 |

| 81 | WX081 | 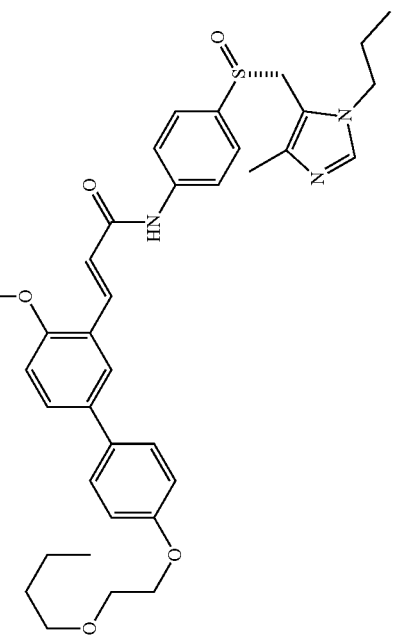 |
| 82 | WX082 | 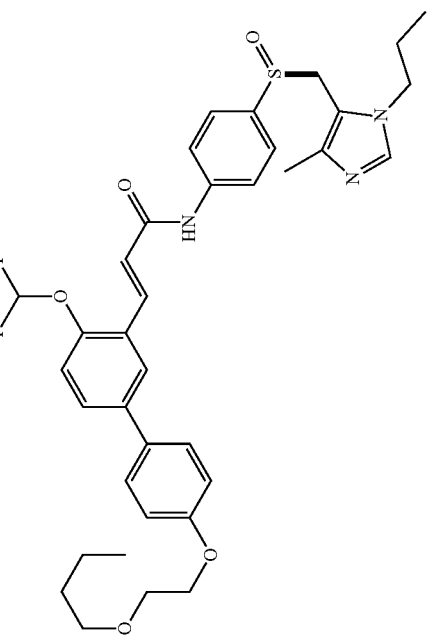 |

-continued
| | |
|---|---|
| WX085 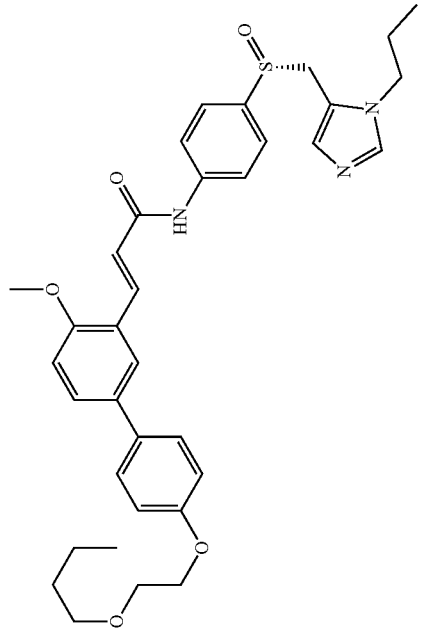 85 | WX086 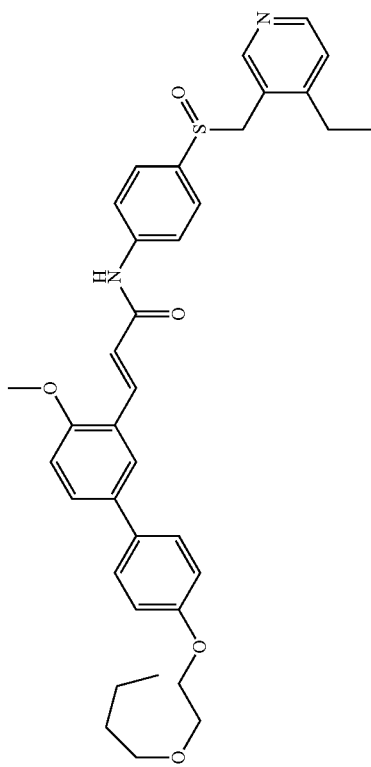 86 |

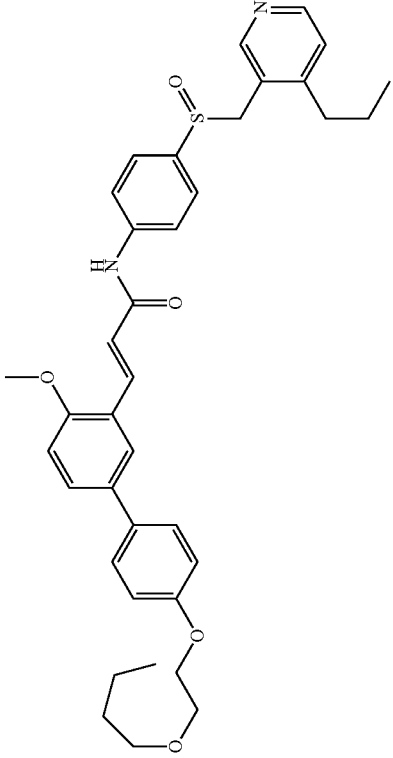
87 WX087
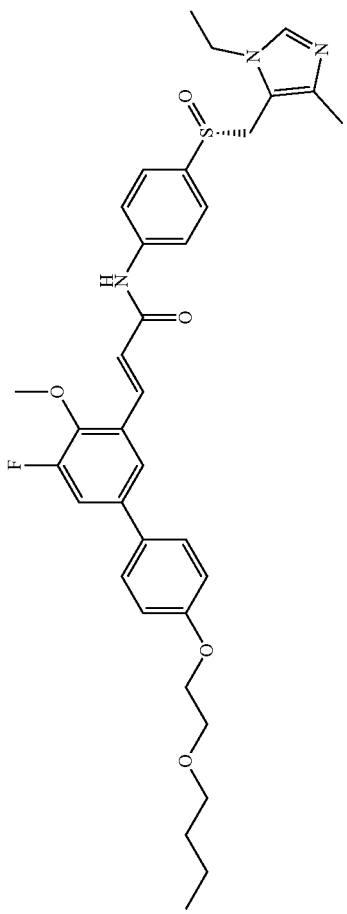
88 WX088
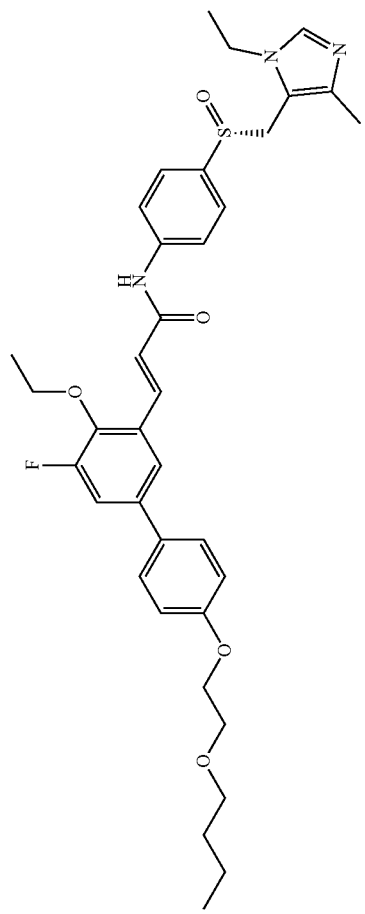
89 WX089

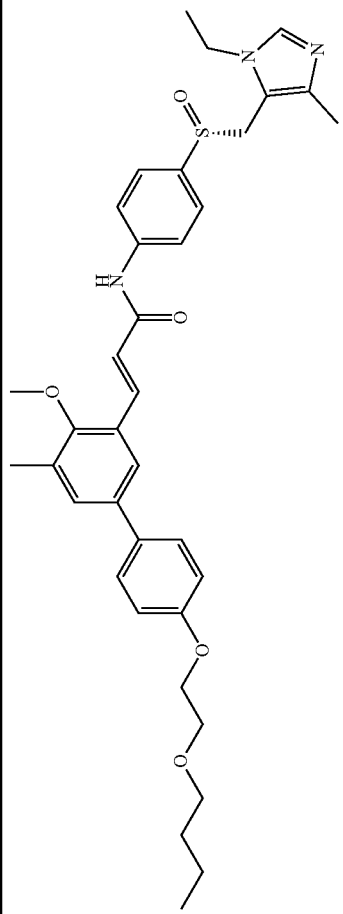
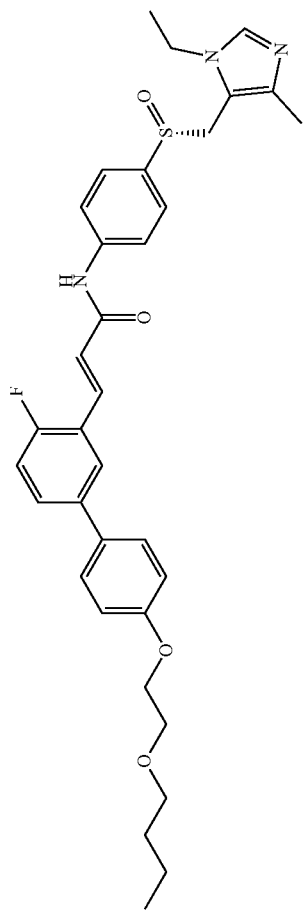
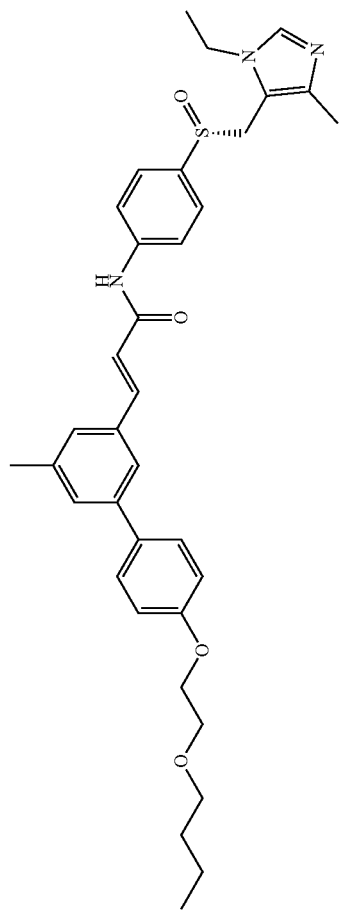

Example 37: WX039, WX040

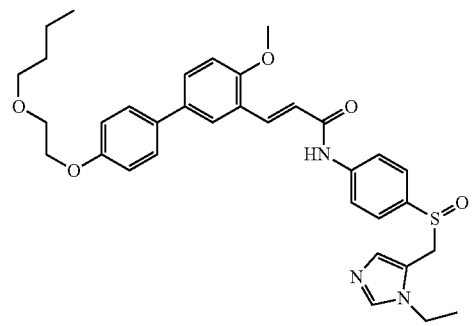

WX039-1

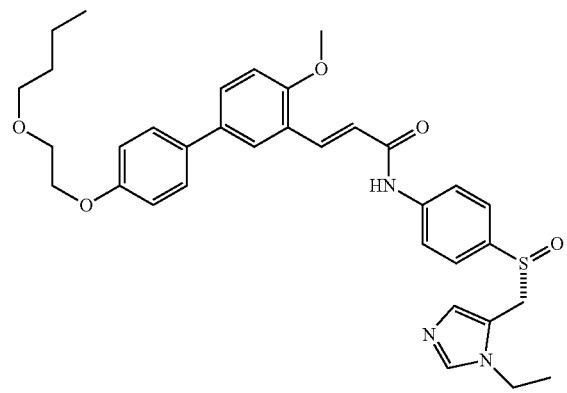 [SMILES: CCCCOCCOc1ccc(-c2ccc(OC)c(/C=C/C(=O)Nc3ccc(S(=O)Cc4cncn4CC)cc3)c2)cc1]

WX039

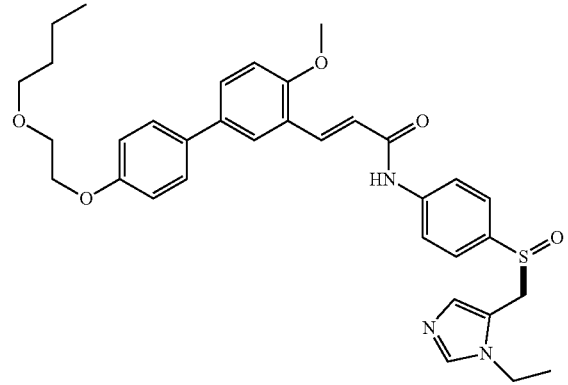

WX040

Step 1: Synthesis of Compound WX039 and WX040

Compound WX039-1 was isolated by supercritical fluid chromatography (separation condition: Column: Chiralpak AS-3 50×4.6 mm I.D., 3 μm, mobile phase: 40% of ethanol (0.05% DEA) in $CO_2$, flow rate: 2.5 mL/min, column temperature: 40° C., wavelength: 220 nm) to obtain the isomers WX039 (retention time: 1.982 min) and WX040 (retention time: 2.416 min). MS-ESI m/z: 603.1; 604.1; 605.1 [M+H]$^+$; $^1$H NMR (WX039, 400 MHz, CDCl$_3$) δ: 9.37 (s, 1H) 8.05 (d, J=15.5 Hz, 1H), 7.80 (d, J=8.8 Hz, 2H), 7.61 (d, J=2.3 Hz, 1H), 7.51 (s, 1H), 7.49 (dd, J=8.7 Hz, J=2.4 Hz, 1H), 7.41 (d, J=8.8 Hz, 2H), 7.29 (d, J=8.5 Hz, 2H), 6.96-6.92 (m, 3H), 6.88 (d, J=15.5 Hz, 1H), 6.55 (s, 1H), 4.15-4.13 (m, 2H), 4.11-3.94 (m, 2H), 3.86 (s, 3H), 3.84-3.82 (m, 2H), 3.80-3.69 (m, 2H), 3.56 (t, J=6.8 Hz, 2H), 1.63-1.59 (m, 2H), 1.42-1.38 (m, 3H), 1.36-1.32 (m, 2H), 0.93 (t, J=7.4 Hz, 3H); $^1$H NMR (WX040, 400 MHz, CDCl$_3$) δ: 9.07 (br s, 1H) 8.05 (d, J=15.5 Hz, 1H), 7.80 (d, J=8.3 Hz, 2H), 7.62 (d, J=2.3 Hz, 1H), 7.53 (s, 1H), 7.50 (dd, J=8.7 Hz, J=2.1 Hz, 1H), 7.43 (d, J=8.5 Hz, 2H), 7.30 (d, J=8.3 Hz, 2H), 6.97-6.94 (m, 3H), 6.88 (d, J=15.5 Hz, 1H), 6.56 (br s, 1H), 4.16-4.13 (m, 2H), 4.11-3.95 (m, 2H), 3.88 (s, 3H), 3.85-3.74 (m, 4H), 3.56 (t, J=6.8 Hz, 2H), 1.63-1.59 (m, 2H), 1.42-1.36 (m, 3H), 1.36-1.32 (m, 2H), 0.93 (t, J=7.4 Hz, 3H).

Example 86: WX086

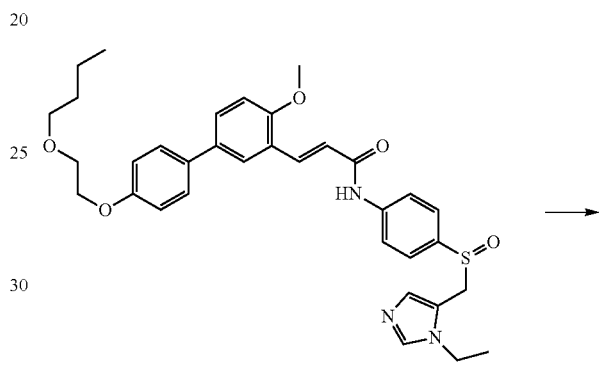

WX039-1

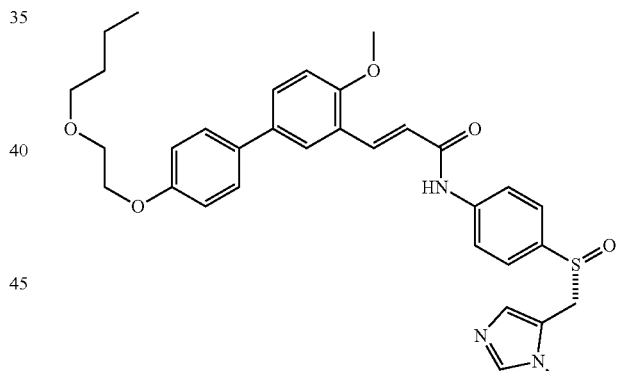

WX039

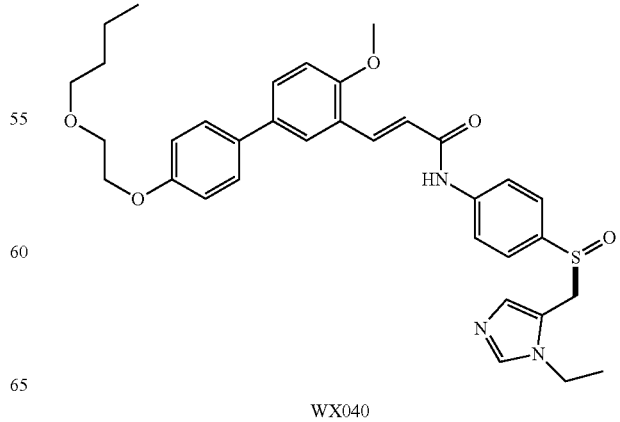

WX040

Step 1: Synthesis of Compound WX086

Compound WX086-1 was isolated by supercritical fluid chromatography (separation condition: Column: Chiralpak AS-3 50×4.6 mm I.D., 3 μm, mobile phase A: CO$_2$, B: 40% of ethanol (0.05% DEA). flow rate: 2.5 mL/min, column temperature: 40° C., wavelength: 220 nm) to obtain the isomers WX086' (retention time: 2.247 min) and WX086 (retention time: 3.248 min). MS-ESI m/z: 613.0, 614.0, 615.0 [M+H]$^+$; $^1$H NMR (400 MHz, CDCl$_3$) δ:8.35 (d, J=5.0 Hz, 1H), 8.02 (d, J=16.1 Hz, 1H), 7.97 (s, 1H), 7.87 (d, J=9.0 Hz, 2H), 7.77 (d, J=2.0 Hz, 1H), 7.60 (dd, 8.5 Hz, 1H), 7.53 (d, J=8.5 Hz, 2H), 7.44 (d, J=9.0 Hz, 2H), 7.32 (d, J=5.0 Hz, 1H), 7.12 (d, J=9.0 Hz, 1H), 7.02 (d, J=8.5 Hz, 2H), 6.97 (d, J=15.6 Hz, 1H), 4.43-4.24 (m, 2H), 4.19-4.11 (m, 2H), 3.97 (s, 3H), 3.82-3.78 (m, 2H), 3.57 (s, 2H), 2.73-2.55 (m, 2H), 1.64-1.55 (m, 2H), 1.48-1.38 (m, 2H), 1.21 (t, J=7.5 Hz, 3H), 0.95 (t, J=7.3 Hz, 3H).

Example 87: WX087

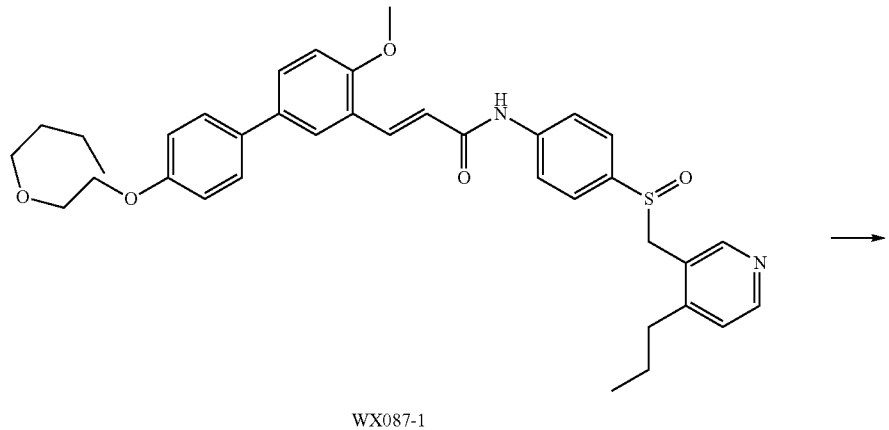

WX087-1

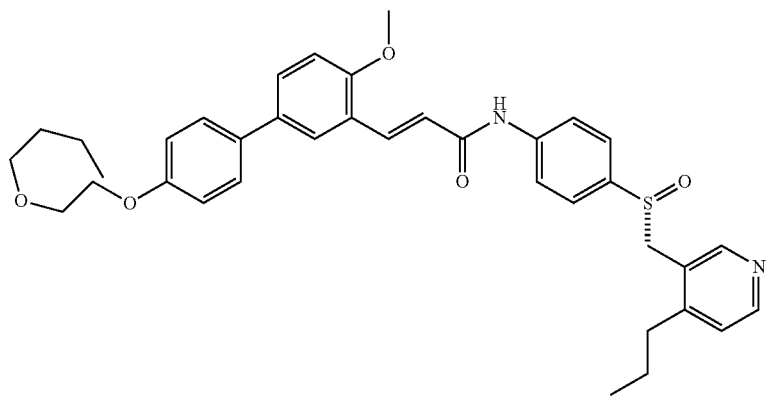 [SMILES: CCCCOCCOc1ccc(-c2ccc(OC)c(/C=C/C(=O)Nc3ccc(S(=O)Cc4cnccc4CCC)cc3)c2)cc1]

WX087'

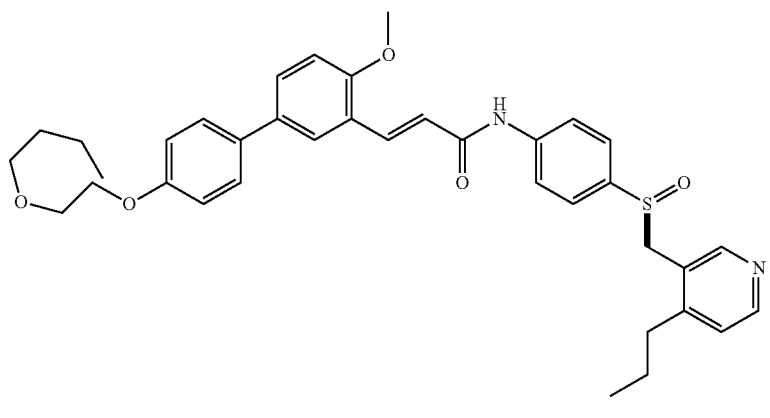

WX087

Step 1: Synthesis of Compound WX087

Compound WX087-1 was isolated by supercritical fluid chromatography (separation condition: Column: Chiralpak AS-3 50×4.6 mm I.D., 3 μm, mobile phase A: $CO_2$, B: 40% of ethanol (0.05% DEA). flow rate: 2.5 mL/min, column temperature: 40° C., wavelength: 220 nm) to obtain the isomers WX087' (retention time: 2.409 min) and WX087 (retention time: 3.392 min). MS-ESI m/z: 627.2, 628.2, 629.2 [M+H]$^+$; $^1$H NMR (400 MHz, $CDCl_3$) δ: 8.41 (br d, J=4.5 Hz, 1H), 8.06 (d, J=15.6 Hz, 1H), 7.94 (br d, J=10.3 Hz, 2H), 7.76 (br d, J=8.5 Hz, 2H), 7.67 (d, J=1.8 Hz, 1H), 7.53 (dd, J=2.0, 8.5 Hz, 1H), 7.46 (d, J=8.5 Hz, 2H), 7.36 (br d, J=8.3 Hz, 2H), 7.12 (br d, J=4.5 Hz, 1H), 6.99 (dd, J=2.9, 8.7 Hz, 3H), 6.78 (d, J=15.6 Hz, 1H), 4.23-4.14 (m, 3H), 4.10-4.04 (m, 1H), 3.93 (s, 3H), 3.82 (t, J=4.8 Hz, 2H), 3.57 (t, J=6.7 Hz, 2H), 2.61-2.53 (m, 2H), 1.64-1.58 (m, 4H), 1.44-1.37 (m, 2H), 1.01-0.96 (m, 2H), 0.96-0.91 (m, 3H).

Example 40: WX006

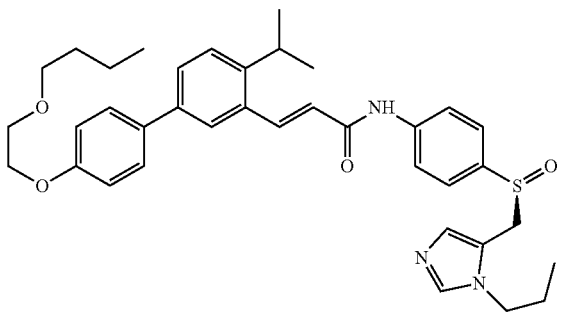

WX006

Synthesis Pathway:

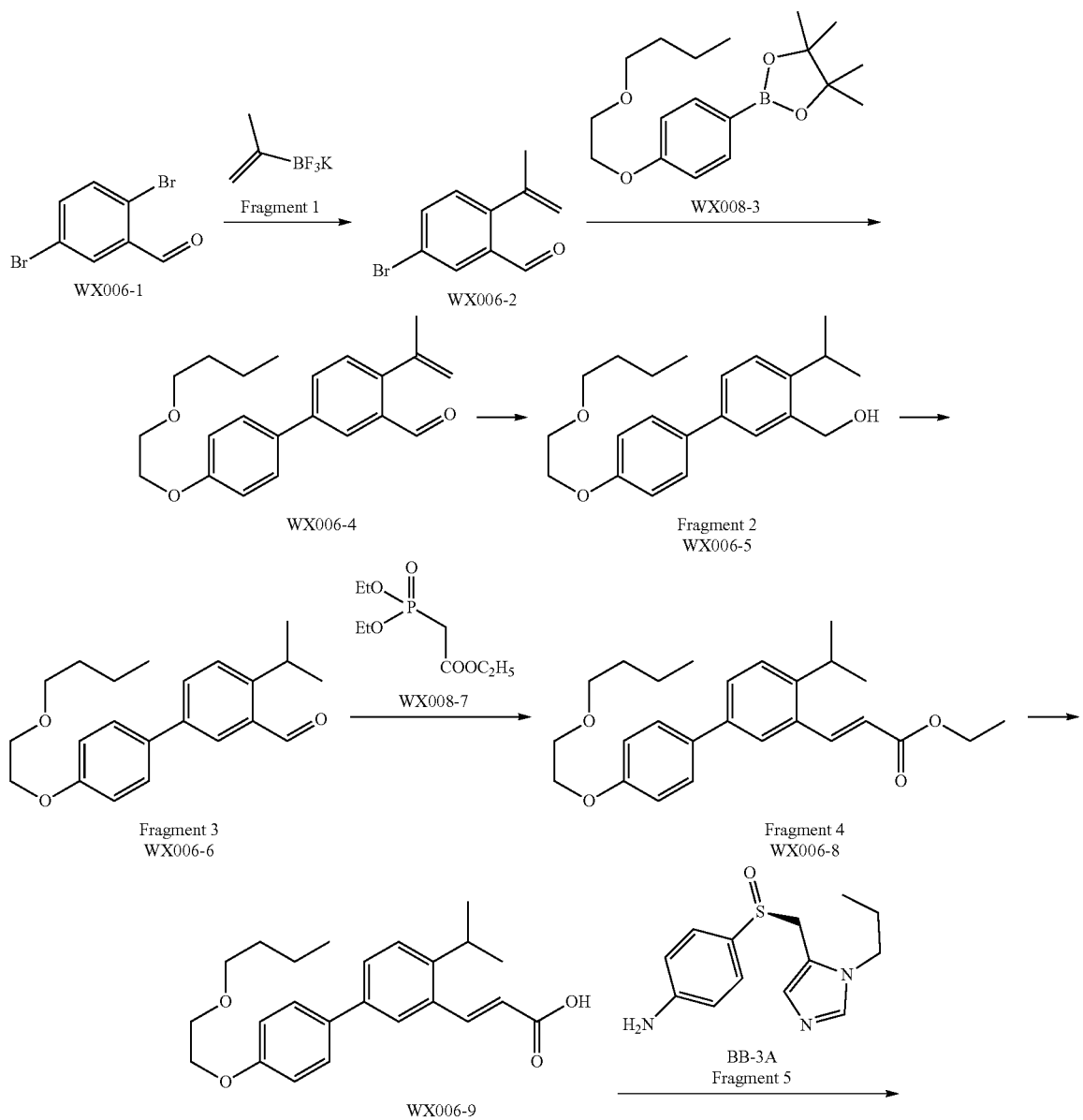

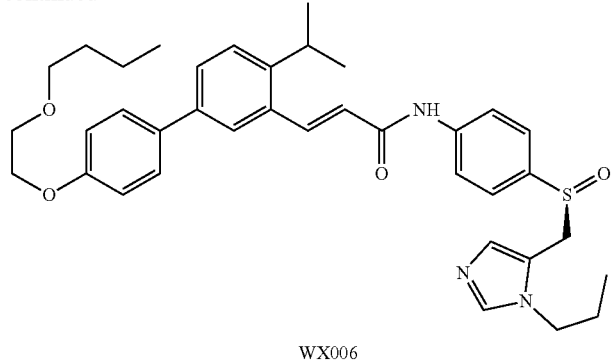

WX006

Step 1: Synthesis of Compound WX006-2

Compound WX006-1 (500.00 mg, 1.89 mmol) and potassium isopropenyl trifluoroborate (195.78 mg, 1.32 mmol) were dissolved in 1,4-dioxane (10 mL) under nitrogen atmosphere, followed by addition of (1,1'-bis(diphenylphosphino)ferrocene)palladium dichloride dichloromethane complex (154.34 mg, 189.00 μL), potassium carbonate (522.43 mg, 3.78 mmol) and water (4 mL). The reaction mixture was heated to 50° C. and stirred for 12 hours under nitrogen atmosphere. After completion of the reaction, the mixture was cooled to room temperature, followed by addition of water (50 mL) and extraction with ethyl acetate (50 mL×2). The organic phases were combined, washed with saturated brine (50 mL×2), dried over anhydrous sodium sulfate, filtered to remove the desiccant and concentrated under reduced pressure. The insoluble material was removed by filtration, and the obtained residue was purified by flash silica gel column chromatography (eluent: ethyl acetate/petroleum ether=1/9) (eluent: ethyl acetate/petroleum ether=0/9-1/9) to obtain the title compound WX006-2 (colorless liquid, 500.00 mg, yield: 77.78%). $^1$H NMR (400 MHz, CDCl$_3$) δ: 10.07 (s, 1H), 7.96 (s, 1H), 7.59-7.57 (d, J=6 Hz, 1H), 7.17-7.15 (d, J=8 Hz, 1H), 5.38 (s, 1H), 4.85 (s, 1H), 2.11 (s, 3H).

Step 2: Synthesis of Compound WX006-4

Compound WX006-2 (500.00 g, 1.47 mmol) and compound WX006-3 (616.18 mg, 1.91 mmol) were dissolved in 1,4-dioxane (6 mL) under nitrogen atmosphere, followed by addition of (1,1'-bis(diphenylphosphino)ferrocene)palladium dichloride dichloromethane complex (120.05 mg, 147.00 μmol), potassium carbonate (406.34 g, 2.94 mmol) and water (3 mL). The reaction mixture was heated to 50° C. and stirred for 16 hours under nitrogen atmosphere. After completion of the reaction, the mixture was cooled to room temperature, followed by addition of water (50 mL) to quenched the reaction, and extracted with ethyl acetate (50 mL×2). The organic phases were combined, washed with saturated brine (50 mL×2), dried over anhydrous sodium sulfate, filtered to remove the desiccant and concentrated under reduced pressure. The insoluble material was removed by filtration, and the obtained residue was purified by flash silica gel column chromatography (eluent: ethyl acetate/petroleum ether=1/9) to obtain the title compound WX006-4 (yellow oily liquid, 232.00 mg, yield: 46.63%). $^1$H NMR (400 MHz, CDCl$_3$) δ: 10.26 (s, 1H), 8.12 (d, J=1.8 Hz, 1H), 7.78-7.74 (m, 1H), 7.57 (d, J=7.5 Hz, 2H), 7.47 (d, J=7.7 Hz, 1H), 7.41 (d, J=8.0 Hz, 1H), 7.27 (s, 1H), 7.05-7.00 (m, 2H), 5.46 (t, J=1.6 Hz, 1H), 4.97-4.94 (m, 1H), 4.19-4.16 (m, 2H), 4.15 (s, 1H), 3.83 (d, J=5.0 Hz, 2H), 3.59-3.55 (m, 2H), 2.22 (s, 3H), 1.66-1.61 (m, 2H), 1.61-1.57 (m, 5H), 1.46-1.36 (m, 3H), 1.34 (s, 1H), 0.98-0.95 (m, 1H), 0.96-0.93 (m, 1H), 0.95-0.93 (m, 1H).

Step 3: Synthesis of Compound WX006-5

Compound WX006-4 (120.00 mg, 354.57 μmol) was dissolved in ethyl acetate (3 mL) at room temperature, and wet palladium on carbon catalyst (100.00 mg, palladium content 10%, water content 50%) was added thereto. The system was displaced with argon three times, followed by displacing with hydrogen three times. The reaction mixture was heated to 50° C. and stirred for 4 hours under hydrogen atmosphere (15 psi). The catalyst was removed by filtration, and the filtrate was concentrated under reduced pressure to obtain the title compound WX006-5 (pale-yellow oily liquid, 110.00 mg). The crude product was used directly in the next step without purification.

Step 4: Synthesis of Compound WX006-6

Compound WX006-5 (100.00 mg, 292.00 μmol) was dissolved in dichloromethane (3 mL) at room temperature, and active manganese dioxide (253.86 mg, 2.92 mmol) was added thereto. The reaction mixture was stirred for 16 hours at room temperature under nitrogen protection. After completion of the reaction, manganese dioxide was removed by filtration, and the filtrate was concentrated under reduced pressure. The obtained residue was purified by preparative thin layer chromatography (developing solvent: ethyl acetate/petroleum ether=1/15) to obtain the title compound WX006-6 (pale-yellow solid, 170.00 mg, yield: 85.50%). $^1$H NMR (400 MHz, CDCl$_3$) δ: 10.43 (s, 1H), 8.01 (d, J=2.0 Hz, 1H), 7.75 (dd, J=2.1, 8.2 Hz, 1H), 7.58-7.45 (m, 2H), 7.38-7.32 (m, 1H), 7.05-6.96 (m, 2H), 4.20-4.14 (m, 2H), 4.04-3.94 (m, 1H), 3.85-3.79 (m, 2H), 3.60-3.52 (m, 2H), 1.70-1.57 (m, 2H), 1.51-1.37 (m, 2H), 1.35 (d, J=6.8 Hz, 4H), 1.04-0.98 (m, 1H), 0.98-0.88 (m, 3H).

Step 5: Synthesis of Compound WX006-8

Compound WX008-7 (210.72 mg, 939.94 μmol) was dissolved in tetrahydrofuran (2 mL) at room temperature. The solution was cooled to 0° C., and sodium hydride (22.56 mg, 939.94 μmol, purity 60%) was added to the above solution. The reaction mixture was warmed to room temperature and stirred for 0.5 hour. A solution prepared by the compound WX006-6 (160.00 mg, 469.97 μmol) and tetrahydrofuran (2 mL) was added to the above mixture. After completion of the addition, the mixture was further stirred for 5 hours. After completion of the reaction, water (25 mL) was added to the mixture to quenched the reaction, and the mixture was extracted with ethyl acetate (20 mL×3). The organic phases were combined, washed with water (20 mL×3), and dried over anhydrous sodium sulfate, followed by filtration to remove the desiccant. The filtrate was concentrated under reduced pressure. The obtained residue was purified by preparative thin layer chromatography (developing solvent: ethyl acetate/petroleum ether=1/15) to obtain the title compound WX006-8 (pale-yellow solid, 160.00 mg, yield 82.93%).

Step 6: Synthesis of Compound WX006-9

Compound WX006-8 (150.00 mg, 365.37 μmol) was dissolved in ethanol (2 mL) at room temperature, and 8 M aqueous sodium hydroxide solution (1.5 mL) was added to the above solution. The reaction mixture was heated to 50° C. and stirred for 4 hours. After completion of the reaction, the mixture was cooled to room temperature, and adjusted to pH=4 with 4 M hydrochloric acid solution, followed by filtration. The precipitate was collected and purified by preparative thin layer chromatography (developing solvent: ethyl acetate/petroleum ether=1/15) to obtain the title compound WX006-9 (pale-yellow solid, 90.00 mg, yield 64.40%). $^1$H NMR (400 MHz, CDCl$_3$) δ: 8.36-8.24 (m, 1H), 7.73 (s, 1H), 7.64-7.46 (m, 3H), 7.46-7.36 (m, 1H), 7.08-6.98 (m, 2H), 6.45 (d, J=15.8 Hz, 1H), 4.26-4.10 (m, 2H), 3.91-3.73 (m, 2H), 3.57 (t, J=6.7 Hz, 2H), 3.47-3.30 (m, 1H), 1.79-1.52 (m, 2H), 1.46-1.37 (m, 2H), 1.37-1.21 (m, 6H), 0.94 (t, J=7.4 Hz, 3H).

Step 7: Synthesis of Compound WX006

Compound WX006-9 (60.00 mg, 227.83 μmol) was dissolved in dichloromethane (2 mL). The solution was cooled to 0° C., and oxalyl chloride (74.57 mg, 587.46 μmol) and N,N-dimethylformamide (21.47 mg, 293.73 μmol) were added to the above solution. After completion of the addition, the reaction mixture was warmed to room temperature and stirred for 2.5 hours under nitrogen atmosphere. A nitrogen stream was introduced to the reaction mixture to remove the solvent. The obtained residue was dissolved in tetrahydrofuran (1 mL), and added to a solution prepared by compound BB-3A (69.62 mg, 264.36 μmol), triethylamine (59.45 mg, 587.46 μmol) and tetrahydrofuran (1 mL). After completion of the addition, the reaction mixture was stirred for 2.5 hours at room temperature. After completion of the reaction, methanol (2 mL) was added to the mixture to quench the reaction, the mixture was concentrated under reduced pressure. The obtained residue was purified by preparative high performance liquid chromatography to obtain the compound WX006. MS-ESI m/z: 628.1; 629.1; 630.1[M+H]$^+$; $^1$H NMR (400 MHz, CDCl$_3$) δ: 8.84 (br s, 1H), 8.33-8.20 (m, 1H), 7.80 (d, J=8.5 Hz, 2H), 7.67-7.29 (m, 8H), 6.99 (d, J=8.8 Hz, 2H), 6.61 (d, J=15.1 Hz, 1H), 6.53 (s, 1H), 4.23-4.11 (m, 3H), 3.99 (d, J=14.1 Hz, 1H), 3.87-3.74 (m, 4H), 3.57 (t, J=6.8 Hz, 2H), 3.45-3.36 (m, 1H), 1.79-1.65 (m, 1H), 1.41 (qd, J=7.3, 14.9 Hz, 2H), 1.29 (d, J=7.0 Hz, 5H), 1.26 (br s, 1H), 1.00-0.83 (m, 6H).

The reference examples in the following table were synthesized according to the synthesis method of the steps 1-7 in Example 40.

| Example | Fragment 1 | Structure | Compound |
|---|---|---|---|
| 41 | ⁀BF$_3$K | [structure] | WX005 |

The reference examples in the following table were synthesized according to the synthesis method of the steps 4-7 in Example 40.

| Example | Fragment 2 | Fragment 3 | Fragment 5 | Structure | Compound |
|---|---|---|---|---|---|
| 42 | BB-4A | | BB-3A | 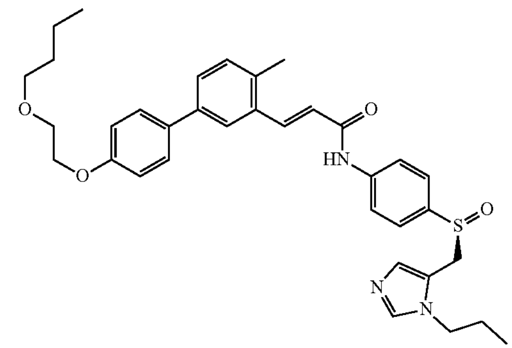 [SMILES: CCCCOCCOc1ccc(-c2ccc(C)c(/C=C/C(=O)Nc3ccc([S@@](=O)Cc4cncn4CCC)cc3)c2)cc1] | WX011 |
| 43 | BB-4B | | BB-3A | 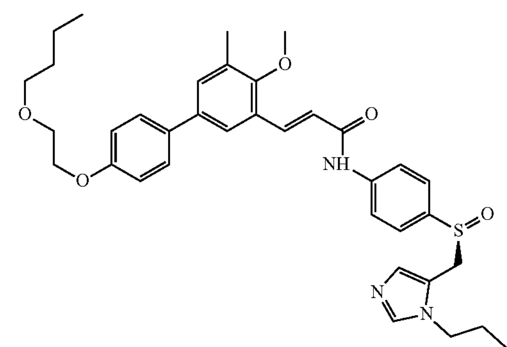 | WX042 |
| 44 | BB-4C | | BB-3A | 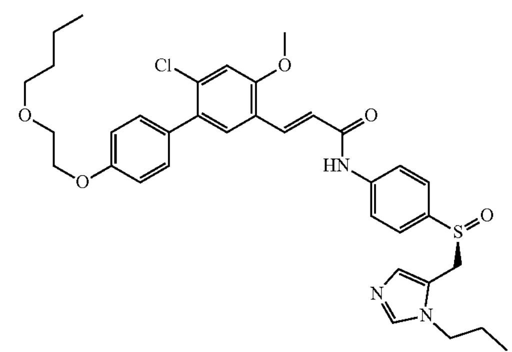 [SMILES: CCCCOCCOc1ccc(-c2cc(/C=C/C(=O)Nc3ccc([S@@](=O)Cc4cncn4CCC)cc3)c(OC)cc2Cl)cc1] | WX043 |

| Example | Fragment 2 | Fragment 3 | Fragment 5 | Structure | Compound |
|---|---|---|---|---|---|
| 45 | N/A | 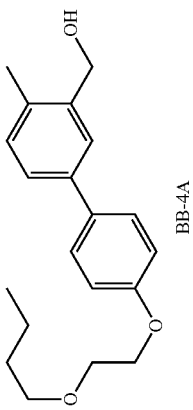 BB-4D | 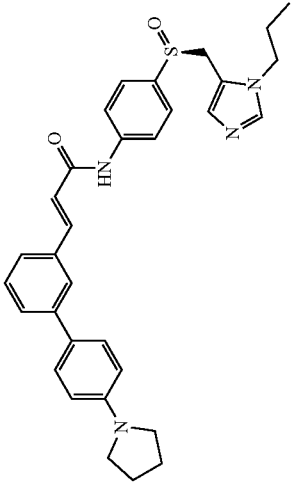 BB-3A | 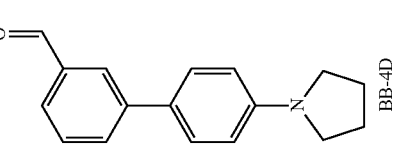 | WX037 |
| 46 | 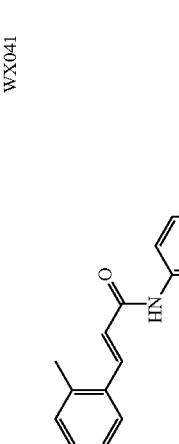 BB-4A | | 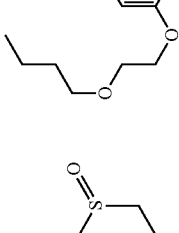 BB-3C | 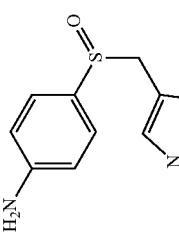 | WX041 |

| Example | Fragment 2 | Fragment 3 | Fragment 5 | Structure | Compound |
|---|---|---|---|---|---|
| 53 | BB-4E | | BB-3A | 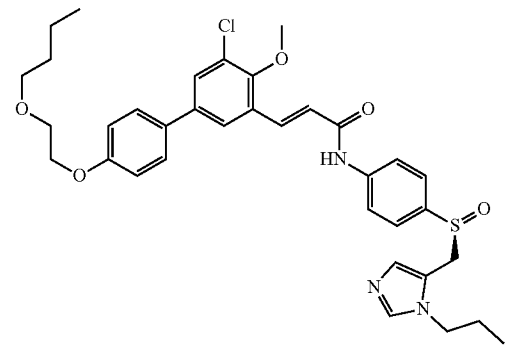 [SMILES: CCCCOCCOc1ccc(-c2cc(Cl)c(OC)c(/C=C/C(=O)Nc3ccc([S@@](=O)Cc4cncn4CCC)cc3)c2)cc1] | WX053 |
| 59 | BB-4G | | BB-3A | 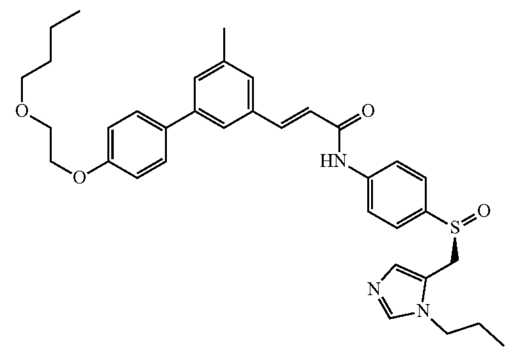 [SMILES: CCCCOCCOc1ccc(-c2cc(C)cc(/C=C/C(=O)Nc3ccc([S@@](=O)Cc4cncn4CCC)cc3)c2)cc1] | WX059 |
| 60 | BB-4F | | BB-3A | 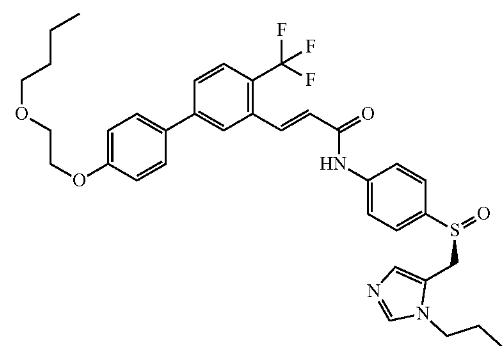 [SMILES: CCCCOCCOc1ccc(-c2ccc(C(F)(F)F)c(/C=C/C(=O)Nc3ccc([S@@](=O)Cc4cncn4CCC)cc3)c2)cc1] | WX060 |

| Example | Fragment 2 | Fragment 3 Fragment 5 | Structure | Compound |
|---|---|---|---|---|
| 70 | BB-4F | BB-3K' | 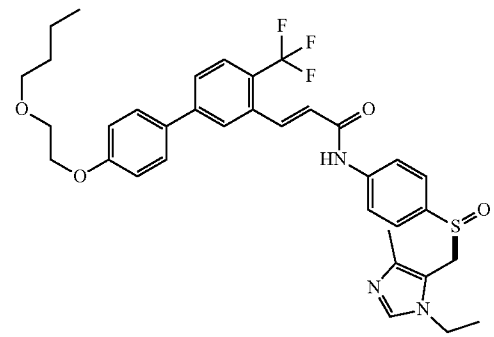 [SMILES: CCCCOCCOc1ccc(-c2ccc(C(F)(F)F)c(/C=C/C(=O)Nc3ccc([S@@](=O)Cc4c(C)ncn4CC)cc3)c2)cc1] | WX070 |
| 71 | BB-4F | BB-3K | 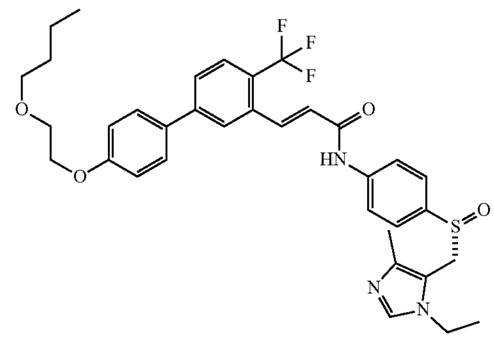 [SMILES: CCCCOCCOc1ccc(-c2ccc(C(F)(F)F)c(/C=C/C(=O)Nc3ccc([S@](=O)Cc4c(C)ncn4CC)cc3)c2)cc1] | WX071 |
| 72 | BB-4H | BB-3K' | 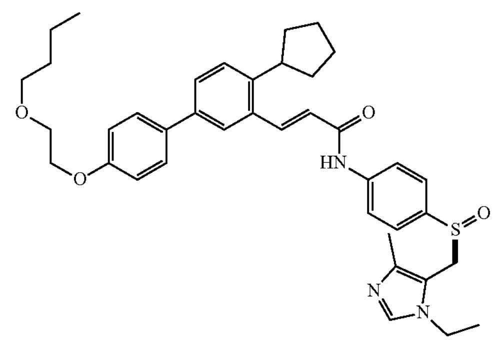 [SMILES: CCCCOCCOc1ccc(-c2ccc(C3CCCC3)c(/C=C/C(=O)Nc3ccc([S@@](=O)Cc4c(C)ncn4CC)cc3)c2)cc1] | WX072 |

| Example | Fragment 2 | Fragment 3 | Fragment 5 | Structure | Compound |
|---|---|---|---|---|---|
| 73 | BB-4H | | BB-3K | 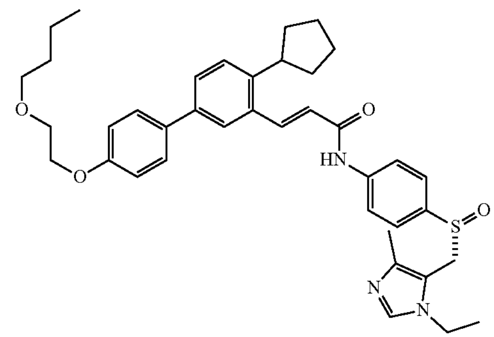 [SMILES: CCCCOCCOc1ccc(-c2ccc(C3CCCC3)c(/C=C/C(=O)Nc3ccc([S@](=O)Cc4c(C)ncn4CC)cc3)c2)cc1] | WX073 |
| 87 | BB-4F | | BB-3J | 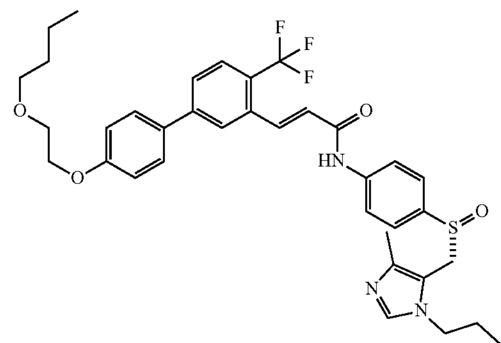 [SMILES: CCCCOCCOc1ccc(-c2ccc(C(F)(F)F)c(/C=C/C(=O)Nc3ccc([S@](=O)Cc4c(C)ncn4CCC)cc3)c2)cc1] | WX087 |
| 88 | BB-4F | | BB-3J | 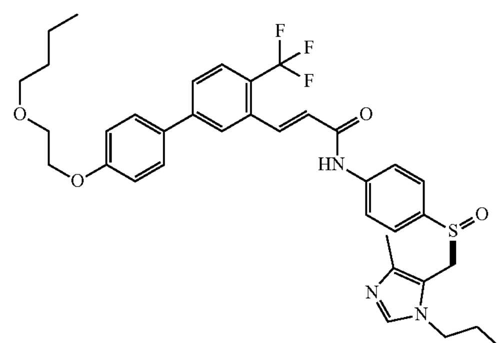 | WX088 |

The reference examples in the following table were synthesized according to the synthesis method of the steps 6-7 in Example 40.

| Example | Fragment 4 | Fragment 5 | Structure | Compound |
|---|---|---|---|---|
| 54 | BB-5A | BB-3K' | 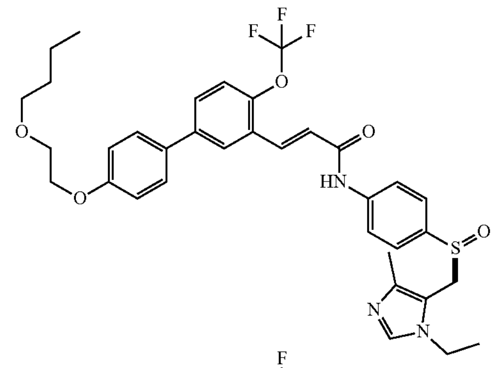 | WX054 |
| 55 | BB-5A | BB-3K | 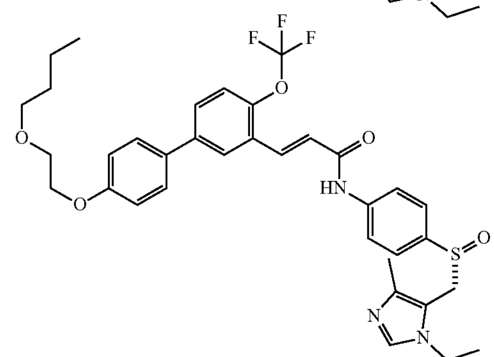 | WX055 |
| 78 | BB-5B | BB-3A | 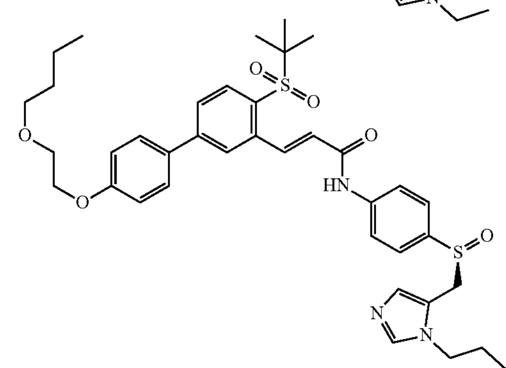 | WX078 |

NMR and MS data for each example

| Example | Comound | NMR | MS m/z: |
|---|---|---|---|
| 2 | WX001 | $^1$H NMR (400 MHz, Methanol-d4) δ: 7.88 (d, J = 8.5 Hz, 2H), 7.82-7.74 (m, 2H), 7.67 (s, 1H), 7.64-7.54 (m, 4H), 7.50-7.44 (m, 3H), 7.05 (d, J = 8.5 Hz, 2H), 6.86 (d, J = 15.6 Hz, 1H), 6.66 (s, 1H), 4.42-4.35 (m, 1H), 4.29-4.21 (m, 1H), 4.19-4.14 (m, 2H), 3.84-3.75 (m, 4H), 3.57 (t, J = 6.7 Hz, 2H), 1.72 (q, J = 7.4 Hz, 2H), 1.64-1.54 (m, 2H), 1.48-1.36 (m, 2H), 0.95 (t, J = 7.4 Hz, 3H), 0.88 (t, J = 7.4 Hz, 3H) | 586.1, 587.1 |
| 3 | WX002 | $^1$H NMR (400 MHz, CDCl3) δ = 9.52 (br s, 1H), 7.85-7.77 (m, 3H), 7.64 (s, 1H), 7.57-7.46 (m, 4H), 7.43-7.36 (m, 2H), 7.30 (br d, J = 8.3 Hz, 2H), 6.98 (br d, J = 8.5 Hz, 2H), 6.76 (br d, J = 15.6 Hz, 1H), 6.51 (br s, 1H), 4.20 (br d, J = 14.3 Hz, 1H), 3.97 (br d, J = 14.3 Hz, 1H), 3.90-3.75 (m, 5H), 1.71 (br d, J = 7.0 Hz, 2H), 0.89 (br t, J = 7.3 Hz, 3H) | 500.2, 501.1 |
| 4 | WX003 | $^1$H NMR (400 MHz, Methanol-d4) δ: 7.90-7.83 (m, 3H), 7.82-7.77 (m, 2H), 7.66 (s, 1H), 7.63-7.56 (m, 1H), 7.56-7.51 (m, 2H), 7.44 (dd, J = 1.6, 8.7 Hz, 2H), 7.26-7.17 (m, 1H), 7.06-6.92 (m, 3H), 6.65 (s, 1H), 4.41-4.32 (m, 1H), 4.27-4.20 (m, 1H), 4.17-4.09 (m, 2H), 3.79 (d, J = 6.0 Hz, 4H), 3.56 (dt, J = 1.3, 6.5 Hz, 2H), 1.77-1.67 (m, 2H), 1.64-1.54 (m, 2H), 1.45-1.34 (m, 2H), 0.94 (t, J = 7.4 Hz, 3H), 0.88 (t, J = 7.3 Hz, 3H) | 604.1, 605.1 |
| 5 | WX004 | $^1$H NMR (400 MHz, CDCl3) δ: 7.90-7.76 (m, 3H), 7.71 (s, 1H), 7.63-7.42 (m, 6H), 7.37 (d, J = 8.0 Hz, 2H), 7.00 (d, J = 8.8 Hz, 2H), 6.69-6.52 (m, 2H), 4.18-3.99 (m, 4H), 3.80 (t, J = 7.3 Hz, 2H), 1.80-1.69 (m, 2H), 1.47 (t, J = 6.9 Hz, 3H), 0.92 (t, J = 7.4 Hz, 3H) | 514.0, 515.0, 516.0 |
| 41 | WX005 | $^1$H NMR (400 MHz, CDCl3) δ: 9.74 (br s, 1H), 8.13 (d, J = 15.3 Hz, 1H), 7.81 (br d, J = 8.5 Hz, 2H), 7.63 (s, 1H), 7.52-7.41 (m, 4H), 7.32-7.27 (m, 3H), 6.97 (d, J = 8.5 Hz, 2H), 6.72 (d, J = 15.3 Hz, 1H), 6.50 (s, 1H), 4.28-3.89 (m, 4H), 3.88-3.72 (m, 4H), 3.57 (t, J = 6.7 Hz, 2H), 2.82 (q, J = 7.4 Hz, 2H), 1.74-1.57 (m, 4H), 1.41 (qd, J = 7.3, 15.0 Hz, 2H), 1.24 (t, J = 7.5 Hz, 3H), 0.98-0.90 (m, 3H), 0.86 (t, J = 7.4 Hz, 3H) | 614.1 615.1 616.1 |
| 40 | WX006 | $^1$H NMR (400 MHz, CDCl3) δ: 8.84 (br s, 1H), 8.33-8.20 (m, 1H), 7.80 (d, J = 8.5 Hz, 2H), 7.67-7.29 (m, 8H), 6.99 (d, J = 8.8 Hz, 2H), 6.61 (d, J = 15.1 Hz, 1H), 6.53 (s, 1H), 4.23-4.11 (m, 3H), 3.99 (d, J = 14.1 Hz, 1H), 3.87-3.74 (m, 4H), 3.57 (t, J = 6.8 Hz, 2H), 3.45-3.36 (m, 1H), 1.79-1.65 (m, 1H), 1.41 (qd, J = 7.3, 14.9 Hz, 2H), 1.29 (d, J = 7.0 Hz, 5H), 1.26 (br s, 1H), 1.00-0.83 (m, 6H) | 628.1, 629.1, 630.1 |
| 6 | WX007 | $^1$H NMR (400 MHz, CDCl$_3$) δ: 7.88-7.77 (m, 3H), 7.69 (s, 1H), 7.60-7.39 (m, 6H), 7.35 (d, J = 8.5 Hz, 2H), 6.98 (d, J = 8.8 Hz, 2H), 6.69 (d, J = 15.3 Hz, 1H), 6.56 (s, 1H), 4.62 (quin, J = 6.0 Hz, 1H), 4.22-4.12 (m, 1H), 4.01 (d, J = 14.1 Hz, 1H), 3.82 (dt, J = 2.5, 7.2 Hz, 2H), 1.74 (sxt, J = 7.3 Hz, 2H), 1.39 (d, J = 6.0 Hz, 7H), 0.91 (t, J = 7.4 Hz, 3H) | 527.7, 528.7 |
| 7 | WX008 | $^1$H NMR (400 MHz, Methanol-d$_4$) δ: 7.88 (d, J = 8.5 Hz, 2H), 7.66 (s, 1H), 7.62 (br. s., 1H), 7.59-7.52 (m, 3H), 7.51-7.36 (m, 5H), 7.03 (d, J = 8.8 Hz, 2H), 6.65 (s, 1H), 4.43-4.34 (m, 1H), 4.29-4.20 (m, 1H), 4.17-4.11 (m, 2H), 3.86-3.72 (m, 4H), 3.56 (t, J = 6.5 Hz, 2H), 2.21 (s, 3H), 1.80-1.67 (m, 2H), 1.63-1.51 (m, 2H), 1.47-1.33 (m, 2H), 0.94 (t, J = 7.4 Hz, 3H), 0.88 (t, J = 7.4 Hz, 3H) | 600.1, 601.1 |
| 8 | WX009 | $^1$H NMR (400 MHz, CDCl3) δ: 8.08 (s, 1H), 7.87-7.76 (m, 3H), 7.71 (s, 1H), 7.58 (d, J = 7.3 Hz, 1H), 7.52 (d, J = 8.8 Hz, 2H), 7.50-7.47 (m, 2H), 7.46-7.42 (m, 1H), 7.37 (d, J = 8.5 Hz, 2H), 7.00 (d, J = 8.8 Hz, 2H), 6.66 (d, J = 15.6 Hz, 1H), 6.59 (s, 1H), 4.19-4.11 (m, 1H), 4.05-4.00 (m, 3H), 3.81 (t, J = 7.2 Hz, 2H), 1.86-1.71 (m, 4H), 1.56-1.48 (m, 2H), 1.01 (t, J = 7.3 Hz, 3H), 0.92 (t, J = 7.4 Hz, 3H) | 541.7, 542.7 |
| 9 | WX010 | $^1$H NMR (400 MHz, CDCl3) δ: 8.62 (s, 1H), 8.14 (s, 1H), 7.85-7.76 (m, 3H), 7.69 (br s, 1H), 7.55 (br d, J = 6.5 Hz, 1H), 7.51 (br d, J = 8.5 Hz, 2H), 7.47-7.42 (m, 2H), 7.40 (br d, J = 8.3 Hz, 2H), 7.01 (br d, J = 8.3 Hz, 2H), 6.71 (br d, J = 15.6 Hz, 1H), 4.35-4.12 (m, 4H), 3.97 (br t, J = 7.2 Hz, 2H), 3.83 (br d, J = 4.3 Hz, 2H), 3.56 (br t, J = 6.5 Hz, 2H), 1.84-1.73 (m, 2H), 1.63-1.56 (m, 2H), 1.47-1.33 (m, 2H), 0.94 (br t, J = 7.2 Hz, 6H) | 587.0, 588.0, 589.0 |

-continued

| Example | Compound | NMR | MS m/z: |
|---|---|---|---|
| 42 | WX011 | ¹H NMR (400 MHz, CDCl3) δ: 10.10 (br s, 1H), 8.06 (d, J = 15.6 Hz, 1H), 7.80 (d, J = 8.5 Hz, 2H), 7.59 (s, 1H), 7.48 (s, 1H), 7.41 (br d, J = 8.5 Hz, 3H), 7.27 (s, 1H), 7.25 (s, 1H), 7.22 (d, J = 8.0 Hz, 1H), 6.94 (d, J = 8.5 Hz, 2H), 6.72 (d, J = 15.3 Hz, 1H), 6.47 (s, 1H), 4.21-4.16 (m, 1H), 4.16-4.12 (m, 2H), 3.91 (d, J = 14.3 Hz, 1H), 3.84-3.80 (m, 2H), 3.80-3.70 (m, 2H), 3.56 (t, J = 6.7 Hz, 2H), 2.43 (s, 3H), 1.73-1.56 (m, 4H), 1.40 (sxt, J = 7.4 Hz, 2H), 0.93 (t, J = 7.3 Hz, 3H), 0.84 (t, J = 7.4 Hz, 3H) | 600.0, 601.0 |
| 10 | WX012 | ¹H NMR (400 MHz, CDCl3) δ: 8.43 (br s, 1H), 7.76 (d, J = 8.5 Hz, 2H), 7.62 (s, 1H), 7.56-7.38 (m, 6H), 7.33 (d, J = 8.5 Hz, 2H), 7.01 (d, J = 8.5 Hz, 2H), 6.56 (s, 1H), 6.30 (s, 1H), 4.18 (t, J = 4.8 Hz, 2H), 4.15-4.09 (m, 1H), 4.02-3.96 (m, 1H), 3.85-3.74 (m, 4H), 3.57 (t, J = 6.7 Hz, 2H), 2.70 (s, 3H), 1.76 (s, 1H), 1.62-1.55 (m, 2H), 1.41 (sxt, J = 7.5 Hz, 2H), 0.97-0.86 (m, 6H) | 600.1, 601.1, 602.1 |
| 11 | WX013 | ¹H NMR (400 MHz, CDCl3) δ:8.59 (br s, 1H), 7.86-7.77 (m, 3H), 7.69 (s, 1H), 7.58-7.41 (m, 6H), 7.35 (d, J = 8.5 Hz, 2H), 7.02 (d, J = 8.8 Hz, 2H), 6.70 (d, J = 15.6 Hz, 1H), 6.57 (s, 1H), 4.21-4.14 (m, 3H), 4.01 (d, J = 14.1 Hz, 1H), 3.85-3.77 (m, 4H), 3.49 (s, 3H), 1.79-1.69 (m, 2H), 0.91 (t, J = 7.4 Hz, 3H) | 543.7, 544.7 |
| 12 | WX014 | ¹H NMR (400 MHz, METHANOL-d4) δ: 7.87-7.78 (m, J = 8.8 Hz, 2H), 7.65 (s, 1H), 7.55-7.47 (m, 4H), 7.45-7.35 (m, J = 8.8 Hz, 2H), 7.22-7.09 (m, 1H), 6.99 (d, J = 8.8 Hz, 2H), 6.65 (s, 1H), 6.30-6.24 (m, 1H), 4.33 (d, J = 14.3 Hz, 1H), 4.19 (d, J = 14.6 Hz, 1H), 4.15-4.07 (m, 2H), 3.82-3.70 (m, 4H), 3.53 (t, J = 6.7 Hz, 2H), 2.57 (s, 3H), 1.74-1.64 (m, 2H), 1.61-1.51 (m, 2H), 1.44-1.26 (m, 2H), 0.95-0.82 (m, 6H) | 618.1, 619.1, 620.0 |
| 13 | WX015 | ¹H NMR (400 MHz, CDCl3) δ: 8.13 (s, 1H), 7.89 (br s, 1H), 7.81 (d, J = 8.5 Hz, 2H), 7.57-7.43 (m, 8H), 7.32 (br d, J = 7.8 Hz, 1H), 6.99 (d, J = 8.5 Hz, 2H), 4.36-4.17 (m, 2H), 3.98 (t, J = 6.7 Hz, 4H), 2.27 (s, 3H), 1.90-1.82 (m, 2H), 1.81-1.70 (m, 2H), 1.06 (t, J = 7.5 Hz, 3H), 0.95 (t, J = 7.3 Hz, 3H) | 543.2, 544.3, 545.2 |
| 14 | WX016 | ¹H NMR (400 MHz, CDCl3) δ: 8.17 (d, J = 15.6 Hz, 1H), 7.80 (d, J = 8.5 Hz, 2H), 7.69 (br s, 1H), 7.51-7.41 (m, 5H), 7.31 (br d, J = 8.0 Hz, 2H), 6.99 (d, J = 8.5 Hz, 2H), 6.77 (br d, J = 15.6 Hz, 1H), 6.51 (br s, 1H), 4.22-4.14 (m, 3H), 3.96 (br d, J = 14.1 Hz, 1H), 3.88-3.75 (m, 5H), 3.57 (t, J = 6.8 Hz, 2H), 1.78-1.66 (m, 2H), 1.62-1.56 (m, 2H), 1.46-1.37 (m, 2H), 0.97-0.86 (m, 6H) | 620.2, 621.1 |
| 1 | WX017 | ¹H NMR (400 MHz, CDCl3) δ: 9.33 (s, 1H), 8.05 (d, J = 15.6 Hz, 1H), 7.80 (d, J = 8.8 Hz, 2H), 7.61 (d, J = 2.3 Hz, 1H), 7.50 (br d, J = 2.3 Hz, 1H), 7.48 (s, 1H), 7.44-7.39 (m, 2H), 7.29 (d, J = 8.8 Hz, 2H), 6.98-6.93 (m, 3H), 6.88 (d, J = 15.8 Hz, 1H), 6.55 (s, 1H), 4.15 (d, J = 4.8 Hz, 2H), 4.14-4.13 (m, 1H), 4.13 (d, J = 2.8 Hz, 1H), 3.97 (d, J = 14.1 Hz, 1H), 3.86 (s, 3H), 3.83-3.79 (m, 1H), 3.79-3.79 (m, 1H), 3.76 (dt, J = 4.0, 7.3 Hz, 2H), 3.56 (t, J = 6.8 Hz, 2H), 1.73-1.66 (m, 2H), 1.65-1.57 (m, 2H), 1.45-1.35 (m, 2H), 0.93 (t, J = 7.4 Hz, 2H), 0.87 (t, J = 7.4 Hz, 3H) | 616.1, 617.1 |
| 15 | WX018 | ¹H NMR (400 MHz, CHLOROFORM-d) δ: 9.85 (br s, 1H), 7.98 (d, J = 15.8 Hz, 1H), 7.80 (d, J = 8.5 Hz, 2H), 7.66 (d, J = 2.0 Hz, 1H), 7.52-7.47 (m, 2H), 7.41 (d, J = 8.8 Hz, 2H), 7.29 (s, 2H), 7.19 (d, J = 8.5 Hz, 1H), 6.95 (d, J = 8.8 Hz, 2H), 6.88 (d, J = 15.8 Hz, 1H), 6.73-6.35 (m, 2H), 4.20 (d, J = 14.1 Hz, 1H), 4.00 (t, J = 6.5 Hz, 2H), 3.94 (d, J = 14.1 Hz, 1H), 3.88-3.73 (m, 2H), 1.84-1.77 (m, 2H), 1.71-1.67 (m, 2H), 1.52 (qd, J = 7.5, 14.9 Hz, 2H), 1.00 (t, J = 7.4 Hz, 3H), 0.87 (t, J = 7.4 Hz, 3H) | 608.0, 609.0, 610.0 |
| 16 | WX019 | ¹H NMR (400 MHz, CDCl3) δ: 8.66 (s, 1H), 7.83 (d, J = 15.6 Hz, 1H), 7.79 (d, J = 8.5 Hz, 2H), 7.68 (s, 1H), 7.56 (br d, J = 7.3 Hz, 1H), 7.54 (s, 1H), 7.52-7.49 (m, 2H), 7.48-7.40 (m, 2H), 7.34 (d, J = 8.5 Hz, 2H), 7.03-6.99 (m, 2H), 6.70 (d, J = 15.6 Hz, 1H), 6.56 (s, 1H), 4.20-4.16 (m, 2H), 4.16-3.98 (m, 2H), 3.90 (q, J = 7.4 Hz, 2H), 3.84-3.80 (m, 2H), 3.59-3.54 (m, 2H), 1.61-1.58 (m, 2H), 1.44-1.36 (m, 5H), 0.94 (t, J = 7.4 Hz, 3H) | 572.0, 573.0 |
| 17 | WX020 | ¹H NMR (400 MHz, CDCl3) δ: 9.70 (s, 1H), 8.15 (d, J = 15.6 Hz, 1H), 7.80 (d, J = 8.8 Hz, 2H), 7.66 (s, 1H), 7.53 (s, 1H), 7.45-7.42 (m, 3H), 7.41 (s, 1H), 7.28 (d, J = 8.8 Hz, 2H), 6.95 (d, J = 8.8 Hz, 2H), 6.79 (d, J = 15.6 Hz, 1H), 6.48 (s, 1H), 4.22-4.01 (m, 2H), 4.00-3.92 (m, 2H), 3.89 (q, J = 7.4 Hz, 2H), 1.84-1.77 (m, 2H), | 562.0, 563.0, 564.0 |

-continued

| Example | Compound | NMR | MS m/z: |
|---|---|---|---|
| | | 1.52 (qd, J = 7.5, 14.9 Hz, 2H), 1.36 (t, J = 7.4 Hz, 3H), 1.00 (t, J = 7.4 Hz, 3H) | |
| 18 | WX021 | $^1$H NMR (400 MHz, CDCl3) δ: 9.64 (s, 1H), 8.17 (d, J = 15.6 Hz, 1H), 7.83 (d, J = 8.8 Hz, 2H), 7.70 (s, 1H), 7.69 (s, 1H), 7.46-7.43 (m, 4H), 7.31 (d, J = 8.4 Hz, 2H), 6.96 (d, J = 8.8 Hz, 2H), 6.82 (d, J = 15.6 Hz, 1H), 6.52 (s, 1H), 4.22-4.02 (m, 2H), 4.01-4.00 (m, 2H), 3.72 (q, J = 7.4 Hz, 2H), 1.84-1.80 (m, 2H), 1.59-1.51 (m, 2H), 1.12-1.04 (m, 1H), 1.36 (t, J = 7.2 Hz, 3H), 0.66-0.64 (m, 2H), 0.33-0.32 (m, 2H). | 588.0, 589.0, 590.0 |
| 19 | WX022 | $^1$H NMR (400 MHz, CDCl3) δ: 9.49 (s, 1H), 8.08 (d, J = 15.6 Hz, 1H), 7.73 (d, J = 8.4 Hz, 2H), 7.60 (s, 1H), 7.43 (s, 1H), 7.37-7.35 (m, 4H), 7.21 (d, J = 8.8 Hz, 2H), 6.88 (d, J = 8.8 Hz, 2H), 6.72 (d, J = 15.6 Hz, 1H), 6.41 (s, 1H), 4.67 (t, J = 5.6 Hz, 1H), 4.56 (t, J = 5.6 Hz, 1H), 4.14-4.06 (m, 3H), 3.86 (d, J = 14 Hz, 1H), 3.75-3.72 (m, 2H), 2.18-2.10 (m, 2H), 1.66-1.62 (m, 2H), 0.79 (t, J = 7.2 Hz, 3H). | 580.0, 581.0, 582.0 |
| 20 | WX023 | $^1$H NMR (400 MHz, CDCl3) δ: 8.73 (s, 1H), 7.70-7.69 (m, 3H), 7.52 (d, J = 8.8 Hz, 2H), 7.47-7.44 (m, 3H), 7.35 (d, J = 8.8 Hz, 2H), 7.02 (d, J = 8.8 Hz, 2H), 6.72 (d, J = 15.6 Hz, 1H), 6.59 (s, 1H), 4.23-4.06 (m, 4H), 3.84 (d, J = 4.8 Hz, 2H), 3.83-3.60 (m, 2H), 3.58 (d, J = 6.8 Hz, 2H), 1.47-1.43 (m, 2H), 1.43-1.31 (m, 2H), 1.39-1.38 (m, 1H), 0.96 (t, J = 7.2 Hz, 3H), 0.35-0.33 (m, 2H), 0.33-0.32 (m, 2H). | 598.0, 599.0 |
| 21 | WX024 | $^1$H NMR (400 MHz, CDCl3) δ: 10.46 (s, 1H), 7.94-7.83 (m, 4H), 7.63-7.47 (m, 6H), 7.2-6.99 (m, 4H), 6.52 (s, 1H), 4.76-4.62 (m, 2H), 4.33-4.15 (m, 4H), 4.01 (t, J = 6.4 Hz, 2H), 3.8 (m, 2H), 2.3-2.1 (m, 2H), 1.72-1.45 (m, 6H), 0.95 (t, J = 7.2 Hz, 3H), 0.80 (t, J = 7.2 Hz, 3H). | 618.1, 619.0, 620.0 |
| 22 | WX025 | $^1$H NMR (400 MHz, CDCl3) δ: 10.19 (br s, 1H), 8.16 (br d, J = 15.3 Hz, 1H), 7.91-7.74 (m, J = 7.5 Hz, 2H), 7.66 (br s, 1H), 7.51 (br s, 1H), 7.48-7.37 (m, 4H), 7.29 (br s, 2H), 6.96 (br d, J = 7.5 Hz, 2H), 6.91-6.76 (m, 1H), 6.47 (br s, 1H), 4.22 (br d, J = 14.1 Hz, 1H), 4.02 (br s, 2H), 3.99-3.89 (m, 1H), 3.89-3.69 (m, 2H), 1.82 (br s, 2H), 1.77-1.64 (m, 2H), 1.63-1.44 (m, 2H), 1.10-0.95 (m, 3H), 0.95-0.79 (m, 3H) | 576.0, 577.0 |
| 23 | WX026 | $^1$H NMR (400 MHz, CDCl3) δ: 9.08 (br s, 1H), 8.04 (d, J = 15.6 Hz, 1H), 7.80 (br d, J = 8.5 Hz, 2H), 7.65 (s, 1H), 7.54-7.47 (m, 2H), 7.47-7.40 (m, 2H), 7.31 (br d, J = 8.5 Hz, 2H), 6.99-6.91 (m, 3H), 6.85 (d, J = 15.6 Hz, 1H), 6.53 (s, 1H), 6.32-6.23 (m, 1H), 6.17-6.10 (m, 1H), 5.99 (s, 1H), 4.27 (dt, J = 3.9, 12.9 Hz, 2H), 4.22-4.12 (m, 1H), 4.07-3.94 (m, 3H), 3.87-3.73 (m, 2H), 1.86-1.71 (m, 4H), 1.53 (qd, J = 7.5, 15.0 Hz, 2H), 1.00 (t, J = 7.4 Hz, 3H), 0.89 (t, J = 7.3 Hz, 3H) | 622.0, 623.0 |
| 24 | WX027 | $^1$H NMR (400 MHz, CDCl3) δ: 9.44 (br s, 1H), 8.15 (d, J = 15.6 Hz, 1H), 7.79 (d, J = 8.8 Hz, 2H), 7.68 (s, 1H), 7.51-7.40 (m, 5H), 7.29 (d, J = 8.5 Hz, 2H), 6.95 (d, J = 8.8 Hz, 2H), 6.78 (d, J = 15.6 Hz, 1H), 6.50 (s, 1H), 4.16 (d, J = 14.1 Hz, 1H), 4.04-3.95 (m, 3H), 3.82 (dt, J = 3.6, 7.3 Hz, 2H), 1.85-1.75 (m, 2H), 1.64-1.59 (m, 2H), 1.52 (qd, J = 7.4, 14.9 Hz, 2H), 1.27 (qd, J = 7.4, 15.1 Hz, 2H), 1.00 (t, J = 7.4 Hz, 3H), 0.90 (t, J = 7.4 Hz, 3H) | 590.0, 591.1, 592.1 |
| 25 | WX028 | $^1$H NMR (400 MHz, CDCl3) δ: 9.34 (br s, 1H), 7.88-7.59 (m, 4H), 7.57-7.45 (m, 4H), 7.44-7.37 (m, 2H), 7.35-7.28 (m, 2H), 6.99 (d, J = 8.5 Hz, 2H), 6.75 (d, J = 15.6 Hz, 1H), 6.53 (s, 1H), 4.20-4.12 (m, 3H), 4.04-3.95 (m, 1H), 3.85-3.78 (m, 4H), 3.56 (t, J = 6.8 Hz, 2H), 1.73-1.53 (m, 4H), 1.46-1.35 (m, 2H), 1.33-1.23 (m, 2H), 0.98-0.85 (m, 6H) | 600.1, 601.1 |
| 26 | WX029 | $^1$H NMR (400 MHz, CDCl3) δ: 9.58 (br s, 1H), 7.84-7.77 (m, 3H), 7.63 (s, 1H), 7.52 (br d, J = 6.5 Hz, 1H), 7.49-7.44 (m, 3H), 7.43-7.36 (m, 2H), 7.34-7.27 (m, 2H), 6.99 (br d, J = 8.5 Hz, 2H), 6.76 (br d, J = 15.3 Hz, 1H), 6.51 (s, 1H), 4.22-4.11 (m, 3H), 4.00 (br d, J = 14.1 Hz, 1H), 3.81 (br t, J = 4.8 Hz, 2H), 3.75-3.60 (m, 2H), 3.56 (br t, J = 6.7 Hz, 2H), 1.93 (td, J = 6.8, 13.6 Hz, 1H), 1.61 (quin, J = 7.1 Hz, 2H), 1.40 (qd, J = 7.4, 14.9 Hz, 2H), 0.93 (t, J = 7.3 Hz, 3H), 0.86 (br dd, J = 6.8, 10.5 Hz, 6H) | 600.1, 601.1 |
| 27 | WX030 | $^1$H NMR (400 MHz, CDCl3) δ: 9.79-9.51 (m, 1H), 8.15 (d, J = 15.6 Hz, 1H), 7.79 (d, J = 8.5 Hz, 2H), 7.65 (s, 1H), 7.47-7.39 (m, 5H), 7.28 (d, J = 8.5 Hz, 2H), 6.94 (d, J = 8.5 Hz, 2H), 6.78 (d, J = 15.6 Hz, 1H), 6.47 (s, 1H), 4.16 (d, J = 14.1 Hz, 1H), 4.05-3.93 (m, 3H), 3.75-3.53 | 590.1, 591.0, 592.0 |

-continued

| Example | Compound | NMR | MS m/z: |
|---|---|---|---|
| | | (m, 2H), 1.96-1.85 (m, 1H), 1.84-1.75 (m, 2H), 1.52 (qd, J = 7.5, 14.9 Hz, 2H), 1.00 (t, J = 7.4 Hz, 3H), 0.83 (dd, J = 6.7, 13.9 Hz, 6H) | |
| 28 | WX031 | $^1$H NMR (400 MHz, CDCl3) δ: 9.08 (br s, 1H), 7.85 (s, 1H), 7.80 (d, J = 8.8 Hz, 2H), 7.66 (s, 1H), 7.59 (d, J = 8.5 Hz, 2H), 7.55-7.50 (m, 2H), 7.49 (d, J = 8.8 Hz, 2H), 7.44-7.39 (m, 2H), 7.00 (d, J = 8.8 Hz, 2H), 6.69 (d, J = 15.6 Hz, 1H), 6.54 (s, 1H), 4.36 (s, 2H), 4.20-4.15 (m, 2H), 3.99 (t, J = 7.4 Hz, 2H), 3.85-3.79 (m, 2H), 3.56 (t, J = 6.7 Hz, 2H), 1.83-1.73 (m, 2H), 1.58 (br s, 2H), 1.43-1.37 (m, 2H), 0.94 (t, J = 7.4 Hz, 6H) | 602.0, 603.0 |
| 29 | WX032 | $^1$H NMR (400 MHz, CDCl3) δ: 9.56 (br s, 1H), 8.10 (d, J = 15.8 Hz, 1H), 7.80 (br d, J = 8.5 Hz, 2H), 7.60 (s, 1H), 7.50-7.36 (m, 4H), 7.27 (br d, J = 8.8 Hz, 2H), 6.98-6.80 (m, 4H), 6.53 (s, 1H), 4.17-3.92 (m, 6H), 3.80 (br t, J = 4.8 Hz, 2H), 3.77-3.66 (m, 2H), 3.55 (t, J = 6.7 Hz, 2H), 1.73-1.55 (m, 4H), 1.45-1.33 (m, 5H), 0.92 (t, J = 7.3 Hz, 3H), 0.85 (t, J = 7.3 Hz, 3H) | 630.1, 631.1, 632.1 |
| 30 | WX033 | $^1$H NMR (400 MHz, CDCl3) δ: 8.463-8.644 (m, 1 H) 8.065-8.224 (m, 1H) 7.860 (br d, J = 8.533 Hz, 2 H) 7.603-7.748 (m, 2 H) 7.442-7.558 (m, 3 H) 7.316 (d, J = 8.282 Hz, 2 H) 7.000 (d, J = 8.784 Hz, 3 H) 6.854 (d, J = 15.560 Hz, 1 H) 6.535-6.673 (m, 1 H) 4.586-4.788 (m, 1 H) 4.108-4.218 (m, 3 H) 3.947-4.040 (m, 1 H) 3.831 (s, 4 H) 3.577 (s, 2 H) 1.698-1.766 (m, 2 H) 1.583-1.679 (m, 2 H) 1.433 (d, J = 6.023 Hz, 8 H) 0.870-1.056 (m, 6 H) | 644.1, 645.1, 646.1 |
| 31 | WX034 | $^1$H NMR (400 MHz, CDCl3) δ: 8.072 (d, J = 15.560 Hz, 1 H) 7.869-7.926 (m, 1 H) 7.681-7.753 (m, 2 H) 7.586-7.632 (m, 1 H) 7.367-7.453 (m, 4 H) 7.278 (d, J = 8.784 Hz, 2 H) 6.881-6.940 (m, 3 H) 6.642-6.725 (m, 1 H) 6.524 (s, 1 H) 4.072-4.121 (m, 2 H) 3.918-4.064 (m, 2 H) 3.666-3.796 (m, 6 H) 3.491 (t, J = 6.776 Hz, 2 H) 2.127 (dd, J = 12.925, 6.400 Hz, 1 H) 1.590-1.711 (m, 2 H) 1.263-1.441 (m, 2 H) 1.024 (d, J = 6.776 Hz, 6 H) 0.848 (dt, J = 16.187, 7.341 Hz, 6 H) | 658.1, 659.0, 660.2 |
| 32 | WX035 | $^1$H NMR (400 MHz, CHLOROFORM-d) δ: 9.44 (br s, 1H), 8.04 (br d, J = 15.8 Hz, 1H), 7.80 (br d, J = 8.3 Hz, 2H), 7.49 (br s, 1H), 7.43 (br d, J = 8.5 Hz, 2H), 7.30 (br d, J = 8.3 Hz, 2H), 7.22 (s, 1H), 7.07 (s, 1H), 6.98 (br d, J = 8.5 Hz, 2H), 6.86 (br d, J = 15.6 Hz, 1H), 6.54 (br s, 1H), 4.23-4.10 (m, 3H), 4.06-3.96 (m, 1H), 3.93 (s, 3H), 3.86 (s, 3H), 3.85-3.80 (m, 2H), 3.80-3.73 (m, 2H), 3.57 (br t, J = 6.7 Hz, 2H), 1.74-1.67 (m, 2H), 1.62 (td, J = 6.9, 14.3 Hz, 2H), 1.40 (qd, J = 7.4, 14.9 Hz, 2H), 0.94 (br t, J = 7.4 Hz, 3H), 0.87 (br t, J = 7.3 Hz, 3H) | 646.0, 647.1. |
| 33 | WX036 | $^1$H NMR (400 MHz, CDCl3) δ: 8.249-8.360 (m, 1 H) 7.978 (d, J = 15.560 Hz, 1 H) 7.705 (d, J = 8.533 Hz, 2 H) 7.401 (s, 1 H) 7.341 (d, J = 2.008 Hz, 1 H) 7.253 (d, J = 8.784 Hz, 2 H) 7.205-7.224 (m, 1 H) 7.026 (s, 1 H) 6.844-6.918 (m, 1 H) 6.773 (d, J = 2.510 Hz, 1 H) 6.728-6.749 (m, 1 H) 6.693-6.728 (m, 1 H) 6.657-6.680 (m, 1 H) 6.489-6.520 (m, 1 H) 4.080 (s, 2 H) 3.997-4.043 (m, 1 H) 3.895-3.970 (m, 1 H) 3.853 (s, 3 H) 3.717-3.760 (m, 2 H) 3.654-3.717 (m, 2 H) 3.488 (t, J = 6.776 Hz, 2 H) 1.605-1.758 (m, 3 H) 1.477-1.559 (m, 4 H) 1.246-1.407 (m, 2 H) 0.844 (dt, J = 19.011, 7.309 Hz, 6 H) | 630.1, 631.1, 632.1 |
| 45 | WX037 | $^1$H NMR (400 MHz, CDCl3) δ: 9.34 (br s, 1H), 7.87-7.76 (m, 3H), 7.66 (s, 1H), 7.55 (br d, J = 6.3 Hz, 1H), 7.52-7.44 (m, 3H), 7.43-7.34 (m, 2H), 7.31 (br d, J = 8.3 Hz, 2H), 6.73 (br d, J = 15.3 Hz, 1H), 6.63 (br d, J = 8.5 Hz, 2H), 6.59-6.50 (m, 1H), 4.22-4.10 (m, 1H), 4.08-3.94 (m, 1H), 3.87-3.71 (m, 2H), 3.34 (br t, J = 6.1 Hz, 4H), 2.04 (br t, J = 6.3 Hz, 5H), 1.79-1.63 (m, 2H), 0.89 (t, J = 7.4 Hz, 3H) | 270.1 (M/2 + H)$^+$ |
| 34 | WX038 | $^1$H NMR (400 MHz, CDCl3) δ: 8.83 (br s, 1H), 8.05 (d, J = 15.8 Hz, 1H), 7.79 (br d, J = 8.5 Hz, 2H), 7.62 (s, 1H), 7.51 (br d, J = 8.5 Hz, 1H), 7.46-7.39 (m, 3H), 7.29 (s, 2H), 7.02-6.93 (m, 3H), 6.83 (d, J = 15.6 Hz, 1H), 4.16 (t, J = 4.8 Hz, 2H), 4.11-3.99 (m, 2H), 3.89 (s, 3H), 3.84-3.74 (m, 4H), 3.56 (t, J = 6.7 Hz, 2H), 1.65-1.53 (m, 7H), 1.40 (qd, J = 7.4, 14.9 Hz, 2H), 0.91 (td, J = 7.3, 17.7 Hz, 6H) | 630.1, 631.1, 632.1 |
| 37 | WX039 | $^1$H NMR (400 MHz, CDCl3) δ: 9.37(s, 1 H) 8.05(d, J = 15.5 Hz, 1H), 7.80 (d, J = 8.8 Hz, 2H), 7.61 (d, J = 2.3 Hz, 1H), 7.51(s, 1H), 7.49(dd, J = 8.7 Hz, J = 2.4 Hz, 1H), | 603.1 604.1 605.1 |

-continued

| Example | Compound | NMR | MS m/z: |
|---|---|---|---|
|  |  | 7.41(d, J = 8.8 Hz, 2H), 7.29(d, J = 8.5 Hz, 2H), 6.96-6.92(m, 3H), 6.88(d, J = 15.5 Hz, 1H), 6.55(s, 1H), 4.15-4.13(m, 2H), 4.11-3.94 (m, 2H), 3.86(s, 3H), 3.84-3.82 (m, 2H), 3.80-3.69(m, 2H), 3.56(t, J = 6.8 Hz, 2H), 1.63-1.59(m, 2H), 1.42-1.38(m, 3H), 1.36-1.32(m, 2H), 0.93(t, J = 7.4 Hz, 3H). |  |
| 37 | WX040 | $^1$H NMR (400 MHz, CDCl3) δ: 9.07(br s, 1 H) 8.05(d, J = 15.5 Hz, 1H), 7.80 (d, J = 8.3 Hz, 2H), 7.62 (d, J = 2.3 Hz, 1H), 7.53(s, 1H), 7.50 (dd, J = 8.7 Hz, J = 2.1 Hz, 1H), 7.43(d, J = 8.5 Hz, 2H), 7.30(d, J = 8.3 Hz, 2H), 6.97-6.94(m, 3H), 6.88(d, J = 15.5 Hz, 1H), 6.56(br s, 1H), 4.16-4.13(m, 2H), 4.11-3.95 (m, 2H), 3.88 (s, 3H), 3.85-3.74 (m, 4H), 3.56 (t, J = 6.8 Hz, 2H), 1.63-1.59 (m, 2H), 1.42-1.36 (m, 3H), 1.36-1.32(m, 2H), 0.93(t, J = 7.4 Hz, 3H). | 603.1 604.0 605.0 |
| 46 | WX041 | $^1$H NMR (400 MHz, CDCl3) δ: 8.68 (S, 1 H), 7.79 (d, J = 8.8 Hz, 2 H), 7.68 (d, J = 1.8 Hz, 1 H), 7.51 (s, 1 H), 7.47 (d, J = 8.5 Hz, 2H), 7.44 (s, 1 H), 7.33 (d, J = 8.8 Hz, 1 H), 7.27 (s, 1 H), 6.99 (d, J = 8.8 Hz, 2H), 6.62(d, J = 15.3 Hz, 1 H), 6.55 (s, 1 H), 4.18-4.15 (m, 2 H), 4.12-3.98 (m, 2 H), 3.88-3.84 (m, 2 H), 3.83-3.81(m, 2 H), 3.56(t, J = 6.8 Hz, 2 H), 2.48(s, 1H), 1.43-1.25 (m, 7H), 0.94 (t, J = 7.4 Hz, 3 H). | 586.0, 587.0 588.1 |
| 43 | WX042 | $^1$H NMR (400 MHz, CDCl3) δ: 9.08 (s, 1 H), 7.97 (d, J = 15.6 Hz, 1 H), 7.73(d, J = 8.8 Hz, 2H), 7.43-7.41 (m, 2 H), 7.36-7.34 (m, 2H), 7.30 (d, J = 1.7 Hz, 1H), 7.24 (d, J = 8.5 Hz, 2 H), 6.90 (d, J = 8.8 Hz, 2H), 6.75 (d, J = 15.8 Hz, 1 H), 6.46 (s, 1H), 4.10-4.08 (m, 2 H), 4.07-3.9 (m, 2H), 3.76-3.73 (m, 2 H), 3.70 (s, 3H), 3.49 (t, J = 6.8 Hz, 2 H), 2.29 (s, 3H), 1.66-1.62 (m, 2H), 1.56-1.52 (m, 2H), 1.36-1.30 (m, 2H), 0.87 (t, J = 7.4 Hz, 3 H), 0.81 (t, J = 7.3 Hz, 3H) | 630.0, 631.0, 632.0 |
| 44 | WX043 | $^1$H NMR (400 MHz, CDCl3) δ: 9.14 (br s, 1H), 7.88 (br d, J = 15.6 Hz, 1H), 7.70 (br d, J = 8.3 Hz, 2H), 7.40 (s, 1H), 7.32 (s, 1H), 7.23 (br s, 1H), 7.22 (br s, 3H), 6.92 (br s, 1H), 6.91-6.87 (m, 2H), 6.73 (br d, J = 15.6 Hz, 1H), 6.44 (s, 1H), 4.09 (br s, 2H), 4.05 (br s, 1H), 3.88 (br d, J = 14.3 Hz, 1H), 3.80 (s, 3H), 3.75 (br s, 2H), 3.70 (br d, J = 6.5 Hz, 2H), 3.49 (br t, J = 6.4 Hz, 2H), 1.64-1.58 (m, 2H), 1.57-1.51 (m, 2H), 1.37-1.29 (m, 2H), 0.87 (br t, J = 7.2 Hz, 3H), 0.81 (br t, J = 7.2 Hz, 3H) | 650.0, 651.0, 652.0 |
| 35 | WX044 | $^1$H NMR (400 MHz, CHLOROFORM-d) δ: 10.28 (br s, 1H), 7.98 (d, J = 15.8 Hz, 1H), 7.81 (br d, J = 8.3 Hz, 2H), 7.76-7.65 (m, 2H), 7.59 (br d, J = 8.0 Hz, 1H), 7.54 (s, 1H), 7.48 (br d, J = 8.5 Hz, 2H), 7.29 (br d, J = 9.0 Hz, 2H), 7.09 (br d, J = 15.6 Hz, 1H), 7.01 (br d, J = 8.8 Hz, 2H), 6.49 (s, 1H), 4.29-4.13 (m, 3H), 3.97 (br d, J = 14.1 Hz, 1H), 3.88-3.70 (m, 4H), 3.57 (t, J = 6.7 Hz, 2H), 1.72 (qd, J = 7.3, 14.6 Hz, 1H), 1.78-1.66 (m, 1H), 1.40 (qd, J = 7.4, 14.9 Hz, 2H), 0.94 (t, J = 7.3 Hz, 3H), 0.89 (br t, J = 7.3 Hz, 3H) | 611.1, 612.0 |
| 36 | WX045 | $^1$H NMR (400 MHz, CDCl3) δ: 8.06 (d, J = 15.6 Hz, 2H), 7.78(d, J = 8.4 Hz, 2H), 7.67 (s, 1H), 7.48-7.31 (m, 6H), 7.01-6.98(m, 3H), 6.82(d, J = 15.6 Hz, 1H), 4.18-4.07 (m, 4H), 3.94 (s, 3H), 3.84-3.81 (m, 4H), 3.58-3.55(m, 2H), 1.45-1.37(m, 7H), 0.93(t, J = 7.4 Hz, 3H). | 616.3, 614.3 |
| 38 | WX046 | $^1$H NMR (400 MHz, CDCl3) δ: 10.53 (br s, 1 H) 7.84-7.94 (m, 1 H) 7.76 (br d, J = 8.03 Hz, 2 H) 7.53 (s, 1 H) 7.40 (s, 2 H) 7.31 (d, J = 7.5 Hz, 2 H) 7.16 (d, J = 8.0 Hz, 2 H) 7.11 (s, 1 H) 6.76-6.95 (m, 3 H) 6.21-6.66 (m, 1 H) 3.89-4.15 (m, 3 H) 3.79-4.15 (m, 3 H) 3.75 (s, 2 H) 3.49 (t, J = 6.2 Hz, 2 H) 1.49-1.60 (m, 2 H) 1.40 (s, 3 H) 1.34 (br s, 2 H) 1.29 (t, J = 6.7 Hz, 3 H) 0.86 (t, J = 7.0 Hz, 3 H). | 652.0, 653.0 |
| 39 | WX047 | 1H NMR (400 MHz, CDCl3) δ: 9.92 (br s, 1H), 8.03 (br d, J = 15.8 Hz, 1H), 7.75 (br d, J = 8.3 Hz, 2H), 7.50 (br s, 1H), 7.43-7.36 (m, 2H), 7.31 (br d, J = 8.5 Hz, 2H), 7.20-7.15 (m, 2H), 6.87 (br d, J = 8.5 Hz, 2H), 6.83 (br s, 1H), 6.79 (br d, J = 15.6 Hz, 1H), 4.07 (br dd, J = 3.9, 9.2 Hz, 3H), 4.01 (q, J = 6.8 Hz, 2H), 3.89-3.80 (m, 3H), 3.77-3.71 (m, 3H), 3.52-3.45 (m, 2H), 1.57-1.51 (m, 2H), 1.47 (s, 3H), 1.33 (br d, J = 6.5 Hz, 5H), 1.30-1.25 (m, 3H), 0.91-0.84 (m, 3H) | 630.1, 631.1 |
| 48 | WX048 | 1H NMR (400 MHz, CDCl3) δ: 9.07 (br s, 1H), 8.06 (d, J = 15.8 Hz, 1H), 7.80 (d, J = 8.5 Hz, 2H), 7.63 (d, J = 2.0 Hz, 1H), 7.53-7.48 (m, 1H), 7.43 (d, J = 8.5 Hz, 1H), 7.54-7.40 (m, 1H), 7.55-7.39 (m, 1H), 7.31 (d, J = 8.5 | 572.0 573.0 |

-continued

| Example | Compound | NMR | MS m/z: |
|---|---|---|---|
| | | Hz, 2H), 6.99-6.92 (m, 3H), 6.88 (d, J = 15.8 Hz, 1H), 6.56 (s, 1H), 4.15 (d, J = 14.1 Hz, 1H), 4.18-3.96 (m, 1H), 4.02-3.96 (m, 2H), 3.88 (s, 3H), 3.78 (dt, J = 3.8, 7.2 Hz, 2H), 1.75 (br d, J = 12.5 Hz, 2H), 1.72-1.66 (m, 2H), 1.52 (qd, J = 7.4, 14.9 Hz, 2H), 1.00 (t, J = 7.4 Hz, 3H), 0.88 (t, J = 7.4 Hz, 3H) | |
| 49 | WX049 | 1H NMR (400 MHz, CDCl3) δ: 9.33 (s, 1H), 8.05 (d, J = 15.6 Hz, 1H), 7.80 (d, J = 8.8 Hz, 2H), 7.61 (d, J = 2.3 Hz, 1H), 7.50 (br d, J = 2.3 Hz, 1H), 7.48 (s, 1H), 7.44-7.39 (m, 2H), 7.29 (d, J = 8.8 Hz, 2H), 6.98-6.93 (m, 3H), 6.88 (d, J = 15.8 Hz, 1H), 6.55 (s, 1H), 4.15 (d, J = 4.8 Hz, 2H), 4.14-4.13 (m, 1H), 4.13 (d, J = 2.8 Hz, 1H), 3.97 (d, J = 14.1 Hz, 1H), 3.83-3.79 (m, 1H), 3.79-3.79 (m, 1H), 3.76 (dt, J = 4.0, 7.3 Hz, 2H), 3.56 (t, J = 6.8 Hz, 2H), 1.73-1.66 (m, 2H), 1.65-1.57 (m, 2H), 1.45-1.35 (m, 2H), 0.93 (t, J = 7.4 Hz, 2H), 0.87 (t, J = 7.4 Hz, 3H)○ | 602.0 603.0 |
| 50 | WX050 | 1H NMR (400 MHz, CDCl3) δ: 9.08 (s, 1H), 8.06 (d, J = 15.8 Hz, 1H), 7.81 (d, J = 8.8 Hz, 2H), 7.63 (d, J = 2.3 Hz, 1H), 7.52-7.49 (m, 1H), 7.49 (s, 1H), 7.43 (d, J = 8.5 Hz, 2H), 7.31 (d, J = 8.8 Hz, 2H), 6.98 (d, J = 6.0 Hz, 2H), 6.96-6.94 (m, 1H), 6.88 (d, J = 15.8 Hz, 1H), 6.57 (s, 1H), 4.19-4.16 (m, 2H), 4.14 (d, J = 7.5 Hz, 1H), 3.99 (d, J = 14.1 Hz, 1H), 3.88 (s, 3H), 3.84-3.81 (m, 2H), 3.78 (dt, J = 2.8, 7.3 Hz, 2H), 3.53 (t, J = 6.8 Hz, 2H), 1.75-1.71 (m, 2H), 1.67-1.61 (m, 2H), 0.96 (t, J = 7.4 Hz, 3H), 0.88 (t, J = 7.4 Hz, 3H). | 602.0 603.1 |
| 51 | WX051 | 1H NMR (400 MHz, CDCl3) δ: 9.14 (br s, 1 H) 7.93 (d, J = 15.5 Hz, 1 H) 7.73 (d, J = 8.7 Hz, 2 H) 7.63 (d, J = 2.0 Hz, 1 H) 7.45 (dd, J = 8.6, 2.1 Hz, 1 H) 7.42 (s, 1 H) 7.37 (d, J = 8.7 Hz, 2 H) 7.24 (d, J = 8.5 Hz, 2 H) 7.14 (d, J = 8.5 Hz, 1 H) 6.92 (d, J = 8.5 Hz, 2 H) 6.77 (d, J = 15.8 Hz, 1 H) 6.31-6.67 (m, 2 H) 3.66-4.17 (m, 8 H) 3.49 (t, J = 6.6 Hz, 2 H) 1.65 (d, J = 7.2 Hz, 2 H) 1.33 (d, J = 7.5 Hz, 2 H) 0.78-0.91 (m, 6 H) | 652.0 653.0 654.0 |
| 52 | WX052 | 1H NMR (400 MHz, CDCl3) δ: 9.90 (br s, 1 H) 7.98 (d, J = 15.5 Hz, 1 H) 7.81 (d, J = 8.7 Hz, 2 H) 7.65 (d, J = 2.2 Hz, 1 H) 7.47-7.52 (m, 2 H) 7.37-7.45 (m, 2 H) 7.29 (s, 1 H) 7.19 (d, J = 8.5 Hz, 1 H) 6.95 (d, J = 8.7 Hz, 2 H) 6.88 (d, J = 15.5 Hz, 1 H) 6.31-6.74 (m, 2 H) 3.90-4.26 (m, 4 H) 3.81 (d, J = 13.05 Hz, 2 H) 1.79-1.91 (m, 2 H) 1.62-1.71 (m, 2 H) 1.06 (t, J = 7.4 Hz, 3 H) 0.87 (t, J = 7.4 Hz, 3 H) | 594.0 595.0 596.1 |
| 53 | WX053 | 1H NMR (400 MHz, CDCl3) δ: 10.35 (s, 1H), 7.96 (d, J = 16 Hz, 1H), 7.82(d, J = 8.0 Hz, 2H), 7.53-7.27(m, 7H), 6.96(d, J = 8.4 Hz, 3H), 6.48(s, 1H), 4.24-3.55(m, 13H), 1.40(d, J = 7.6 Hz, 2H), 0.96-0.86(m, 6H). | 651.0 652.0 |
| 54 | WX054 | 1H NMR (400 MHz, CDCl3) δ: 9.84 (br s, 1H), 8.00 (d, J = 15.6 Hz, 1H), 7.82 (br d, J = 8.3 Hz, 2H), 7.68 (s, 1H), 7.53 (dd, J = 1.9, 8.4 Hz, 1H), 7.48 (s, 1H), 7.43 (br d, J = 8.5 Hz, 2H), 7.37-7.28 (m, 3H), 7.00 (d, J = 8.5 Hz, 2H), 6.84 (d, J = 15.8 Hz, 1H), 4.21-4.11 (m, 3H), 4.00-3.90 (m, 3H), 3.86-3.80 (m, 2H), 3.57 (t, J = 6.8 Hz, 2H), 1.65 (br d, J = 2.8 Hz, 2H), 1.53 (s, 3H), 1.46-1.35 (m, 5H), 0.95 (t, J = 7.4 Hz, 3H) | 670.0 671.0 |
| 55 | WX055 | 1H NMR (400 MHz, CDCl3) δ: 10.03 (br s, 1H), 7.99 (br d, J = 15.6 Hz, 1H), 7.82 (br d, J = 8.3 Hz, 3H), 7.67 (s, 1H), 7.53 (br d, J = 8.5 Hz, 1H), 7.48 (s, 1H), 7.42 (br d, J = 8.5 Hz, 3H), 6.99 (br d, J = 8.5 Hz, 3H), 6.85 (br d, J = 15.8 Hz, 1H), 4.21-4.14 (m, 3H), 3.99-3.90 (m, 3H), 3.83 (br t, J = 4.6 Hz, 2H), 3.57 (br t, J = 6.7 Hz, 2H), 1.64 (br d, J = 6.8 Hz, 2H), 1.52 (s, 3H), 1.45-1.35 (m, 5H), 0.95 (t, J = 7.4 Hz, 3H) | 670.0 671.0 |
| 56 | WX056 | 1H NMR (400 MHz, CDCl3) δ: 8.38 (br s, 1H), 8.06 (br d, J = 15.8 Hz, 1H), 7.92 (br s, 2H), 7.76 (br d, J = 7.8 Hz, 2H), 7.67 (br s, 1H), 7.54 (br d, J = 8.5 Hz, 1H), 7.47 (br d, J = 8.3 Hz, 2H), 7.35 (br d, J = 7.5 Hz, 2H), 7.11 (br s, 1H), 7.00 (br d, J = 8.3 Hz, 4H), 6.78 (br d, J = 15.8 Hz, 1H), 4.21-4.08 (m, 4H), 3.94 (s, 3H), 3.89-3.78 (m, 2H), 3.87-3.77 (m, 1H), 3.57 (t, J = 6.7 Hz, 3H), 2.26 (br s, 4H), 1.62 (td, J = 6.9, 14.5 Hz, 6H), 1.46-1.36 (m, 6H) | 599.0 600.0 |
| 57 | WX057 | 1H NMR (400 MHz, CDCl3) δ: 8.07-7.92 (m, 2H), 4.20-4.17 (m, 2H), 3.98-3.92 (m, 3H), 3.84 (br t, J = 3.9 Hz, 2H), 3.58 (dt, J = 1.6, 6.7 Hz, 2H), 2.96-2.86 (m, 1H), 1.64 (br d, J = 7.0 Hz, 2H), 1.52 (s, 3H), 1.47-1.40 (m, 2H), 1.40-1.36 (m, 3H), 1.30 (dd, J = 2.8, 7.0 Hz, 4H), 1.27 (br s, 2H), 1.13 (dd, J = 1.9, 6.7 Hz, 3H), 0.99-0.91 (m, 3H) | 675.9 676.0 |

-continued

| Example | Comound | NMR | MS m/z: |
|---|---|---|---|
| 58 | WX058 | 1H NMR (400 MHz, CDCl3) δ: 9.41 (br s, 1H), 8.22 (d, J = 15.6 Hz, 1H), 7.61 (br d, J = 8.8 Hz, 1H), 7.49 (br d, J = 1.3 Hz, 1H), 7.36-7.27 (m, 3H), 7.11-7.07 (m, 1H), 6.77 (br d, J = 8.5 Hz, 1H), 6.52 (d, J = 15.6 Hz, 1H), 6.33 (s, 1H), 3.96 (t, J = 4.8 Hz, 1H), 3.93-3.75 (m, 1H), 3.62 (t, J = 4.6 Hz, 1H), 3.58-3.52 (m, 1H), 3.36 (t, J = 6.7 Hz, 1H), 3.19-3.10 (m, 1H), 1.53-1.45 (m, 1H), 1.45-1.39 (m, 1H), 1.25-1.17 (m, 1H), 1.08 (d, J = 6.8 Hz, 1H), 0.77-0.69 (m, 4H), 0.70-0.63 (m, 1H) | 659.9 662.0 |
| 59 | WX059 | 1H NMR (400 MHz, CDCl3) δ: 0.93 (dt, J = 16.00, 7.43 Hz, 6 H) 1.41 (dq, J = 14.90, 7.41 Hz, 2 H) 1.62-1.67 (m, 2 H) 1.73 (sxt, J = 7.33 Hz, 2 H) 2.42 (s, 3 H) 3.57 (t, J = 6.78 Hz, 2 H) 3.75-3.89 (m, 4 H) 4.01 (d, J = 14.05 Hz, 1 H) 4.12-4.22 (m, 3 H) 6.56 (s, 1 H) 6.68 (d, J = 15.56 Hz, 1 H) 7.00 (d, J = 8.78 Hz, 2 H) 7.32-7.39 (m, 3 H) 7.46-7.54 (m, 4 H) 7.76-7.85 (m, 3 H) 8.64 (s, 1 H) | 599.8. 600.8 |
| 60 | WX060 | 1H NMR (400 MHz, CDCl3) δ: 10.70 (s, 1H), 8.16-8.08 (m, 1H), 7.83-7.75 (m, J = 8.5 Hz, 2H), 7.72-7.65 (m, 2H), 7.55 (br d, J = 8.0 Hz, 1H), 7.49-7.39 (m, 3H), 7.26-7.18 (m, J = 8.5 Hz, 2H), 6.96 (d, J = 8.5 Hz, 2H), 6.83 (d, J = 15.6 Hz, 1H), 6.44 (s, 1H), 4.23-4.17 (m, 1H), 4.17-4.10 (m, 2H), 3.93-3.84 (m, 1H), 3.82 (t, J = 4.8 Hz, 2H), 3.80-3.69 (m, 2H), 3.56 (t, J = 6.8 Hz, 2H), 1.71-1.57 (m, 4H), 1.45-1.33 (m, 2H), 0.93 (t, J = 7.3 Hz, 3H), 0.81 (t, J = 7.5 Hz, 3H) | 654.0, 655.0 |
| 61 | WX061 | 1H NMR (400 MHz, CDCl3) δ: 10.58 (br s, 1 H) 7.88 (d, J = 15.8 Hz, 1 H) 7.75 (d, J = 8.5 Hz, 2 H) 7.53 (d, J = 2.2 Hz, 1 H) 7.36-7.43 (m, 2 H) 7.30 (d, J = 8.5 Hz, 2 H) 7.16 (d, J = 8.7 Hz, 2 H) 7.09 (d, J = 8.5 Hz, 1 H) 6.88 (d, J = 8.5 Hz, 2 H) 6.83 (d, J = 15.8 Hz, 1 H) 6.19-6.64 (m, 1 H) 3.79-4.15 (m, 6 H) 3.69-3.78 (m, 2 H) 3.49 (t, J = 6.6 Hz, 2 H) 1.49-1.60 (m, 2 H) 1.40 (s, 3 H) 1.31-1.36 (m, 2 H) 1.28 (t, J = 7.2 Hz, 3 H) 0.86 (t, J = 7.4 Hz, 3 H) | 652.0 653.0 654.0 |
| 62 | WX062 | 1H NMR (400 MHz, CDCl3) δ: 10.49 (br s, 1 H) 7.89 (d, J = 15.8 Hz, 1 H) 7.76 (d, J = 8.2 Hz, 2 H) 7.54 (d, J = 1.7 Hz, 1 H) 7.37-7.44 (m, 2 H) 7.32 (d, J = 8.5 Hz, 2 H) 7.16 (d, J = 8.5 Hz, 2 H) 7.10 (d, J = 8.53 Hz, 1 H) 6.87 (b d, J = 8.53 Hz, 2 H) 6.83 (d, J = 15.8 Hz, 1 H) 6.22-6.64 (m, 1 H) 3.78-4.15 (m, 6 H) 1.70-1.78 (m, 2 H) 1.40 (s, 3 H) 1.29 (t, J = 7.2 Hz, 3 H) 0.99 (t, J = 7.4 Hz, 3 H) | 594.0 595.0 596.0 |
| 63 | WX063 | 1H NMR (400 MHz, CDCl3) δ: 10.43 (br s, 1 H) 7.89 (d, J = 15.81 Hz, 1 H) 7.76 (br d, J = 8.53 Hz, 2 H) 7.54 (d, J = 2.01 Hz, 1 H) 7.38-7.45 (m, 2 H) 7.32 (d, J = 8.53 Hz, 2 H) 7.17 (d, J = 8.78 Hz, 2 H) 7.10 (d, J = 8.53 Hz, 1 H) 6.87 (d, J = 8.53 Hz, 2 H) 6.82 (d, J = 15.81 Hz, 1 H) 6.23-6.66 (m, 1 H) 3.80-4.14 (m, 6 H) 1.77-1.83 (m, 2 H) 1.40 (s, 3 H) 1.29 (t, J = 7.40 Hz, 3 H) 0.99 (t, J = 7.40 Hz, 3 H) | 594.0 595.0 596.0 |
| 64 | WX064 | 1H NMR (400 MHz, CDCl3) δ: 10.14 (br s, 1 H) 7.97 (d, J = 15.8 Hz, 1 H) 7.80 (d, J = 8.5 Hz, 2 H) 7.64 (d, J = 2.0 Hz, 1 H) 7.45-7.53 (m, 2 H) 7.40 (d, J = 8.5 Hz, 2 H) 7.26 (d, J = 3.5 Hz, 1 H) 7.18 (d, J = 8.5 Hz, 1 H) 6.96 (d, J = 8.7 Hz, 2 H) 6.90 (d, J = 15.8 Hz, 1 H) 6.29-6.76 (m, 2 H) 3.70-4.24 (m, 8 H) 3.52 (t, J = 6.7 Hz, 2 H) 1.56-1.75 (m, 4 H) 0.95 (t, J = 7.4 Hz, 3 H) 0.86 (t, J = 7.4 Hz, 3 H) | 638.0 639.0 640.0 |
| 65 | WX065 | 1H NMR (400 MHz, CDCl3) δ: 9.98 (br s, 1H), 8.05 (d, J = 15.8 Hz, 1H), 7.83 (br d, J = 8.5 Hz, 2H), 7.57 (d, J = 1.5 Hz, 1H), 7.50-7.45 (m, 2H), 7.39 (d, J = 8.5 Hz, 2H), 7.27-7.23 (m, 2H), 6.98-6.93 (m, 3H), 6.90 (d, J = 12.0 Hz, 1H), 4.18-4.11 (m, 3H), 3.97-3.88 (m, 3H), 3.84-3.79 (m, 5H), 3.52 (t, J = 6.8 Hz, 2H), 1.70-1.62 (m, 2H), 1.55 (s, 3H), 1.36 (t, J = 7.3 Hz, 3H), 0.95 (t, J = 7.4 Hz, 3H) | 602.1, 603.0, 604.0 |
| 66 | WX066 | 1H NMR (400 MHz, CDCl3) δ: 9.83 (br s, 1H), 9.81-9.72 (m, 1H), 8.05 (d, J = 15.6 Hz, 1H), 7.83 (br d, J = 8.3 Hz, 2H), 7.58 (d, J = 1.8 Hz, 1H), 7.50-7.45 (m, 2H), 7.40 (br d, J = 8.5 Hz, 2H), 7.30-7.25 (m, 2H), 6.99-6.86 (m, 4H), 4.18-4.15 (m, 2H), 4.14-3.93 (m, 2H), 3.93-3.88 (m, 2H), 3.84 (s, 3H), 3.83-3.79 (m, 2H), 3.52 (t, J = 6.8 Hz, 2H), 1.71-1.62 (m, 2H), 1.56 (s, 3H), 1.37 (t, J = 7.3 Hz, 3H), 0.95 (t, J = 7.4 Hz, 3H) | 602.1, 603.0, 604.0 |
| 67 | WX067 | 1H NMR (400 MHz, CDCl3) δ: 8.64 (br s, 1H), 8.13 (br d, J = 15.6 Hz, 1H), 7.81 (br d, J = 8.0 Hz, 2H), 7.67 (s, 1H), 7.54-7.49 (m, 2H), 7.46 (br d, J = 7.5 Hz, 2H), 7.34 | 616.1, 617.1, 618.1 |

-continued

| Example | Compound | NMR | MS m/z: |
|---|---|---|---|
| | | (br d, J = 7.8 Hz, 2H), 7.02-6.95 (m, 3H), 6.83 (br d, J = 15.1 Hz, 1H), 6.59 (s, 1H), 4.18 (br s, 2H), 4.17-4.15 (m, 2H), 4.14-3.99 (m, 2H), 3.84 (br s, 2H), 3.79 (br t, J = 7.2 Hz, 2H), 3.54 (br t, J = 6.5 Hz, 2H), 1.76-1.70 (m, 2H), 1.67 (br d, J = 7.5 Hz, 2H), 1.49 (br t, J = 6.8 Hz, 3H), 0.97 (br t, J = 7.4 Hz, 3H), 0.90 (br t, J = 7.2 Hz, 3H) | |
| 68 | WX068 | 1H NMR (400 MHz, CDCl3) δ: 9.22 (br s, 1H), 8.03 (d, J = 15.6 Hz, 1H), 7.74 (br d, J = 8.5 Hz, 2H), 7.54 (s, 1H), 7.43-7.32 (m, 4H), 7.21 (s, 1H), 6.94-6.82 (m, 3H), 6.76 (d, J = 15.6 Hz, 1H), 4.11-4.06 (m, 2H), 4.06-4.02 (m, 2H), 4.11-3.89 (m, 1H), 3.84-3.77 (m, 1H), 3.81 (q, J = 7.0 Hz, 1H), 3.74 (br t, J = 4.8 Hz, 2H), 3.49 (t, J = 6.8 Hz, 2H), 1.61-1.55 (m, 4H), 1.53 (s, 3H), 1.36 (br t, J = 7.0 Hz, 4H), 1.32-1.27 (m, 1H), 1.33-1.26 (m, 3H), 0.90-0.83 (m, 1H), 0.87 (t, J = 7.3 Hz, 2H) | 630.1 631.1 |
| 69 | WX069 | 1H NMR (400 MHz, CDCl3) δ: 8.54 (br s, 1H), 8.11 (d, J = 15.6 Hz, 1H), 7.79 (d, J = 8.5 Hz, 2H), 7.64 (d, J = 2.3 Hz, 1H), 7.49 (dd, J = 2.3, 8.5 Hz, 1H), 7.44 (d, J = 8.8 Hz, 2H), 7.41 (s, 1H), 7.29 (d, J = 8.8 Hz, 2H), 6.98 (d, J = 8.8 Hz, 2H), 6.95 (s, 1H), 6.79 (d, J = 15.8 Hz, 1H), 4.19-4.16 (m, 2H), 4.15-4.11 (m, 2H), 4.10-4.01 (m, 2H), 3.84-3.80 (m, 2H), 3.77 (t, J = 7.3 Hz, 2H), 3.52 (t, J = 6.8 Hz, 2H), 1.76-1.65 (m, 4H), 1.63 (s, 3H), 1.48 (t, J = 7.0 Hz, 3H), 0.95 (t, J = 7.5 Hz, 3H), 0.90 (t, J = 7.4 Hz, 3H) | 630.1, 631.1, 632.1, |
| 70 | WX070 | 1H NMR (400 MHz, CDCl3) δ: 11.10 (br s, 1H), 8.17-8.09 (m, 1H), 7.82 (br d, J = 8.0 Hz, 2H), 7.68 (d, J = 7.5 Hz, 1H), 7.67-7.65 (m, 1H), 7.56 (br d, J = 8.0 Hz, 1H), 7.47 (s, 1H), 7.41 (d, J = 9.0 Hz, 2H), 7.21 (d, J = 8.5 Hz, 2H), 6.97 (d, J = 8.5 Hz, 2H), 6.82 (d, J = 15.6 Hz, 1H), 4.23-4.11 (m, 3H), 3.98-3.79 (m, 5H), 3.57 (t, J = 6.8 Hz, 2H), 1.67-1.58 (m, 2H), 1.47-1.31 (m, 8H), 0.94 (t, J = 7.3 Hz, 3H) | 654.0 655.0 |
| 71 | WX071 | 1H NMR (400 MHz, CDCl3) δ: 11.15 (br s, 1H), 8.13 (br d, J = 15.1 Hz, 1H), 7.82 (br d, J = 8.5 Hz, 2H), 7.72-7.60 (m, 2H), 7.55 (br d, J = 8.0 Hz, 1H), 7.47 (s, 1H), 7.44-7.36 (m, J = 8.5 Hz, 2H), 7.24-7.17 (m, J = 8.5 Hz, 2H), 6.96 (br d, J = 8.5 Hz, 2H), 6.83 (br d, J = 15.6 Hz, 1H), 4.27-4.08 (m, 3H), 3.94 (q, J = 7.0 Hz, 2H), 3.89-3.78 (m, 3H), 3.57 (br t, J = 6.5 Hz, 2H), 1.62 (quin, J = 7.0 Hz, 2H), 1.48-1.29 (m, 8H), 0.94 (t, J = 7.3 Hz, 3H) | 654.0 655.0 |
| 72 | WX072 | 1H NMR (400 MHz, CDCl3) δ: 8.36 (br s, 1H), 8.28 (d, J = 15.1 Hz, 1H), 7.80 (d, J = 8.5 Hz, 2H), 7.66 (d, J = 1.8 Hz, 1H), 7.53 (dd, J = 1.9, 8.2 Hz, 1H), 7.51-7.45 (m, 3H), 7.40 (d, J = 8.3 Hz, 1H), 7.32 (d, J = 8.8 Hz, 2H), 7.05-6.96 (m, 2H), 6.56 (d, J = 15.3 Hz, 1H), 4.21-4.16 (m, 2H), 4.13-3.99 (m, 2H), 3.93-3.85 (m, 2H), 3.85-3.81 (m, 2H), 3.57 (t, J = 6.8 Hz, 2H), 3.42 (td, J = 8.7, 17.3 Hz, 1H), 2.14-2.04 (m, 2H), 1.90-1.80 (m, 2H), 1.79-1.71 (m, 2H), 1.67-1.61 (m, 3H), 1.45-1.37 (m, 5H), 0.95 (t, J = 7.4 Hz, 3H) | 654.1 655.0 |
| 73 | WX073 | 1H NMR (400 MHz, CDCl3) δ: 8.29 (d, J = 15.3 Hz, 1H), 7.80 (d, J = 8.5 Hz, 2H), 7.66 (d, J = 1.8 Hz, 1H), 7.56-7.52 (m, 1H), 7.51-7.45 (m, 2H), 7.40 (d, J = 8.3 Hz, 1H), 7.32 (d, J = 8.5 Hz, 2H), 7.00 (d, J = 8.5 Hz, 2H), 6.55 (d, J = 15.1 Hz, 1H), 4.21-4.15 (m, 2H), 4.13-4.00 (m, 2H), 3.88 (q, J = 7.0 Hz, 2H), 3.85-3.81 (m, 2H), 3.57 (t, J = 6.8 Hz, 2H), 3.47-3.38 (m, 1H), 2.14-2.04 (m, 2H), 1.91-1.81 (m, 2H), 1.80-1.69 (m, 2H), 1.67-1.61 (m, 6H), 1.44-1.36 (m, 5H), 0.95 (t, J = 7.4 Hz, 3H) | 654.1 655.0 |
| 74 | WX074 | 1H NMR (400 MHz, CDCl3) δ: 10.80 (br s, 1 H) 7.95 (d, J = 15.8 Hz, 1 H) 7.83 (d, J = 8.5 Hz, 2 H) 7.59 (d, J = 2.0 Hz, 1 H) 7.43-7.49 (m, 2 H) 7.37 (d, J = 8.5 Hz, 2 H) 7.23 (d, J = 8.5 Hz, 2 H) 7.16 (d, J = 8.2 Hz, 1 H) 6.96 (d, J = 8.7 Hz, 2 H) 6.91 (d, J = 15.8 Hz, 1 H) 6.29-6.71 (m, 1 H) 3.86-4.23 (m, 6 H) 3.78-3.85 (m, 2 H) 3.52 (t, J = 6.7 Hz, 2 H) 1.58-1.73 (m, 2 H) 1.45 (s, 3 H) 1.36 (s, 3 H) 0.95 (t, J = 7.4 Hz, 3 H) | 638.0 639.0 640.0 |
| 75 | WX075 | 1H NMR (400 MHz, CDCl3) δ: 0.82 (t, J = 7.40 Hz, 3 H) 0.87 (t, J = 7.40 Hz, 3 H) 1.33 (dq, J = 15.09, 7.43 Hz, 2 H) 1.53 (s, 3 H) 1.59 (br s, 3 H) 1.61-1.69 (m, 2 H) 3.49 (t, J = 6.65 Hz, 2 H) 3.68-3.77 (m, 4 H) 3.80 (s, 3 H) 3.91-4.06 (m, 2 H) 4.07-4.11 (m, 2 H) 6.78 (d, J = 15.81 Hz, 1 H) 6.89-6.92 (m, 2 H) 7.18-7.24 (m, 3 H) 7.33-7.37 (m, 3 H) 7.43 (dd, J = 8.53, 2.26 Hz, 1 H) 7.54 (d, J = 2.01 Hz, 1 H) 7.73 (d, J = 8.53 Hz, 2 H) 7.98 (d, J = 15.56 Hz, 1 H) 9.07 (br s, 1 H) | 629.8, 630.1 |

| Example | Comound | NMR | MS m/z: |
|---|---|---|---|
| 76 | WX076 | 1H NMR (400 MHz, CDCl3) δ: 0.82 (t, J = 7.40 Hz, 3 H) 0.87 (t, J = 7.40 Hz, 3 H) 1.33 (dq, J = 15.09, 7.43 Hz, 2 H) 1.53 (s, 3 H) 1.59 (br s, 3 H) 1.61-1.69 (m, 2 H) 3.49 (t, J = 6.65 Hz, 2 H) 3.68-3.77 (m, 4 H) 3.80 (s, 3 H) 3.91-4.06 (m, 2H) 4.07-4.11 (m, 2 H) 6.78 (d, J = 15.81 Hz, 1 H) 6.89-6.92 (m, 2 H) 7.18-7.24 (m, 3 H) 7.33-7.37 (m, 3 H) 7.43 (dd, J = 8.53, 2.26 Hz, 1 H) 7.54 (d, J = 2.01 Hz, 1 H) 7.73 (d, J = 8.53 Hz, 2 H) 7.98 (d, J = 15.56 Hz, 1 H) 9.07 (br s, 1 H) | 629.8, 630.1 |
| 78 | WX078 | 1H NMR (400 MHz, CDCl3) δ: 8.58 (d, J = 15.6 Hz, 1H), 8.07 (d, J = 8.3 Hz, 1H), 7.86-7.73 (m, 3H), 7.70 (d, J = 8.5 Hz, 1H), 7.55 (d, J = 8.5 Hz, 2H), 7.50 (s, 1H), 7.32 (br d, J = 8.5 Hz, 2H), 7.04 (d, J = 8.5 Hz, 2H), 6.67 (d, J = 15.3 Hz, 1H), 6.52 (s, 1H), 4.24-3.95 (m, 4H), 3.87-3.77 (m, 5H), 3.58 (t, J = 6.7 Hz, 2H), 3.36-3.24 (m, 1H), 1.80-1.69 (m, 3H), 1.67-1.62 (m, 2H), 1.46-1.38 (m, 2H), 1.33 (d, J = 6.8 Hz, 6H), 0.95 (t, J = 7.4 Hz, 3H), 0.90 (t, J = 7.4 Hz, 3H) | 692.0 693.0 |
| 79 | WX079 | 1H NMR (400 MHz, CDCl3) δ: 0.96 (br s, 4 H) 1.22-1.48 (m, 2 H) 1.58 (br s, 6 H) 2.33 (br s, 2 H) 3.45-3.74 (m, 1 H) 3.74-4.00 (m, 9 H) 4.16 (br s, 2 H) 6.97 (br s, 4 H) 7.35-7.45 (m, 2 H) 7.49 (br s, 2 H) 7.59 (br s, 1 H) 7.74-7.96 (m, 2 H) 8.07 (br s, 1 H) 10.11 (br s, 1 H) 9.82-10.38 (m, 1 H) | 615.8, 616.8 |
| 80 | WX080 | 1H NMR (400 MHz, CDCl3) δ: 10.42 (br s, 1 H) 7.89 (d, J = 15.5 Hz, 1 H) 7.75 (d, J = 8.5 Hz, 2 H)) 7.53 (d, J = 2.01 Hz, 1 H) 7.36 (s, 1 H) 7.31 (d, J = 8.5 Hz, 2 H) 7.16 (d, J = 8.5 Hz, 2 H) 7.10 (d, J = 8.5 Hz, 1 H) 6.89 (d, J = 8.5 Hz, 2 H) 6.83 (d, J = 15.5 Hz, 1 H) 6.20-6.68 (m, 1 H) 3.72-4.12 (m, 8 H) 3.45 (t, J = 6.7 Hz, 2 H) 1.51-1.68 (m, 4 H) 1.41 (s, 3 H) 0.88 (t, J = 7.2 Hz, 3 H) 0.79 (t, J = 7.2 Hz, 3 H) | 652.1 653.0 654.0 |
| 81 | WX081 | 1H NMR (400 MHz, CDCl3) δ: 10.25 (br s, 1 H) 7.90 (d, J = 15.5 Hz, 1 H) 7.75 (d, J = 8.5 Hz, 2 H) 7.55 (s, 1 H) 7.41 (d, J = 8.5 Hz, 1 H) 7.37 (s, 1 H) 7.32 (d, J = 8.5 Hz, 2 H) 7.16 (d, J = 8.5 Hz, 2 H) 7.11 (d, J = 8.5 Hz, 1 H) 6.89 (d, J = 8.5 Hz, 2 H) 6.83 (d, J = 15.5 Hz, 1 H) 6.20-6.67 (m, 1 H) 3.67-4.15 (m, 8 H) 3.49 (t, J = 6.7 Hz, 2 H) 1.59-1.68 (m, 2 H) 1.49-1.58 (m, 2 H) 1.42 (s, 3 H) 1.25-1.38 (m, 2 H) 0.86 (t, J = 7.2 Hz, 3 H) 0.80 (t, J = 7.5 Hz, 3 H) | 666.0 667.1 668.2 |
| 82 | WX082 | 1H NMR (400 MHz, CDCl3) δ: 9.78 (br s, J = 17.5 Hz, 1 H) 7.91 (d, J = 15.5 Hz, 1 H) 7.74 (d, J = 8.5 Hz, 2 H) 7.58 (d, J = 2.0 Hz, 1 H) 7.42 (dd, J = 8.5, 2.0 Hz, 1 H) 7.36 (s, 1 H) 7.34 (d, J = 8.5 Hz, 2 H) 7.17 (s, 1 H) 7.13 (s, 2 H) 6.90 (d, J = 8.5 Hz, 2 H) 6.80 (d, J = 16.0 Hz, 1 H) 6.46 (s, 1 H) 3.83-4.19 (m, 4 H) 3.65-3.81 (m, 4 H) 3.44-3.53 (m, 2 H) 1.62-1.68 (m, 5 H) 1.52-1.58 (m, 2 H) 1.33 (d, J = 15.06, 7.5 Hz, 2 H) 0.85-0.91 (m, 3 H) 0.78-0.84 (m, 3 H) | 666.0 667.1 668.2 |
| 83 | WX083 | 1H NMR (400 MHz, CDCl3) δ: 10.18 (br s, 1H), 8.15 (dd, J = 2.0, 15.3 Hz, 1H), 7.81 (d, J = 8.5 Hz, 2H), 7.75-7.68 (m, 2H), 7.59 (d, J = 8.5 Hz, 1H), 7.48-7.42 (m, 3H), 7.29-7.22 (m, 3H), 7.00 (d, J = 8.5 Hz, 2H), 6.76 (d, J = 15.3 Hz, 1H), 4.22-3.94 (m, 1H), 3.86-3.82 (m, 1H), 3.90-3.76 (m, 1H), 3.58 (t, J = 6.8 Hz, 2H), 1.67-1.59 (m, 4H), 1.50 (s, 3H), 1.46-1.37 (m, 2H), 0.95 (t, J = 7.4 Hz, 3H), 0.86 (t, J = 7.4 Hz, 3H) | 668.0 690.0 |
| 84 | WX084 | 1H NMR (400 MHz, CDCl3) δ: 10.29 (br s, 1H), 7.99 (br d, J = 13.8 Hz, 1H), 7.65 (br d, J = 8.3 Hz, 2H), 7.57-7.51 (m, 2H), 7.42 (br d, J = 8.0 Hz, 1H), 7.29 (s, 1H), 7.14-7.05 (m, 3H), 6.83 (d, J = 8.5 Hz, 2H), 6.62 (d, J = 15.3 Hz, 1H), 4.02 (t, J = 4.6 Hz, 1H), 4.05-3.90 (m, 1H), 3.78-3.71 (m, 1H), 3.78-3.71 (m, 1H), 3.68 (br t, J = 4.8 Hz, 1H), 3.70-3.66 (m, 1H), 3.42 (t, J = 6.8 Hz, 2H), 1.56-1.50 (m, 2H), 1.50-1.44 (m, 3H), 1.32 (s, 3H), 1.28-1.22 (m, 2H), 0.82-0.75 (m, 4H), 0.69 (t, J = 7.4 Hz, 3H) | 668.0 690.0 |
| 85 | WX085 | 1H NMR (400 MHz, CDCl3) δ: 0.69-0.95 (m, 7 H) 1.32 (br d, J = 6.53 Hz, 2 H) 1.45-1.68 (m, 4 H) 3.48 (br s, 2 H) 3.62-3.80 (m, 8 H) 3.92 (br d, J = 13.55 Hz, 1 H) 4.06 (br s, 4 H) 6.48 (br s, 1 H) 7.15-7.57 (m, 8 H) 7.74 (br d, J = 7.03 Hz, 2 H) 7.98 (br d, J = 15.56 Hz, 1 H) 9.59 (br s, 1 H) | 615.8, 616.1 |
| 86 | WX086 | 1H NMR (400 MHz, CDCl3) δ: 8.35 (d, J = 5.0 Hz, 1H), 8.02 (d, J = 16.1 Hz, 1H), 7.97 (s, 1H), 7.87 (d, J = 9.0 Hz, 2H), 7.77 (d, J = 2.0 Hz, 1H), 7.60 (dd, J = 2.0, 8.5 Hz, | 613.0, 614.0 615.0 |

| Example | Compound | NMR | MS m/z: |
|---|---|---|---|
| | | 1H), 7.53 (d, J = 8.5 Hz, 2H), 7.44 (d, J = 9.0 Hz, 2H), 7.32 (d, J = 5.0 Hz, 1H), 7.12 (d, J = 9.0 Hz, 1H), 7.02 (d, J = 8.5 Hz, 2H), 6.97 (d, J = 15.6 Hz, 1H), 4.43-4.24 (m, 2H), 4.19-4.11 (m, 2H), 3.97 (s, 3H), 3.82-3.78 (m, 2H), 3.57 (s, 2H), 2.73-2.55 (m, 2H), 1.64-1.55 (m, 2H), 1.48-1.38 (m, 2H), 1.21 (t, J = 7.5 Hz, 3H), 0.95 (t, J = 7.3 Hz, 3H) | |
| 87 | WX087 | 1H NMR (400 MHz, CDCl3)δ: 8.41 (br d, J = 4.5 Hz, 1H), 8.06 (d, J = 15.6 Hz, 1H), 7.94 (br d, J = 10.3 Hz, 2H), 7.76 (br d, J = 8.5 Hz, 2H), 7.67 (d, J = 1.8 Hz, 1H), 7.53 (dd, J = 2.0, 8.5 Hz, 1H), 7.46 (d, J = 8.5 Hz, 2H), 7.36 (br d, J = 8.3 Hz, 2H), 7.12 (br d, J = 4.5 Hz, 1H), 6.99 (dd, J = 2.9, 8.7 Hz, 3H), 6.78 (d, J = 15.6 Hz, 1H), 4.23-4.14 (m, 3H), 4.10-4.04 (m, 1H), 3.93 (s, 3H), 3.82 (t, J = 4.8 Hz, 2H), 3.57 (t, J = 6.7 Hz, 2H), 2.61-2.53 (m, 2H), 1.64-1.58 (m, 4H), 1.44-1.37 (m, 2H), 1.01-0.96 (m, 2H), 0.96-0.91 (m, 3H) | 627.2, 628.2 629.2 |
| 88 | WX088 | $^1$H NMR (400 MHz, CHLOROFORM-d) δ = 8.04-7.95 (m, 1H), 8.00 (d, J = 15.6 Hz, 1H), 7.80 (d, J = 8.4 Hz, 2H), 7.47 (s, 1H), 7.44 (s, 1H), 7.42 (s, 2H), 7.33-7.29 (m, 3H), 7.00 (d, J = 8.8 Hz, 2H), 6.83 (d, J = 16.4 Hz, 1H), 4.20-4.14 (m, 2H), 4.12 (s, 1H), 4.01 (s, 1H), 3.98 (s, 3H), 3.92 (q, J = 7.4 Hz, 2H), 3.85-3.81 (m, 2H), 3.57 (t, J = 6.6 Hz, 2H), 1.67-1.62 (m, 2H), 1.60 (br s, 4H), 1.46-1.37 (m, 5H), 0.98-0.92 (m, 1H), 0.95 (t, J = 7.4 Hz, 2H) | 634.1 |
| 89 | WX089 | 1H NMR (400 MHz, DMSO-d6) δ = 10.56 (s, 1H), 7.92-7.78 (m, 3H), 7.75-7.58 (m, 5H), 7.44 (br d, J = 8.5 Hz, 2H), 7.13-6.98 (m, 3H), 4.33 (br d, J = 14.3 Hz, 1H), 4.23-4.07 (m, 5H), 3.91 (br d, J = 6.8 Hz, 2H), 3.80-3.63 (m, 2H), 3.50-3.43 (m, 2H), 1.63 (s, 3H), 1.51 (quin, J = 6.9 Hz, 2H), 1.41-1.26 (m, 8H), 0.89 (t, J = 7.4 Hz, 3H) | 648.1 |
| 90 | WX090 | $^1$H NMR (400 MHz, DMSO-d$_6$) δ ppm 0.89 (t, J = 7.40 Hz, 3 H) 1.23-1.30 (m, 3 H) 1.30-1.39 (m, 2 H) 1.47-1.55 (m, 2 H) 1.60 (s, 3 H) 2.34 (s, 3 H) 3.46 (t, J = 6.65 Hz, 2 H) 3.70-3.73 (m, 2 H) 3.74 (s, 3 H) 3.82-3.92 (m, 2 H) 4.13 (t, J = 4.64 Hz, 2 H) 4.17 (s, 1 H) 4.24-4.30 (m, 1 H) 6.97-7.04 (m, 2 H) 7.05 (s, 1 H) 7.42 (d, J = 8.78 Hz, 2 H) 7.56 (s, 2 H) 7.61 (d, J = 8.78 Hz, 2 H) 7.70 (d, J = 1.76 Hz, 1 H) 7.80 (s, 1 H) 7.83-7.88 (m, 2 H) 10.51 (s, 1 H) | 630.1 |
| 91 | WX091 | $^1$H NMR (400 MHz, DMSO-d$_6$) δ = 10.59 (s, 1H), 7.95 (br d, J = 5.2 Hz, 1H), 7.85 (d, J = 8.8 Hz, 2H), 7.75-7.69 (m, 2H), 7.65 (d, J = 8.8 Hz, 2H), 7.55 (s, 1H), 7.42 (d, J = 8.8 Hz, 2H), 7.39-7.35 (m, 1H), 7.10-7.02 (m, 3H), 4.31-4.23 (m, 1H), 4.18-4.10 (m, 3H), 3.97-3.79 (m, 2H), 3.75-3.68 (m, 2H), 3.46 (t, J = 6.4 Hz, 2H), 1.60 (s, 3H), 1.55-1.46 (m, 2H), 1.38-1.30 (m, 2H), 1.30-1.25 (m, 3H), 0.88 (t, J = 7.4 Hz, 3H) | 604.1 |
| 92 | WX092 | $^1$H NMR (400 MHz, DMSO-d$_6$) δ = 10.49 (s, 1H), 7.85 (d, J = 8.5 Hz, 2H), 7.72-7.62 (m, 4H), 7.56 (s, 1H), 7.51 (s, 1H), 7.46-7.37 (m, 3H), 7.06 (d, J = 8.8 Hz, 2H), 6.93 (d, J = 15.6 Hz, 1H), 4.32-4.22 (m, 1H), 4.20-4.10 (m, 3H), 3.93-3.82 (m, 2H), 3.78-3.68 (m, 2H), 3.48 (t, J = 6.5 Hz, 2H), 2.42 (s, 3H), 1.61 (s, 3H), 1.56-1.46 (m, 2H), 1.40-1.24 (m, 5H), 0.89 (t, J = 7.3 Hz, 3H) | 600.1 |

Experimental Example 1: CCR2/CCR5 In Vitro Test

Experimental Purpose:

The intracellular calcium signal was detected by FLIPR, and the $IC_{50}$ value of the compound was used as an index to evaluate the inhibitory effect of the compound on CCR2 and CCR5 receptors.

Experimental Materials:

1. Cell line: The cells were inoculated and incubated in a 5% $CO_2$ incubator at 37° C. overnight.

CCR2/CCR5 density: 1 M (20 k/well)

| Target | Clone# | Passage# | Host |
|---|---|---|---|
| CCR2 | C7 | P6 | HEK293 |
| CCR5 | C13 | P4 | HEK293 |

2. Reagents: Fluo-4 Direct, (Invitrogen, Cat #F10471)

3. Equipment and Devices:

384 well Poly-D-Lysine protein coating plate, Greiner #781946

384 compound plate, Greiner #781280

FLIPR, Molecular Device

ECHO, Labcyte

4. Compounds:

The compound was dissolved in DMSO to prepare a 10 mM solution, and the compound solution was placed in a nitrogen box.

| Compound_ID | Purity | Amount_In_mg |
|---|---|---|
| Cenicriviroc | 97.00 | 1.15 |

Agonist reference compounds:

| MCP-1 | Sigma | SRP3109 | 10 uM stock in $H_2O$ |
| RANTES | Sigma | SRP3269 | 10 uM stock in $H_2O$ |

Experimental Procedures and Methods:

Preparation of probenecid in FLIPR assay buffer: 1 mL of FLIPR assay buffer was added to 77 mg of probenecid to prepare a 250 mM solution, which is prepared fresh daily.

2× (8 µM) Fluo-4 Direct™ Loading Buffer (per 10 mL)
Thaw a bottle of Fluo-4 Direct™ crystal (F10471).
Add 10 mL of FLIPR assay buffer to the vial.
Add 0.2 mL of probenecid to each 10 mL of Fluo-Direct. The final concentration of the assay was 2.5 mM.
Rotate it and place for >5 minutes (in absence of light).
Prepare fresh daily.

Experimental Procedures:

(a) Prepare agonist compound:

MCP-1 was diluted in FLIPR assay buffer 1:2 into 10 points, starting at 0.5 uM (final 100 nM). RANTES was diluted in FLIPR assay buffer 1:3 into 10 points, starting at 0.5 uM (final 100 nM). 20 uL of serially diluted compound buffer was added to each well of the DRC plate according to the compound plate map.

(b) Prepare antagonist compound: antagonist reference compound

Standard compound was diluted in DMSO 1:3 into 11 points, starting at 1 mM. Test compound was diluted in DMSO 1:3 into 11 points, starting at 2 mM. 250 nL of compound solution was transferred into a cell plate using Echo (Greiner #781946).

(c) Take the cell plate out of the incubator, and gently dispense 20 uL of 2× Fluo-4 Direct wash-free loading buffer into a 384-well cell culture plate using a pipette. The final cell plate is 40 µL in volume.

(d) Incubate for 50 minutes at 37° C. under 5% $CO_2$, and for 10 minutes at room temperature.

(e) Take the cell plate out of the incubator, and place it in FLIPR. Place the composite plate and the tip box in FLIPR.

(f) For DRC plate:

1) Run the program on FLIPRTETRA.
2) Read the fluorescent signal.
3) Transfer 10 µL of compound from the DRC plate to the cell plate.
4) Read the fluorescent signal.
5) Calculate the "maximum−minimum" from Read 90 to the maximum allowed. Use FLIPR to calculate the EC80 value of each cell line.
6) Prepare 5×$EC_{80}$ concentration of the agonist reference compound.

(g) For the composite plate (1-add):

1) Run the program on FLIPRTETRA.
2) Transfer 10 µl, of 5×EC80 concentration of the agonist reference compound from the composite plate to the cell plate.
3) Read the fluorescent signal.
4) Calculate the "maximum−minimum" from Read 90 to the maximum allowed.

(h) Analyze the data using Prism, and calculate the $IC_{50}$ value of the compound.

The experimental results are shown in Table 1:

TABLE 1

| Compound | $IC_{50}$ (nM) test results detected by FLIPR | |
|---|---|---|
| | CCR2 | CCR5 |
| WX001 | 29.9 | 9.3 |
| WX002 | 318.6 | 113.2 |
| WX003 | 21.6 | 3.0 |
| WX004 | 152.8 | 7.1 |
| WX005 | 12.1 | 3.4 |
| WX006 | 32.1 | 3.3 |
| WX007 | 65.2 | 6.4 |
| WX008 | 17.3 | 1.5 |
| WX009 | 63.2 | 9.4 |
| WX010 | 214.2 | 17.2 |
| WX011 | 61.0 | 2.6 |
| WX012 | 51.0 | 5.4 |
| WX013 | 983.7 | 14.2 |
| WX014 | 257.8 | 7.9 |
| WX015 | 62.0 | 65.1 |
| WX016 | 75.1 | 4.5 |
| WX017 | 13.0 | 7.9 |
| WX018 | 43.5 | 7.3 |
| WX019 | 9.3 | 50.9 |
| WX020 | 68.1 | 8.2 |
| WX021 | 64.5 | 8.8 |
| WX022 | 204.9 | 10.1 |
| WX023 | 37.1 | 53.3 |
| WX024 | 63.1 | 1.3 |
| WX025 | 127.0 | 7.4 |
| WX026 | 175.4 | 3.2 |
| WX027 | 207.2 | 13.6 |
| WX028 | 86.4 | 15.5 |
| WX029 | 167.5 | 34.2 |
| WX030 | 300.3 | 15.9 |
| WX031 | 237.3 | 95.9 |
| WX032 | 28.6 | 8.1 |
| WX033 | 56.3 | 11.8 |
| WX034 | 30.0 | 10.0 |
| WX035 | 214.6 | 16.1 |
| WX036 | 64.9 | 13.3 |
| WX037 | 62.2 | 44.2 |
| WX038 | 42.5 | 12.5 |
| WX039 | 70.1 | 760.0 |
| WX040 | 11.3 | 10.5 |
| WX041 | 22.5 | 21.4 |
| WX042 | 52.8 | 4.0 |
| WX043 | 249.6 | 9.1 |
| WX044 | 293.2 | 16.1 |
| WX045 | 77.6 | 14.8 |
| WX046 | 1.1 | 2.8 |
| WX047 | 8.2 | 6.7 |
| WX048 | 11.8 | 2.6 |
| WX049 | 13.3 | 9.2 |
| WX050 | 12.6 | 20.8 |
| WX051 | 5.5 | 1.4 |
| WX052 | 80.8 | 11.9 |
| WX053 | 5.9 | 1.3 |
| WX054 | 43.4 | 9.2 |
| WX055 | 7.6 | 6.4 |
| WX056 | 71.1 | 16.6 |
| WX057 | 24.7 | 3.5 |
| WX058 | 28.2 | 5.7 |
| WX059 | 9.9 | 8.5 |
| WX060 | 18.5 | 4.1 |
| WX061 | 8.9 | 15.2 |
| WX062 | 84.5 | 20.5 |
| WX063 | 9.4 | 1.4 |
| WX064 | 12.8 | 6.1 |
| WX065 | 49.6 | 68.0 |
| WX066 | 6.5 | 10.1 |
| WX067 | 16.8 | 0.9 |
| WX068 | 36.0 | 18.4 |
| WX069 | 35.3 | 1.0 |
| WX070 | 39.2 | 8.4 |
| WX071 | 4.5 | 3.4 |
| WX072 | 11.9 | 5.9 |
| WX073 | 11.9 | 6.5 |

TABLE 1-continued

IC$_{50}$ (nM) test results detected by FLIPR

| Compound | CCR2 | CCR5 |
|---|---|---|
| WX074 | 5.4 | 3.5 |
| WX075 | 17.3 | 2.4 |
| WX076 | 42.2 | 8.5 |
| WX078 | 25.4 | 1.3 | trifugation at 3000 g for 15 minutes at 4° C. The plasma concentration was determined by LC-MS/MS. The pharmacokinetic parameters were calculated by the non-compartment model linear logarithmic trapezoidal method using WinNonlin™ Version 6.3 (Pharsight, Mountain View, Calif.) pharmacokinetic software.

Table 2 shows the pharmacokinetic parameters of the test compounds WX017, WX047, WX079 and the reference compound in rats.

TABLE 2

Pharmacokinetic parameters in rats

| | Intravenous injection (2 mg/kg) | | | Oral (10 mg/kg) | | | |
|---|---|---|---|---|---|---|---|
| | Plasma clearance (mL/min/kg) | Half-life (h) | Area Under a Curve (0-inf, nM · h) | Peak concentrationn (M) | Peak time (h) | Area Under a Curve (0-inf/0-last, nM · h) | Bioavailability |
| Reference Compound (Cenicriviroc) | 1.57 | 5.48 | 31344 | 3323 | 4.0 | 31956 | 20.4% |
| WX017 | 0.4 | 3.69 | 135732 | 30750 | 1.5 | 331778 | 48.9% |
| WX047 | 0.520 | 3.06 | 101904 | 20750 | 5.0 | 204785 | 40.4% |
| WX079 | 0.224 | 9.47 | 255072 | 27300 | 3.0 | 404142 | 32.6% |
| WX088 | 0.328 | 6.63 | 150423 | 12185 | 3.0 | 122101 | 15.7% |

TABLE 1-continued

IC$_{50}$ (nM) test results detected by FLIPR

| Compound | CCR2 | CCR5 |
|---|---|---|
| WX079 | 5.6 | 5.8 |
| WX080 | 25.1 | 15.1 |
| WX081 | 12.5 | 5.5 |
| WX082 | 53.4 | 11.4 |
| WX083 | 28.9 | 2.1 |
| WX084 | 51.2 | 4.6 |
| WX085 | 5.2 | 5.6 |
| WX086 | 13.0 | 1.8 |
| WX087 | 66.0 | 2.1 |
| WX088 | 3.5 | 4.3 |
| WX089 | 15.0 | ND |
| WX090 | 5.5 | 6.9 |
| WX091 | 4.7 | 4.4 |
| WX092 | 3.9 | 10.1 |

Conclusion: The compounds of the present invention have significant antagonism to CCR2 and CCR5 receptors.

Experimental Example 2: Comparative Pharmacokinetics Study in Rats

SD male rats were used as the test animals in this study. The drug concentrations in plasma of the rats by intravenous or oral administration of test compounds WX017, WX047, WX079, WX088 and reference compound at different time points were quantitatively determined by LC/MS/MS, which were used to evaluate the pharmacokinetic profile of the two test drugs in rats.

A clear solution of the test compound was injected into SD rats via the tail vein (overnight fasting, 7-10 weeks old), and the test compound was orally administered to the SD rats (overnight fasting, 7-10 weeks old). Approximately 200 µL of blood was collected from the jugular vein or tail vein of the animals 0.0833, 0.25, 0.5, 1, 2, 4, 6, 8 and 24 hours after administration, and was placed in an anticoagulant tube containing EDTA-K2. The plasma was collected by cen- The experimental results showed that the plasma clearance of WX017, WX047, WX079 and WX088 was lower than that of the reference compound, which was 25%, 33%, 14% and 21% of the reference compound, respectively; the oral plasma system of exposure (AUC$_{0-inf}$) of WX017, WX047, WX079 and WX088 was 10.4, 6.4, 12.6 and 3.8 times, as that of the reference compound, respectively. Therefore, in rodent rats, the pharmacokinetics of WX017, WX047, WX079 and WX088 are significantly better than that of the reference compound.

Experimental Example 3: Comparative Pharmacokinetics Study in Cynomolgus Monkeys Male cynomolgus monkeys were used as the test animals in this study. The drug concentrations in plasma of the cynomolgus monkeys by intravenous or oral administration of test compound WX047 and reference compound at different time points were quantitatively determined by LC/MS/MS, which were used to evaluate the pharmacokinetic profile of the two test drugs in cynomolgus monkeys.

A clear solution of the test compound was injected into cynomolgus monkeys via t the cephalic or saphenous vein (overnight fasting, 2.5-7 kg), and the test compound was intragastrically administered to the cynomolgus monkeys (overnight fasting, 7-10 weeks old). Approximately 400 µL of blood was collected from the peripheral vein of the animals 0.0833, 0.25, 0.5, 1, 2, 4, 6, 8, 12 and 24 hours after administration, and transferred into an commercial centrifuge tube containing EDTA-K2*2H$_2$O anticoagulation. The plasma was collected by centrifugation at 3000 g for 10 minutes at 4° C. The plasma concentration was determined by LC-MS/MS. The pharmacokinetic parameters were calculated by the non-compartment model linear logarithmic trapezoidal method using WinNonlin™ Version 6.3 (Pharsight, Mountain View, Calif.) pharmacokinetic software.

Table 3 shows the pharmacokinetic parameters of the test compound WX047 and the reference compound in cynomolgus monkeys.

TABLE 3

| | Intravenous injection (1 mg/kg) | | | Oral (3 mg/kg) | | | |
|---|---|---|---|---|---|---|---|
| | Plasma clearance (mL/min/kg) | Half-life (h) | Area Under a Curve (0-inf, nM · h) | Peak concentrationn (M) | Peak time (h) | Area Under a Curve (0-inf/0-last, nM · h) | Bioavailability |
| Reference Compound (Cenicriviroc) | 8.74 | 5.37 | 2766 | 99.6 | 2.0 | 424 | 5.11 |
| WX047 | 9.11 | 1.66 | 3149 | 1080 | 2.0 | 3678 | 38.9 |

Pharmacokinetic parameters in rats

The experimental results showed that the bioavailability of WX047 was 7.6 times as that of the reference compound; the oral plasma system of exposure ($AUC_{0-inf}$) of WX047 was 10.8 times as that of the reference compound. Therefore, the pharmacokinetic of WX047 in cynomolgus monkeys are significantly better than that of the reference compound.

Experimental Example 4 Inhibition Effect on the Activity of Human Liver Microsomal Cytochrome P450 Isoezymes (CYP1A2, CYP2C9, CYP2C19, CYP2D6 and CYP3A4)

A total of 5 specific probe substrates for CYP's five isozymes, Phenacetin (CYP1A2), Diclofenac (CYP2C9), (S)-Mexantine (S)-Mephenytoin, CYP2C19), Dextromethorphan (CYP2D6) and Midazolam (CYP3A4) were incubated with human liver microsomes and test compounds, respectively, and reduced nicotinamide adenine dinucleotide phosphate (NADPH) was added to initiate the reaction. After the reaction, the sample was processed and liquid chromatography tandem mass spectrometry (LC-MS/MS) was used to quantitatively detect the eight metabolites produced by the specific substrate, Acetaminophen and 4'-hydroxydiclofenac, 4'-hydroxymephenytoin, Dextrorphan and 1'-hydroxymidazolam, in order to calculate the corresponding half maximal inhibitory concentration ($IC_{50}$).

TABLE 4

| | $IC_{50}$ (µM) | | | | |
|---|---|---|---|---|---|
| Compound ID | CYP1A2 | CYP2C9 | CYP2C19 | CYP2D6 | CYP3A4-M |
| Reference Compound (Cenicriviroc) | >50 | >50 | >50 | >50 | 5.6 |
| WX047 | >50 | >50 | >50 | >50 | >50 |
| WX079 | >50 | >50 | >50 | >50 | 28.3 |

Experimental Conclusion: The reference compound has a weak inhibitory effect on CYP3A4, while WX047 and WX079 have no risk on inhibiting five isoenzymes (CYP1A2, CYP2B6, CYP2C8, CYP2C9, CYP2C19, CYP2D6 and CYP3A4) of human liver microsomal cytochrome P450, which are better than the reference compound.

What is claimed is:

1. A compound as shown in formula (I) or a pharmaceutically acceptable salt thereof, wherein,

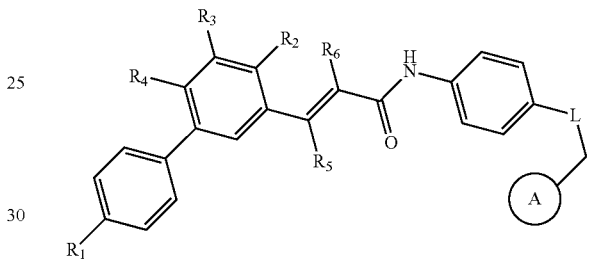

(I)

$R_1$ is selected from the group consisting of $C_{1-6}$ alkoxy and 5-6 membered heterocycloalkyl, each of which is optionally substituted by 1, 2 or 3 R;

each of $R_2$, $R_3$ and $R_4$ is independently H, halogen, OH, CN, or selected from the group consisting of $C_{1-6}$ alkyl, $C_{1-6}$ alkoxy, $C_{1-6}$ alkylthio, $C_{1-6}$ alkyl-S(=O)—, $C_{1-6}$ alkyl-S(=O)$_2$- and $C_{3-6}$ cycloalkyl, each of which is optionally substituted by 1, 2 or 3 R;

each of $R_5$ and $R_6$ is independently H, or $C_{1-3}$ alkyl, which is optionally substituted by 1, 2 or 3 R ring A is

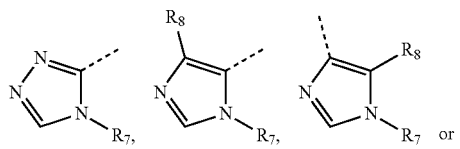

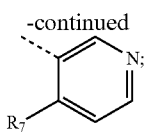

R₇ is C₁₋₆ alkyl, which is optionally substituted by 1, 2 or 3 R;

R₈ is H, or C₁₋₆ alkyl, which is optionally substituted by 1, 2 or 3 R;

L is —S(=O)— or —S(=O)₂—;

R is halogen, OH, or selected from the group consisting of C₁₋₆ alkyl, C₁₋₆ heteroalkyl and C₃₋₆ cycloalkyl, each of which is optionally substituted by 1, 2 or 3 R';

R' is F, Cl, Br, I, OH, CH₂F, CHF₂ or CF₃;

each of the "hetero" in the 5-6 membered heterocycloalkyl is independently —NH—, —O— or N;

in any of the above cases, the number of the heteroatom or the heteroatom group is independently 1, 2 or 3.

2. The compound as shown in formula (I) or the pharmaceutically acceptable salt thereof according to claim 1, wherein, R is F, Cl, Br, I, OH, or selected from the group consisting of C₁₋₃ alkyl, C₁₋₄ alkoxy and C₃₋₆ cycloalkyl, each of which is optionally substituted by 1, 2 or 3 R'.

3. The compound as shown in formula (I) or the pharmaceutically acceptable salt thereof according to claim 2, wherein, R is F, Cl, Br, I, OH, or selected from the group consisting of Me,

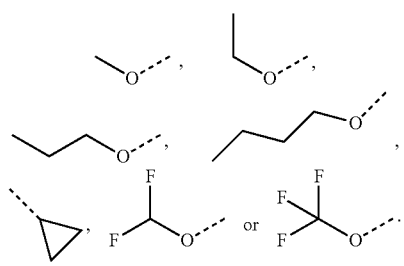

each of which is optionally substituted by 1, 2 or 3 R'.

4. The compound as shown in formula (I) or the pharmaceutically acceptable salt thereof according to claim 3, wherein, R is F, Cl, Br, I, OH, CH₃, CH₂F, CHF₂, CF₃,

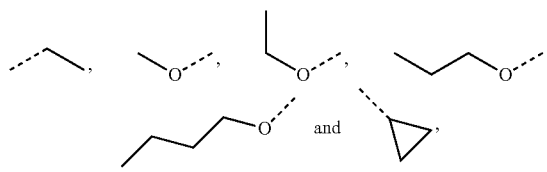

5. The compound as shown in formula (I) or the pharmaceutically acceptable salt thereof according to claim 1, wherein, R₁ is selected from the group consisting of C₁₋₄ alkoxy and pyrrolidinyl, each of which is optionally substituted by 1, 2 or 3 R.

6. The compound as shown in formula (I) or the pharmaceutically acceptable salt thereof according to claim 5, wherein, R₁ is selected from the group consisting of

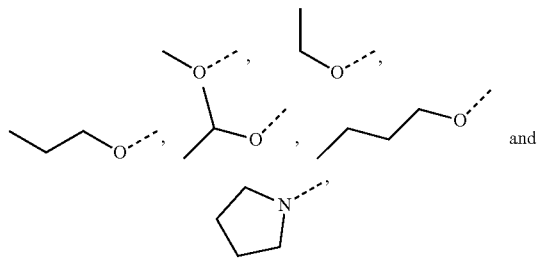

each of which is optionally substituted by 1, 2 or 3 R.

7. The compound as shown in formula (I) or the pharmaceutically acceptable salt thereof according to claim 6, wherein, R₁ is

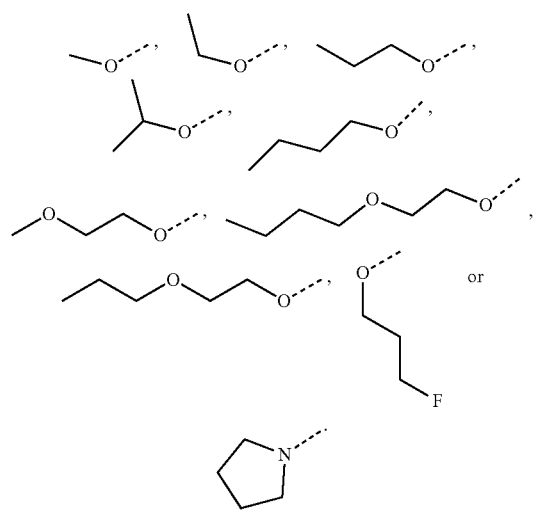

8. The compound as shown in formula (I) or the pharmaceutically acceptable salt thereof according to claim 1, wherein, each of R₂, R₃ and R₄ is independently H, halogen, OH, CN, or selected from the group consisting of C₁₋₃ alkyl, C₁₋₃ alkoxy, C₁₋₃ alkylthio, C₁₋₃ alkyl-S(=O)—, C₁₋₃ alkyl-S(=O)₂— and C₄₋₅ cycloalkyl, each of which is optionally substituted by 1, 2 or 3 R.

9. The compound as shown in formula (I) or the pharmaceutically acceptable salt thereof according to claim 8, wherein, each of R₂, R₃ and R₄ is independently H, F, Cl, Br, I, OH, CN, or selected from the group consisting of Me,

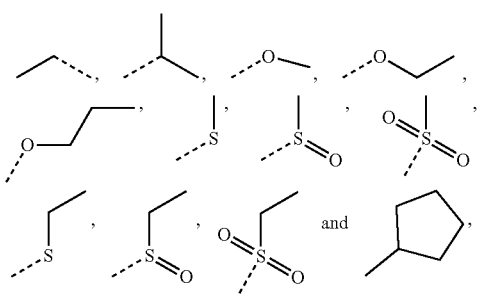

each of which is optionally substituted by 1, 2 or 3 R.

10. The compound as shown in formula (I) or the pharmaceutically acceptable salt thereof according to claim 9, wherein, each of $R_2$, $R_3$ and $R_4$ is independently H, F, Cl, Br, I, OH, CN, Me,

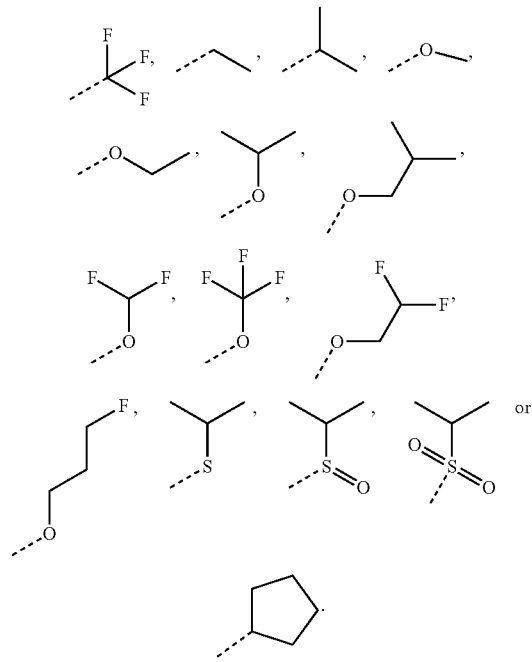

11. The compound as shown in formula (I) or the pharmaceutically accentahle salt thereof according to claim 10, wherein, $R_2$ is H, F, Cl, OH, CN, Me,

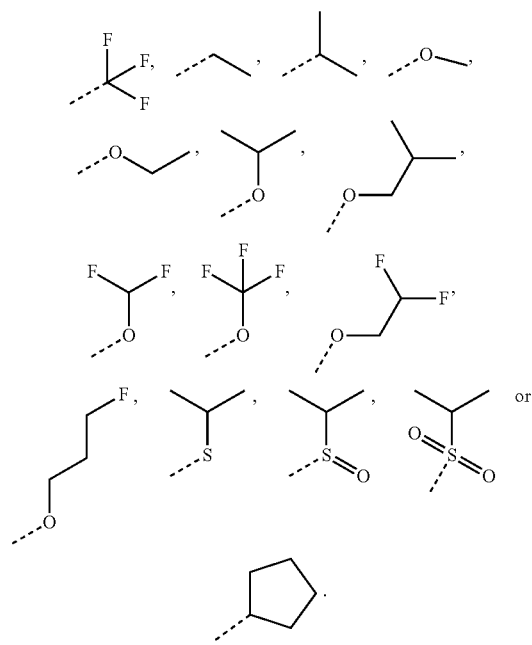

12. The compound as shown in formula (I) or the pharmaceutically acceptable salt thereof according to claim 10, wherein, $R_3$ is H, F, Cl, Me or

13. The compound as shown in formula (I) or the pharmaceutically acceptable salt thereof according to claim 10, wherein, $R_4$ is H or Cl.

14. The compound as shown in formula (I) or the pharmaceutically acceptable salt thereof according to claim 1, wherein, each of $R_5$ and $R_6$ is independently H or Me.

15. The compound as shown in formula (I) or the pharmaceutically acceptable salt thereof according to claim 1, wherein, $R_7$ is selected from the group consisting of Me,

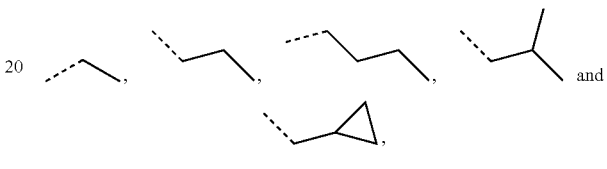

each of which is optionally substituted by 1, 2 or 3 R.

16. The compound as shown in formula (I) or the pharmaceutically acceptable salt thereof according to claim 15, wherein, $R_7$ is Me,

17. The compound as shown in formula (I) or the pharmaceutically acceptable salt thereof according to claim 1, wherein, $R_8$ is H, or selected from the group consisting of Me and

each of which is optionally substituted by 1, 2 or 3 R.

18. The compound as shown in formula (I) or the pharmaceutically acceptable salt thereof according to claim 17, wherein, $R_8$ is H, Me or

19. The compound as shown in formula (I) or the pharmaceutically acceptable salt thereof according to claim 1, wherein, ring A is

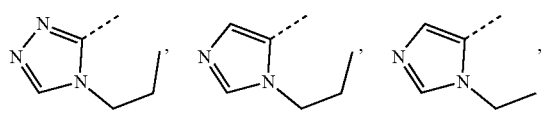

315
-continued
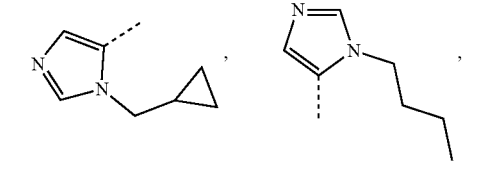
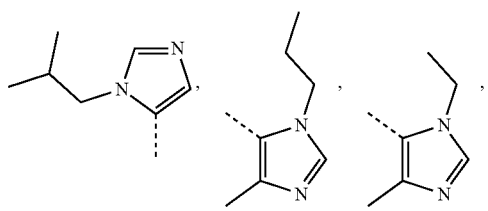
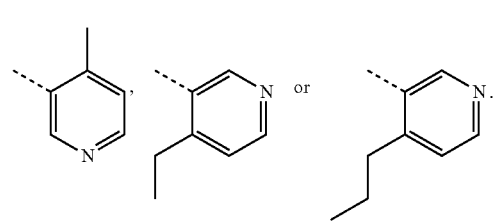
316
-continued
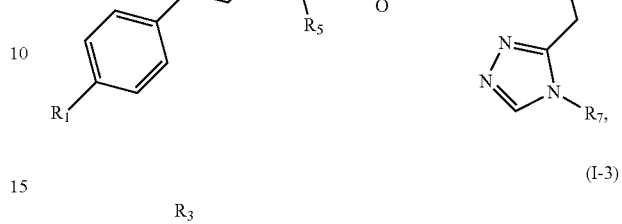
(I-2)
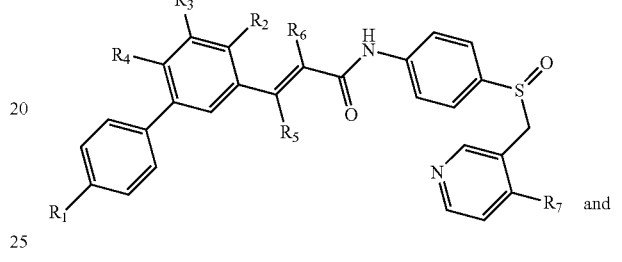
(I-3)
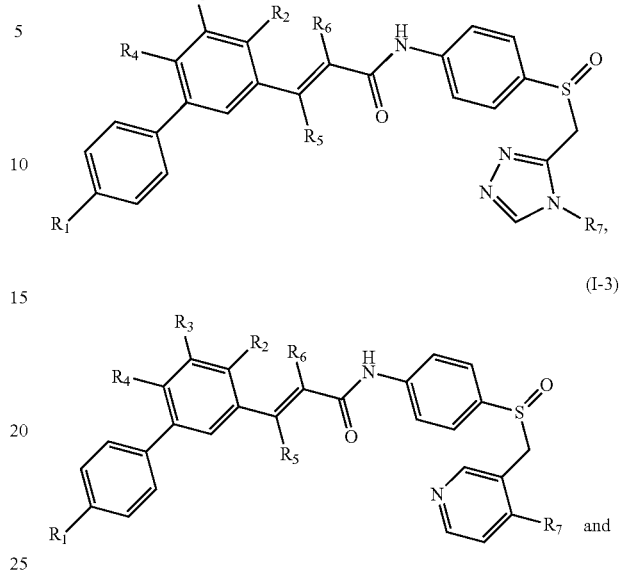
(I-4)
wherein,
R₁, R₂, R₃, R₄, R₅, R₆, R₇ and R₈ are as defined in claim 1.
20. The compound or the pharmaceutically acceptable salt thereof according to claim 1, which is selected from the group consisting of
(I-1)
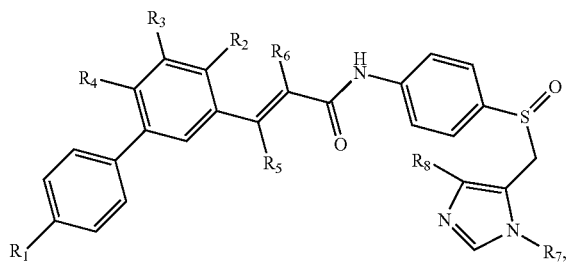
21. A compound shown as the following formula or a pharmaceutically acceptable salt thereof, which is selected from the group consisting of
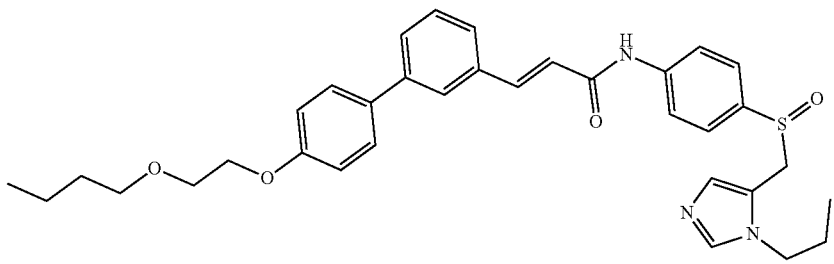
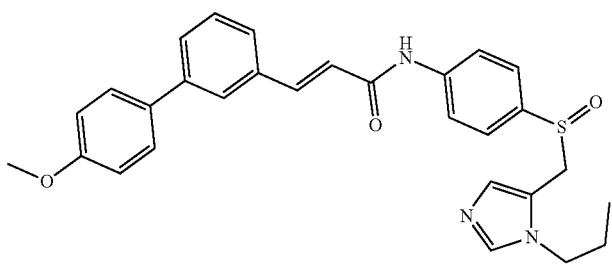

-continued
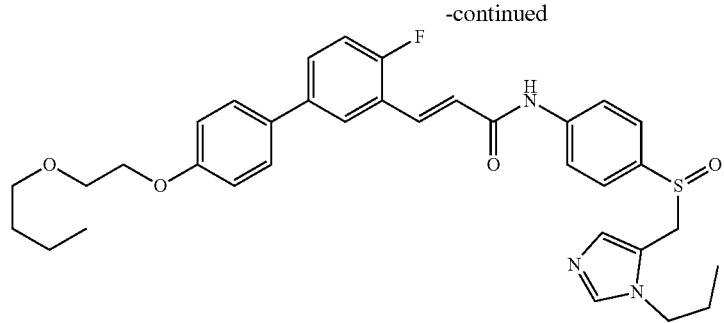
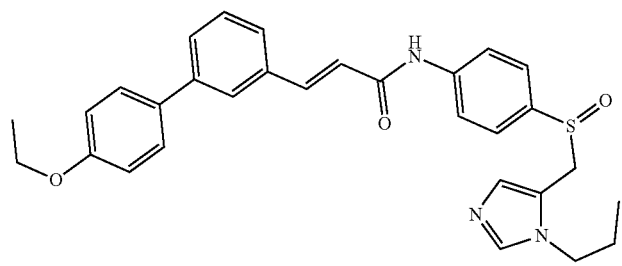
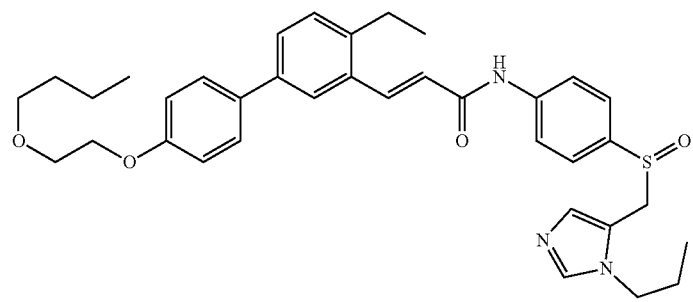
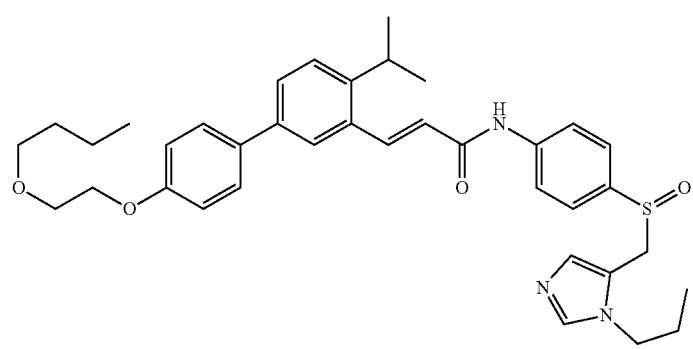
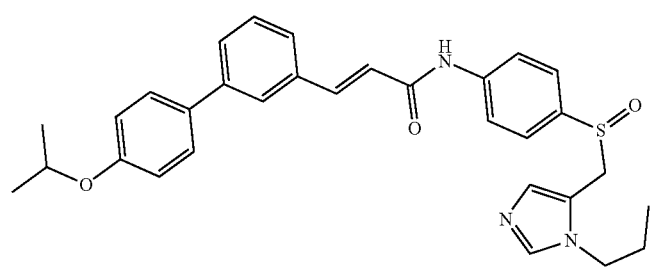

-continued
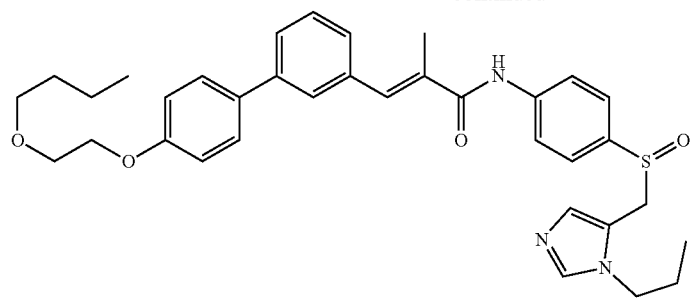
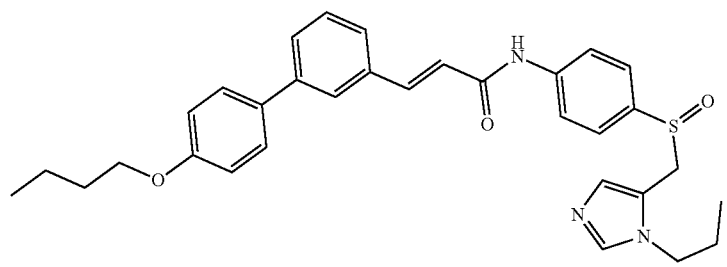
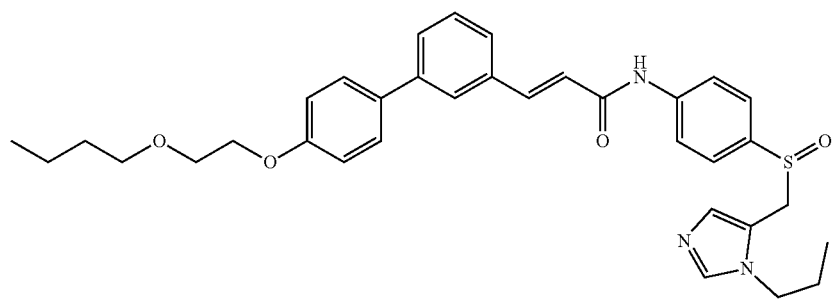
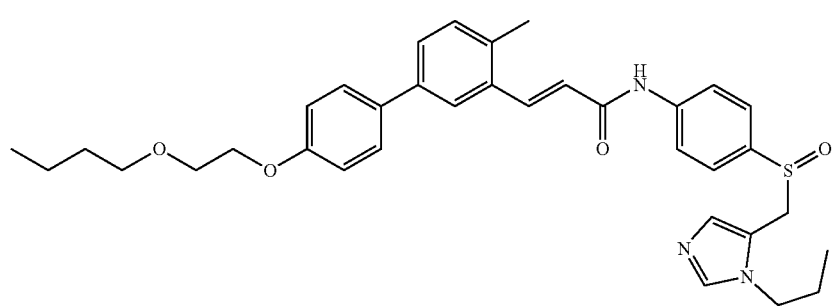
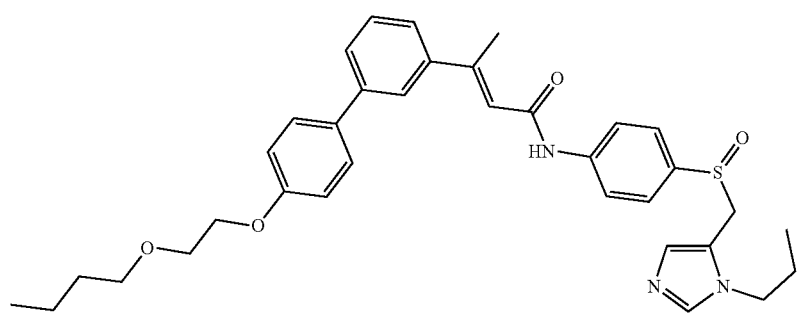

321
322
-continued
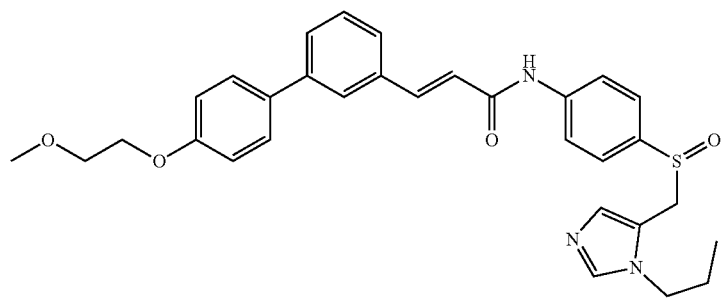
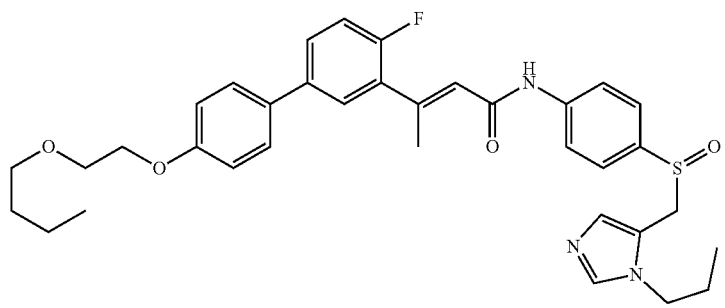
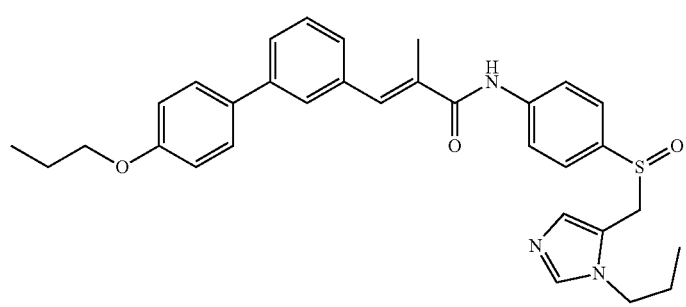
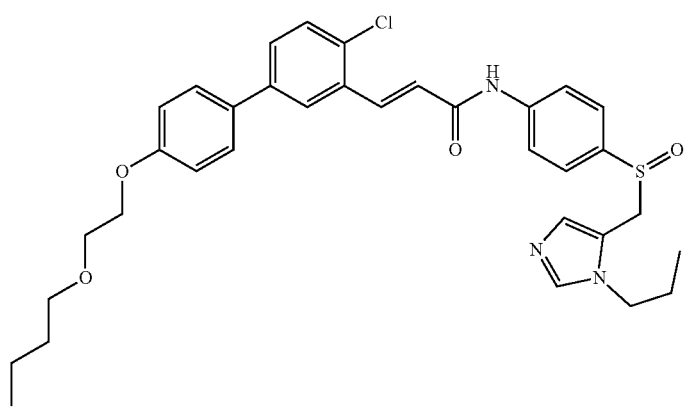
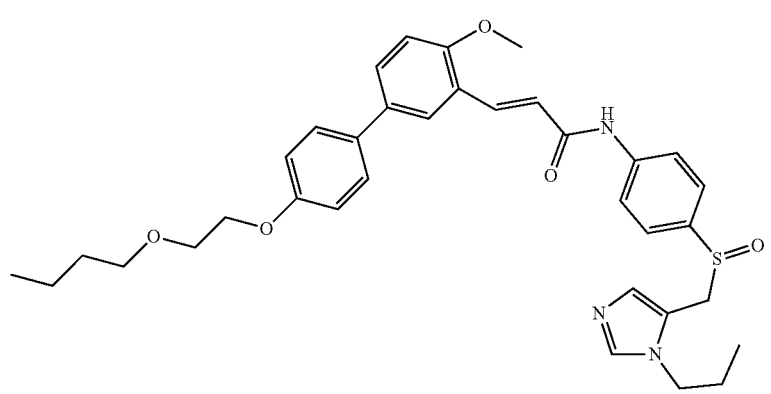

-continued
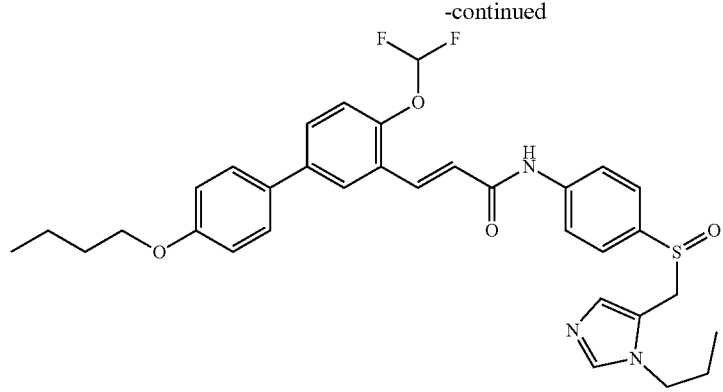
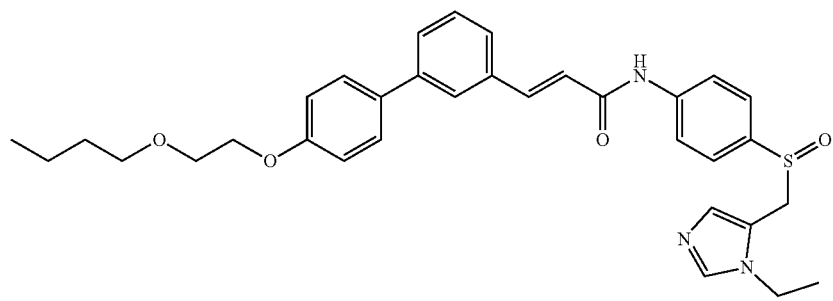
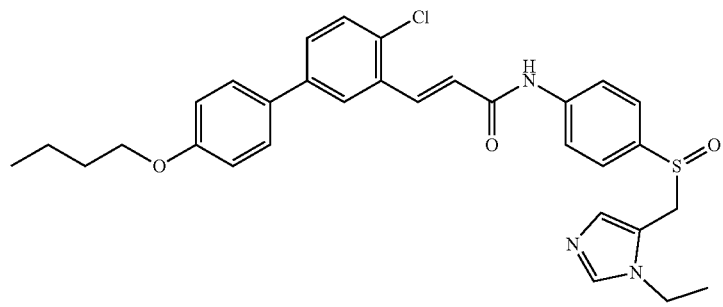
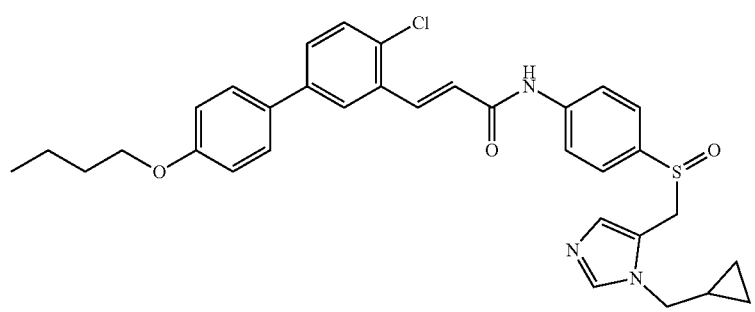
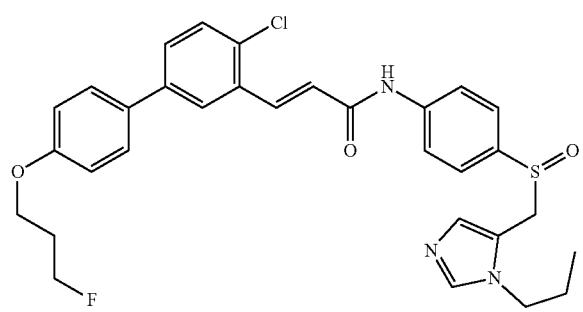

-continued
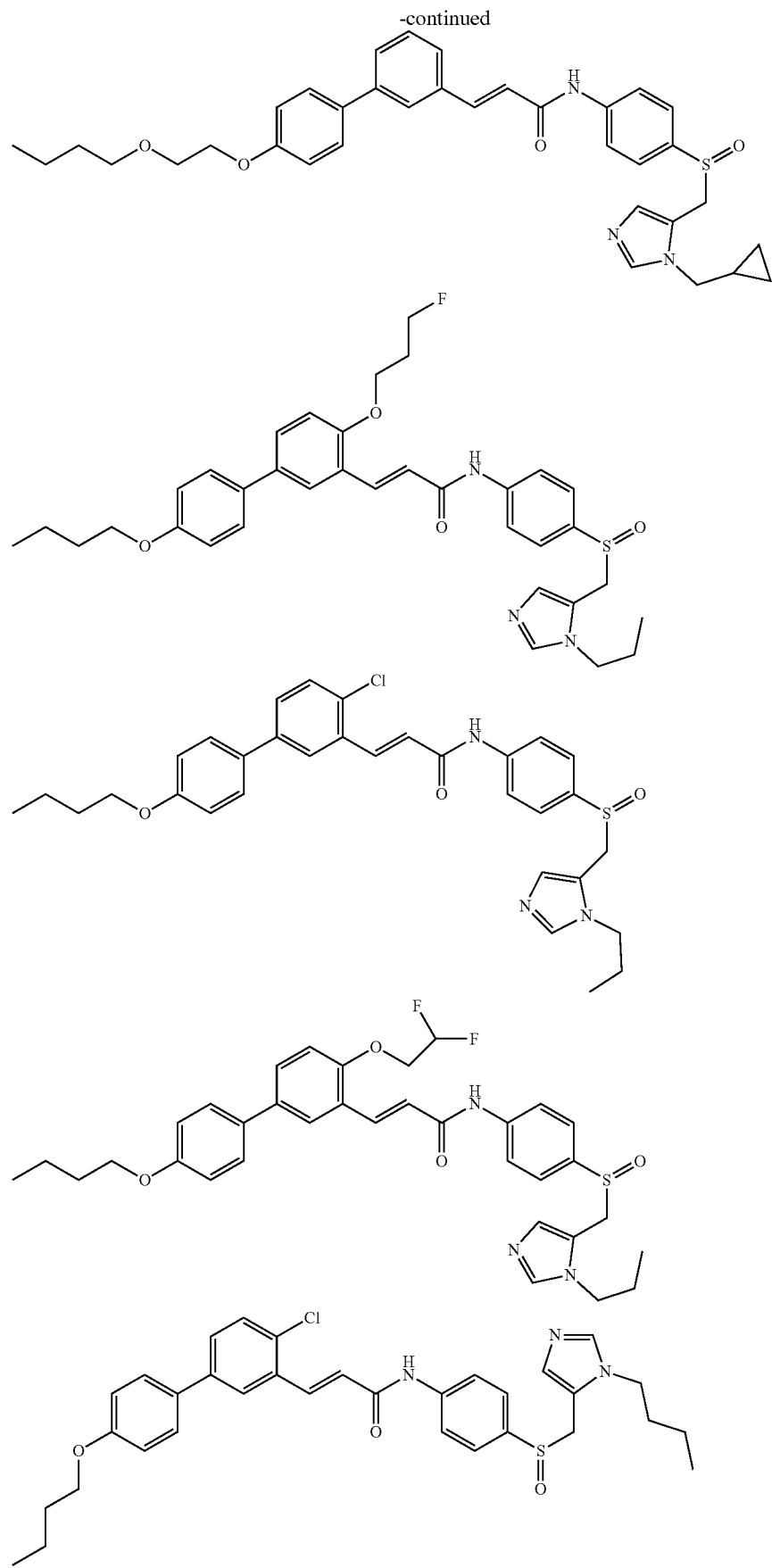

-continued
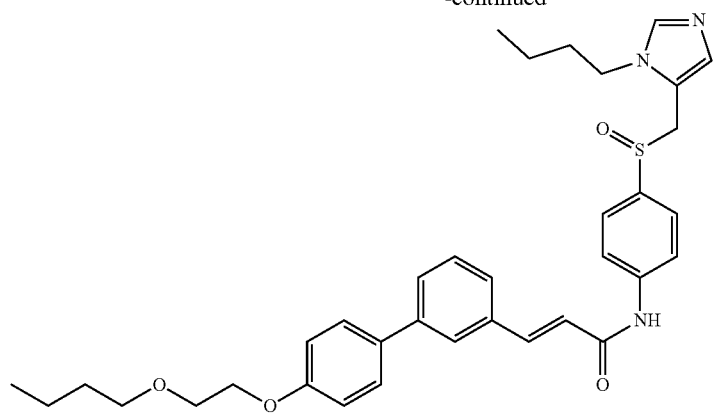
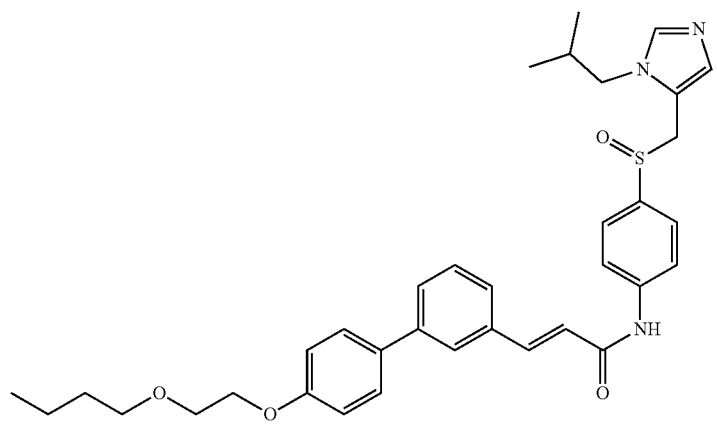
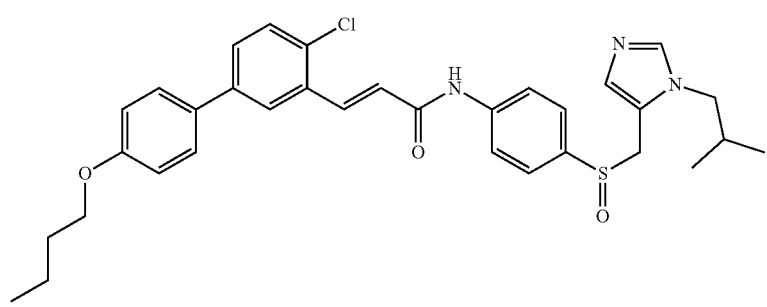
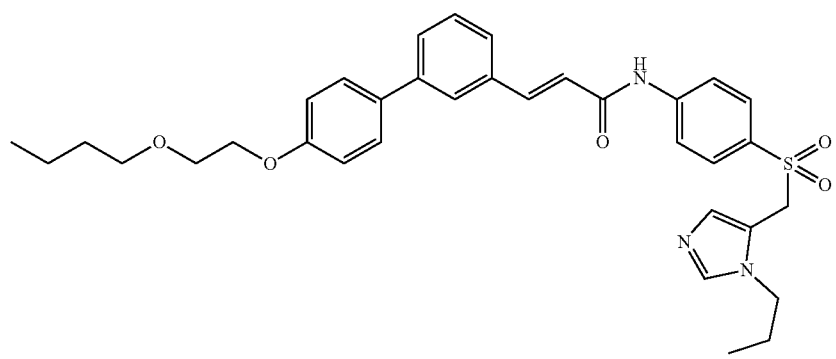

-continued
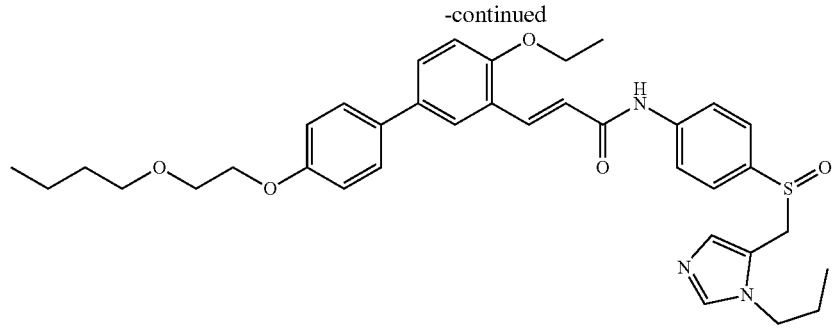
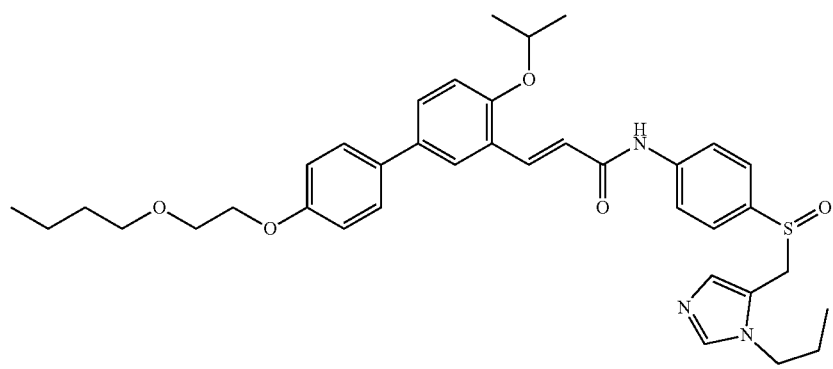
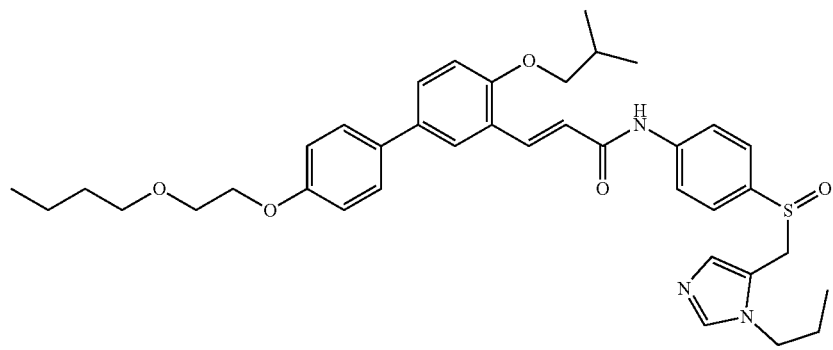
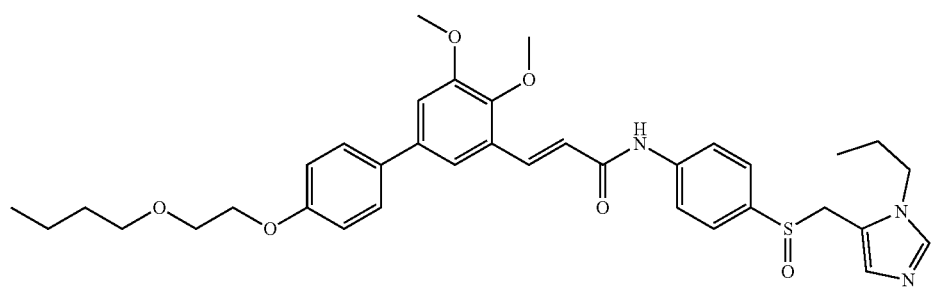
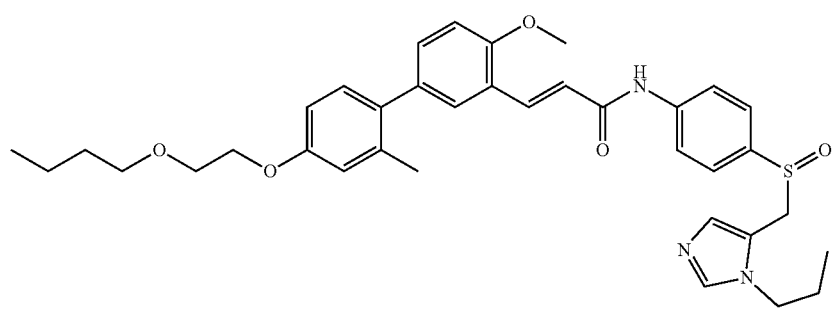

331
-continued
332
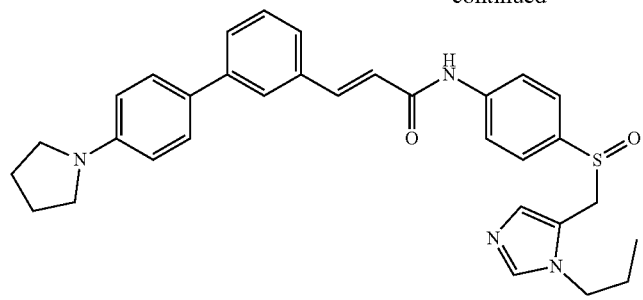
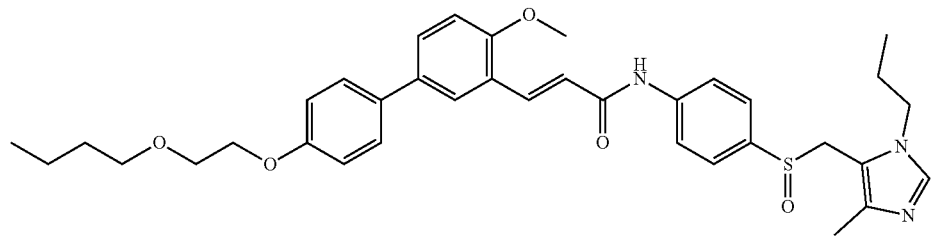
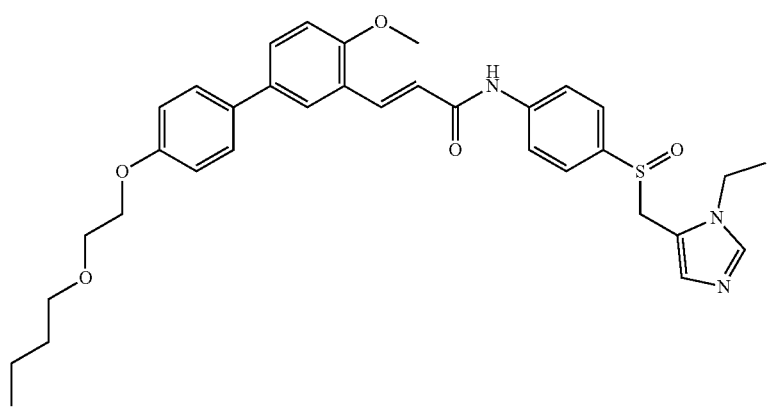
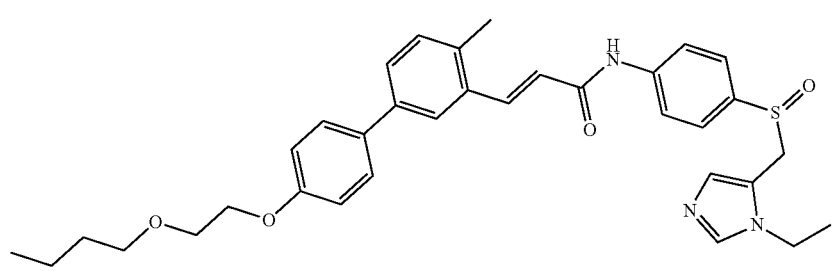
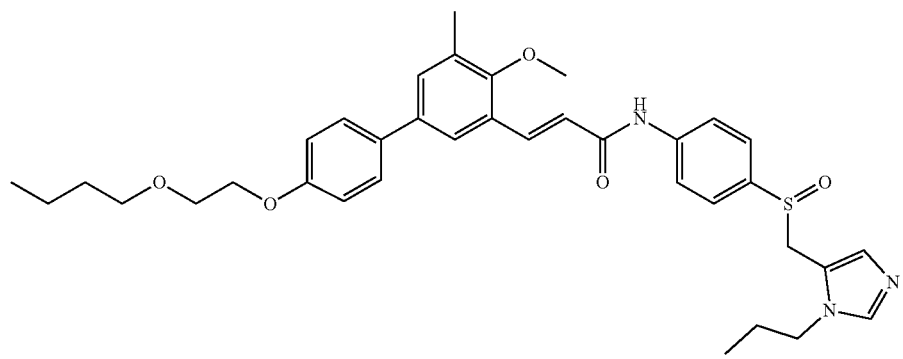

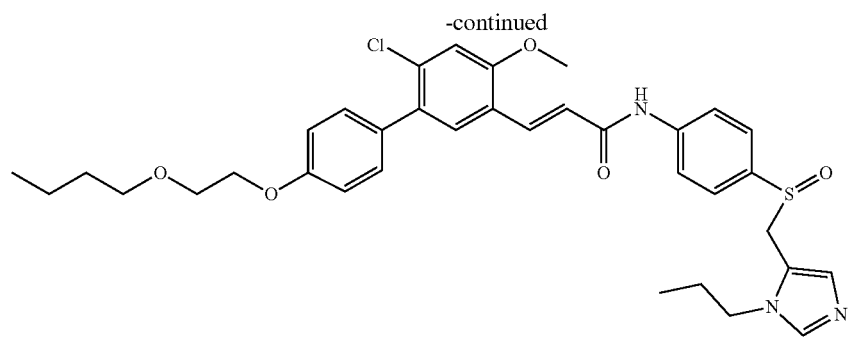
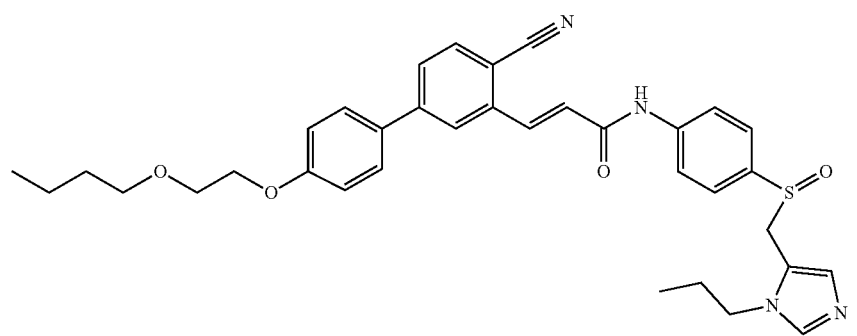
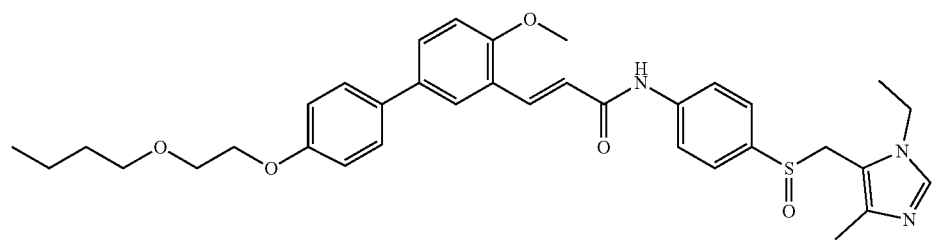
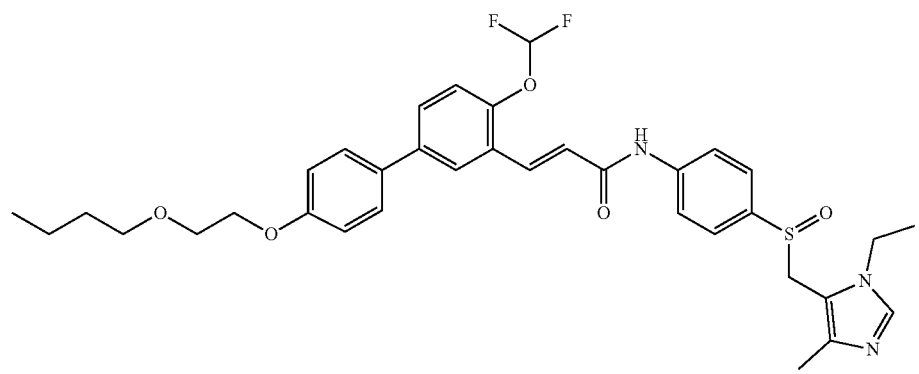
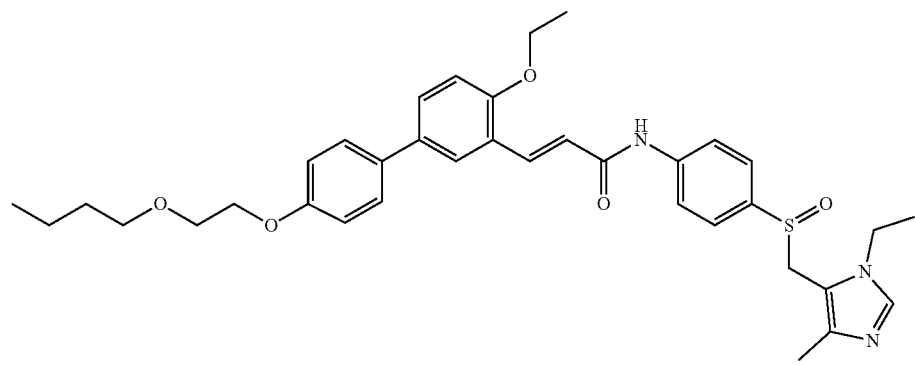

-continued
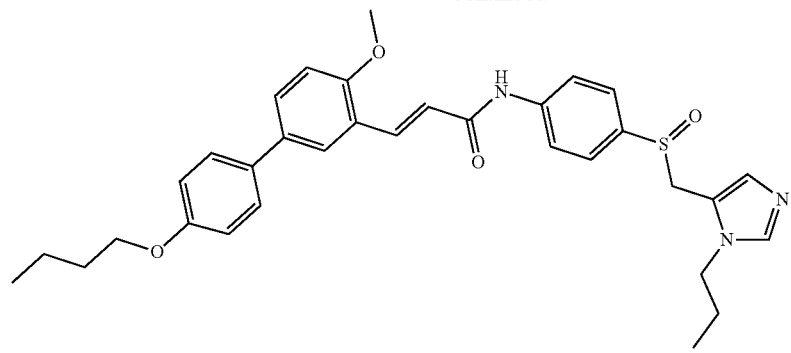
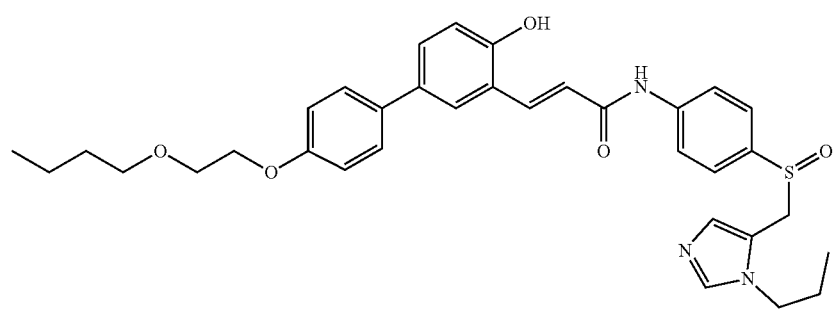
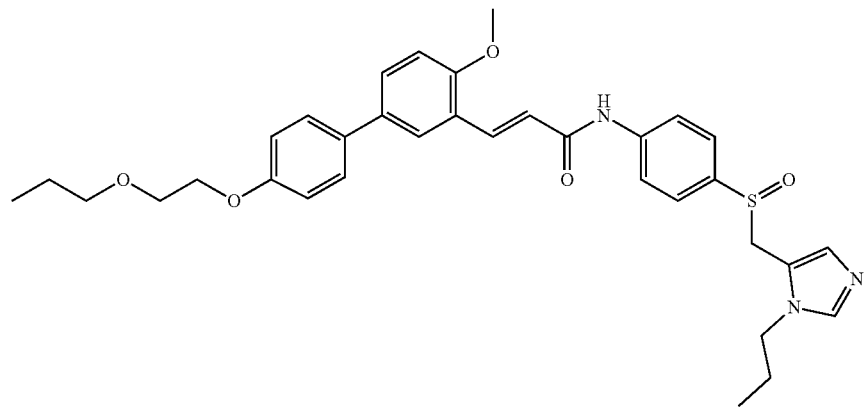
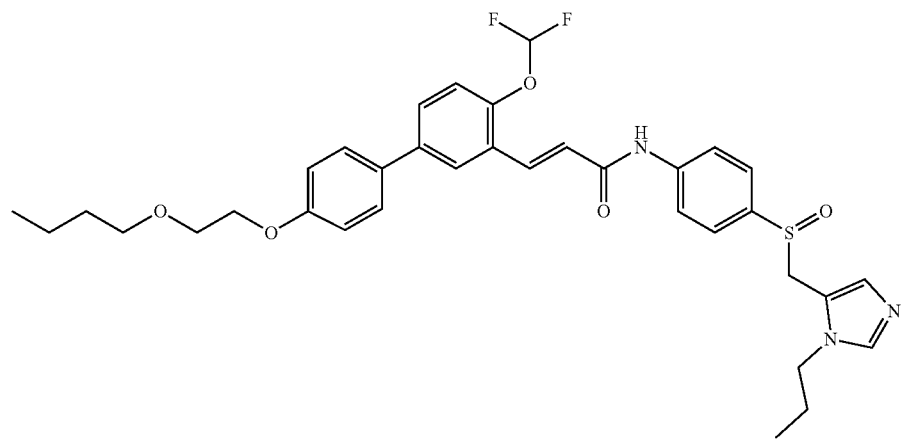

-continued
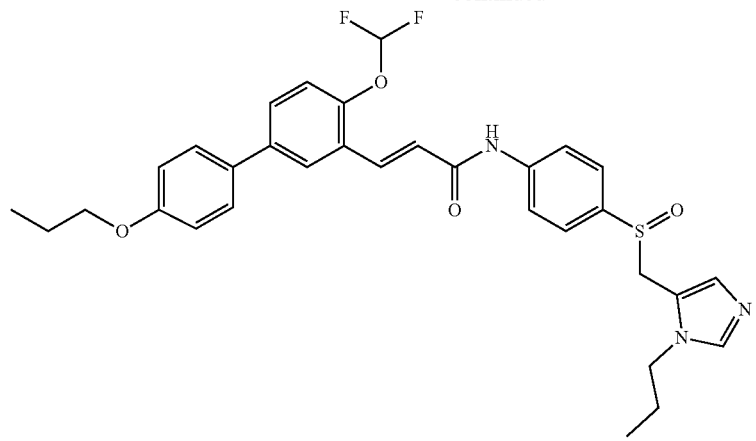
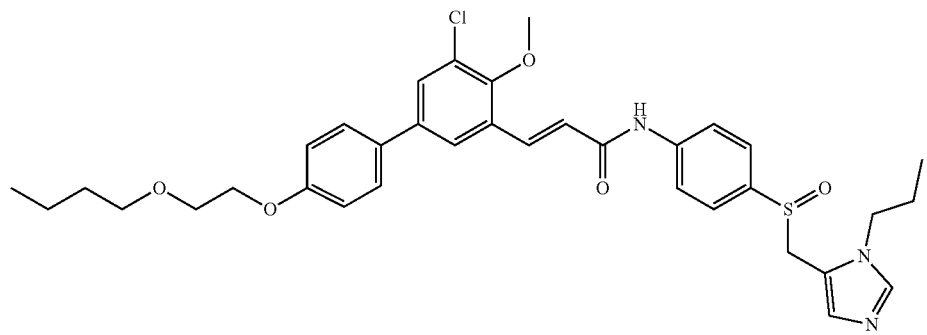
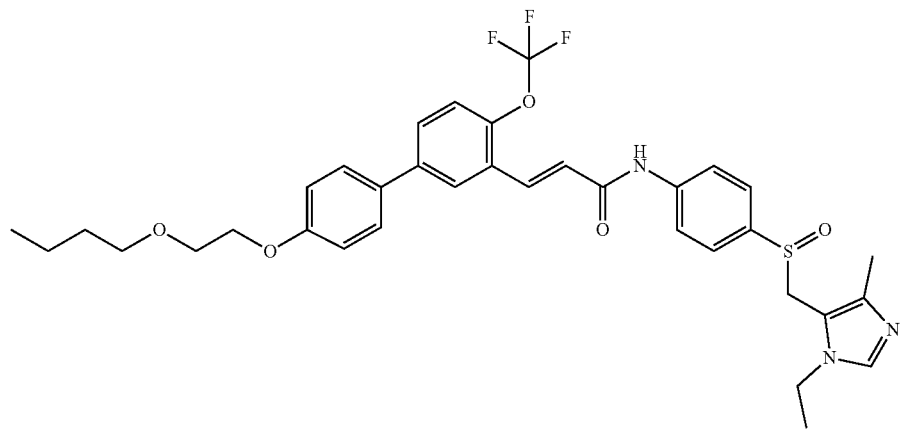
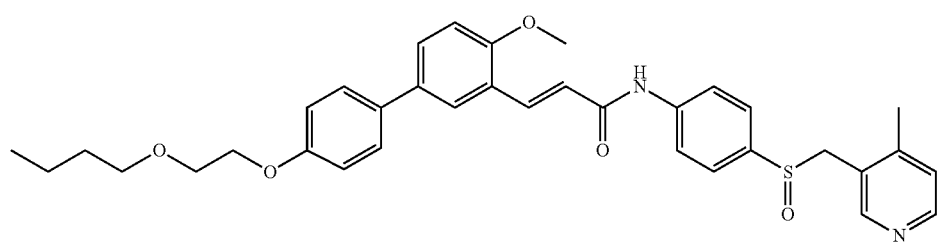

-continued
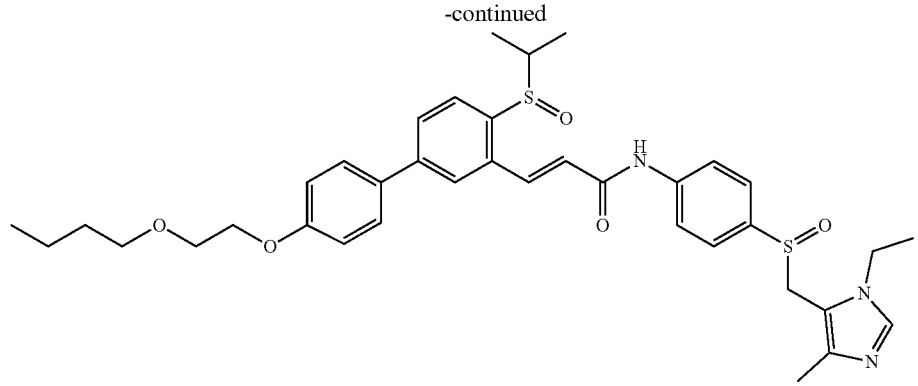
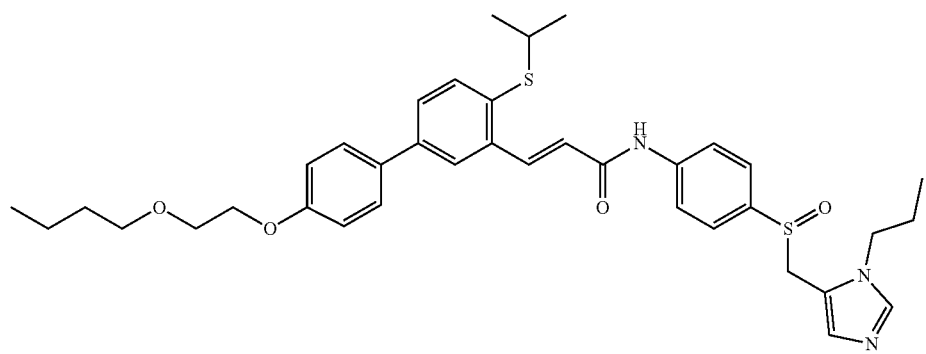
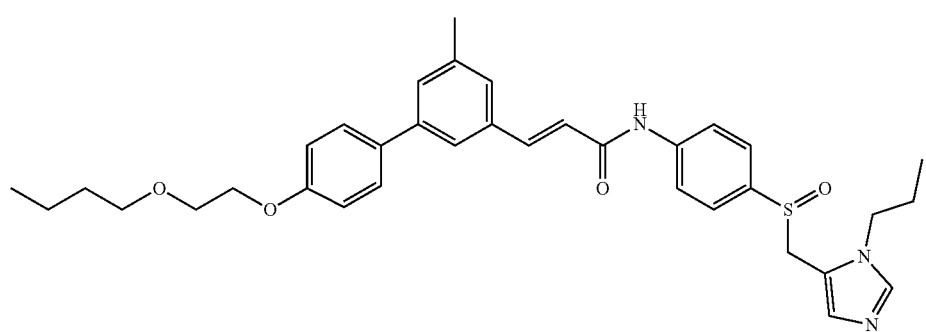
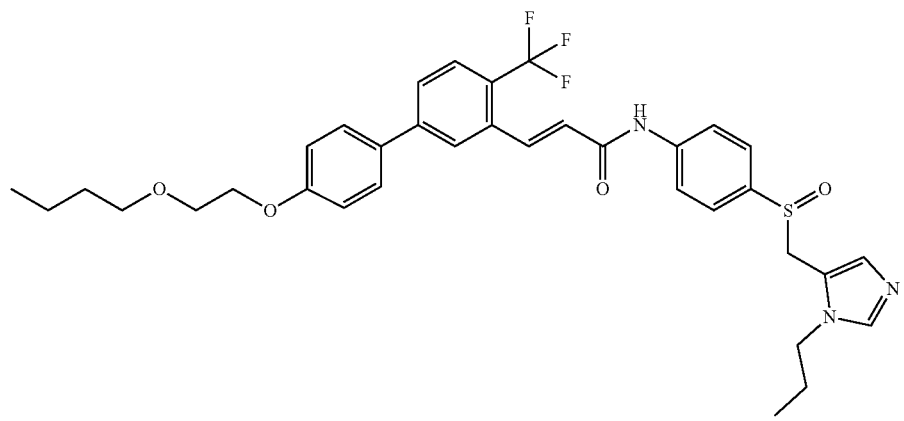

-continued
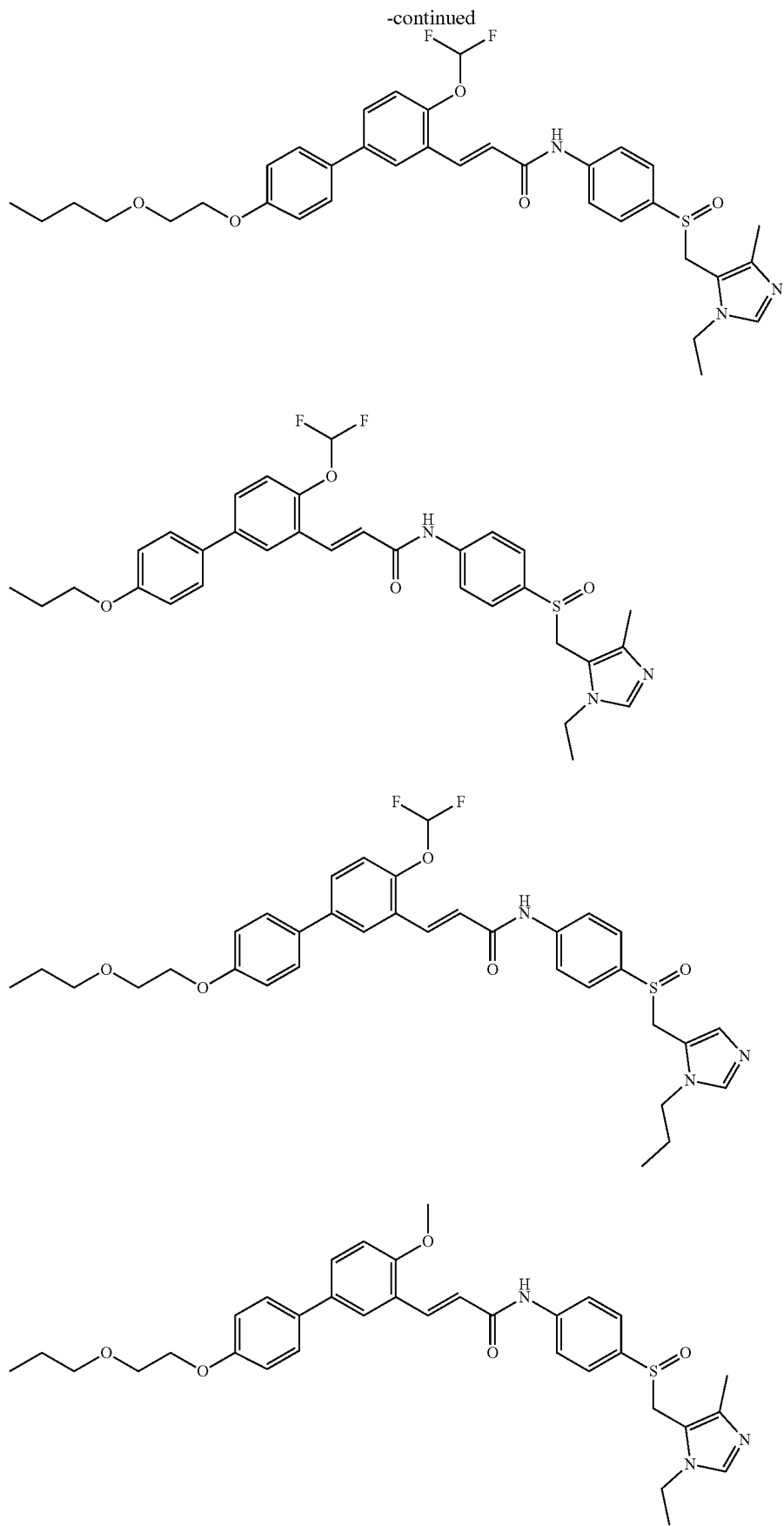

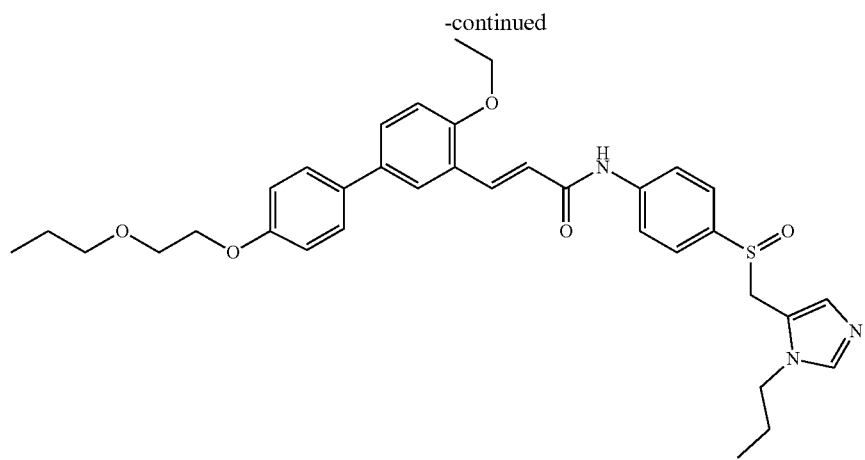
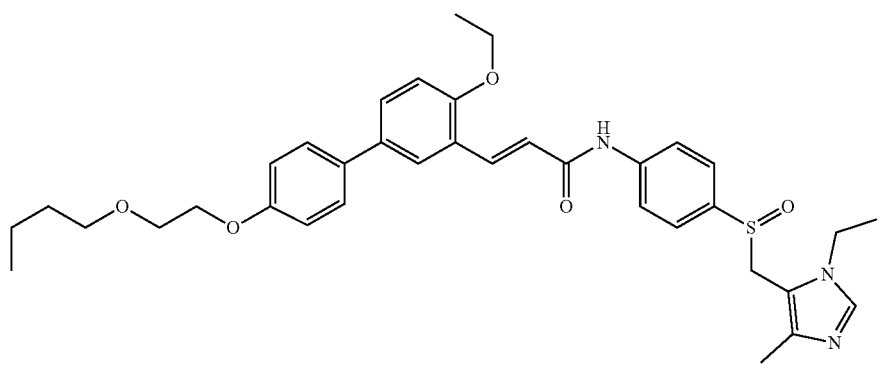
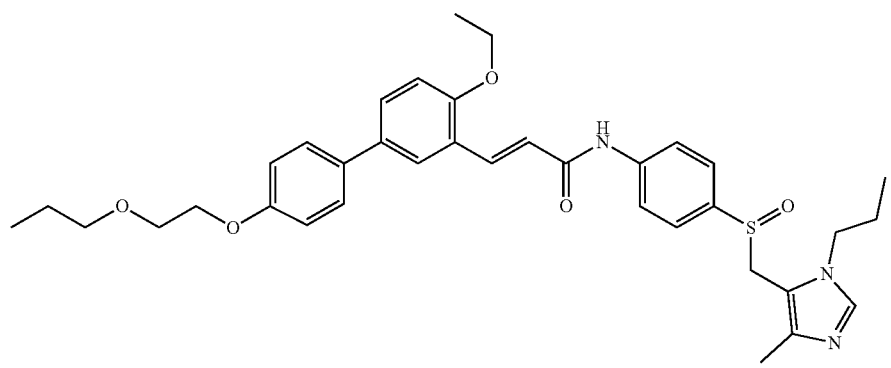
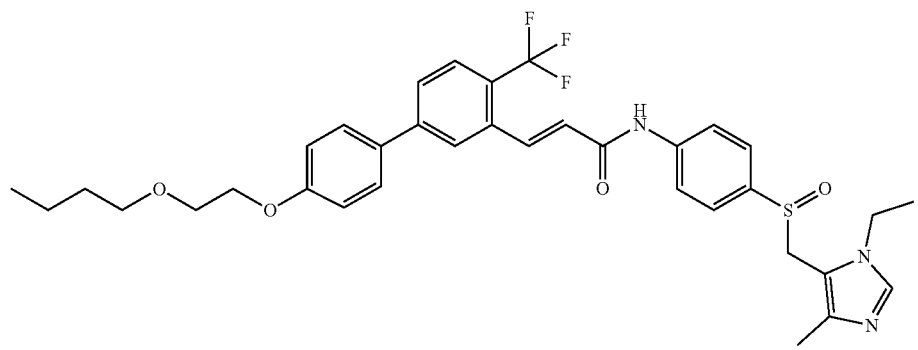

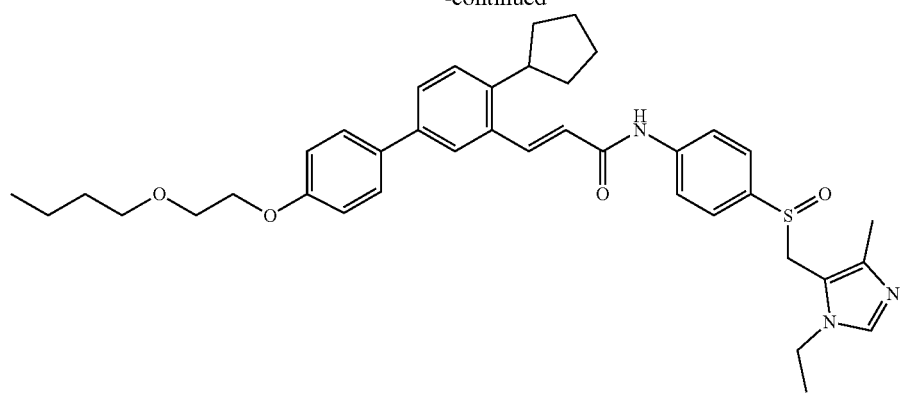
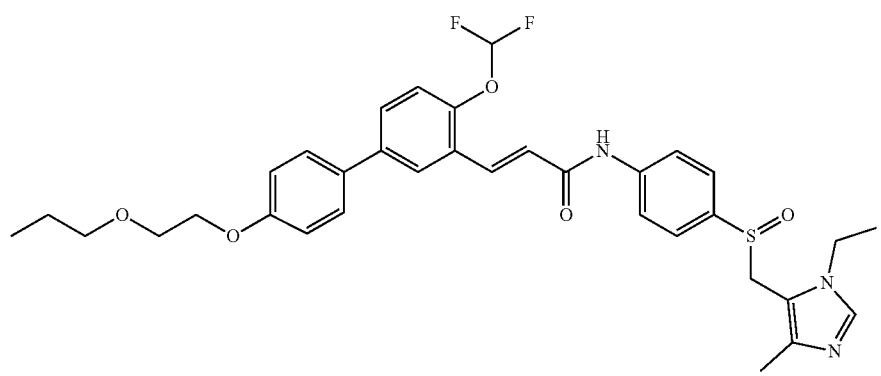
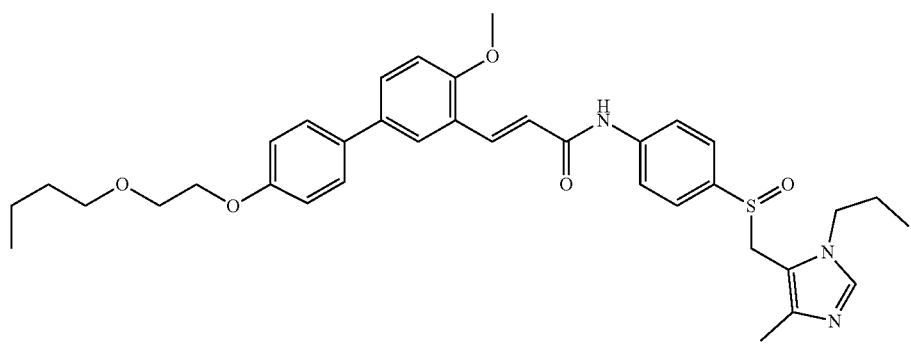
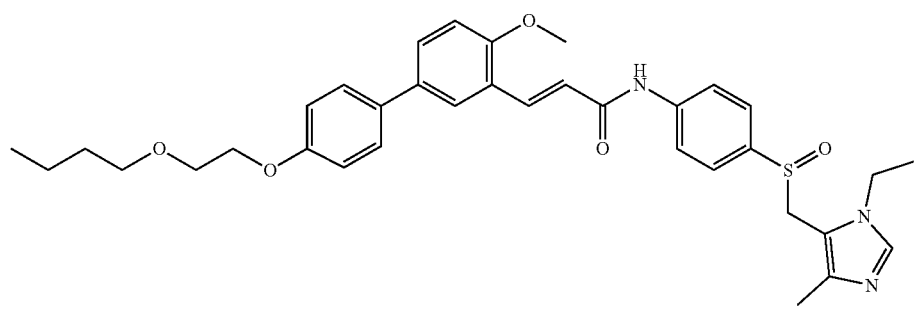

-continued
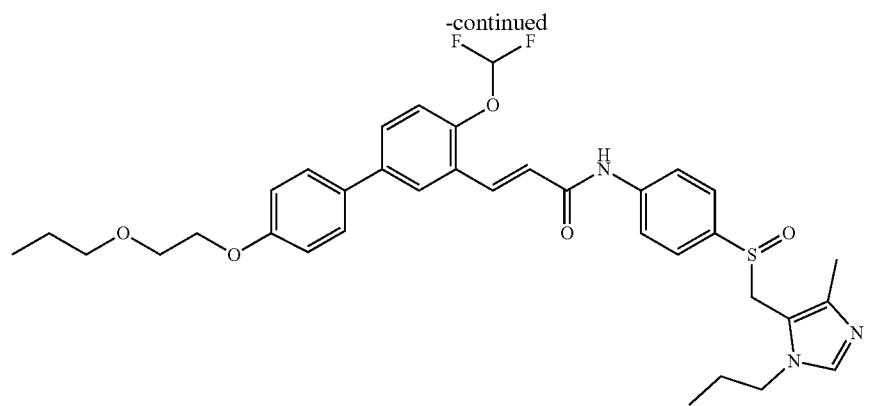
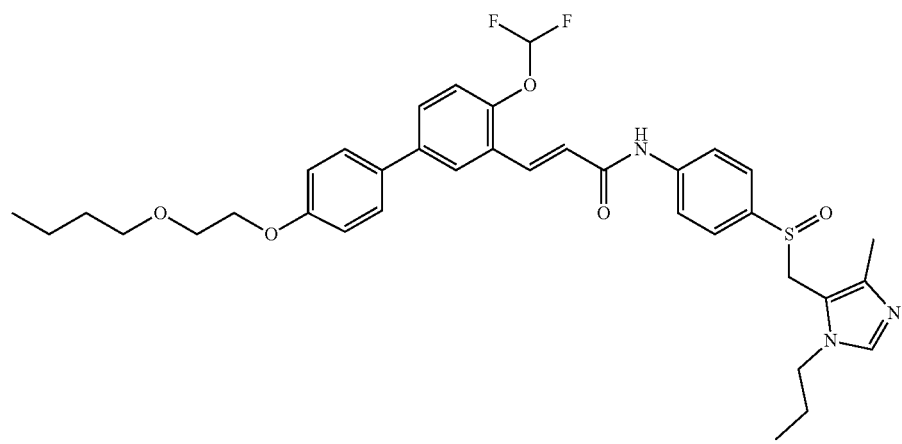
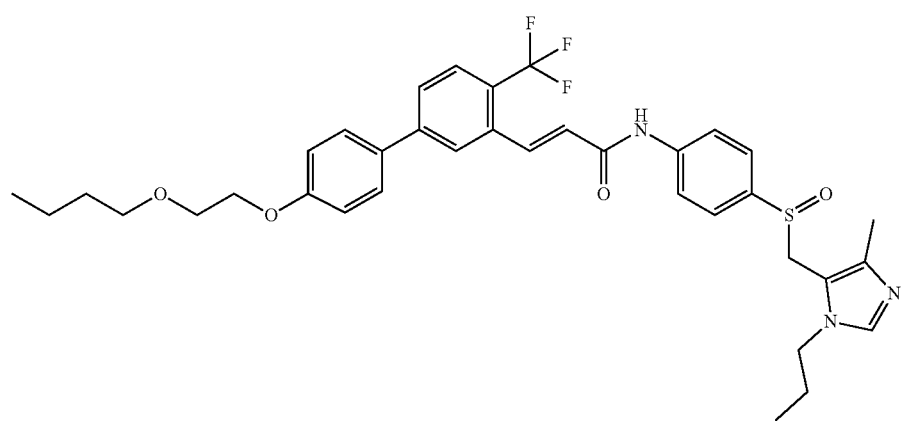
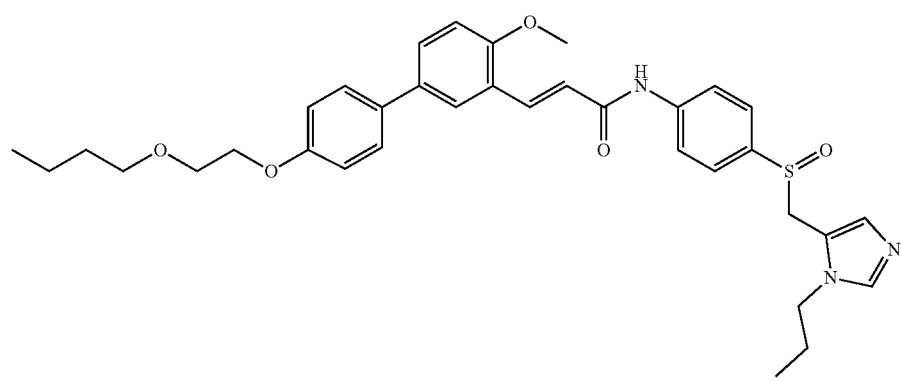

-continued
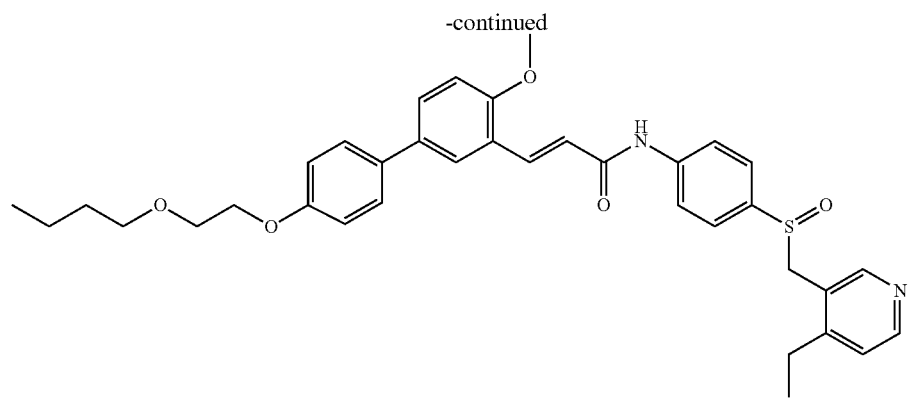
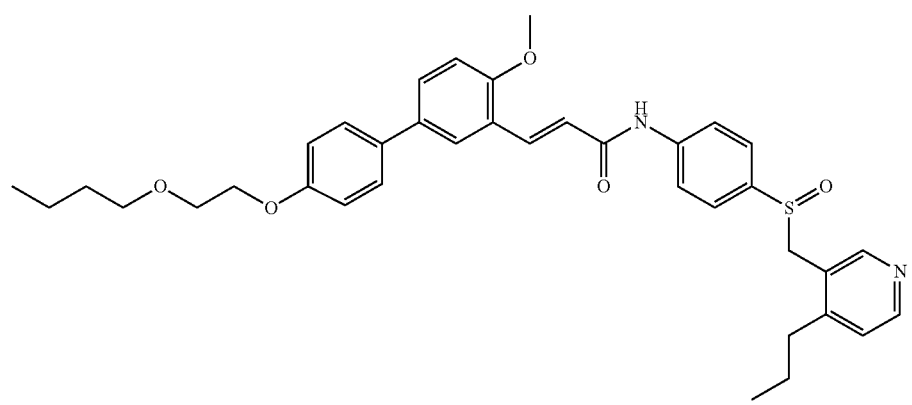
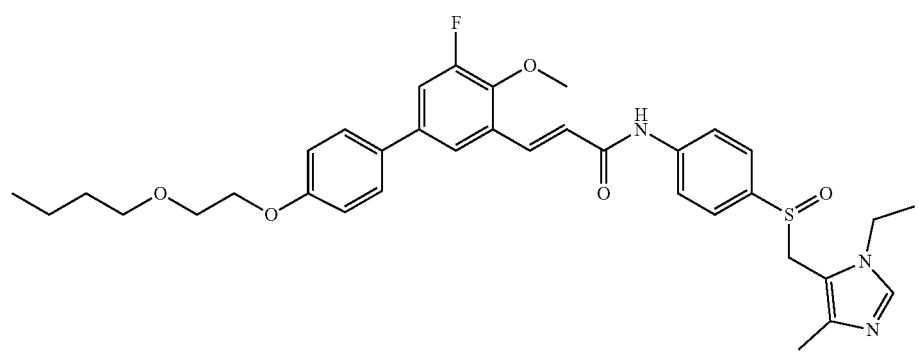
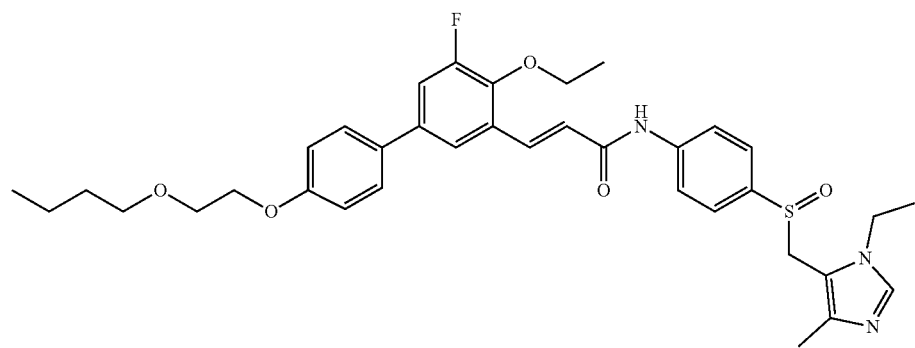

-continued
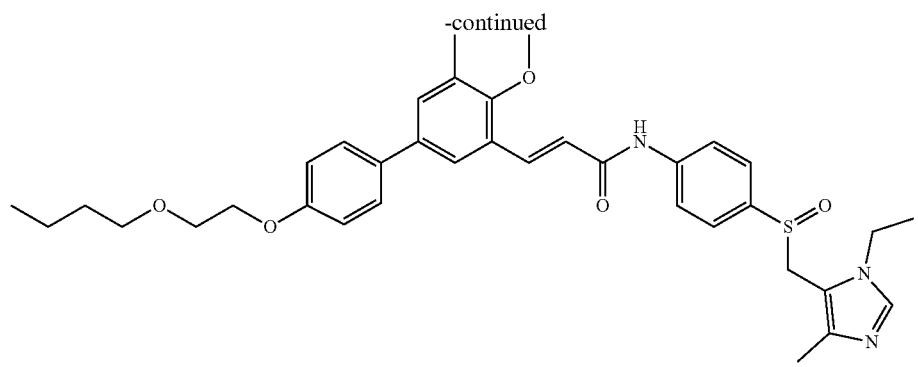
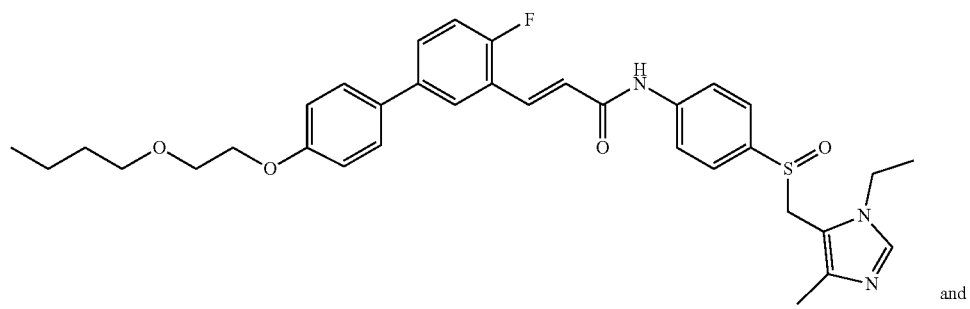
and
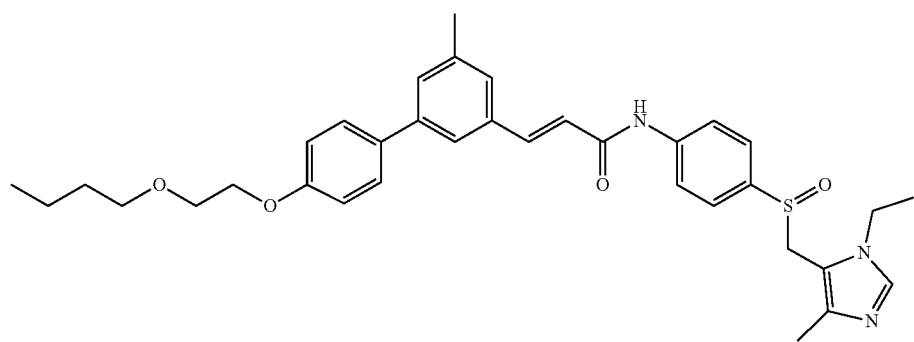
22. A compound or the pharmaceutically acceptable salt thereof, which is selected from the group consisting of
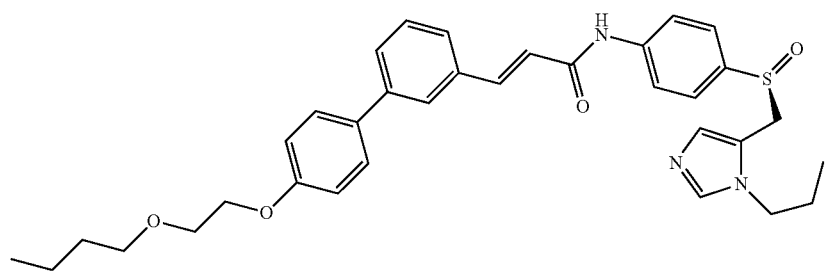
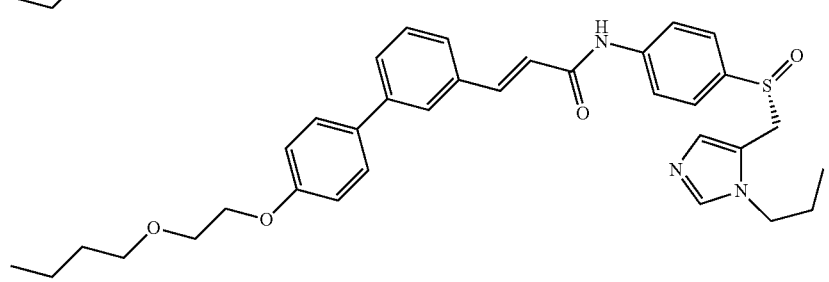

353
354
-continued
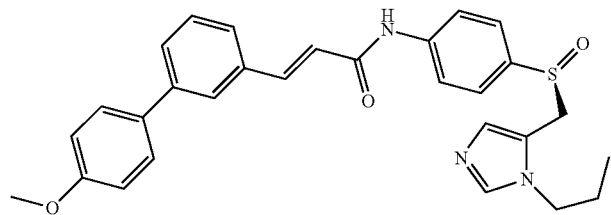
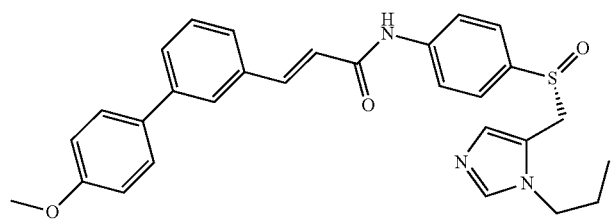
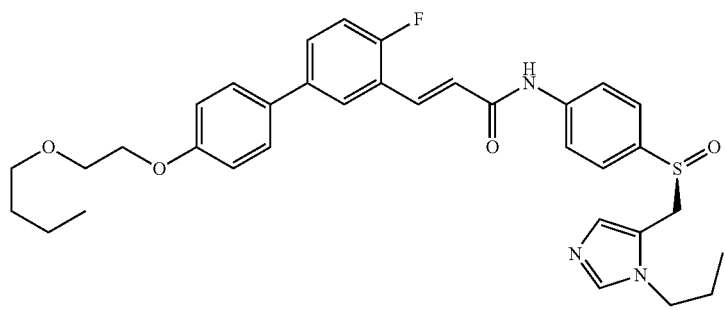
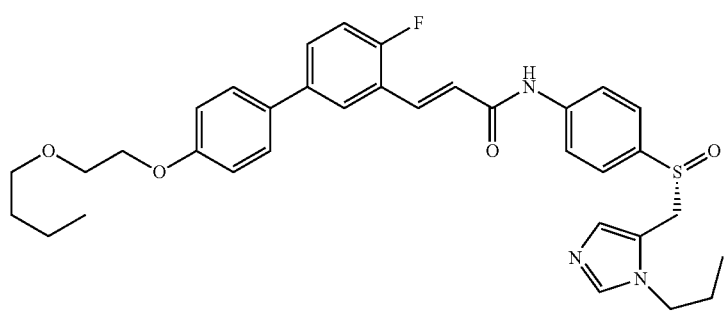
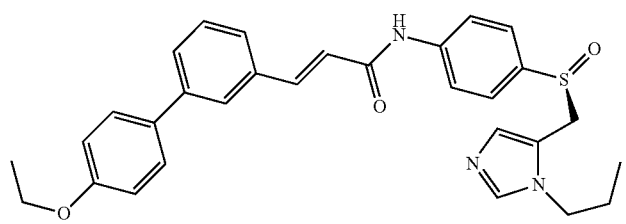
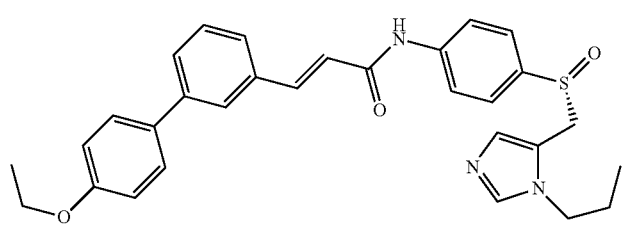

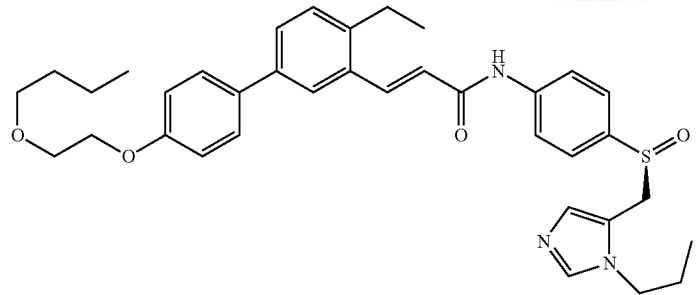
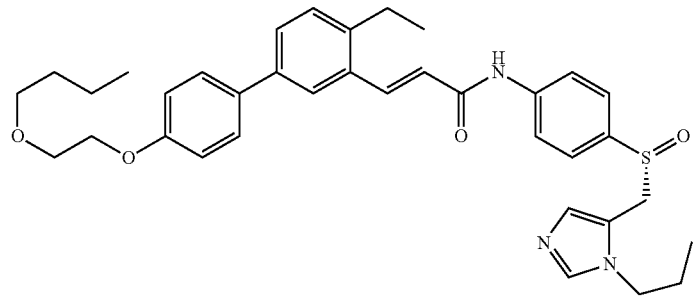
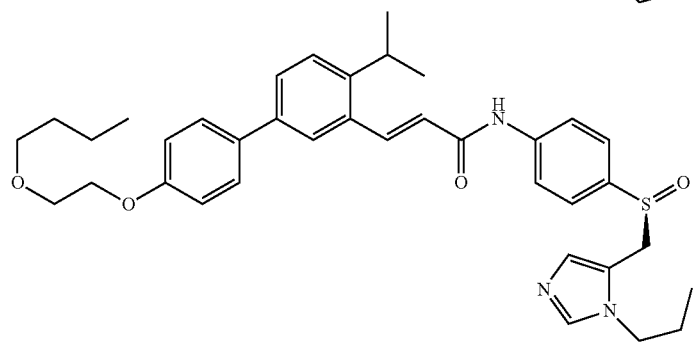
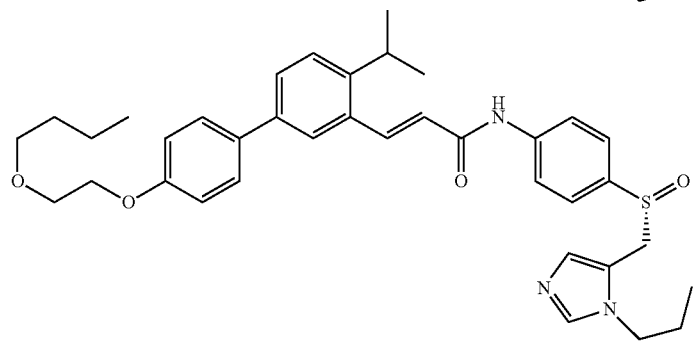
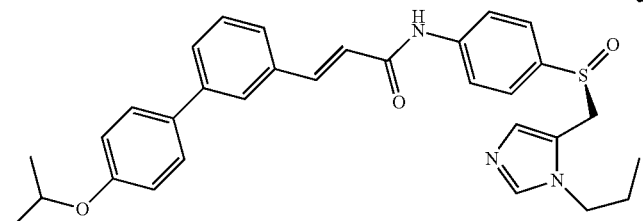
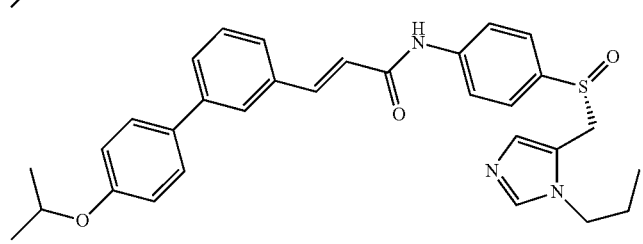

-continued
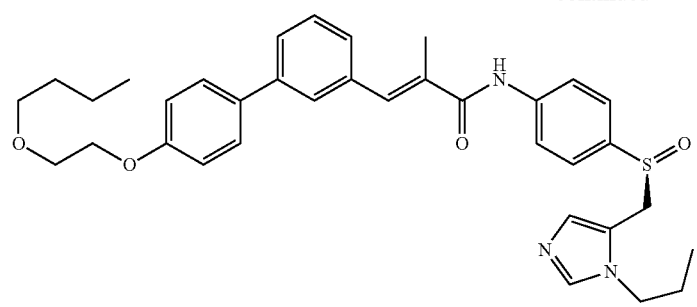
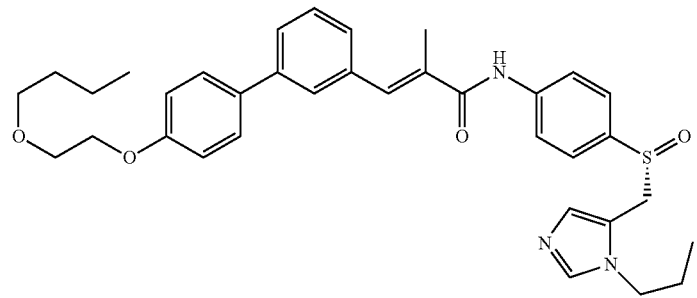
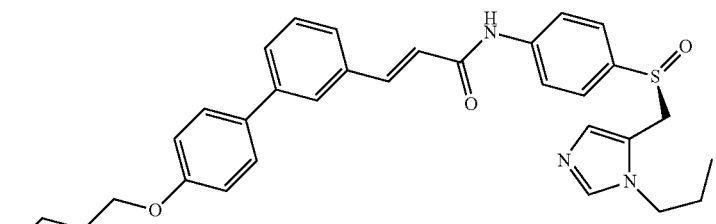
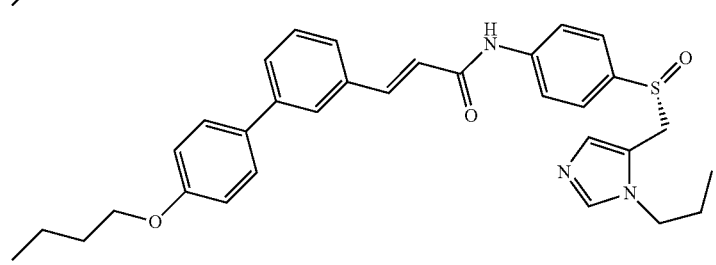
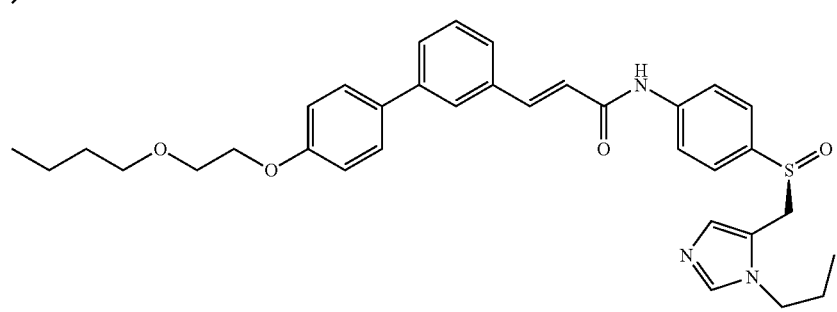
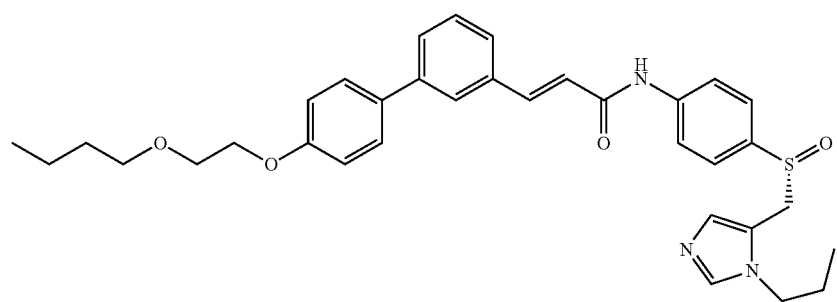

-continued
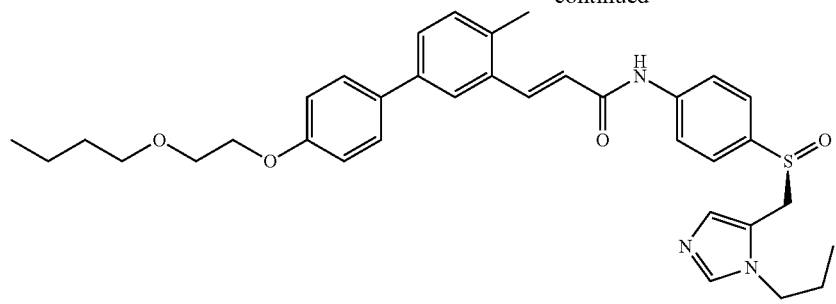
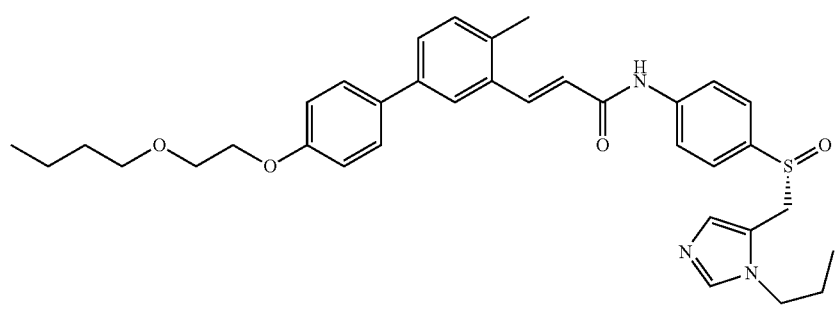
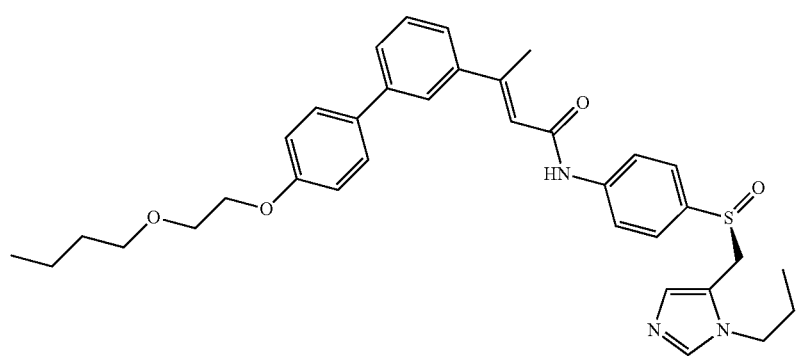
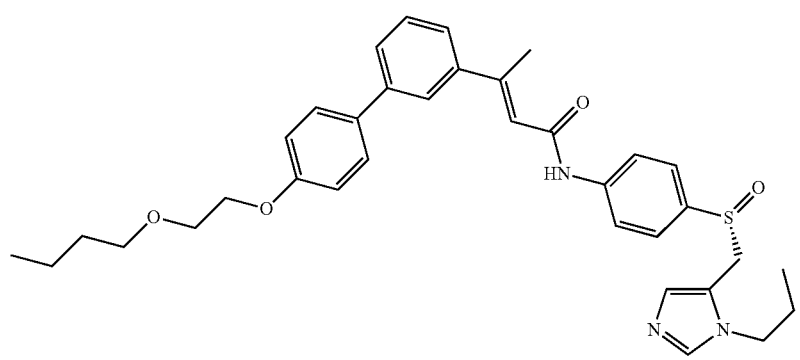
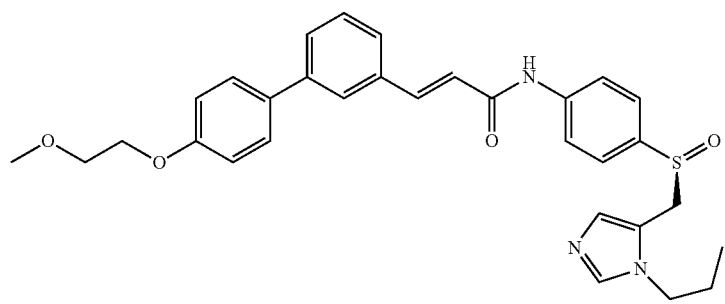

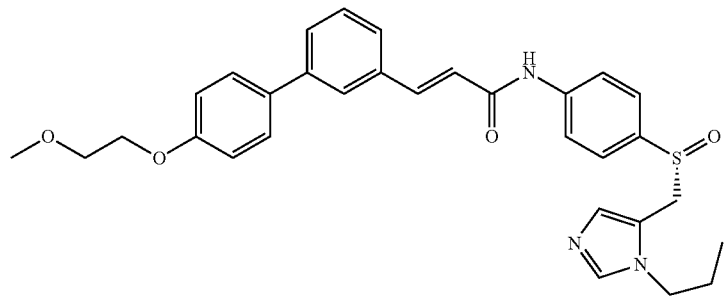
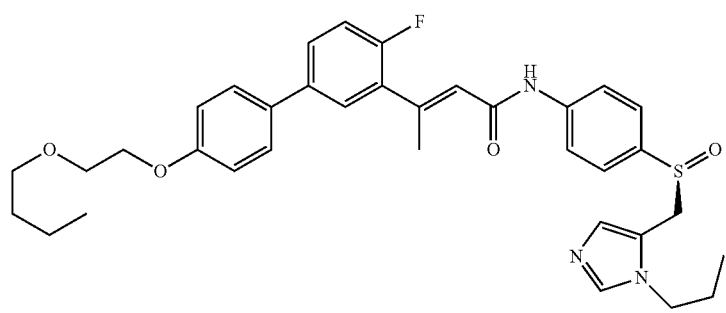
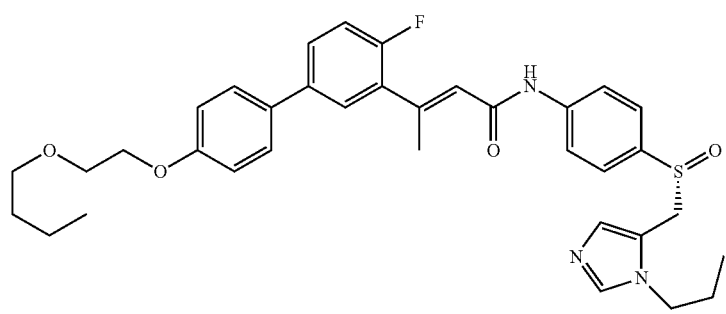
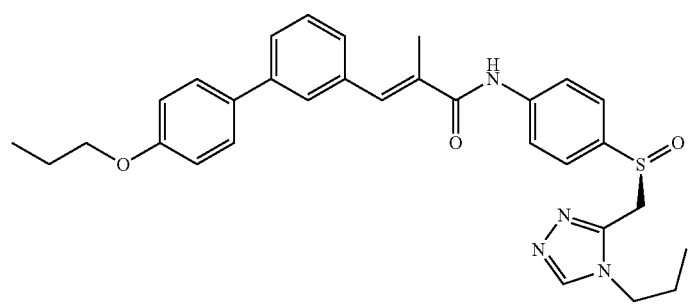
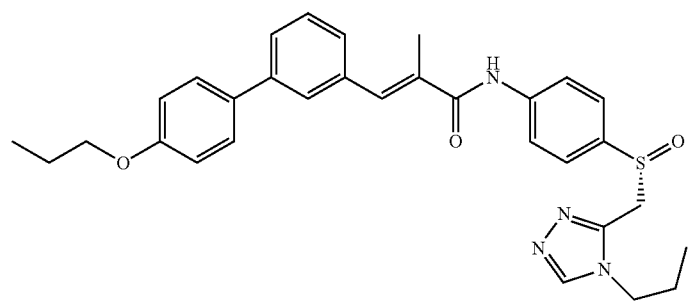

-continued
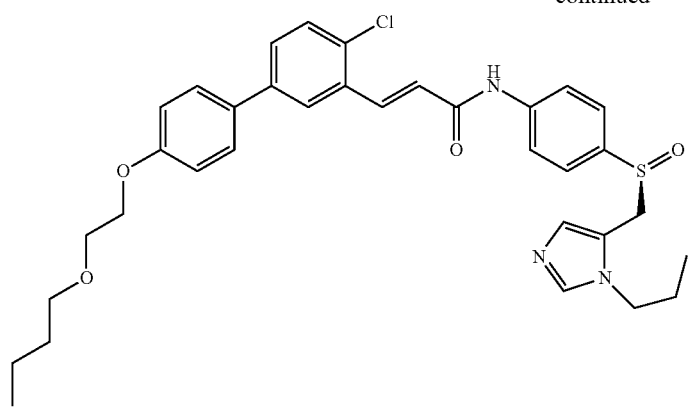
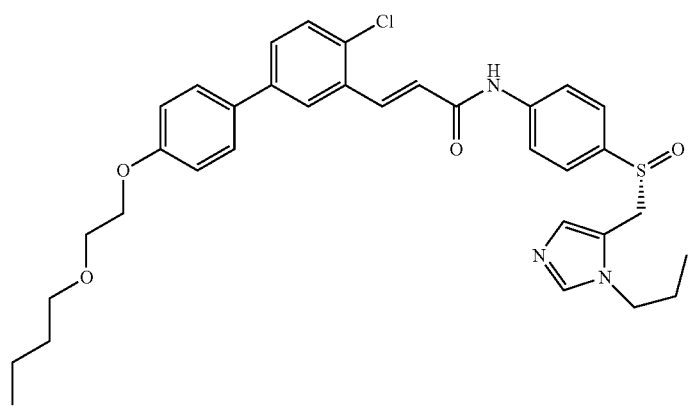
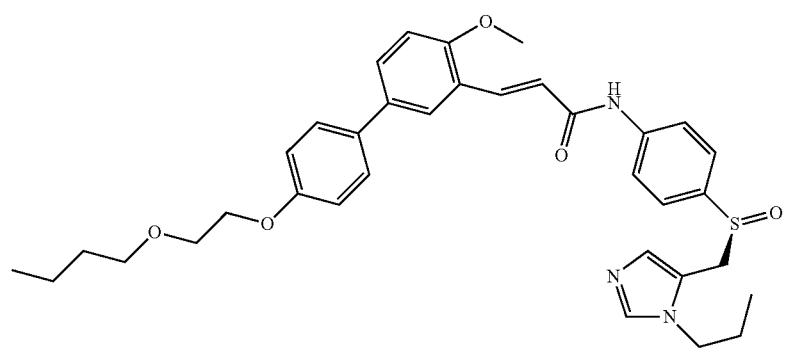
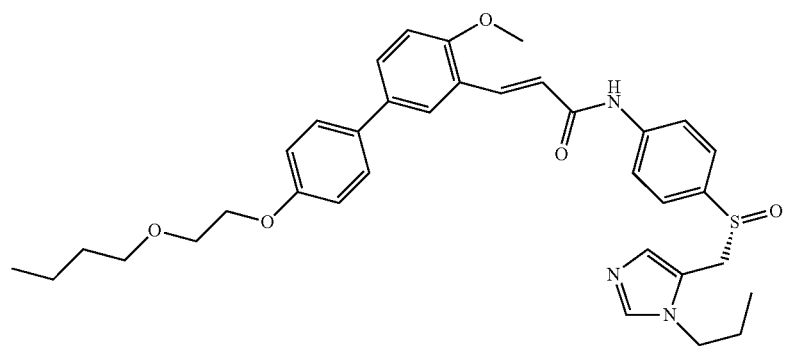

-continued
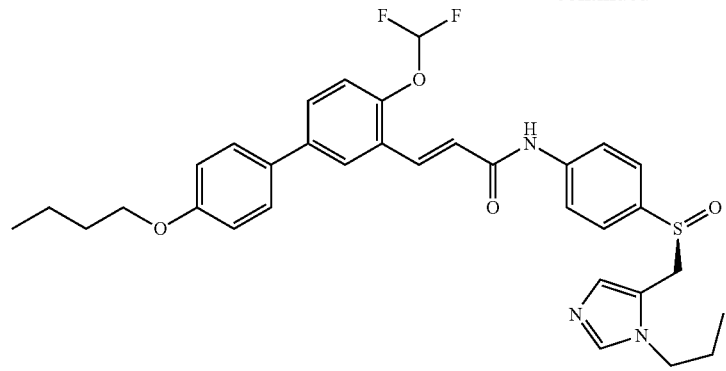
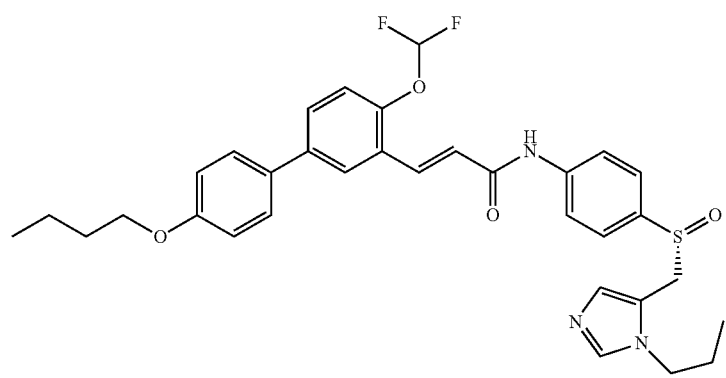
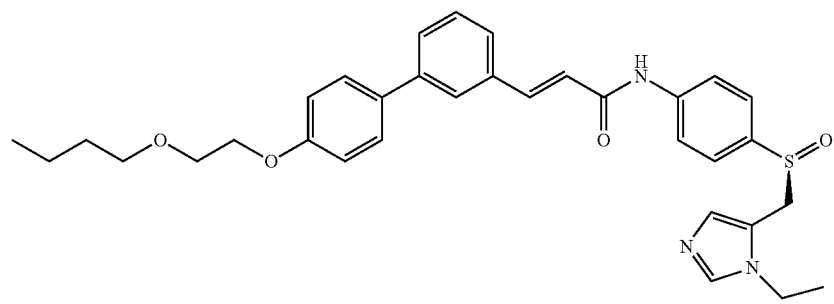
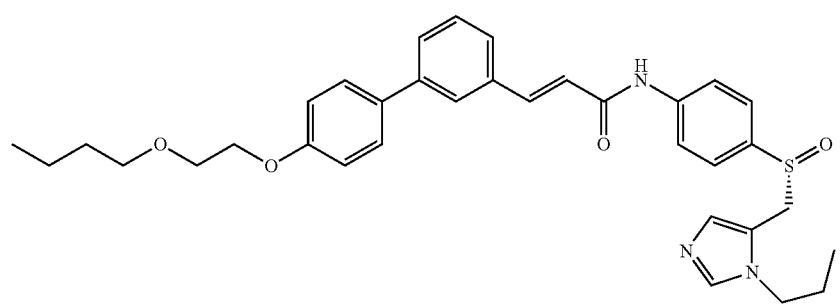
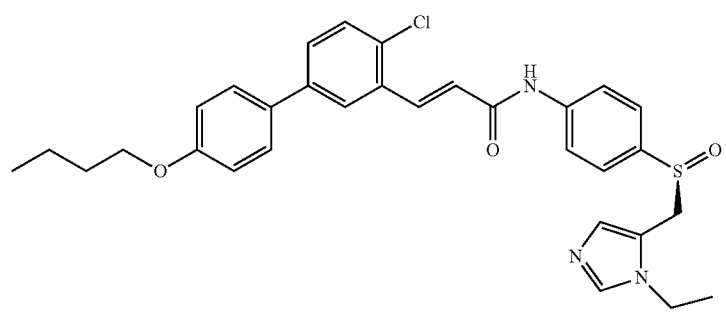

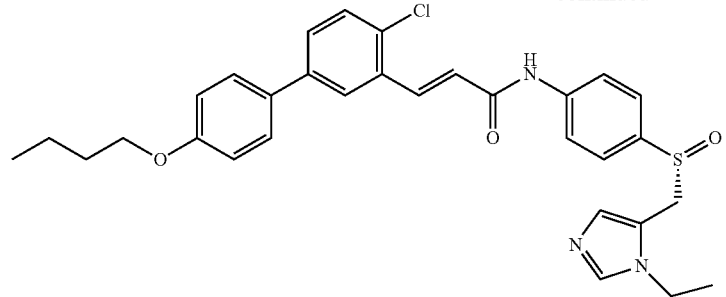
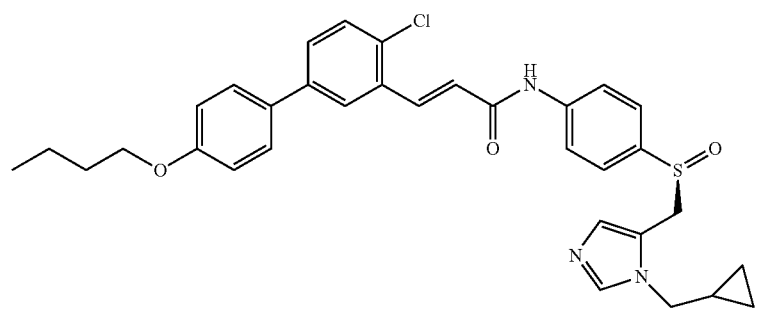
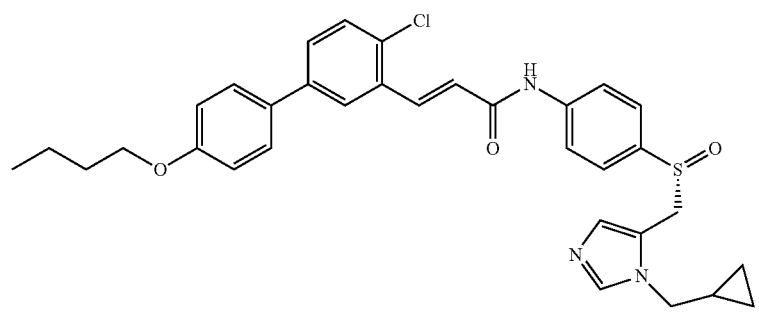
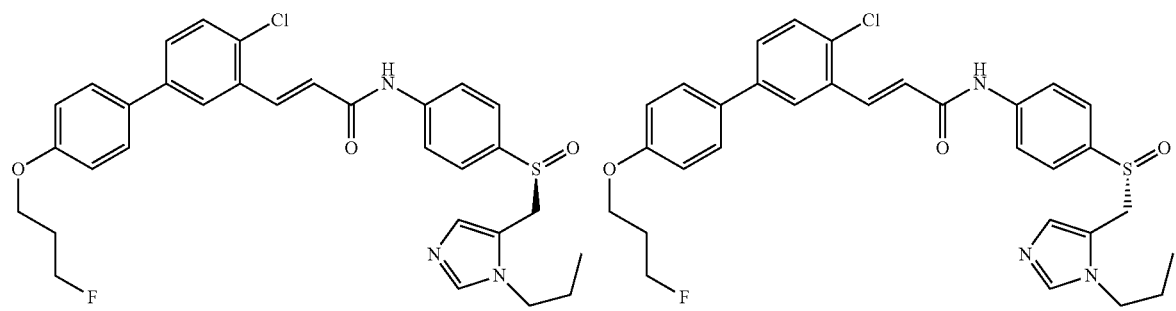
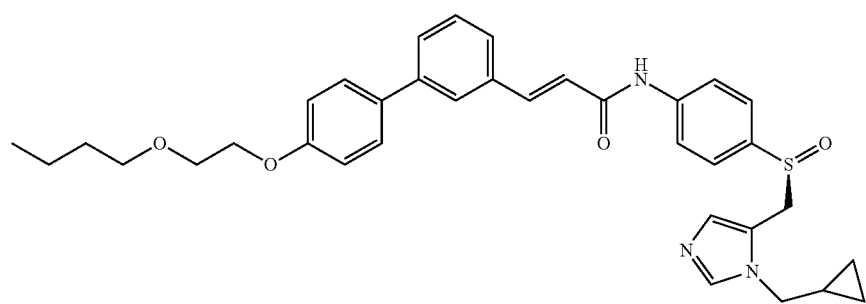

-continued
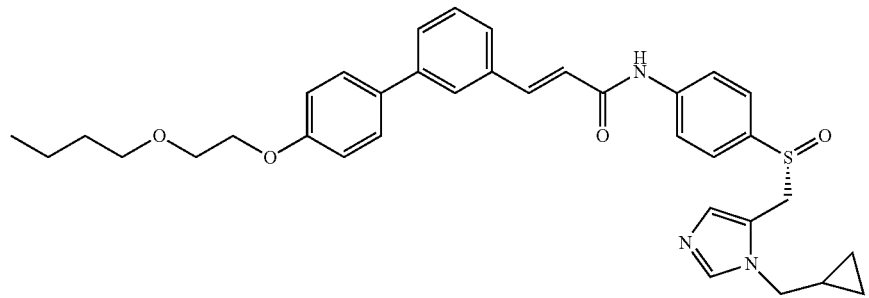
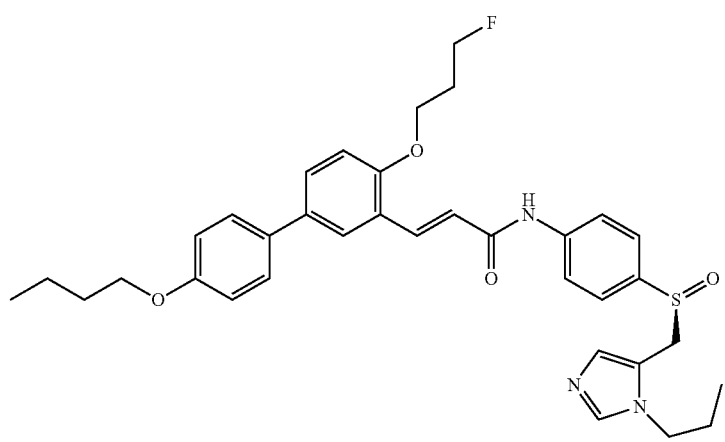
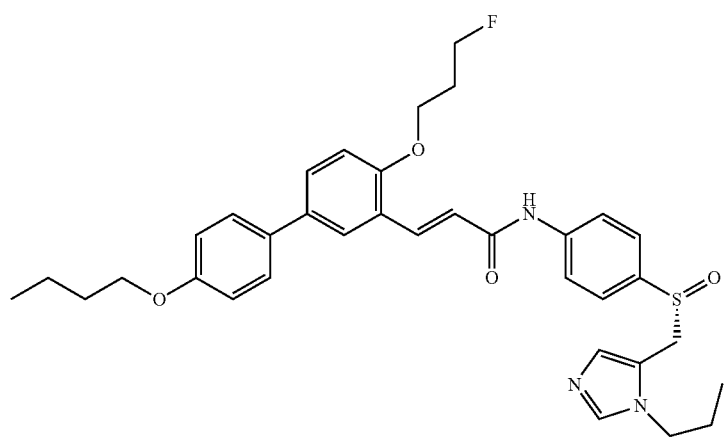
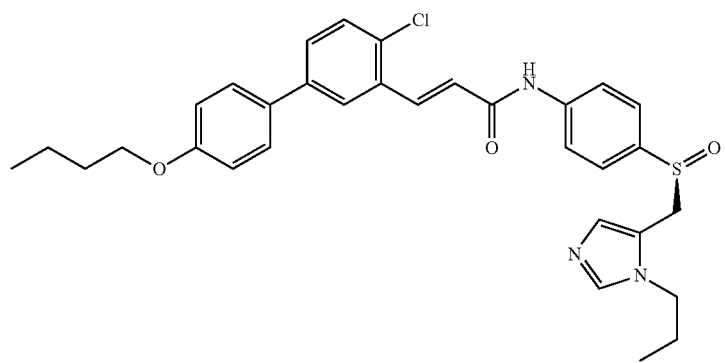

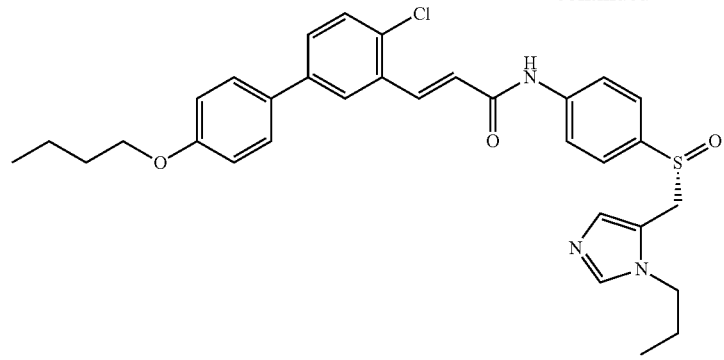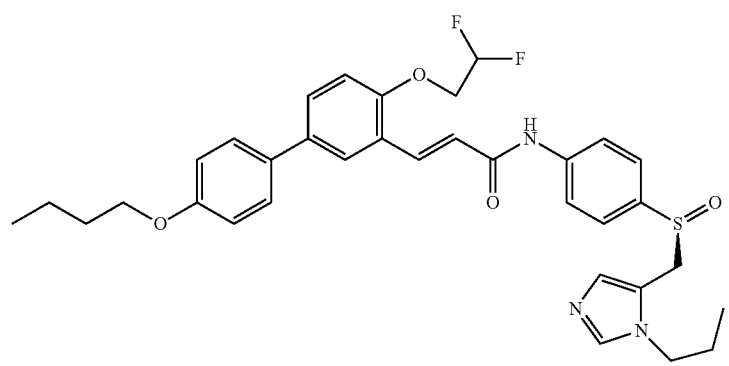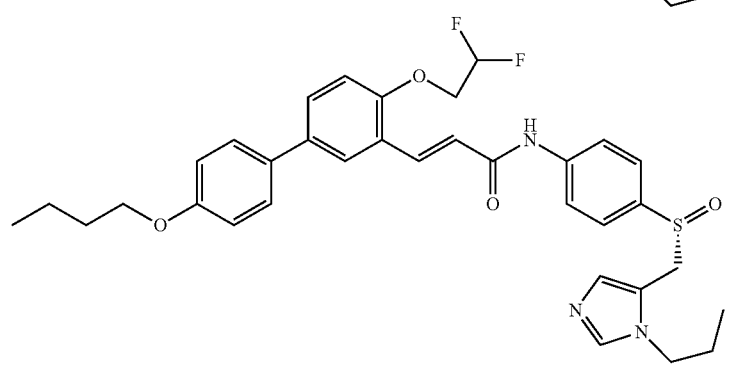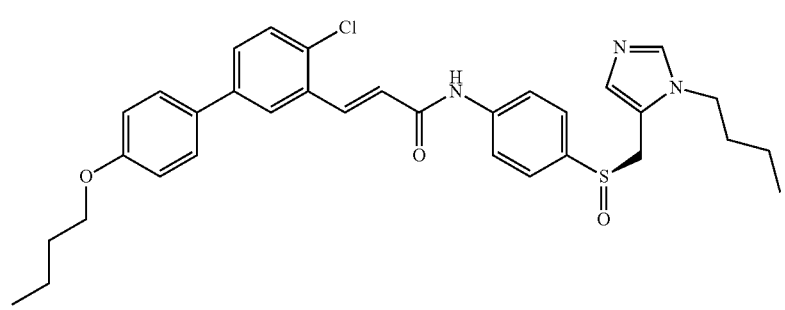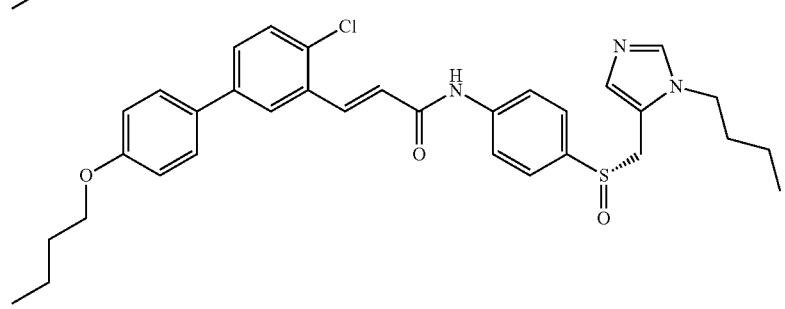

-continued
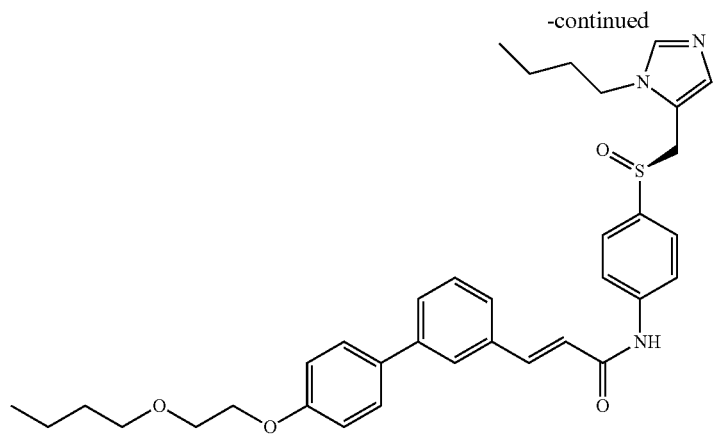
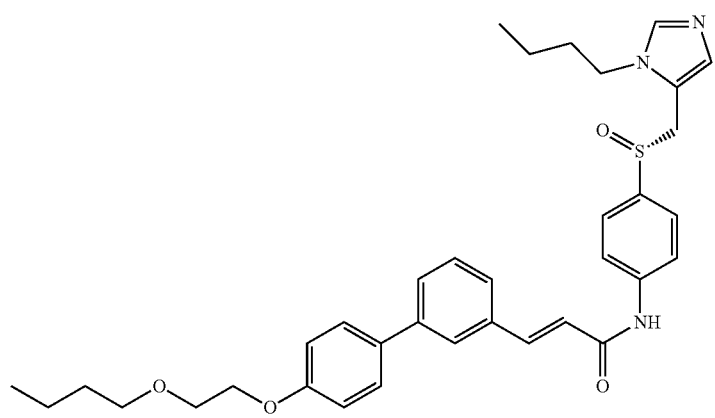
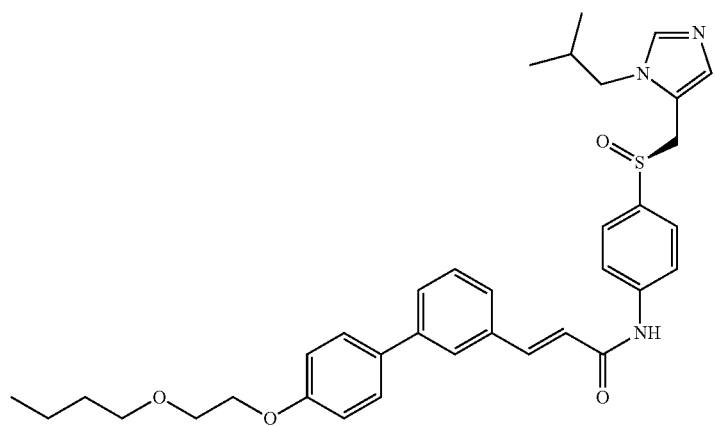
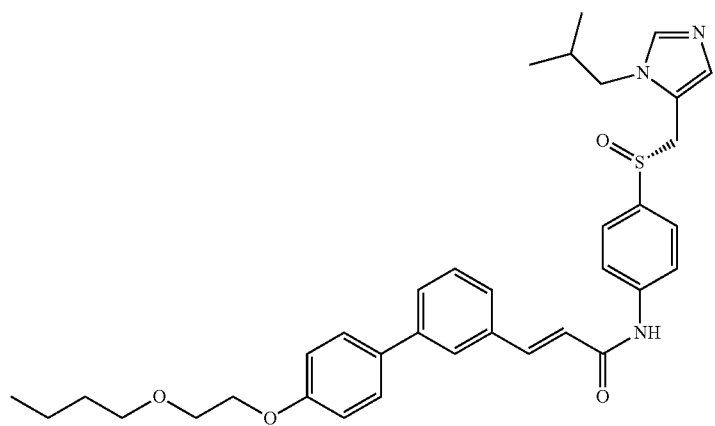

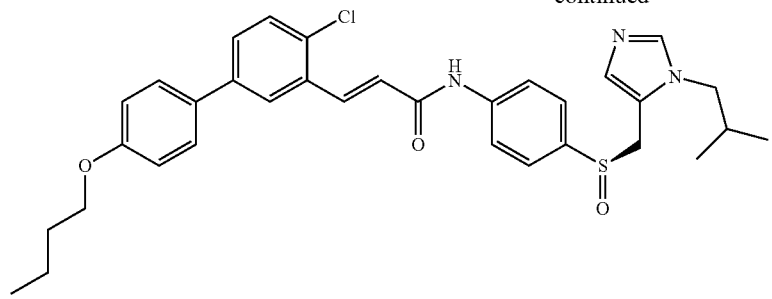
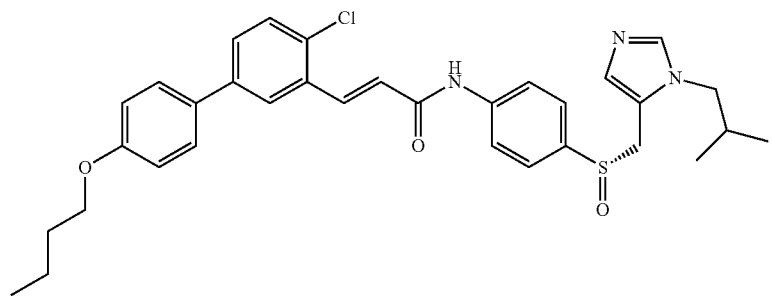
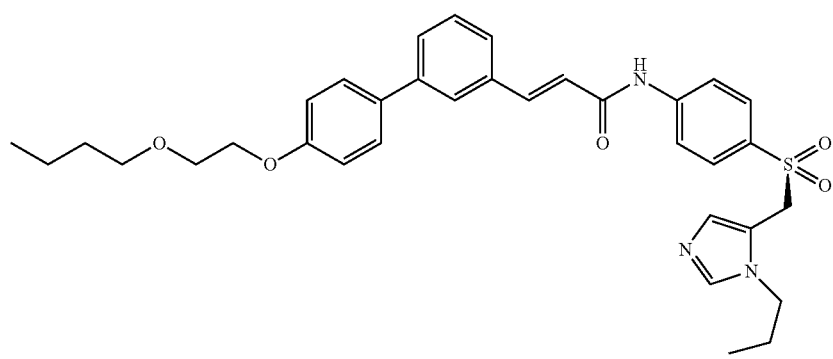
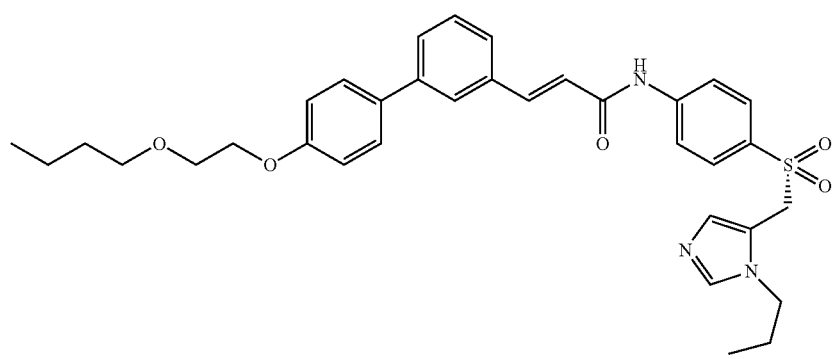
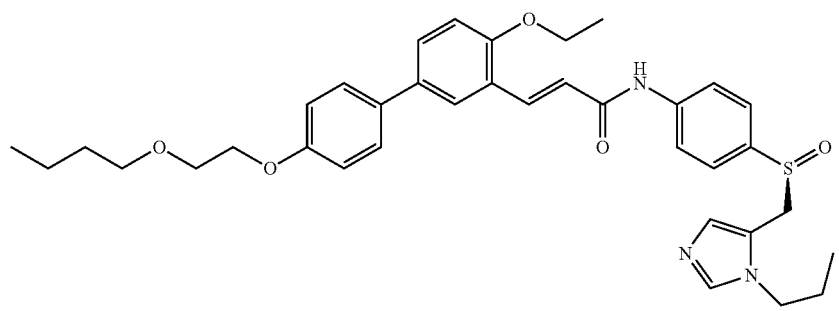

-continued
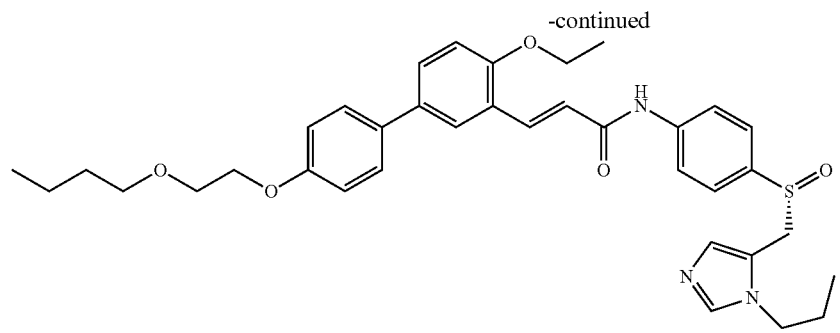
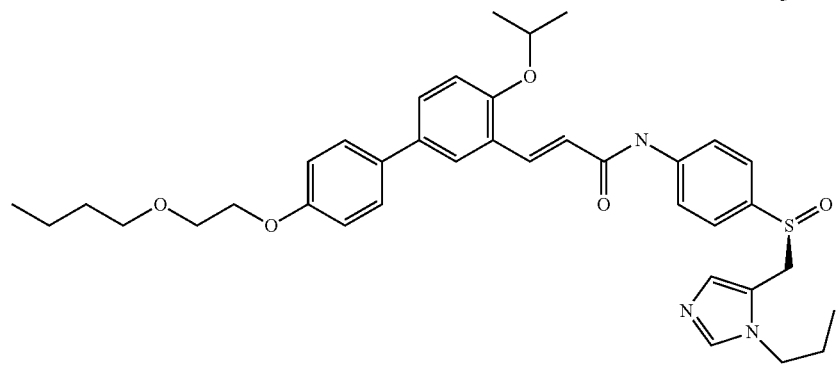
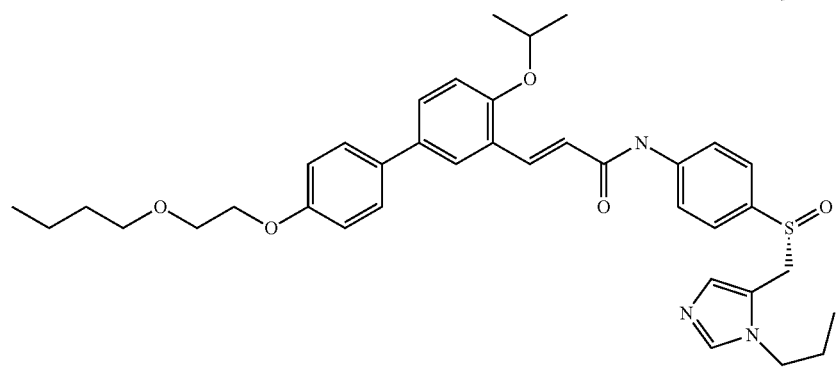
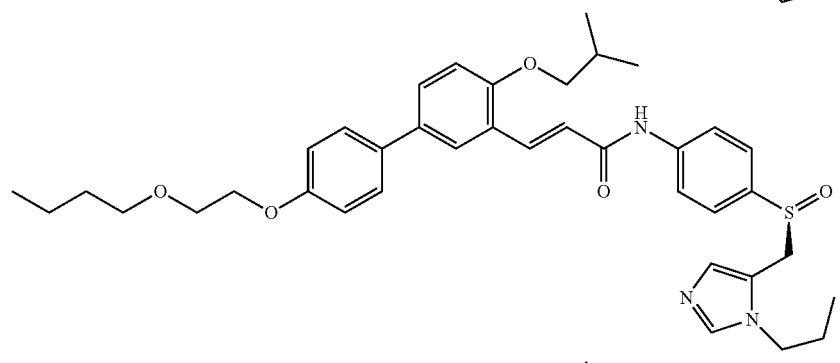
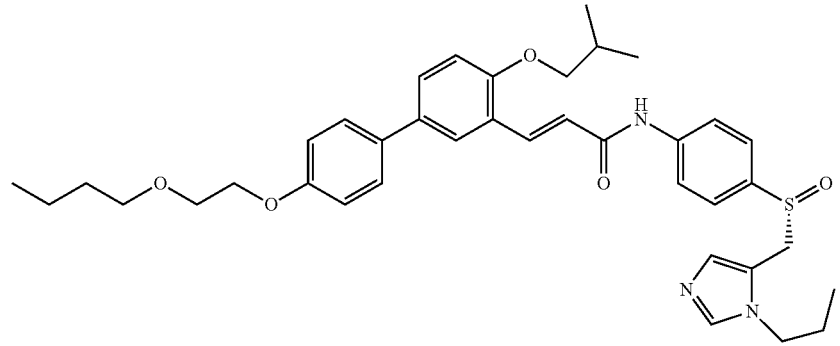

-continued
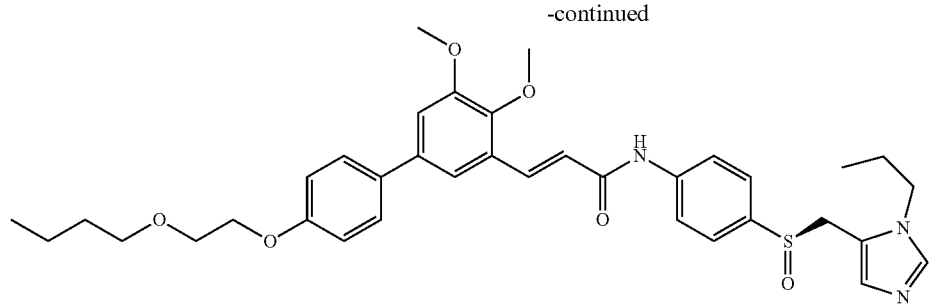
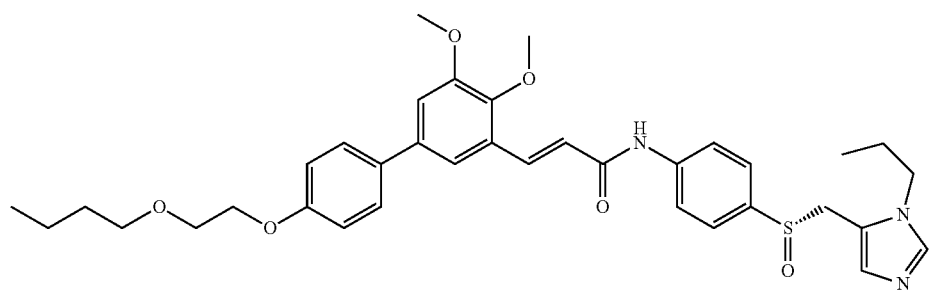
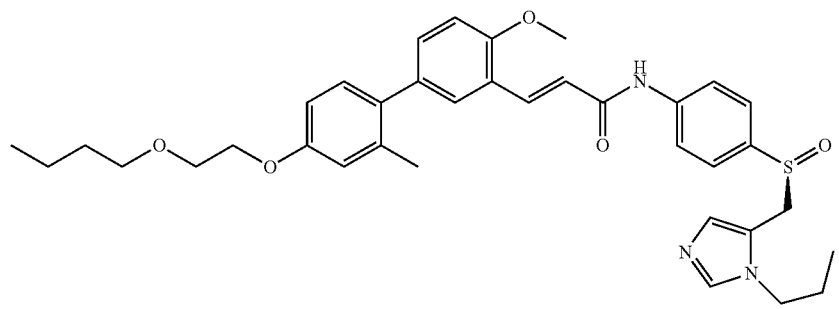
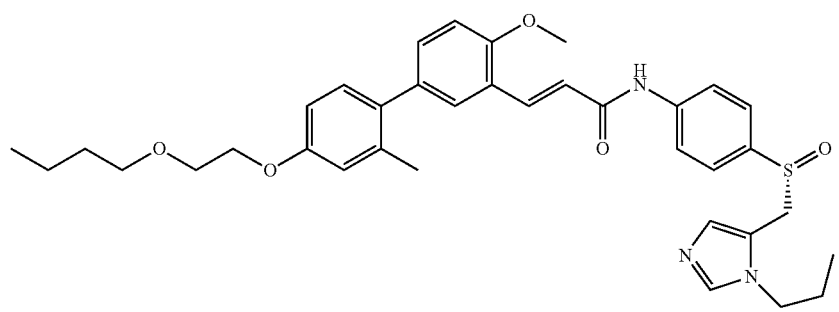
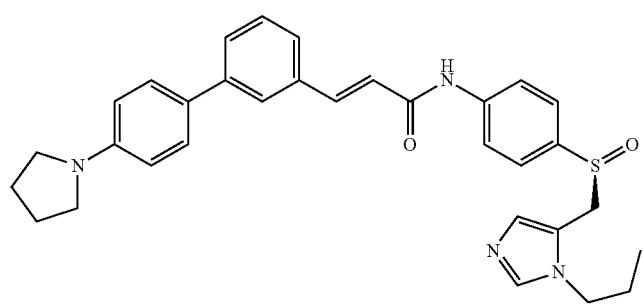

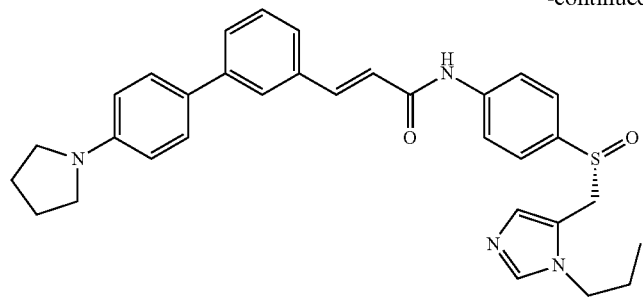
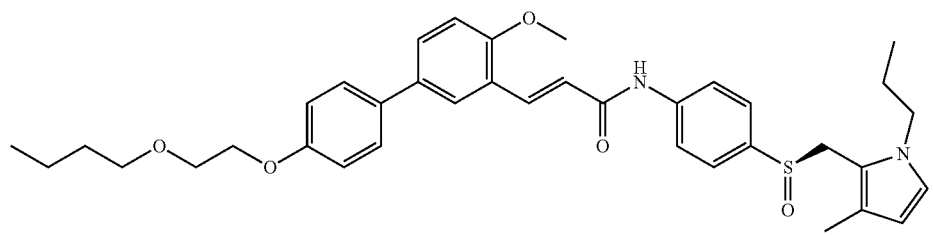
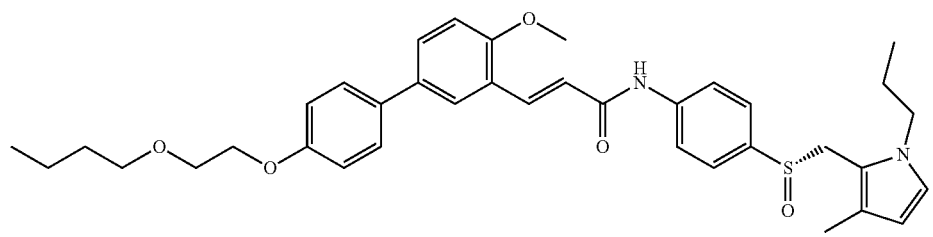
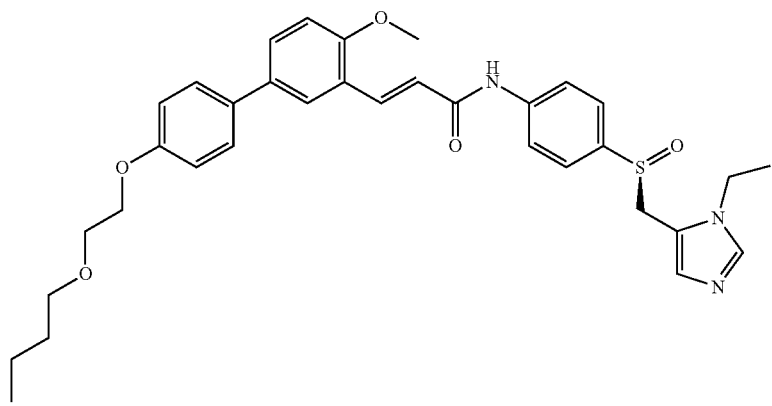
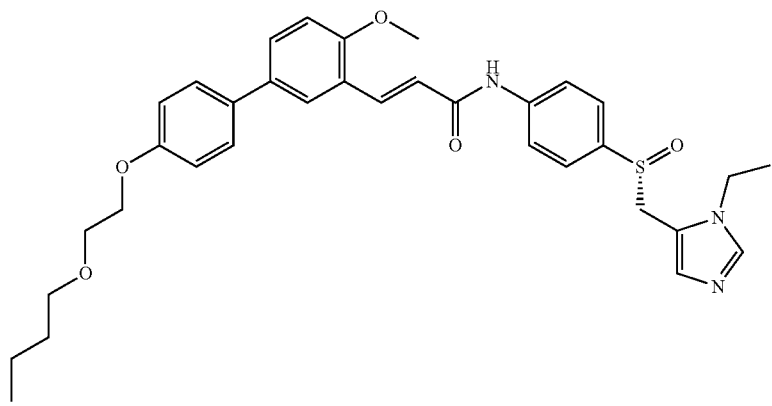

-continued
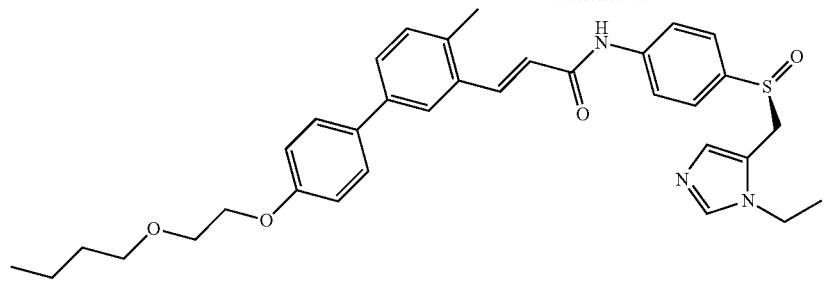
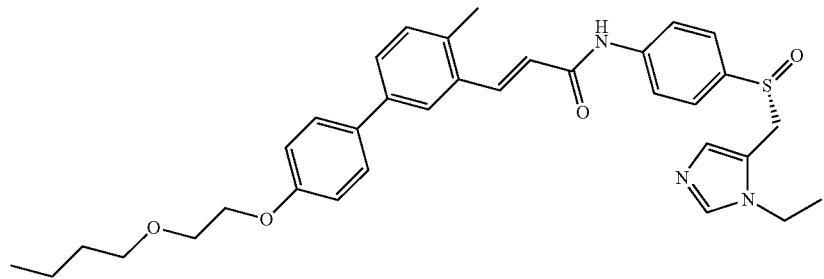
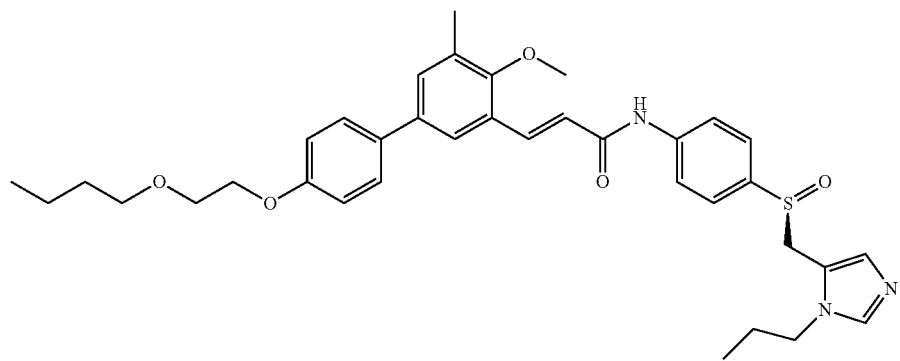
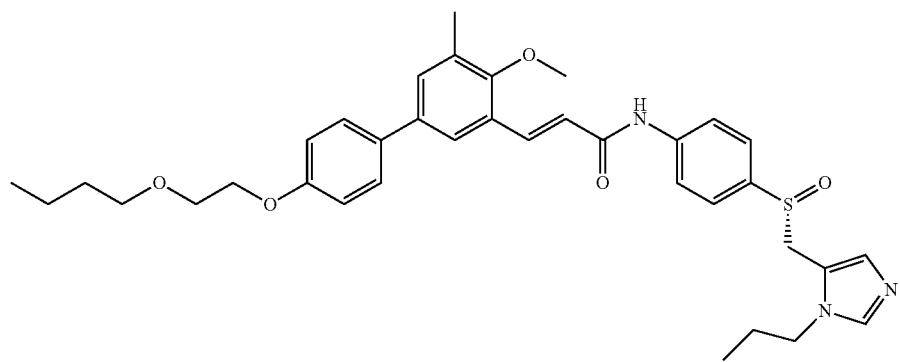
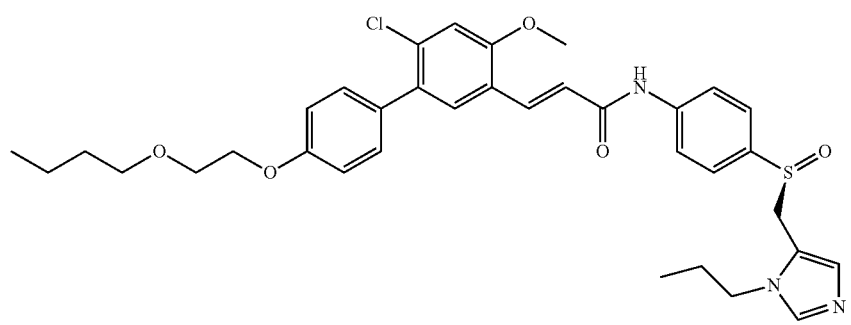

-continued
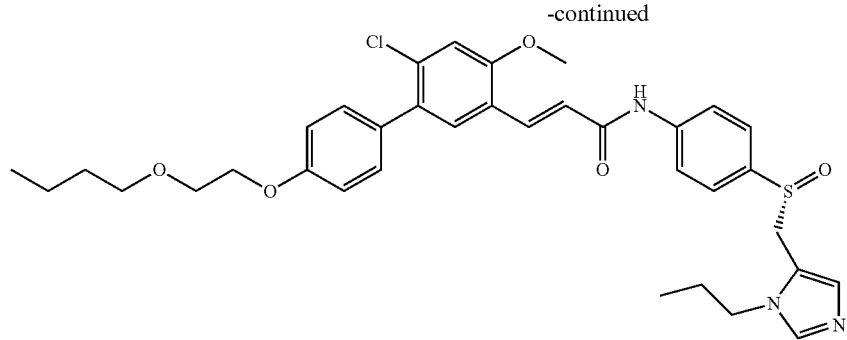
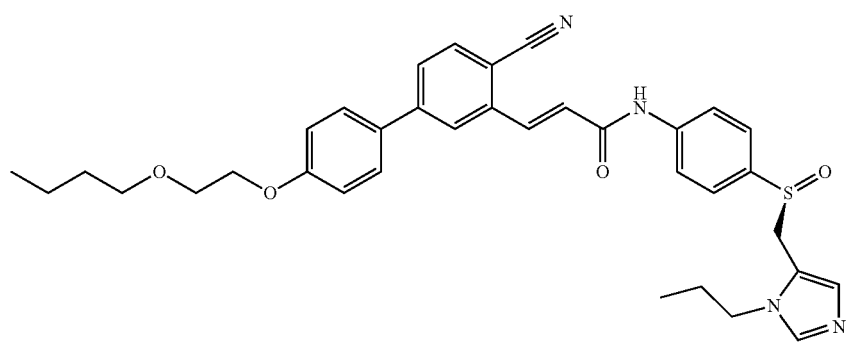
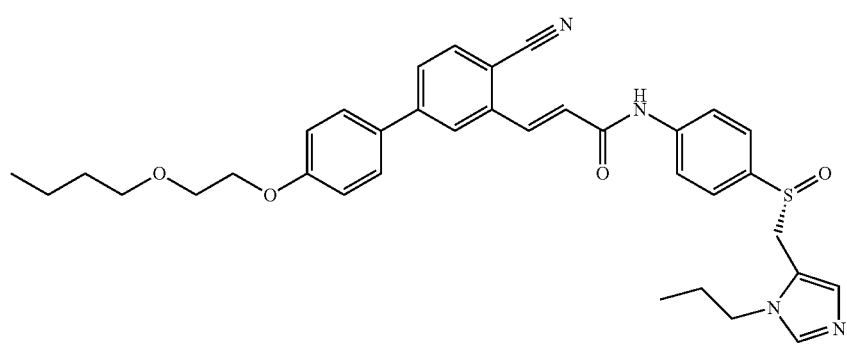
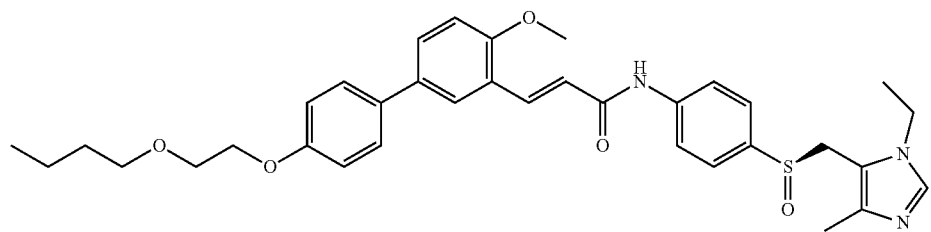
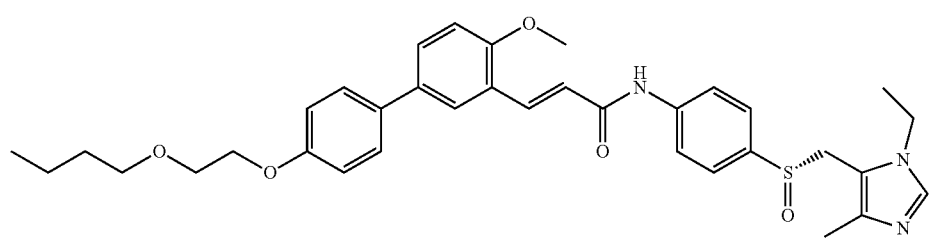

-continued
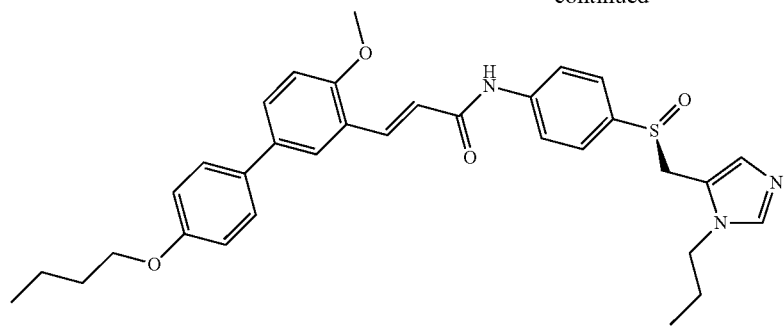
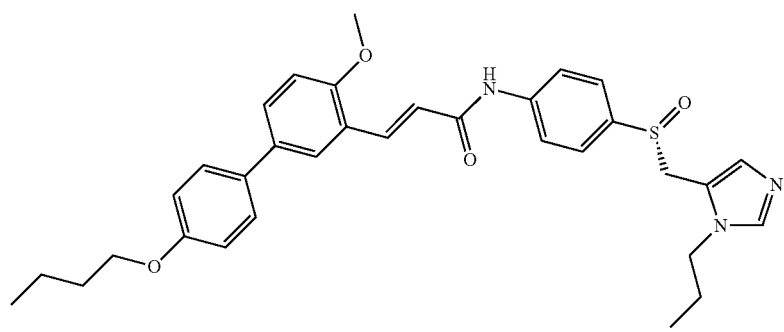
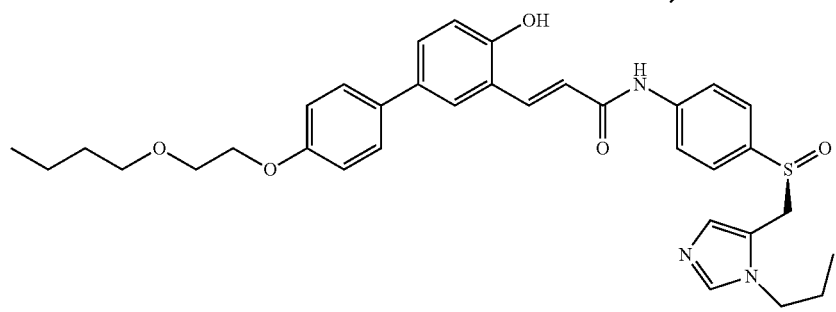
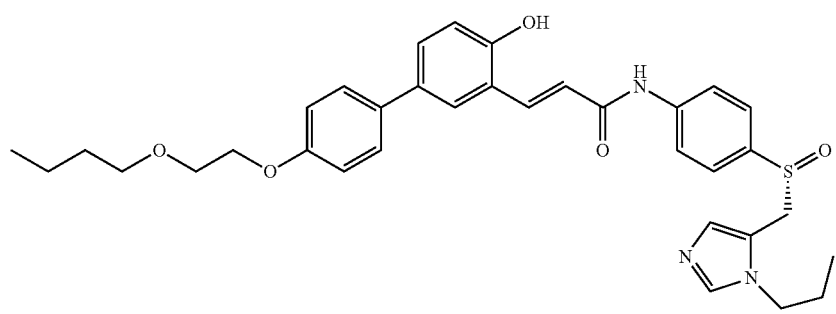
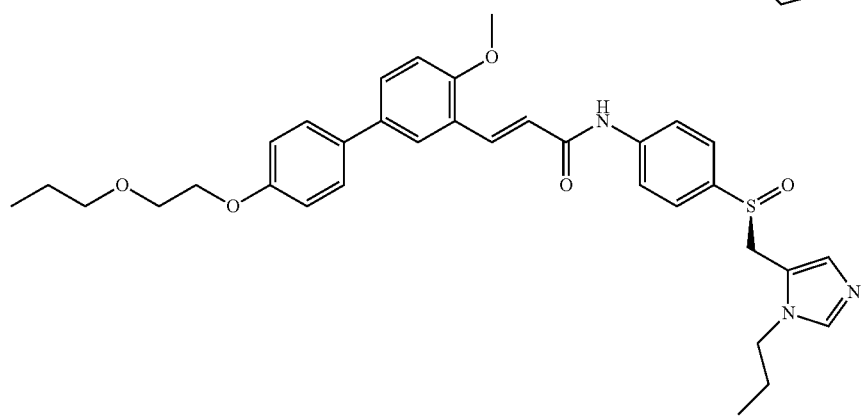

-continued
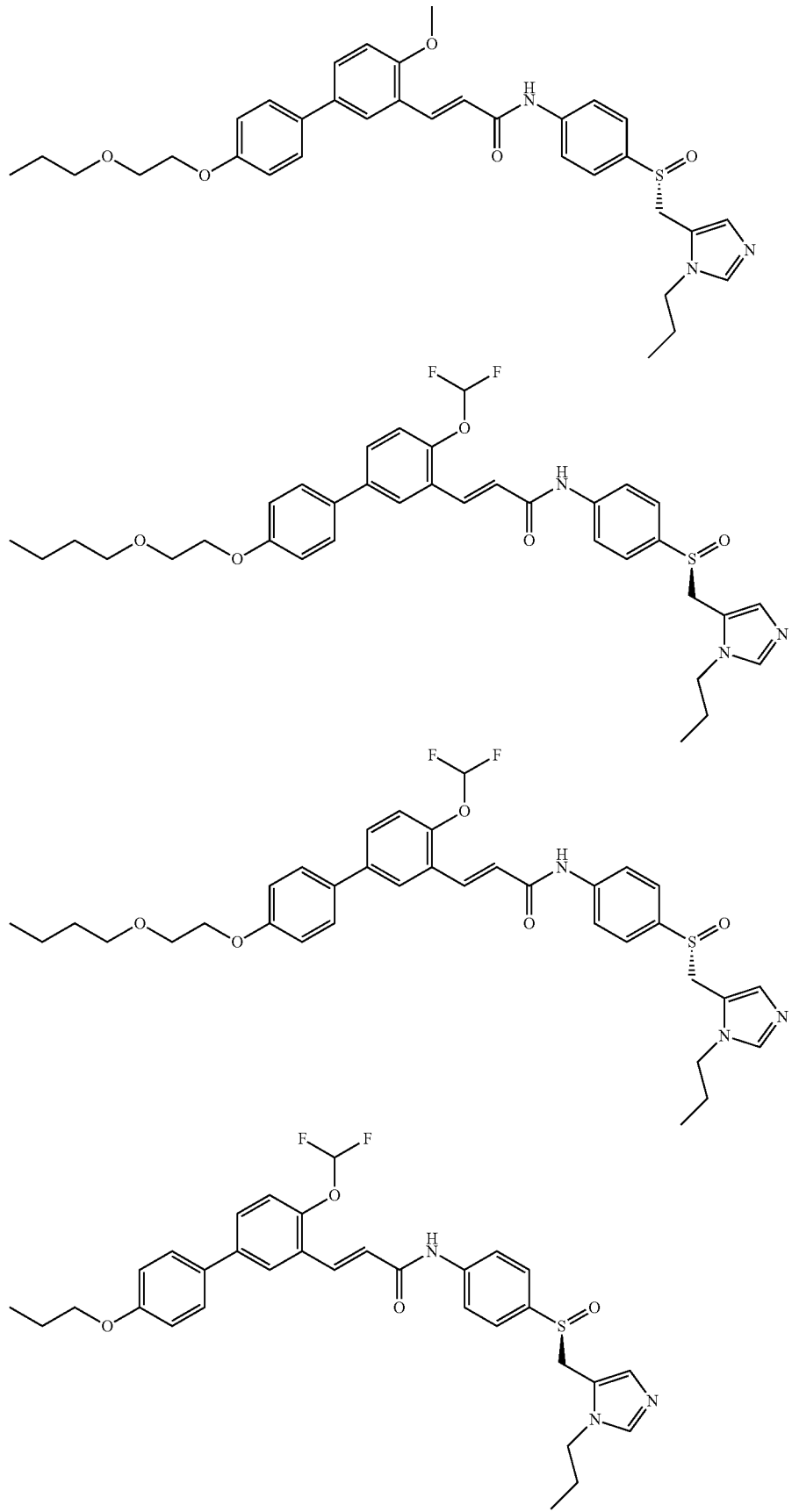

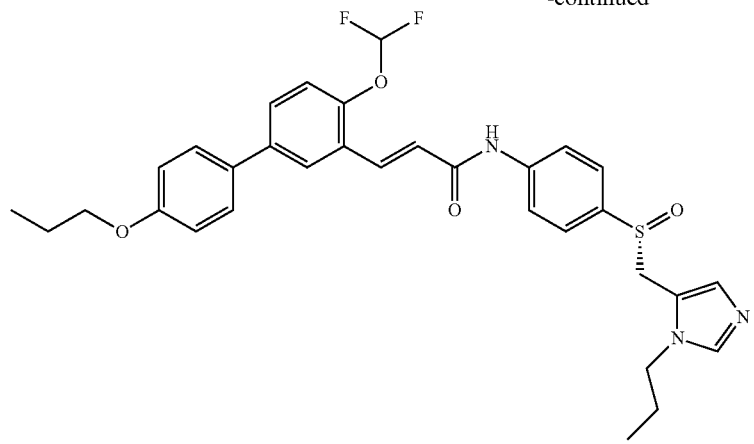
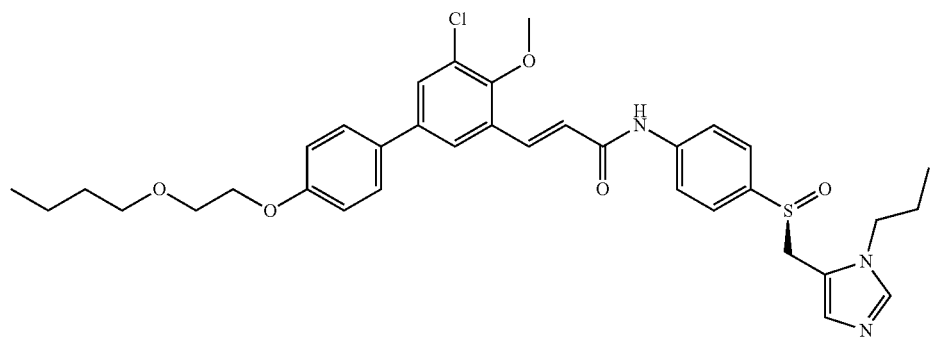
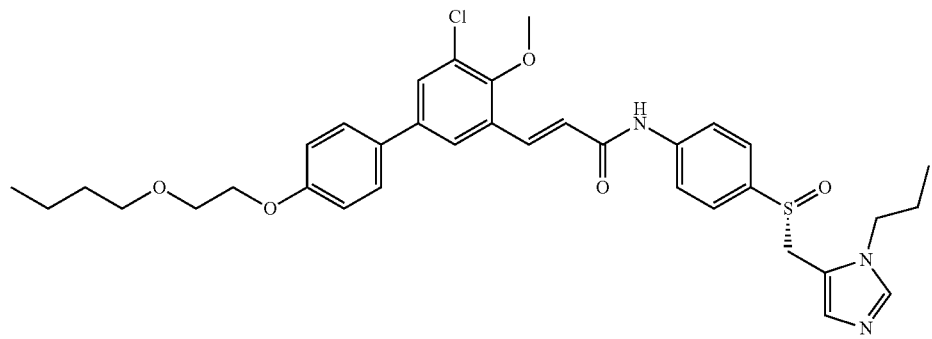
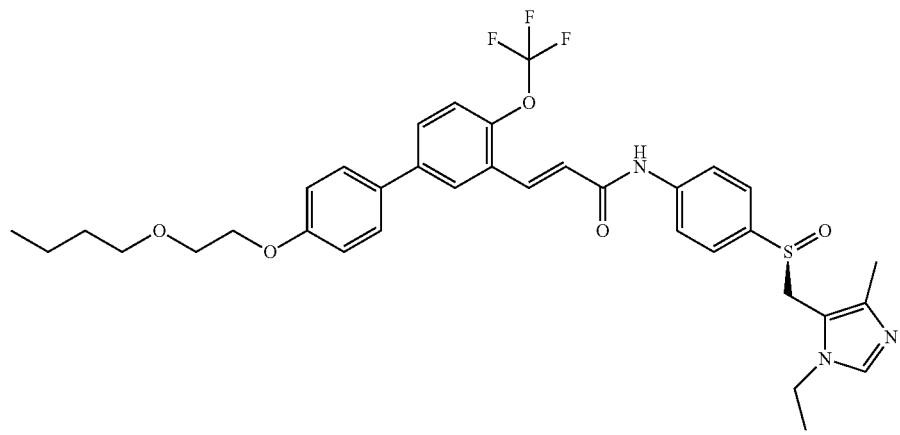

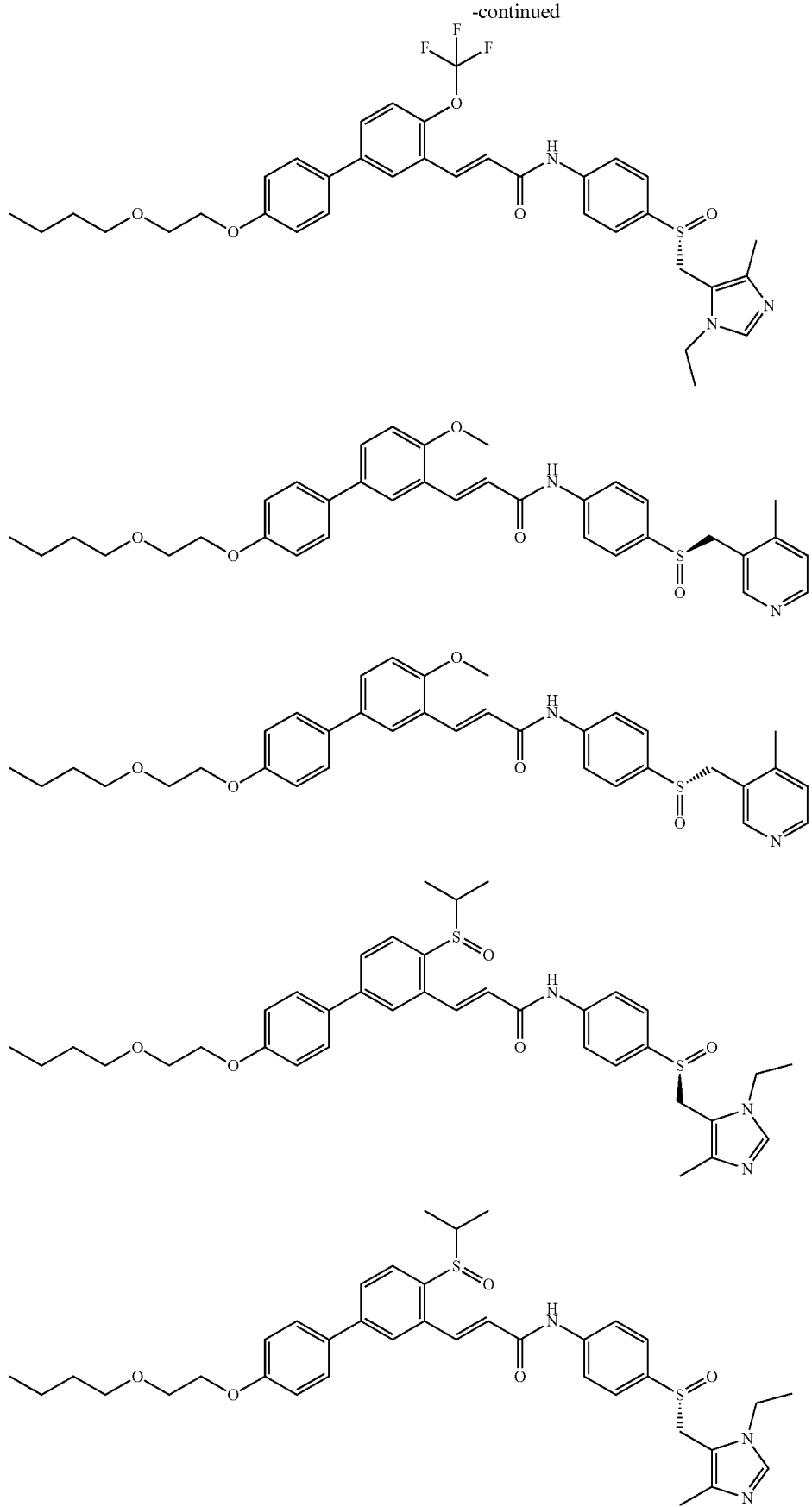

-continued
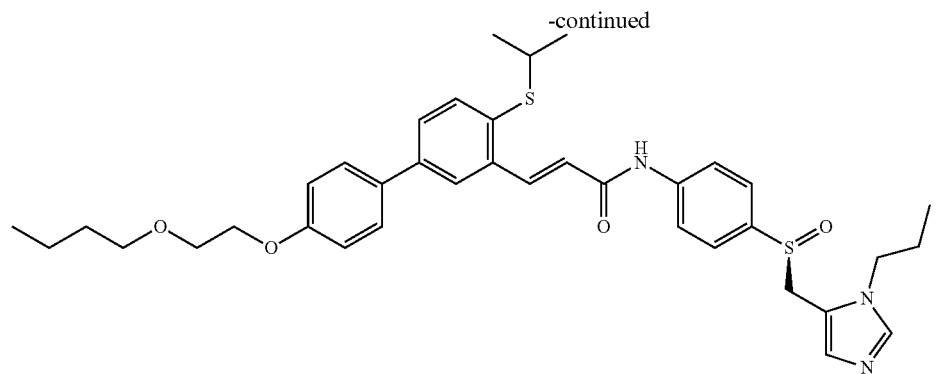
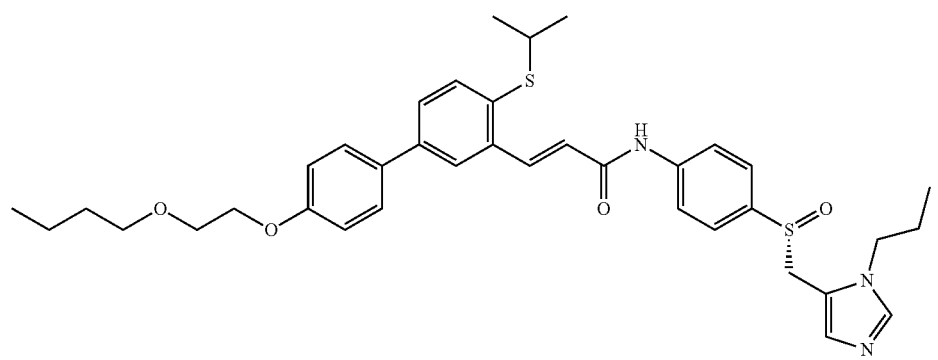
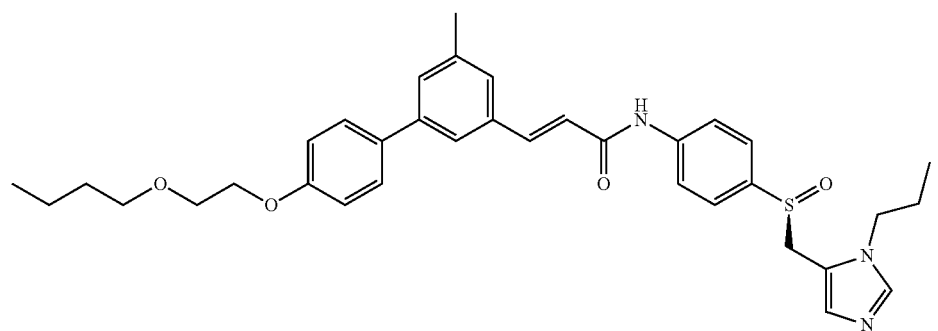
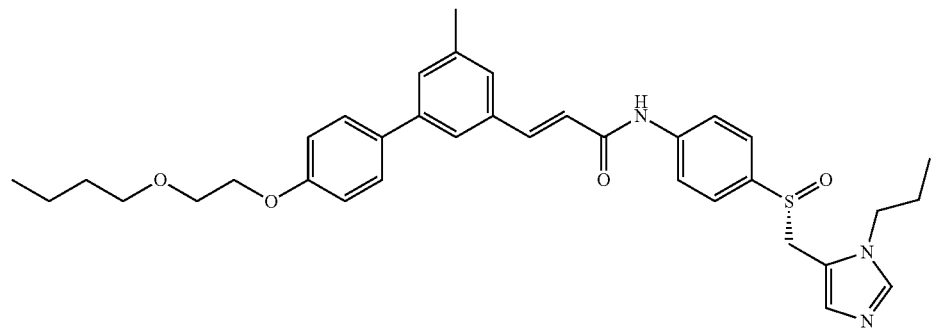

-continued
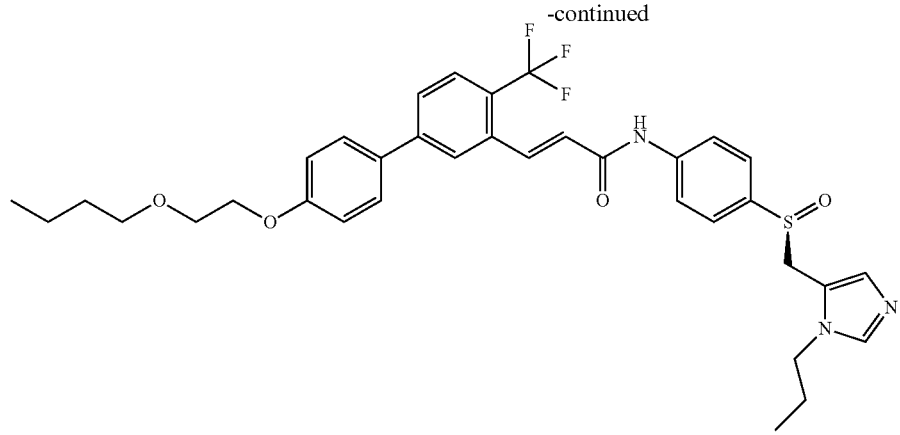
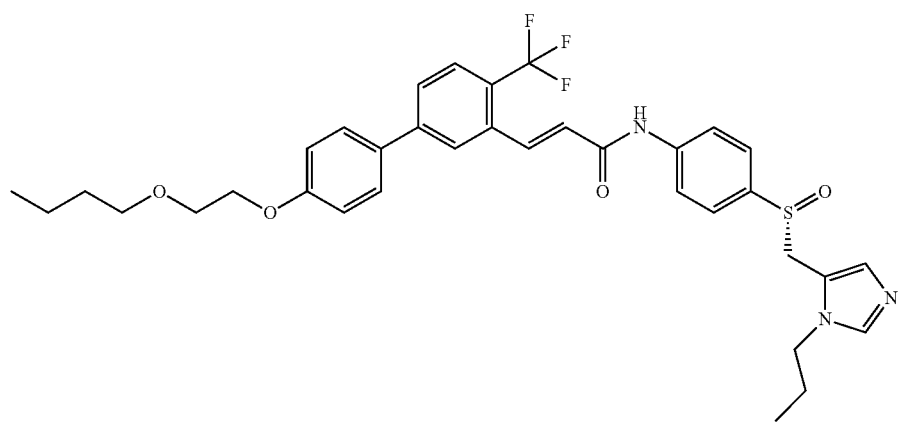
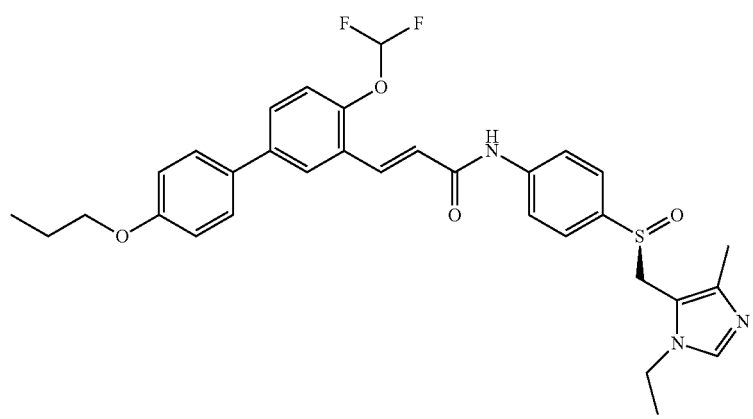
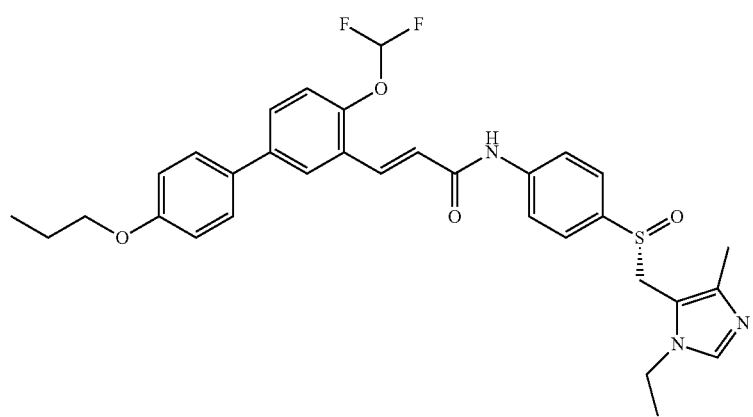

-continued
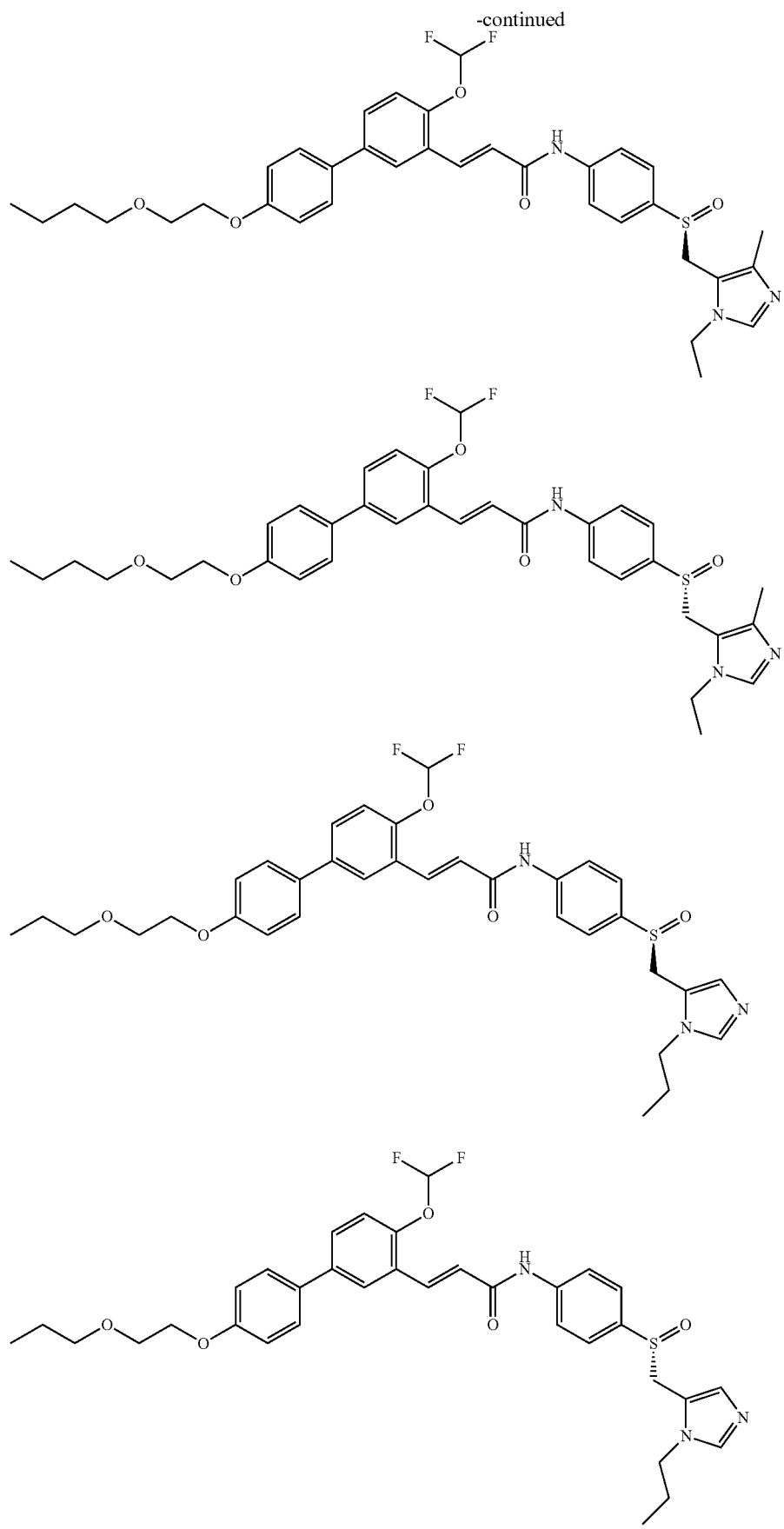

-continued
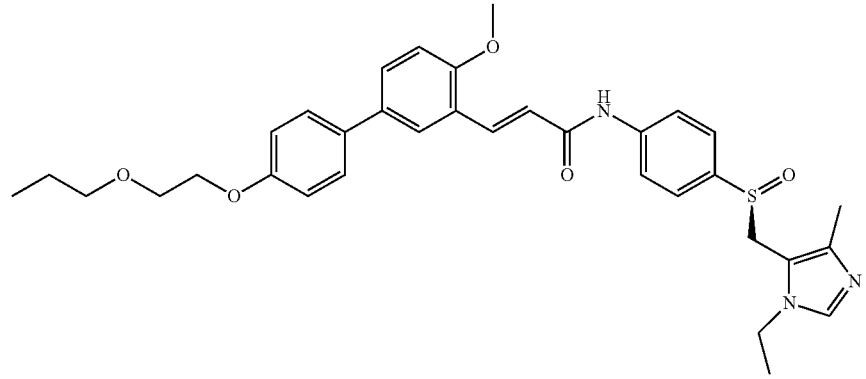
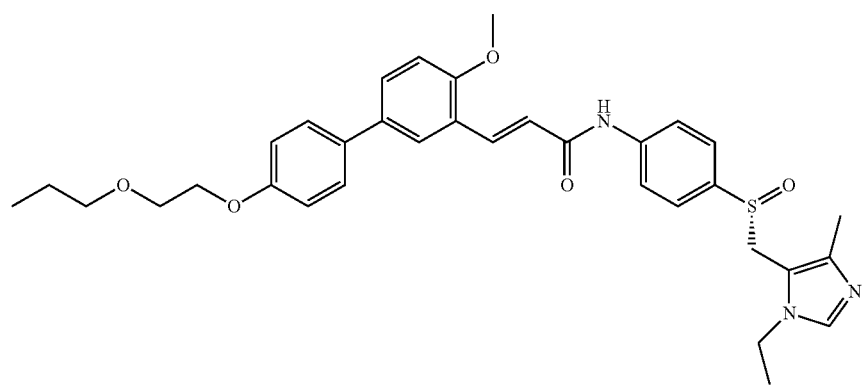
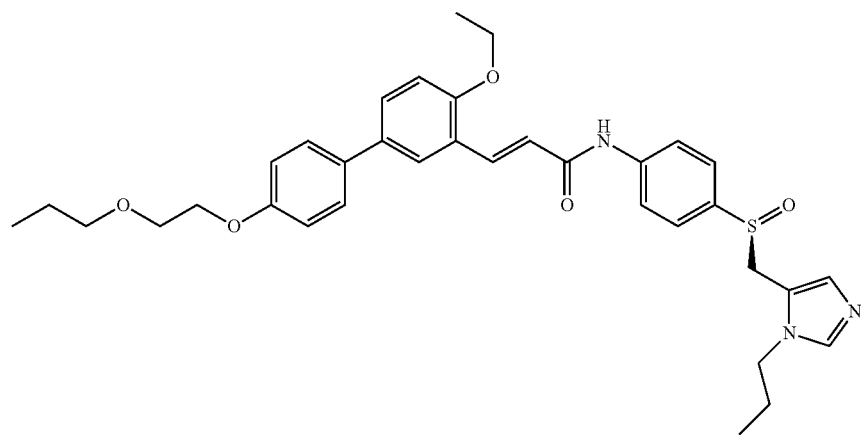
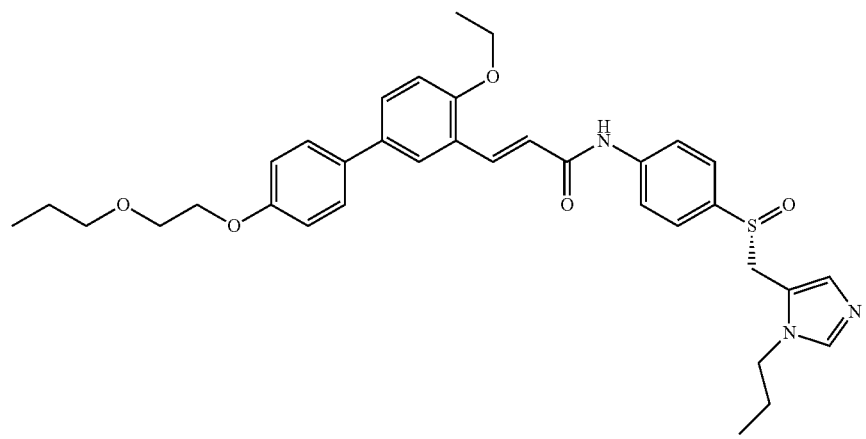

-continued
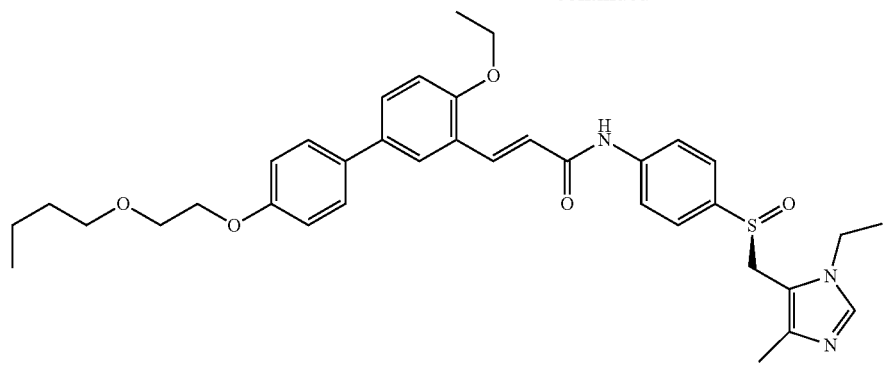
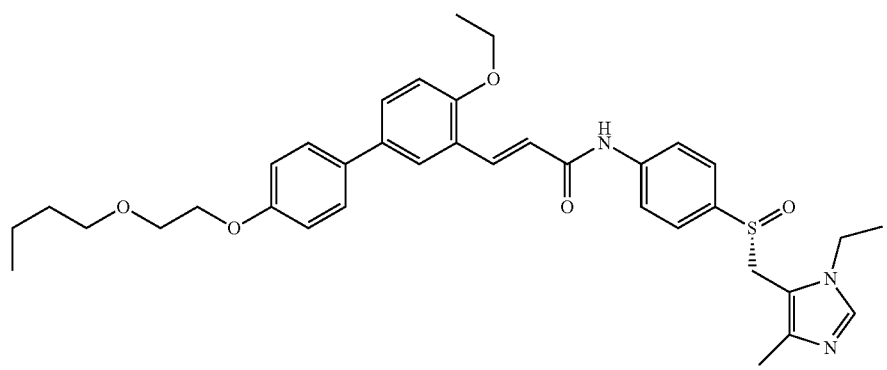
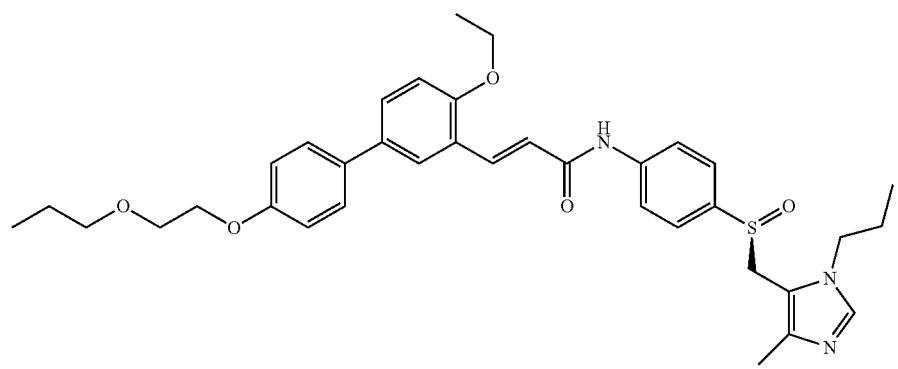
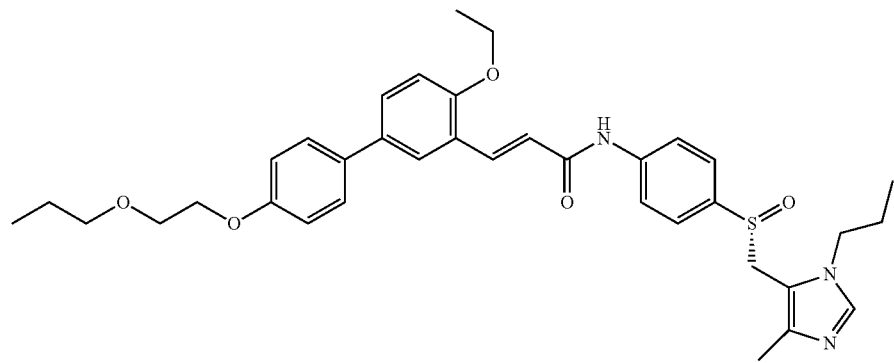

-continued
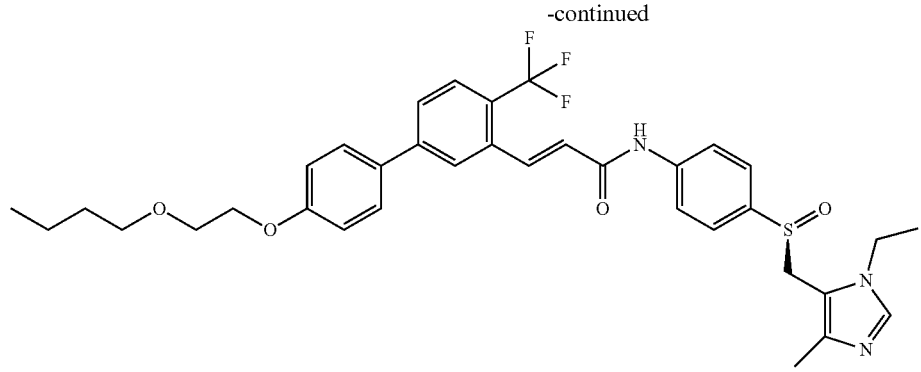
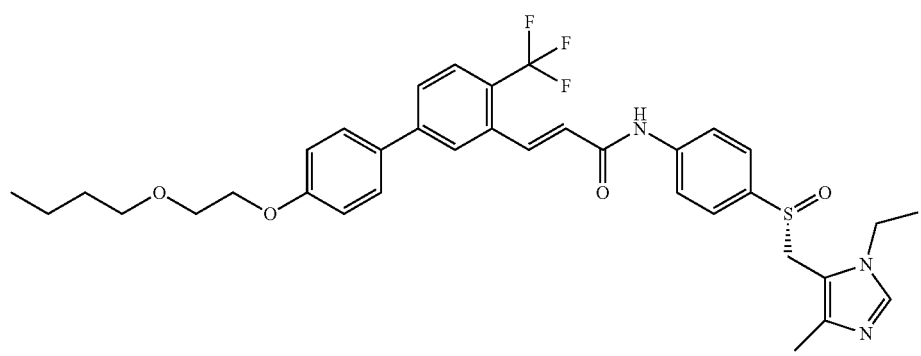
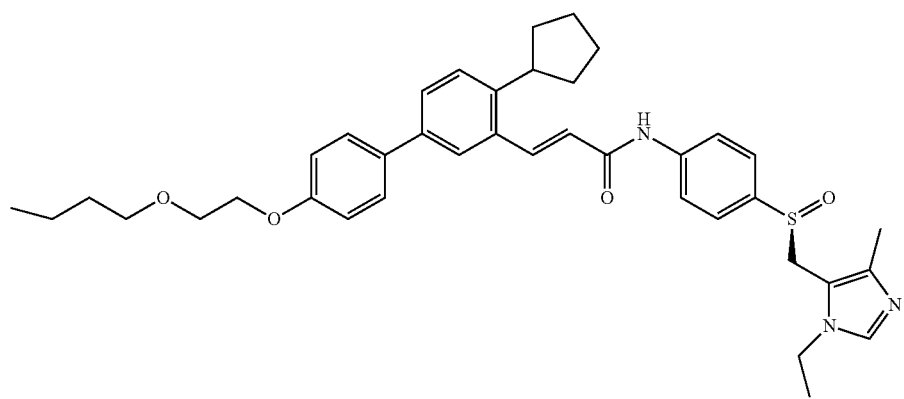
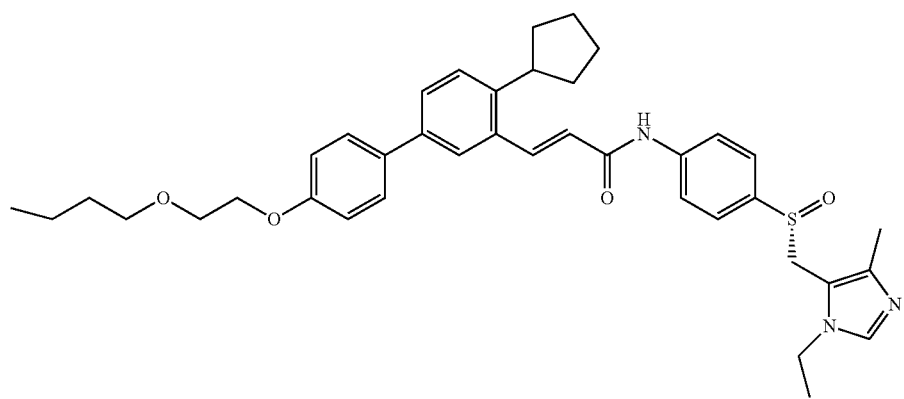

-continued
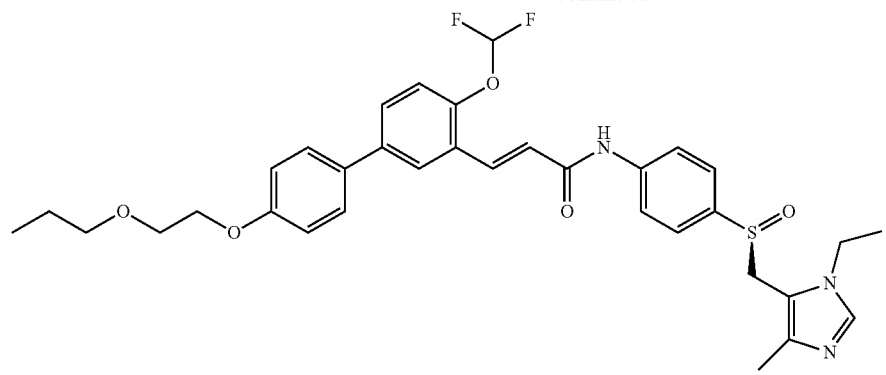
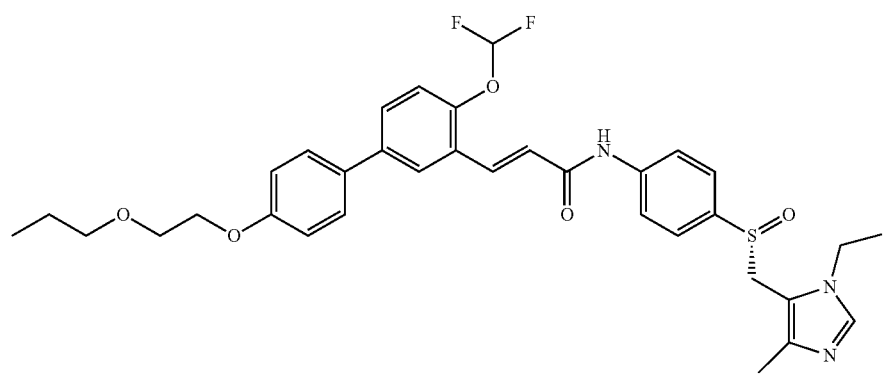
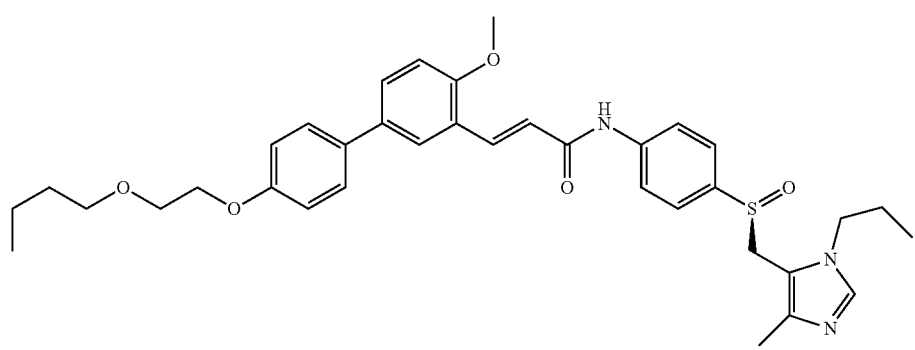
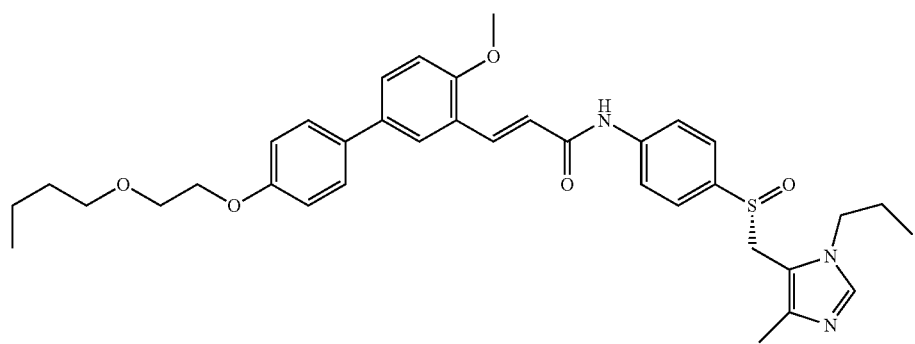

-continued
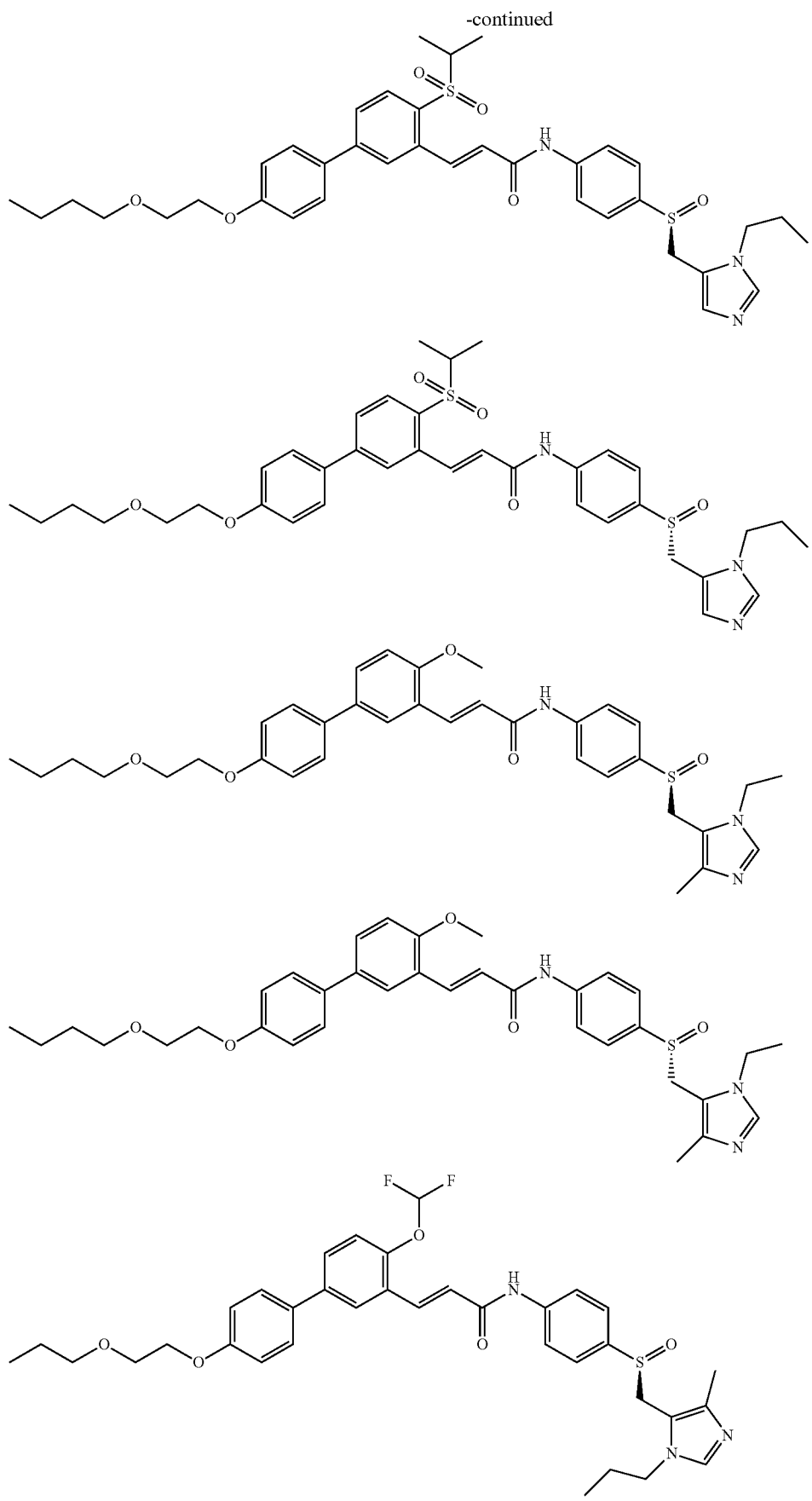

-continued
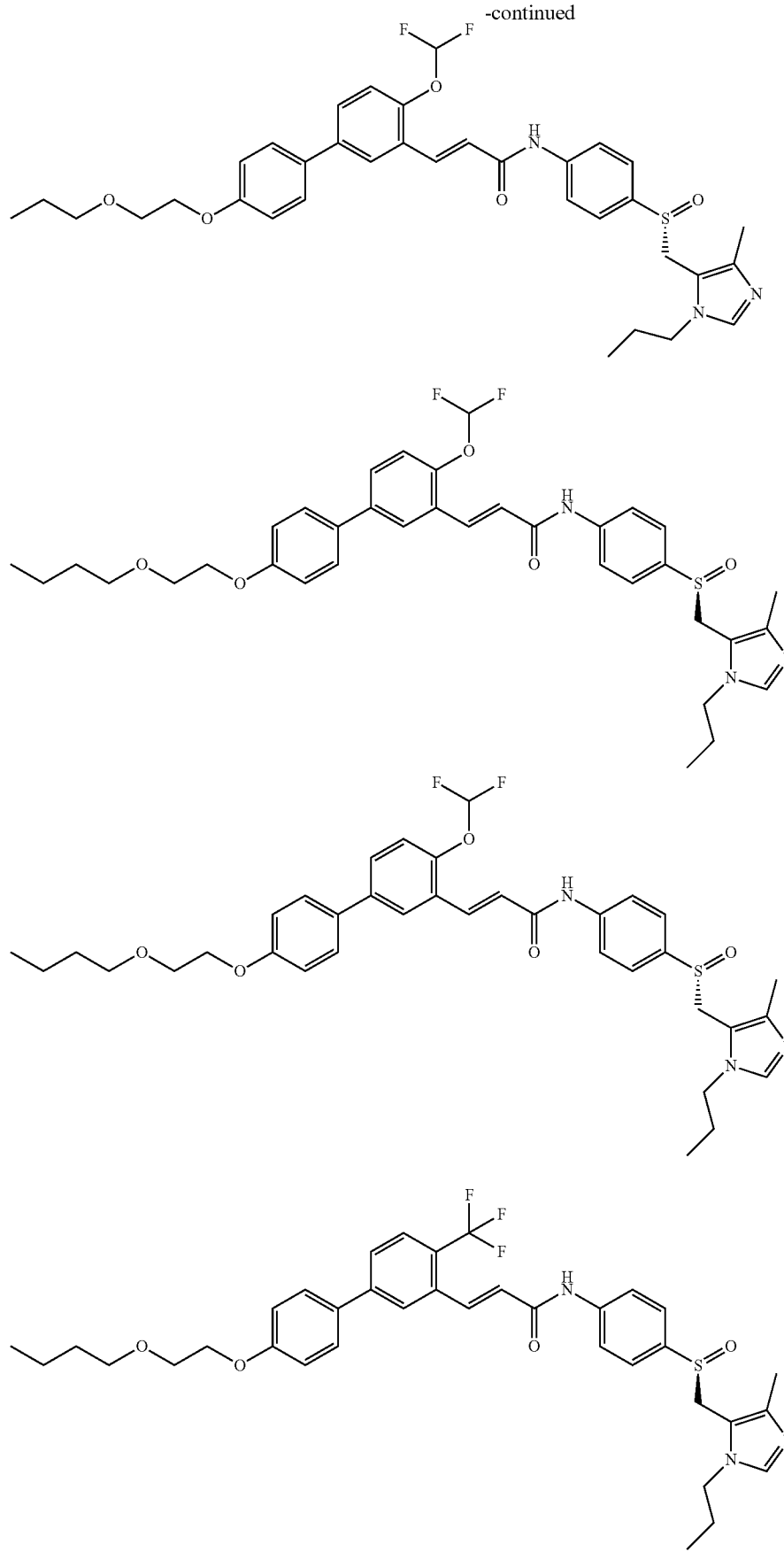

-continued
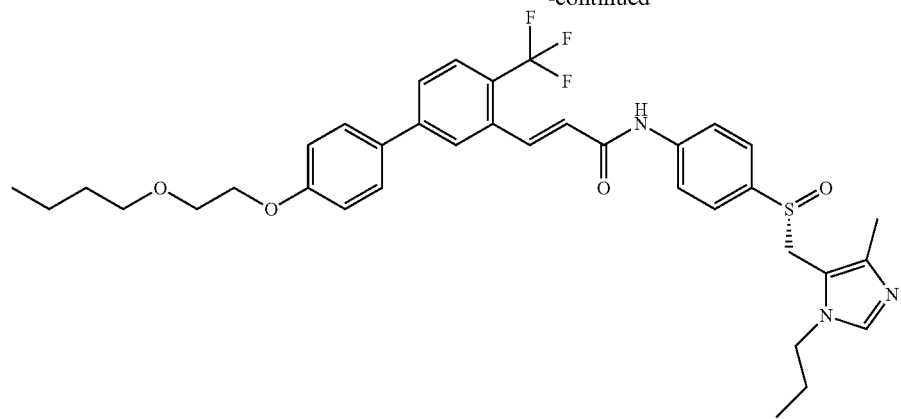
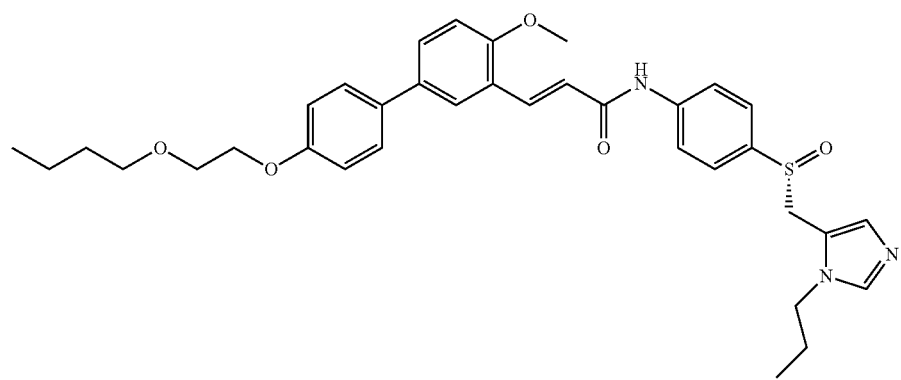
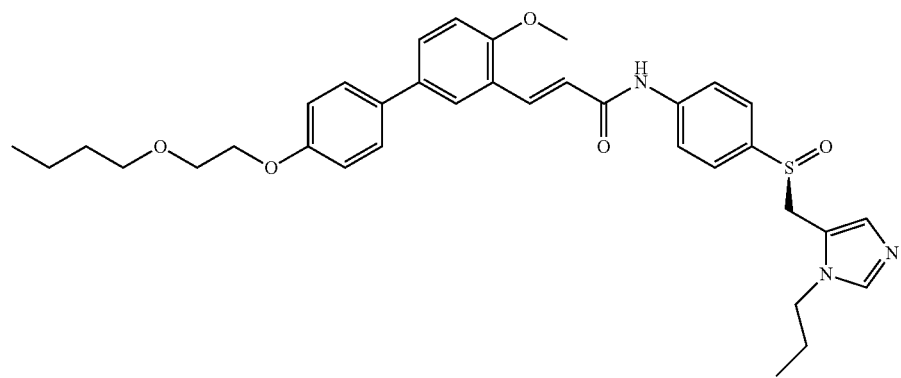
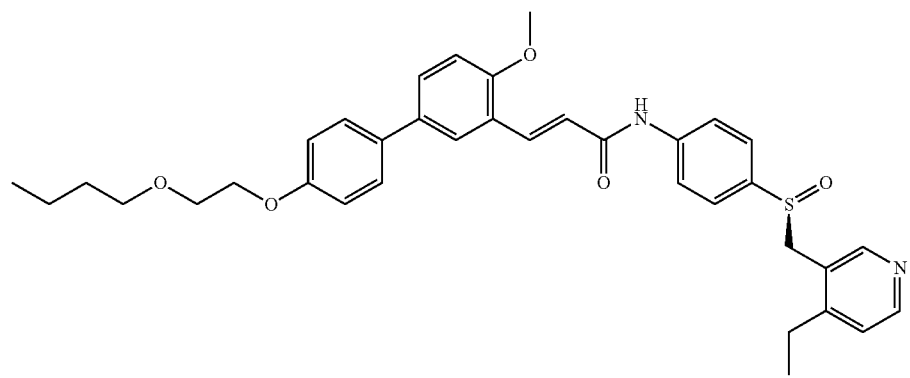

-continued
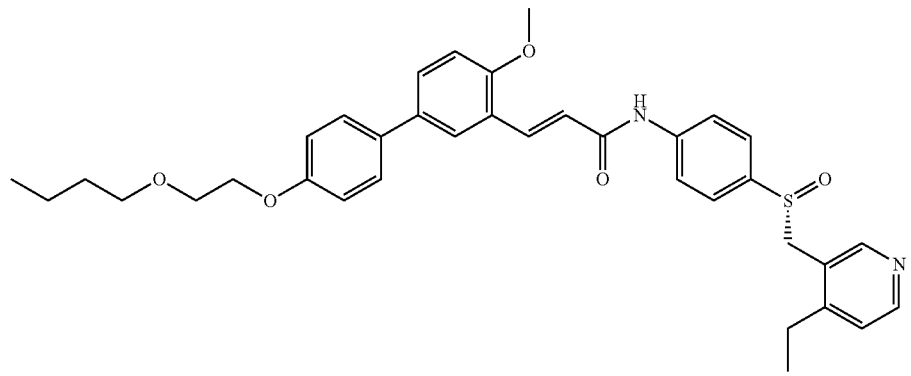
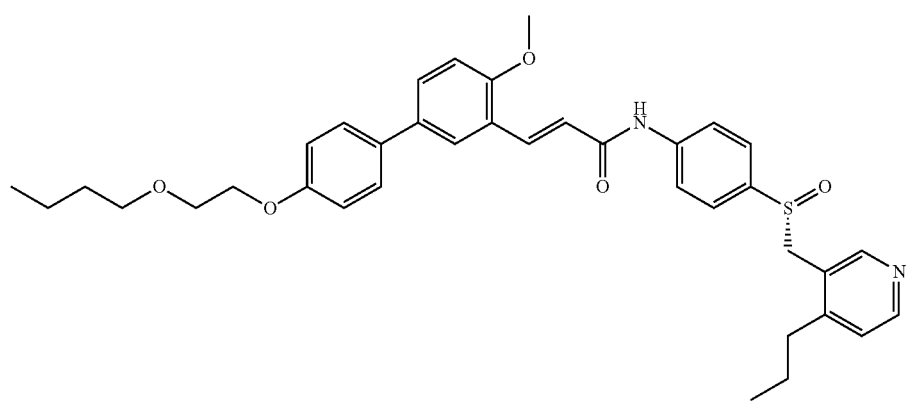
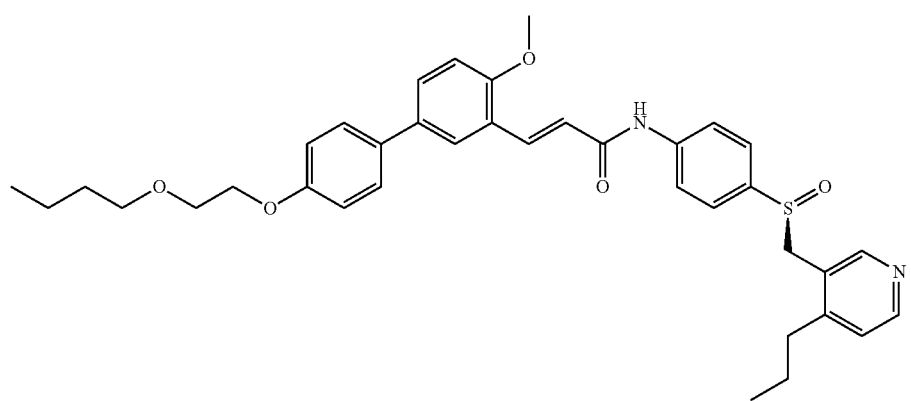
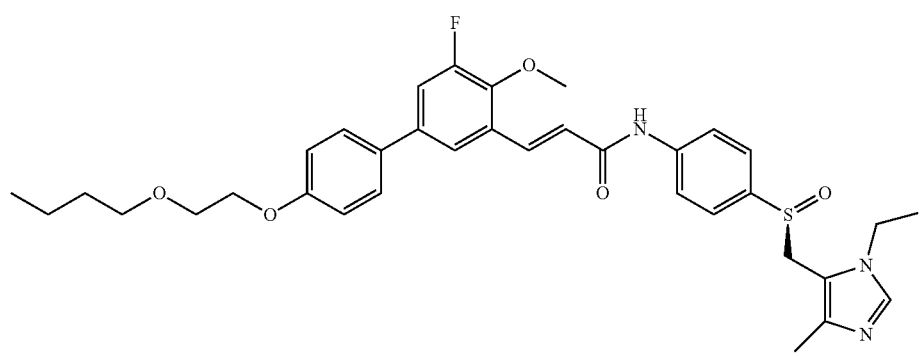

-continued
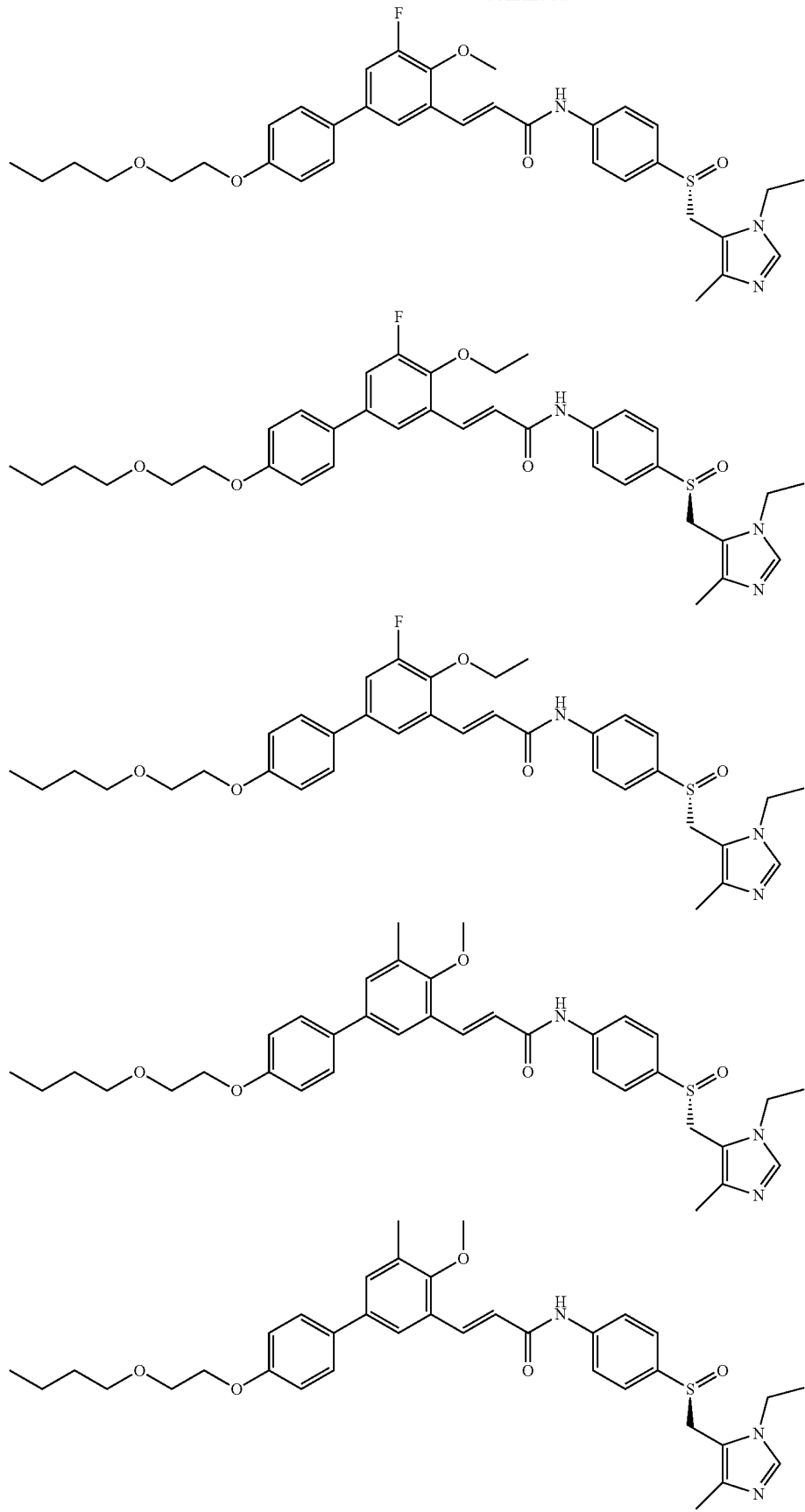

-continued

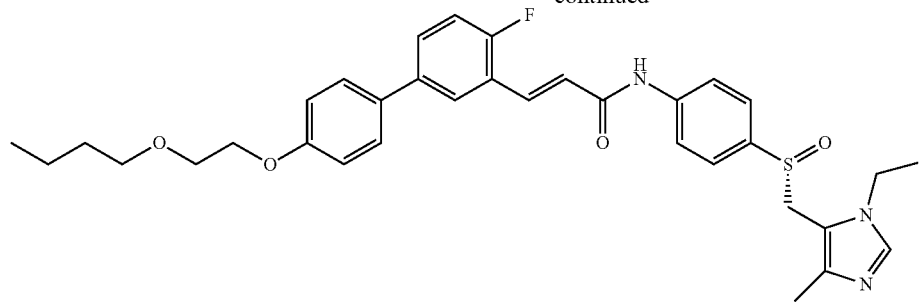

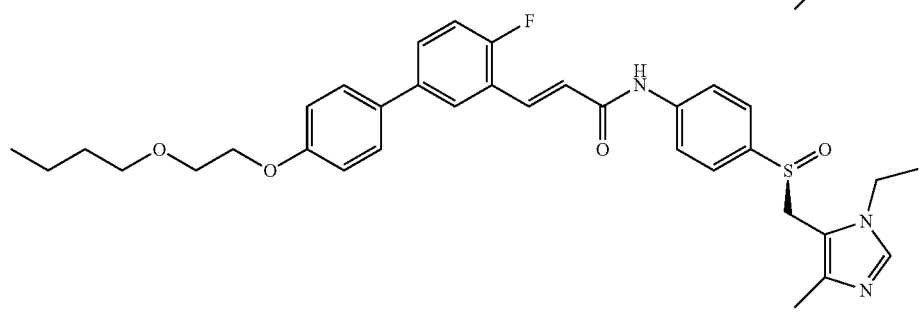

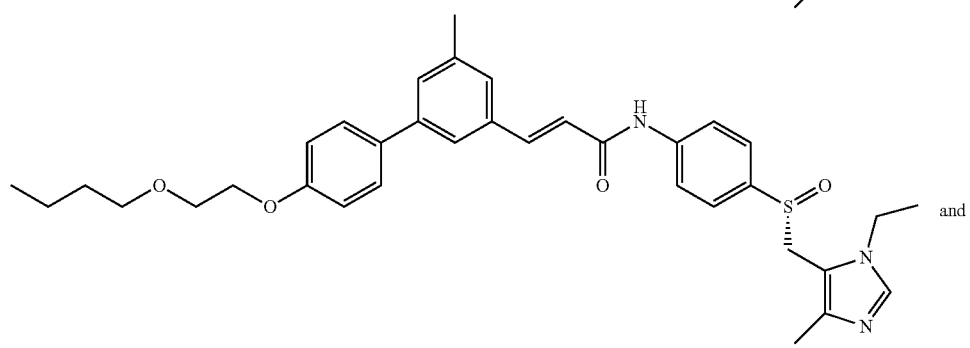

and

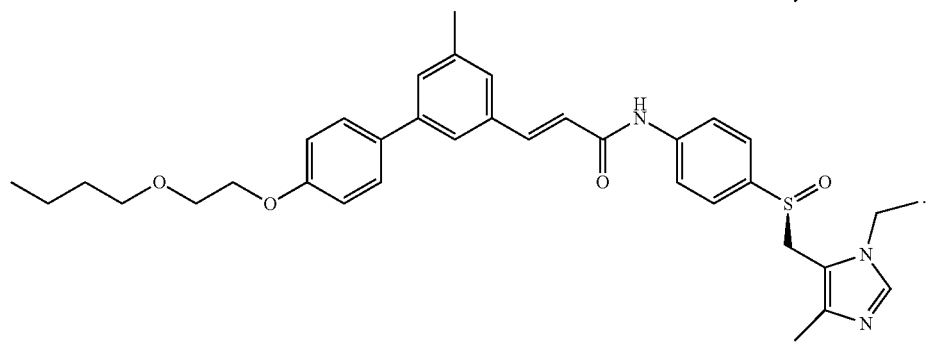

.

23. A pharmaceutical composition, comprising a therapeutically effective amount of the compound or the pharmaceutically acceptable salt thereof according to claim 1, and a pharmaceutically acceptable carrier.

24. A method of treating CCR2 and/or CCR5 related disease in a subject in need thereof, comprising administering a pharmaceutically effective amount of the compound or the pharmaceutically acceptable salt thereof according to claim 1.

25. A method of treating CCR2 and/or CCR5 related disease in a subject in need thereof, comprising administering a pharmaceutically effective amount of the pharmaceutical composition according to claim 23 to the subject.

* * * * *